(12) United States Patent
Moshgabadi et al.

(10) Patent No.: US 11,526,504 B1
(45) Date of Patent: Dec. 13, 2022

(54) SEARCH-TIME FIELD EXTRACTION IN A DATA INTAKE AND QUERY SYSTEM

(71) Applicant: Splunk Inc., San Francisco, CA (US)

(72) Inventors: Amin Moshgabadi, San Diego, CA (US); Baibhav Gautam, El Sobrante, CA (US); Hema Krishnamurthy Mohan, San Mateo, CA (US); Joshua Vertes, San Diego, CA (US)

(73) Assignee: Splunk Inc., San Francisco, CA (US)

( * ) Notice: Subject to any disclaimer, the term of this patent is extended or adjusted under 35 U.S.C. 154(b) by 0 days.

(21) Appl. No.: 17/246,154

(22) Filed: Apr. 30, 2021

(51) Int. Cl.
*G06F 16/00* (2019.01)
*G06F 16/242* (2019.01)
*G06F 3/0482* (2013.01)
*G06F 16/25* (2019.01)
*G06F 16/245* (2019.01)

(52) U.S. Cl.
CPC ........ *G06F 16/2428* (2019.01); *G06F 3/0482* (2013.01); *G06F 16/245* (2019.01); *G06F 16/252* (2019.01)

(58) Field of Classification Search
CPC .......................... G06F 16/26; G06F 16/24578
See application file for complete search history.

(56) References Cited

U.S. PATENT DOCUMENTS

| | | | |
|---|---|---|---|
| 7,937,344 B2 | 5/2011 | Baum et al. | |
| 8,112,425 B2 | 2/2012 | Baum et al. | |
| 8,751,529 B2 | 6/2014 | Zhang et al. | |
| 8,788,525 B2 | 7/2014 | Neels et al. | |
| 9,215,240 B2 | 12/2015 | Merza et al. | |
| 9,286,413 B1 | 3/2016 | Coates et al. | |
| 10,127,258 B2 | 11/2018 | Lamas et al. | |
| 11,016,650 B1 | 5/2021 | Kritzer et al. | |
| 2010/0241351 A1 | 9/2010 | Meisels et al. | |

(Continued)

OTHER PUBLICATIONS

Bitincka, Ledion et al., "Optimizing Data Analysis with a Semi-structured Time Series Database," self-published, first presented at "Workshop on Managing Systems via Log Analysis and Machine Learning Techniques (SLAML)", Vancouver, British Columbia, Oct. 3, 2010.

(Continued)

*Primary Examiner* — Cheryl Lewis
(74) *Attorney, Agent, or Firm* — Knobbe Martens Olson & Bear LLP

(57) ABSTRACT

An improved data intake and query system that can perform and display ingest-time and search-time field extraction, redaction, copy, and/or categorization is described herein. As described herein, ingest-time field extraction, redaction, copy, and/or categorization may refer to field or field value extraction, redaction, copy, and/or categorization that is performed by a log observer system of the data intake and query system on raw machine data as the raw machine data is ingested or received from a publisher. As described herein, search-time field extraction, redaction, copy, and/or categorization may refer to field or field value extraction, redaction, copy, and/or categorization that is performed by the log observer system and/or other components of the improved data intake and query system on historical raw machine data that has already been ingested and indexed by the improved data intake and query system.

20 Claims, 60 Drawing Sheets

(56) References Cited

U.S. PATENT DOCUMENTS

| | | | |
|---|---|---|---|
| 2013/0227582 A1* | 8/2013 | Daly | G06F 9/4881 |
| | | | 718/103 |
| 2015/0341212 A1 | 11/2015 | Hsiao et al. | |
| 2016/0110732 A1 | 4/2016 | Dravneek et al. | |
| 2018/0032570 A1 | 2/2018 | Miller et al. | |
| 2018/0095610 A1* | 4/2018 | Wieder | G06F 3/04855 |
| 2018/0213044 A1 | 7/2018 | George et al. | |
| 2019/0098106 A1 | 3/2019 | Mungel et al. | |
| 2019/0236149 A1 | 8/2019 | Kuruvada et al. | |
| 2020/0104402 A1 | 4/2020 | Burnett et al. | |
| 2021/0027503 A1* | 1/2021 | Kumaresan | G06F 40/177 |

OTHER PUBLICATIONS

Carraso, David, "Exploring Splunk," published by CITO Research, New York, NY, Apr. 2012.

SLAML 10 Reports, Workshop On Managing Systems via Log Analysis and Machine Learning Techniques. ;login: Feb. 2011—Conference Reports—vol. 36, No. 1, pp. 104-110.

Splunk Enterprise Overview 8.0.0—splunk > turn data into doing—copyright 2020 Splunk Inc.—in 17 pages—Retrieved from Splunk Documentation <URL: https://doc.splunk.com/Documentation> on May 20, 2020.

Splunk Cloud User Manual 8.0.2004—splunk> turn data in doing - copyright 2020 Splunk Inc.—in 66 pages—Retrieved from Splunk Documentation <URL: httgs://does.splunk.com/Documentation> on May 20, 2020.

Splunk Quick Reference Guide, updated 2019, available online at https://www.splunk.com/pdfs/solution-guides/splunk-quick-reference-guide.pdf, retrieved May 20, 2020.

U.S. Appl. No. 17/246,229** filed Apr. 30, 2021.

U.S. Appl. No. 17/246,334** filed Apr. 30, 2021.

* cited by examiner

| Time 2135 | Host 2136 | Source 2137 | Source Type 2138 | Event 2139 |
|---|---|---|---|---|
| 10/10/2000 1:55 p.m. | www1 | access.log | access_combined | 127.0.0.1 - frank [10/Oct/2000:13:55:36-0700] "GET/apache.gif HTTP/1.0" 200 2326 0.0947 |
| 10/10/2000 1:56 p.m. | www2 | access.log | access_combined | 127.0.0.1 - bob [10/Oct/2000:13:56:36-0700] "GET/mickey_mouse.gif HTTP/1.0" 200 2980 0.0899 |
| 10/10/2000 1:57 p.m. | www2 | access.log | access_combined | 127.0.0.1 - carlos [10/Oct/2000:13:57:36-0700] "GET/donald_duck.gif HTTP/1.0" 200 2900 0.0857 |
| 10/10/2000 1:58 p.m. | www2 | error.log | apache_error | [Sunday Oct 10 1:58:33 2010] [error] [client 127.10.1.1.015] File does not exist: /home/reba/public_html/images/daffy_duck.gif |

FIG. 21C

| Data Summary | | | |
|---|---|---|---|
| Hosts (5) | Sources (8) | Sourcetypes (3) | × |
| ( filter ) | | | |
| Host ◇ | | Count ◇ | Last Update ◇ |
| mailsv | ⫶⌄ | 9,829 | 4/29/14 1:32:47.000 PM |
| vendor_sales | ⫶⌄ | 30,244 | 4/29/14 1:32:46.000 PM |
| www1 | ⫶⌄ | 24,221 | 4/29/14 1:32:44.000 PM |
| www2 | ⫶⌄ | 22,595 | 4/29/14 1:32:47.000 PM |
| www3 | ⫶⌄ | 22,975 | 4/29/14 1:32:45.000 PM |

FIG. 24B

New Pivot 1,776,004 of 1,776,004 events matched                                              Save As ▾  Clear

Filters: All time

Split Rows: component

Split Columns: group

Column Values: Count of Event O...

| component | NULL | conf | deploy-connections | deploy-server | map | mpool | per_host_thruput | per_index_thruput | per_source_thruput | per_sourcetype_thruput | pipeline | queue | realtime_search_data |
|---|---|---|---|---|---|---|---|---|---|---|---|---|---|
| BucketMover | 4 | 0 | 0 | 0 | 0 | 0 | 0 | 0 | 0 | 0 | 0 | 0 | 0 |
| DatabaseDirectoryManager | 4 | 0 | 0 | 0 | 0 | 0 | 0 | 0 | 0 | 0 | 0 | 0 | 0 |
| DateParserVerbose | 562 | 0 | 0 | 0 | 0 | 0 | 0 | 0 | 0 | 0 | 0 | 0 | 0 |
| DiskMon | 3 | 0 | 0 | 0 | 0 | 0 | 0 | 0 | 0 | 0 | 0 | 0 | 0 |
| IndexConfig | 1 | 0 | 0 | 0 | 0 | 0 | 0 | 0 | 0 | 0 | 0 | 0 | 0 |
| LicenseUsage | 2872 | 0 | 972 | 2916 | 972 | 972 | 4621 | 2843 | 9314 | 9306 | 18797 | 12206 | 972 |
| Metrics | 0 | 1 | 0 | 0 | 0 | 0 | 0 | 0 | 0 | 0 | 0 | 0 | 0 |
| OneShotWriter | 12226 | 0 | 0 | 0 | 0 | 0 | 0 | 0 | 0 | 0 | 0 | 0 | 0 |
| TailingProcessor | 2 | 0 | 0 | 0 | 0 | 0 | 0 | 0 | 0 | 0 | 0 | 0 | 0 |
| WatchedFile | 18 | 0 | 0 | 0 | 0 | 0 | 0 | 0 | 0 | 0 | 0 | 0 | 0 |
| cached | 5 | 0 | 0 | 0 | 0 | 0 | 0 | 0 | 0 | 0 | 0 | 0 | 0 |
| decorators | 2 | 0 | 0 | 0 | 0 | 0 | 0 | 0 | 0 | 0 | 0 | 0 | 0 |
| utils | 1 | 0 | 0 | 0 | 0 | 0 | 0 | 0 | 0 | 0 | 0 | 0 | 0 |
| view | 6 | 0 | 0 | 0 | 0 | 0 | 0 | 0 | 0 | 0 | 0 | 0 | 0 |

20 per page ▾   Format ▾

SEARCH-TIME FIELD EXTRACTION IN A DATA INTAKE AND QUERY SYSTEM

RELATED APPLICATIONS

Any and all applications for which a foreign or domestic priority claim is identified in the Application Data Sheet as filed with the present application are incorporated by reference under 37 CFR 1.57 and made a part of this specification.

FIELD

At least one embodiment of the present disclosure pertains to one or more tools for facilitating searching and analyzing large sets of data to locate data of interest.

BACKGROUND

Information technology (IT) environments can include diverse types of data systems that store large amounts of diverse data types generated by numerous devices. For example, a big data ecosystem may include databases such as MySQL and Oracle databases, cloud computing services such as Amazon web services (AWS), and other data systems that store passively or actively generated data, including machine-generated data ("machine data"). The machine data can include performance data, diagnostic data, or any other data that can be analyzed to diagnose equipment performance problems, monitor user interactions, and to derive other insights.

The large amount and diversity of data systems containing large amounts of structured, semi-structured, and unstructured data relevant to any search query can be massive, and continues to grow rapidly. This technological evolution can give rise to various challenges in relation to managing, understanding and effectively utilizing the data. To reduce the potentially vast amount of data that may be generated, some data systems pre-process data based on anticipated data analysis needs. In particular, specified data items may be extracted from the generated data and stored in a data system to facilitate efficient retrieval and analysis of those data items at a later time. At least some of the remainder of the generated data is typically discarded during pre-processing.

However, storing massive quantities of minimally processed or unprocessed data (collectively and individually referred to as "raw data") for later retrieval and analysis is becoming increasingly more feasible as storage capacity becomes more inexpensive and plentiful. In general, storing raw data and performing analysis on that data later can provide greater flexibility because it enables an analyst to analyze all of the generated data instead of only a fraction of it.

Although the availability of vastly greater amounts of diverse data on diverse data systems provides opportunities to derive new insights, it also gives rise to technical challenges to search and analyze the data. Tools exist that allow an analyst to search data systems separately and collect results over a network for the analyst to derive insights in a piecemeal manner. However, UI tools that allow analysts to quickly search and analyze large set of raw machine data to visually identify data subsets of interest, particularly via straightforward and easy-to-understand sets of tools and search functionality do not exist.

BRIEF DESCRIPTION OF THE DRAWINGS

The present disclosure is illustrated by way of example, and not limitation, in the figures of the accompanying drawings, in which like reference numerals indicate similar elements.

FIG. 21C provides a visual representation of the manner in which a pipelined search language or query operates, in accordance with example embodiments.

FIG. 24B is an interface diagram of an example user interface for a data summary dialog that enables a user to select various data sources, in accordance with example embodiments.

FIGS. 25, 26, 27A-27D, 28, 29, 30, and 31 are interface diagrams of example report generation user interfaces, in accordance with example embodiments.

FIG. 33B is an interface diagram of an example user interface of an incident review dashboard, in accordance with example embodiments.

DETAILED DESCRIPTION

Figure 1:
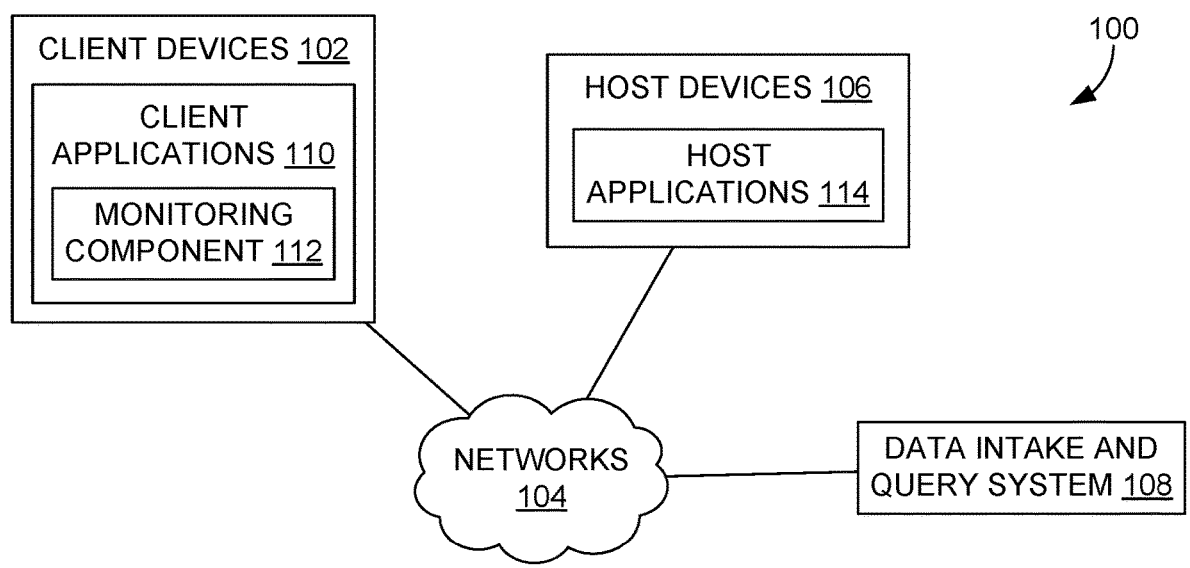
FIG. 1 is a block diagram of an example networked computer environment, in accordance with example embodiments.7

Embodiments are described herein according to the following outline:

1.0. General Overview
2.0. Operating Environment
  2.1. Host Devices
  2.2. Client Devices
  2.3. Client Device Applications
  2.4. Data Intake and Query System Overview
3.0. Data Intake and Query System Architecture
  3.1. Intake System
    3.1.1 Forwarder
    3.1.2 Data Retrieval Subsystem
    3.1.3 Ingestion Buffer
    3.1.4 Streaming Data Processors
  3.2. Indexing System
    3.2.1. Indexing System Manager
    3.2.2. Indexing Nodes
      3.2.2.1 Indexing Node Manager
      3.2.2.2 Partition Manager
      3.2.2.3 Indexer and Data Store
    3.2.3. Bucket Manager
  3.3 Query System
    3.3.1. Query System Manager
    3.3.2. Search Head
      3.3.2.1 Search Master
      3.3.2.2 Search Manager
    3.3.3. Search Nodes
    3.3.4. Cache Manager
    3.3.5. Search Node Monitor and Catalog
  3.4. Common Storage
  3.5. Data Store Catalog
  3.6. Query Acceleration Data Store
4.0. Data Intake and Query System Functions
  4.1. Ingestion
    4.1.1 Publication to Intake Topic(s)
    4.1.2 Transmission to Streaming Data Processors
    4.1.3 Messages Processing
    4.1.4 Transmission to Subscribers
    4.1.5 Data Resiliency and Security
    4.1.6 Message Processing Algorithm
  4.2. Indexing
    4.2.1. Containerized Indexing Nodes
    4.2.2. Moving Buckets to Common Storage
    4.2.3. Updating Location Marker in Ingestion Buffer
    4.2.4. Merging Buckets
  4.3. Querying
    4.3.1. Containerized Search Nodes
    4.3.2. Identifying Buckets for Query Execution
    4.3.4. Hashing Bucket Identifiers for Query Execution
    4.3.5. Mapping Buckets to Search Nodes
    4.3.6. Obtaining Data for Query Execution
    4.3.7. Caching Search Results
  4.4. Data Ingestion, Indexing, and Storage Flow
    4.4.1. Input
    4.4.2. Parsing
    4.4.3. Indexing
  4.5. Query Processing Flow
  4.6. Pipelined Search Language
  4.7. Field Extraction
  4.8. Example Search Screen
  4.9. Data Models
  4.10. Acceleration Techniques
    4.10.1. Aggregation Technique
    4.10.2. Keyword Index
    4.10.3. High Performance Analytics Store
      4.10.3.1 Extracting Event Data Using Posting
    4.10.4. Accelerating Report Generation
  4.12. Security Features
  4.13. Data Center Monitoring
  4.14. IT Service Monitoring
  4.15. Ingest-Time Processing
  4.16. Other Architectures
5.0. Terminology
6.0. Example Embodiments 1.0. General Overview Modern data centers and other computing environments can comprise anywhere from a few host computer systems to thousands of systems configured to process data, service requests from remote clients, and perform numerous other computational tasks. During operation, various components within these computing environments often generate significant volumes of machine data. Machine data is any data produced by a machine or component in an information technology (IT) environment and that reflects activity in the IT environment. For example, machine data can be raw machine data that is generated by various components in IT environments, such as servers, sensors, routers, mobile devices, Internet of Things (IoT) devices, etc. Machine data can include system logs, network packet data, sensor data, application program data, error logs, stack traces, system performance data, etc. In general, machine data can also include performance data, diagnostic information, and many other types of data that can be analyzed to diagnose performance problems, monitor user interactions, and to derive other insights.

A number of tools are available to analyze machine data. In order to reduce the size of the potentially vast amount of machine data that may be generated, many of these tools typically pre-process the data based on anticipated data-analysis needs. For example, pre-specified data items may be extracted from the machine data and stored in a database to facilitate efficient retrieval and analysis of those data items at search time. However, the rest of the machine data typically is not saved and is discarded during pre-processing. As storage capacity becomes progressively cheaper and more plentiful, there are fewer incentives to discard these portions of machine data and many reasons to retain more of the data.

This plentiful storage capacity is presently making it feasible to store massive quantities of minimally processed machine data for later retrieval and analysis. In general, storing minimally processed machine data and performing analysis operations at search time can provide greater flexibility because it enables an analyst to search all of the machine data, instead of searching only a pre-specified set of data items. This may enable an analyst to investigate different aspects of the machine data that previously were unavailable for analysis.

However, analyzing and searching massive quantities of machine data presents a number of challenges. For example, a data center, servers, or network appliances may generate many different types and formats of machine data (e.g., system logs, network packet data (e.g., wire data, etc.), sensor data, application program data, error logs, stack traces, system performance data, operating system data, virtualization data, etc.) from thousands of different components, which can collectively be very time-consuming to analyze. In another example, mobile devices may generate large amounts of information relating to data accesses, application performance, operating system performance, network performance, etc. There can be millions of mobile devices that report these types of information.

These challenges can be addressed by using an event-based data intake and query system, such as the SPLUNK® ENTERPRISE system developed by Splunk Inc. of San Francisco, Calif. The SPLUNK® ENTERPRISE system is the leading platform for providing real-time operational intelligence that enables organizations to collect, index, and search machine data from various websites, applications, servers, networks, and mobile devices that power their businesses. The data intake and query system is particularly useful for analyzing data which is commonly found in system log files, network data, and other data input sources. Although many of the techniques described herein are explained with reference to a data intake and query system similar to the SPLUNK® ENTERPRISE system, these techniques are also applicable to other types of data systems.

In the data intake and query system, machine data are collected and stored as "events". An event comprises a portion of machine data and is associated with a specific point in time. The portion of machine data may reflect activity in an IT environment and may be produced by a component of that IT environment, where the events may be searched to provide insight into the IT environment, thereby improving the performance of components in the IT environment. Events may be derived from "time series data," where the time series data comprises a sequence of data points (e.g., performance measurements from a computer system, etc.) that are associated with successive points in time. In general, each event has a portion of machine data that is associated with a timestamp that is derived from the portion of machine data in the event. A timestamp of an event may be determined through interpolation between temporally proximate events having known timestamps or may be determined based on other configurable rules for associating timestamps with events.

In some instances, machine data can have a predefined format, where data items with specific data formats are stored at predefined locations in the data. For example, the machine data may include data associated with fields in a database table. In other instances, machine data may not have a predefined format (e.g., may not be at fixed, predefined locations), but may have repeatable (e.g., non-random) patterns. This means that some machine data can comprise various data items of different data types that may be stored at different locations within the data. For example, when the data source is an operating system log, an event can include one or more lines from the operating system log containing machine data that includes different types of performance and diagnostic information associated with a specific point in time (e.g., a timestamp).

Examples of components which may generate machine data from which events can be derived include, but are not limited to, web servers, application servers, databases, firewalls, routers, operating systems, and software applications that execute on computer systems, mobile devices, sensors, Internet of Things (IoT) devices, etc. The machine data generated by such data sources can include, for example and without limitation, server log files, activity log files, configuration files, messages, network packet data, performance measurements, sensor measurements, etc.

The data intake and query system uses a flexible schema to specify how to extract information from events. A flexible schema may be developed and redefined as needed. Note that a flexible schema may be applied to events "on the fly," when it is needed (e.g., at search time, index time, ingestion time, etc.). When the schema is not applied to events until search time, the schema may be referred to as a "late-binding schema."

During operation, the data intake and query system receives machine data from any type and number of sources (e.g., one or more system logs, streams of network packet data, sensor data, application program data, error logs, stack traces, system performance data, etc.). The system parses the machine data to produce events each having a portion of machine data associated with a timestamp. The system stores the events in a data store. The system enables users to run queries against the stored events to, for example, retrieve events that meet criteria specified in a query, such as criteria indicating certain keywords or having specific values in defined fields. As used herein, the term "field" refers to a location in the machine data of an event containing one or more values for a specific data item. A field may be referenced by a field name associated with the field. As will be described in more detail herein, a field is defined by an extraction rule (e.g., a regular expression) that derives one or more values or a sub-portion of text from the portion of machine data in each event to produce a value for the field for that event. The set of values produced are semantically-related (such as IP address), even though the machine data in each event may be in different formats (e.g., semantically-related values may be in different positions in the events derived from different sources).

As described above, the system stores the events in a data store. The events stored in the data store are field-searchable, where field-searchable herein refers to the ability to search the machine data (e.g., the raw machine data) of an event based on a field specified in search criteria. For example, a search having criteria that specifies a field name "UserID" may cause the system to field-search the machine data of events to identify events that have the field name "UserID." In another example, a search having criteria that specifies a field name "UserID" with a corresponding field value "12345" may cause the system to field-search the machine data of events to identify events having that field-value pair (e.g., field name "UserID" with a corresponding field value of "12345"). Events are field-searchable using one or more configuration files associated with the events. Each configuration file includes one or more field names, where each field name is associated with a corresponding extraction rule and a set of events to which that extraction rule applies. The set of events to which an extraction rule applies may be identified by metadata associated with the set of events. For example, an extraction rule may apply to a set of events that are each associated with a particular host, source, or source type. When events are to be searched based on a particular field name specified in a search, the system uses one or more configuration files to determine whether there is an extraction rule for that particular field name that applies to each event that falls within the criteria of the search. If so, the event is considered as part of the search results (and additional processing may be performed on that event based on criteria specified in the search). If not, the next event is similarly analyzed, and so on.

As noted above, the data intake and query system utilizes a late-binding schema while performing queries on events. One aspect of a late-binding schema is applying extraction rules to events to extract values for specific fields during search time. More specifically, the extraction rule for a field can include one or more instructions that specify how to extract a value for the field from an event. An extraction rule can generally include any type of instruction for extracting values from events. In some cases, an extraction rule comprises a regular expression, where a sequence of characters form a search pattern. An extraction rule comprising a regular expression is referred to herein as a regex rule. The system applies a regex rule to an event to extract values for a field associated with the regex rule, where the values are extracted by searching the event for the sequence of characters defined in the regex rule.

In the data intake and query system, a field extractor may be configured to automatically generate extraction rules for certain fields in the events when the events are being created, indexed, or stored, or possibly at a later time. Alternatively, a user may manually define extraction rules for fields using a variety of techniques. In contrast to a conventional schema for a database system, a late-binding schema is not defined at data ingestion time. Instead, the late-binding schema can be developed on an ongoing basis until the time a query is actually executed. This means that extraction rules for the fields specified in a query may be provided in the query itself, or may be located during execution of the query. Hence, as a user learns more about the data in the events, the user can continue to refine the late-binding schema by adding new fields, deleting fields, or modifying the field extraction rules for use the next time the schema is used by the system. Because the data intake and query system maintains the underlying machine data and uses a late-binding schema for searching the machine data, it enables a user to continue investigating and learn valuable insights about the machine data.

In some embodiments, a common field name may be used to reference two or more fields containing equivalent and/or similar data items, even though the fields may be associated with different types of events that possibly have different data formats and different extraction rules. By enabling a common field name to be used to identify equivalent and/or similar fields from different types of events generated by disparate data sources, the system facilitates use of a "common information model" (CIM) across the disparate data sources (further discussed with respect to FIG. 23A).

2.0. Operating Environment

FIG. 1 is a block diagram of an example networked computer environment 100, in accordance with example embodiments. It will be understood that FIG. 1 represents one example of a networked computer system and other embodiments may use different arrangements.

The networked computer system 100 comprises one or more computing devices. These one or more computing devices comprise any combination of hardware and software configured to implement the various logical components described herein. For example, the one or more computing devices may include one or more memories that store instructions for implementing the various components described herein, one or more hardware processors configured to execute the instructions stored in the one or more memories, and various data repositories in the one or more memories for storing data structures utilized and manipulated by the various components.

In some embodiments, one or more client devices 102 are coupled to one or more host devices 106 and a data intake and query system 108 via one or more networks 104. Networks 104 broadly represent one or more LANs, WANs, cellular networks (e.g., LTE, HSPA, 3G, and other cellular technologies), and/or networks using any of wired, wireless, terrestrial microwave, or satellite links, and may include the public Internet.

2.1. Host Devices

In the illustrated embodiment, a system 100 includes one or more host devices 106. Host devices 106 may broadly include any number of computers, virtual machine instances, and/or data centers that are configured to host or execute one or more instances of host applications 114. In general, a host device 106 may be involved, directly or indirectly, in processing requests received from client devices 102. Each host device 106 may comprise, for example, one or more of a network device, a web server, an application server, a database server, etc. A collection of host devices 106 may be configured to implement a network-based service. For example, a provider of a network-based service may configure one or more host devices 106 and host applications 114 (e.g., one or more web servers, application servers, database servers, etc.) to collectively implement the network-based application.

In general, client devices 102 communicate with one or more host applications 114 to exchange information. The communication between a client device 102 and a host application 114 may, for example, be based on the Hypertext Transfer Protocol (HTTP) or any other network protocol. Content delivered from the host application 114 to a client device 102 may include, for example, HTML documents, media content, etc. The communication between a client device 102 and host application 114 may include sending various requests and receiving data packets. For example, in general, a client device 102 or application running on a client device may initiate communication with a host application 114 by making a request for a specific resource (e.g., based on an HTTP request), and the application server may respond with the requested content stored in one or more response packets.

In the illustrated embodiment, one or more of host applications 114 may generate various types of performance data during operation, including event logs, network data, sensor data, and other types of machine data. For example, a host application 114 comprising a web server may generate one or more web server logs in which details of interactions between the web server and any number of client devices 102 is recorded. As another example, a host device 106 comprising a router may generate one or more router logs that record information related to network traffic managed by the router. As yet another example, a host application 114 comprising a database server may generate one or more logs that record information related to requests sent from other host applications 114 (e.g., web servers or application servers) for data managed by the database server.

2.2. Client Devices

Client devices 102 of FIG. 1 represent any computing device capable of interacting with one or more host devices 106 via a network 104. Examples of client devices 102 may include, without limitation, smart phones, tablet computers, handheld computers, wearable devices, laptop computers, desktop computers, servers, portable media players, gaming devices, and so forth. In general, a client device 102 can provide access to different content, for instance, content provided by one or more host devices 106, etc. Each client device 102 may comprise one or more client applications 110, described in more detail in a separate section hereinafter.

2.3. Client Device Applications

In some embodiments, each client device 102 may host or execute one or more client applications 110 that are capable of interacting with one or more host devices 106 via one or more networks 104. For instance, a client application 110 may be or comprise a web browser that a user may use to navigate to one or more websites or other resources provided by one or more host devices 106. As another example, a client application 110 may comprise a mobile application or "app." For example, an operator of a network-based service hosted by one or more host devices 106 may make available one or more mobile apps that enable users of client devices 102 to access various resources of the network-based service. As yet another example, client applications 110 may include background processes that perform various operations without direct interaction from a user. A client application 110 may include a "plug-in" or "extension" to another application, such as a web browser plug-in or extension.

In some embodiments, a client application 110 may include a monitoring component 112. At a high level, the monitoring component 112 comprises a software component or other logic that facilitates generating performance data related to a client device's operating state, including monitoring network traffic sent and received from the client device and collecting other device and/or application-specific information. Monitoring component 112 may be an integrated component of a client application 110, a plug-in, an extension, or any other type of add-on component. Monitoring component 112 may also be a stand-alone process.

In some embodiments, a monitoring component 112 may be created when a client application 110 is developed, for example, by an application developer using a software development kit (SDK). The SDK may include custom monitoring code that can be incorporated into the code implementing a client application 110. When the code is converted to an executable application, the custom code implementing the monitoring functionality can become part of the application itself.

In some embodiments, an SDK or other code for implementing the monitoring functionality may be offered by a provider of a data intake and query system, such as a system 108. In such cases, the provider of the system 108 can implement the custom code so that performance data generated by the monitoring functionality is sent to the system 108 to facilitate analysis of the performance data by a developer of the client application or other users.

In some embodiments, the custom monitoring code may be incorporated into the code of a client application 110 in a number of different ways, such as the insertion of one or more lines in the client application code that call or otherwise invoke the monitoring component 112. As such, a developer of a client application 110 can add one or more lines of code into the client application 110 to trigger the monitoring component 112 at desired points during execution of the application. Code that triggers the monitoring component may be referred to as a monitor trigger. For instance, a monitor trigger may be included at or near the beginning of the executable code of the client application 110 such that the monitoring component 112 is initiated or triggered as the application is launched, or included at other points in the code that correspond to various actions of the client application, such as sending a network request or displaying a particular interface.

In some embodiments, the monitoring component 112 may monitor one or more aspects of network traffic sent and/or received by a client application 110. For example, the monitoring component 112 may be configured to monitor data packets transmitted to and/or from one or more host applications 114. Incoming and/or outgoing data packets can be read or examined to identify network data contained within the packets, for example, and other aspects of data packets can be analyzed to determine a number of network performance statistics. Monitoring network traffic may enable information to be gathered particular to the network performance associated with a client application 110 or set of applications.

In some embodiments, network performance data refers to any type of data that indicates information about the network and/or network performance. Network performance data may include, for instance, a URL requested, a connection type (e.g., HTTP, HTTPS, etc.), a connection start time, a connection end time, an HTTP status code, request length, response length, request headers, response headers, connection status (e.g., completion, response time(s), failure, etc.), and the like. Upon obtaining network performance data indicating performance of the network, the network performance data can be transmitted to a data intake and query system 108 for analysis.

Upon developing a client application 110 that incorporates a monitoring component 112, the client application 110 can be distributed to client devices 102. Applications generally can be distributed to client devices 102 in any manner, or they can be pre-loaded. In some cases, the application may be distributed to a client device 102 via an application marketplace or other application distribution system. For instance, an application marketplace or other application distribution system might distribute the application to a client device based on a request from the client device to download the application.

Examples of functionality that enables monitoring performance of a client device are described in U.S. patent application Ser. No. 14/524,748, entitled "UTILIZING PACKET HEADERS TO MONITOR NETWORK TRAFFIC IN ASSOCIATION WITH A CLIENT DEVICE", filed on 27 Oct. 2014, and which is hereby incorporated by reference in its entirety for all purposes.

In some embodiments, the monitoring component 112 may also monitor and collect performance data related to one or more aspects of the operational state of a client application 110 and/or client device 102. For example, a monitoring component 112 may be configured to collect device performance information by monitoring one or more client device operations, or by making calls to an operating system and/or one or more other applications executing on a client device 102 for performance information. Device performance information may include, for instance, a current wireless signal strength of the device, a current connection type and network carrier, current memory performance information, a geographic location of the device, a device orientation, and any other information related to the operational state of the client device.

In some embodiments, the monitoring component 112 may also monitor and collect other device profile information including, for example, a type of client device, a manufacturer, and model of the device, versions of various software applications installed on the device, and so forth.

In general, a monitoring component 112 may be configured to generate performance data in response to a monitor trigger in the code of a client application 110 or other triggering application event, as described above, and to store the performance data in one or more data records. Each data record, for example, may include a collection of field-value pairs, each field-value pair storing a particular item of performance data in association with a field for the item. For example, a data record generated by a monitoring component 112 may include a "networkLatency" field (not shown in the Figure) in which a value is stored. This field indicates a network latency measurement associated with one or more network requests. The data record may include a "state" field to store a value indicating a state of a network connection, and so forth for any number of aspects of collected performance data.

2.4. Data Intake and Query System Overview

The data intake and query system 108 can process and store data received data from the data sources client devices 102 or host devices 106, and execute queries on the data in response to requests received from one or more computing devices. In some cases, the data intake and query system 108 can generate events from the received data and store the events in buckets in a common storage system. In response to received queries, the data intake and query system can assign one or more search nodes to search the buckets in the common storage.

In certain embodiments, the data intake and query system 108 can include various components that enable it to provide stateless services or enable it to recover from an unavailable or unresponsive component without data loss in a time efficient manner. For example, the data intake and query system 108 can store contextual information about its various components in a distributed way such that if one of the components becomes unresponsive or unavailable, the data intake and query system 108 can replace the unavailable component with a different component and provide the replacement component with the contextual information. In this way, the data intake and query system 108 can quickly recover from an unresponsive or unavailable component while reducing or eliminating the loss of data that was being processed by the unavailable component.

3.0. Data Intake and Query System Architecture

Figure 2:
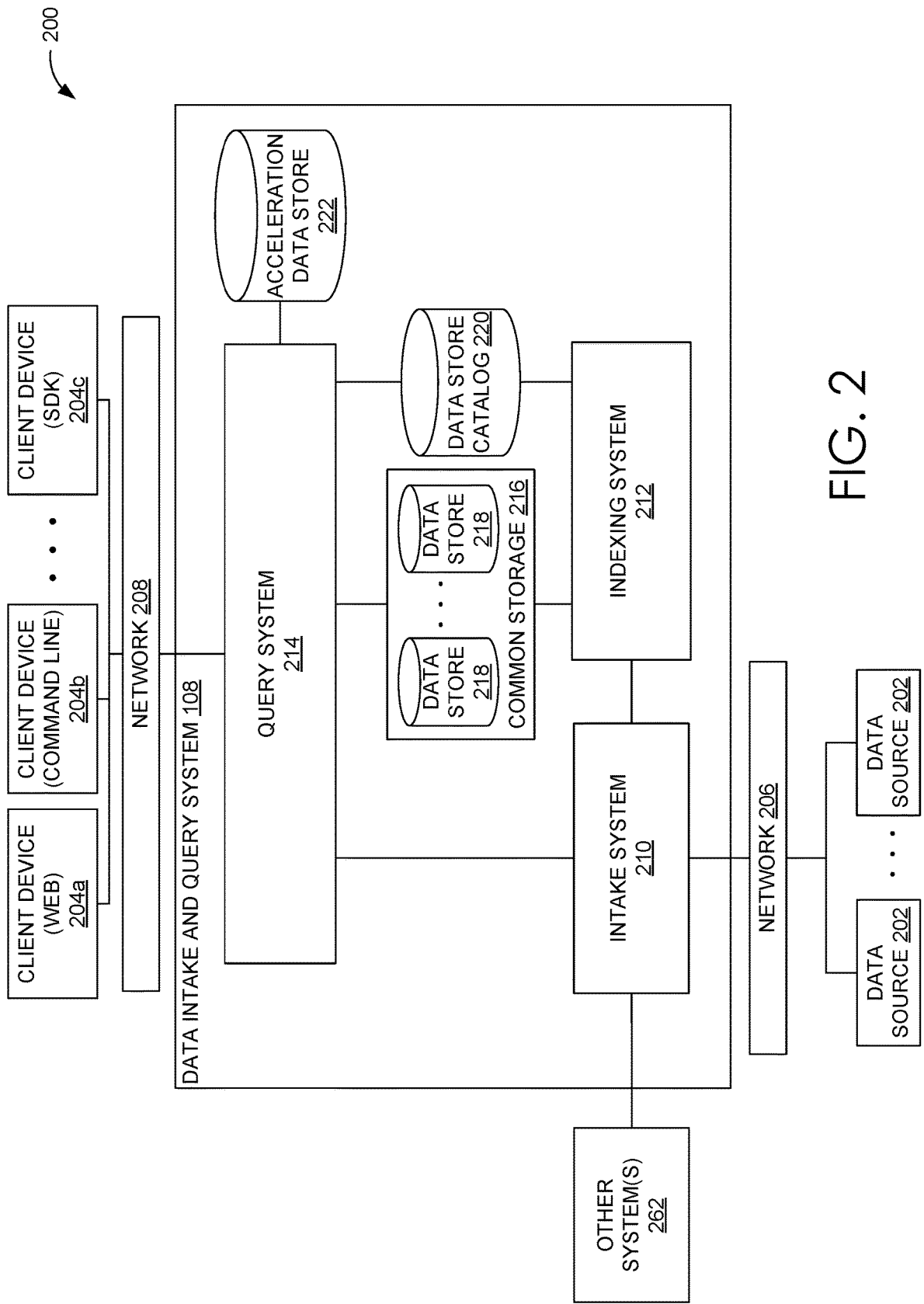
FIG. 2 is a block diagram of an example data intake and query system, in accordance with example embodiments.

FIG. 2 is a block diagram of an embodiment of a data processing environment 200. In the illustrated embodiment, the environment 200 includes data sources 202 and client devices 204a, 204b, 204c (generically referred to as client device(s) 204) in communication with a data intake and query system 108 via networks 206, 208, respectively. The networks 206, 208 may be the same network, may correspond to the network 104, or may be different networks. Further, the networks 206, 208 may be implemented as one or more LANs, WANs, cellular networks, intranetworks, and/or internetworks using any of wired, wireless, terrestrial microwave, satellite links, etc., and may include the Internet.

Each data source 202 broadly represents a distinct source of data that can be consumed by the data intake and query system 108. Examples of data sources 202 include, without limitation, data files, directories of files, data sent over a network, event logs, registries, streaming data services (examples of which can include, by way of non-limiting example, Amazon's Simple Queue Service ("SQS") or Kinesis™ services, devices executing Apache Kafka™ software, or devices implementing the Message Queue Telemetry Transport (MQTT) protocol, Microsoft Azure EventHub, Google Cloud PubSub, devices implementing the Java Message Service (JMS) protocol, devices implementing the Advanced Message Queuing Protocol (AMQP)), performance metrics, etc.

The client devices 204 can be implemented using one or more computing devices in communication with the data intake and query system 108, and represent some of the different ways in which computing devices can submit queries to the data intake and query system 108. For example, the client device 204a is illustrated as communicating over an Internet (Web) protocol with the data intake and query system 108, the client device 204b is illustrated as communicating with the data intake and query system 108 via a command line interface, and the client device 204b is illustrated as communicating with the data intake and query system 108 via a software developer kit (SDK). However, it will be understood that the client devices 204 can communicate with and submit queries to the data intake and query system 108 in a variety of ways.

The data intake and query system 108 can process and store data received data from the data sources 202 and execute queries on the data in response to requests received from the client devices 204. In the illustrated embodiment, the data intake and query system 108 includes an intake system 210, an indexing system 212, a query system 214, common storage 216 including one or more data stores 218, a data store catalog 220, and a query acceleration data store 222.

As mentioned, the data intake and query system 108 can receive data from different sources 202. In some cases, the data sources 202 can be associated with different tenants or customers. Further, each tenant may be associated with one or more indexes, hosts, sources, sourcetypes, or users. For example, company ABC, Inc. can correspond to one tenant and company XYZ, Inc. can correspond to a different tenant. While the two companies may be unrelated, each company may have a main index and test index associated with it, as well as one or more data sources or systems (e.g., billing system, CRM system, etc.). The data intake and query system 108 can concurrently receive and process the data from the various systems and sources of ABC, Inc. and XYZ, Inc.

In certain cases, although the data from different tenants can be processed together or concurrently, the data intake and query system 108 can take steps to avoid combining or co-mingling data from the different tenants. For example, the data intake and query system 108 can assign a tenant identifier for each tenant and maintain a separation between the data using the tenant identifier. In some cases, the tenant identifier can be assigned to the data at the data sources 202, or can be assigned to the data by the data intake and query system 108 at ingest.

As will be described in greater detail herein, at least with reference to FIGS. 3A and 3B, the intake system 210 can receive data from the data sources 202, perform one or more preliminary processing operations on the data, and communicate the data to the indexing system 212, query system 214, or to other systems 262 (which may include, for example, data processing systems, telemetry systems, real-time analytics systems, data stores, databases, etc., any of which may be operated by an operator of the data intake and query system 108 or a third party). The intake system 210 can receive data from the data sources 202 in a variety of formats or structures. In some embodiments, the received data corresponds to raw machine data, structured or unstructured data, correlation data, data files, directories of files, data sent over a network, event logs, registries, messages published to streaming data sources, performance metrics, sensor data, image and video data, etc. The intake system 210 can process the data based on the form in which it is received. In some cases, the intake system 210 can utilize one or more rules to process data and to make the data available to downstream systems (e.g., the indexing system 212, query system 214, etc.). Illustratively, the intake system 210 can enrich the received data. For example, the intake system may add one or more fields to the data received from the data sources 202, such as fields denoting the host, source, sourcetype, index, or tenant associated with the incoming data. In certain embodiments, the intake system 210 can perform additional processing on the incoming data, such as transforming structured data into unstructured data (or vice versa), identifying timestamps associated with the data, removing extraneous data, parsing data, indexing data, separating data, categorizing data, routing data based on criteria relating to the data being routed, and/or performing other data transformations, etc.

As will be described in greater detail herein, at least with reference to FIG. 4, the indexing system 212 can process the data and store it, for example, in common storage 216. As part of processing the data, the indexing system can identify timestamps associated with the data, organize the data into buckets or time series buckets, convert editable buckets to non-editable buckets, store copies of the buckets in common storage 216, merge buckets, generate indexes of the data, etc. In addition, the indexing system 212 can update the data store catalog 220 with information related to the buckets (pre-merged or merged) or data that is stored in common storage 216, and can communicate with the intake system 210 about the status of the data storage.

As will be described in greater detail herein, at least with reference to FIG. 5, the query system 214 can receive queries that identify a set of data to be processed and a manner of processing the set of data from one or more client devices 204, process the queries to identify the set of data, and execute the query on the set of data. In some cases, as part of executing the query, the query system 214 can use the data store catalog 220 to identify the set of data to be processed or its location in common storage 216 and/or can retrieve data from common storage 216 or the query acceleration data store 222. In addition, in some embodiments, the query system 214 can store some or all of the query results in the query acceleration data store 222.

As mentioned and as will be described in greater detail below, the common storage 216 can be made up of one or more data stores 218 storing data that has been processed by the indexing system 212. The common storage 216 can be configured to provide high availability, highly resilient, low loss data storage. In some cases, to provide the high availability, highly resilient, low loss data storage, the common storage 216 can store multiple copies of the data in the same and different geographic locations and across different types of data stores (e.g., solid state, hard drive, tape, etc.). Further, as data is received at the common storage 216 it can be automatically replicated multiple times according to a replication factor to different data stores across the same and/or different geographic locations. In some embodiments, the common storage 216 can correspond to cloud storage, such as Amazon Simple Storage Service (S3) or Elastic Block Storage (EBS), Google Cloud Storage, Microsoft Azure Storage, etc.

In some embodiments, indexing system 212 can read to and write from the common storage 216. For example, the indexing system 212 can copy buckets of data from its local or shared data stores to the common storage 216. In certain embodiments, the query system 214 can read from, but cannot write to, the common storage 216. For example, the query system 214 can read the buckets of data stored in common storage 216 by the indexing system 212, but may not be able to copy buckets or other data to the common storage 216. In some embodiments, the intake system 210 does not have access to the common storage 216. However, in some embodiments, one or more components of the intake system 210 can write data to the common storage 216 that can be read by the indexing system 212.

As described herein, such as with reference to FIGS. 5B and 5C, in some embodiments, data in the data intake and query system 108 (e.g., in the data stores of the indexers of the indexing system 212, common storage 216, or search nodes of the query system 214) can be stored in one or more time series buckets. Each bucket can include raw machine data associated with a time stamp and additional information about the data or bucket, such as, but not limited to, one or more filters, indexes (e.g., TSIDX, inverted indexes, keyword indexes, etc.), bucket summaries, etc. In some embodiments, the bucket data and information about the bucket data is stored in one or more files. For example, the raw machine data, filters, indexes, bucket summaries, etc. can be stored in respective files in or associated with a bucket. In certain cases, the group of files can be associated together to form the bucket.

The data store catalog 220 can store information about the data stored in common storage 216, such as, but not limited to an identifier for a set of data or buckets, a location of the set of data, tenants or indexes associated with the set of data, timing information about the data, etc. For example, in embodiments where the data in common storage 216 is stored as buckets, the data store catalog 220 can include a bucket identifier for the buckets in common storage 216, a location of or path to the bucket in common storage 216, a time range of the data in the bucket (e.g., range of time between the first-in-time event of the bucket and the last-in-time event of the bucket), a tenant identifier identifying a customer or computing device associated with the bucket, and/or an index (also referred to herein as a partition) associated with the bucket, etc. In certain embodiments, the data intake and query system 108 includes multiple data store catalogs 220. For example, in some embodiments, the data intake and query system 108 can include a data store catalog 220 for each tenant (or group of tenants), each partition of each tenant (or group of indexes), etc. In some cases, the data intake and query system 108 can include a single data store catalog 220 that includes information about buckets associated with multiple or all of the tenants associated with the data intake and query system 108.

The indexing system 212 can update the data store catalog 220 as the indexing system 212 stores data in common storage 216. Furthermore, the indexing system 212 or other computing device associated with the data store catalog 220 can update the data store catalog 220 as the information in the common storage 216 changes (e.g., as buckets in common storage 216 are merged, deleted, etc.). In addition, as described herein, the query system 214 can use the data store catalog 220 to identify data to be searched or data that satisfies at least a portion of a query. In some embodiments, the query system 214 makes requests to and receives data from the data store catalog 220 using an application programming interface ("API").

The query acceleration data store 222 can store the results or partial results of queries, or otherwise be used to accelerate queries. For example, if a user submits a query that has no end date, the system can query system 214 can store an initial set of results in the query acceleration data store 222. As additional query results are determined based on additional data, the additional results can be combined with the initial set of results, and so on. In this way, the query system 214 can avoid re-searching all of the data that may be responsive to the query and instead search the data that has not already been searched.

In some environments, a user of a data intake and query system 108 may install and configure, on computing devices owned and operated by the user, one or more software applications that implement some or all of these system components. For example, a user may install a software application on server computers owned by the user and configure each server to operate as one or more of intake system 210, indexing system 212, query system 214, common storage 216, data store catalog 220, or query acceleration data store 222, etc. This arrangement generally may be referred to as an "on-premises" solution. That is, the system 108 is installed and operates on computing devices directly controlled by the user of the system. Some users may prefer an on-premises solution because it may provide a greater level of control over the configuration of certain aspects of the system (e.g., security, privacy, standards, controls, etc.). However, other users may instead prefer an arrangement in which the user is not directly responsible for providing and managing the computing devices upon which various components of system 108 operate.

In certain embodiments, one or more of the components of a data intake and query system 108 can be implemented in a remote distributed computing system. In this context, a remote distributed computing system or cloud-based service can refer to a service hosted by one more computing resources that are accessible to end users over a network, for example, by using a web browser or other application on a client device to interface with the remote computing resources. For example, a service provider may provide a data intake and query system 108 by managing computing resources configured to implement various aspects of the system (e.g., intake system 210, indexing system 212, query system 214, common storage 216, data store catalog 220, or query acceleration data store 222, etc.) and by providing access to the system to end users via a network. Typically, a user may pay a subscription or other fee to use such a service. Each subscribing user of the cloud-based service may be provided with an account that enables the user to configure a customized cloud-based system based on the user's preferences. When implemented as a cloud-based service, various components of the system 108 can be implemented using containerization or operating-system-level virtualization, or other virtualization technique. For example, one or more components of the intake system 210, indexing system 212, or query system 214 can be implemented as separate software containers or container instances. Each container instance can have certain resources (e.g., memory, processor, etc.) of the underlying host computing system assigned to it, but may share the same operating system and may use the operating system's system call interface. Each container may provide an isolated execution environment on the host system, such as by providing a memory space of the host system that is logically isolated from memory space of other containers. Further, each container may run the same or different computer applications concurrently or separately, and may interact with each other. Although reference is made herein to containerization and container instances, it will be understood that other virtualization techniques can be used. For example, the components can be implemented using virtual machines using full virtualization or paravirtualization, etc. Thus, where reference is made to "containerized" components, it should be understood that such components may additionally or alternatively be implemented in other isolated execution environments, such as a virtual machine environment.

3.1. Intake System

As detailed below, data may be ingested at the data intake and query system 108 through an intake system 210 configured to conduct preliminary processing on the data, and make the data available to downstream systems or components, such as the indexing system 212, query system 214, third party systems, etc.

Figure 3A:
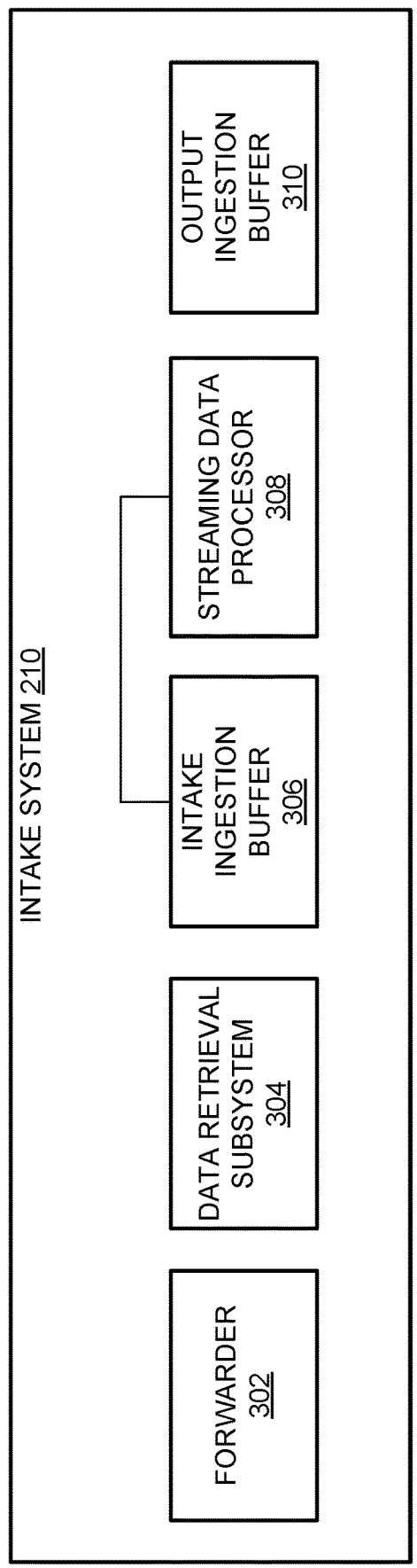
FIG. 3A is a block diagram of one embodiment an intake system.

One example configuration of an intake system 210 is shown in FIG. 3A. As shown in FIG. 3A, the intake system 210 includes a forwarder 302, a data retrieval subsystem 304, an intake ingestion buffer 306, a streaming data processor 308, and an output ingestion buffer 310. As described in detail below, the components of the intake system 210 may be configured to process data according to a streaming data model, such that data ingested into the data intake and query system 108 is processed rapidly (e.g., within seconds or minutes of initial reception at the intake system 210) and made available to downstream systems or components. The initial processing of the intake system 210 may include search or analysis of the data ingested into the intake system 210. For example, the initial processing can transform data ingested into the intake system 210 sufficiently, for example, for the data to be searched by a query system 214, thus enabling "real-time" searching for data on the data intake and query system 108 (e.g., without requiring indexing of the data). Various additional and alternative uses for data processed by the intake system 210 are described below.

Although shown as separate components, the forwarder 302, data retrieval subsystem 304, intake ingestion buffer 306, streaming data processors 308, and output ingestion buffer 310, in various embodiments, may reside on the same machine or be distributed across multiple machines in any combination. In one embodiment, any or all of the components of the intake system can be implemented using one or more computing devices as distinct computing devices or as one or more container instances or virtual machines across one or more computing devices. It will be appreciated by those skilled in the art that the intake system 210 may have more of fewer components than are illustrated in FIGS. 3A and 3B. In addition, the intake system 210 could include various web services and/or peer-to-peer network configurations or inter container communication network provided by an associated container instantiation or orchestration platform. Thus, the intake system 210 of FIGS. 3A and 3B should be taken as illustrative. For example, in some embodiments, components of the intake system 210, such as the ingestion buffers 306 and 310 and/or the streaming data processors 308, may be executed by one more virtual machines implemented in a hosted computing environment. A hosted computing environment may include one or more rapidly provisioned and released computing resources, which computing resources may include computing, networking and/or storage devices. A hosted computing environment may also be referred to as a cloud computing environment. Accordingly, the hosted computing environment can include any proprietary or open source extensible computing technology, such as Apache Flink or Apache Spark, to enable fast or on-demand horizontal compute capacity scaling of the streaming data processor 308.

In some embodiments, some or all of the elements of the intake system 210 (e.g., forwarder 302, data retrieval subsystem 304, intake ingestion buffer 306, streaming data processors 308, and output ingestion buffer 310, etc.) may reside on one or more computing devices, such as servers, which may be communicatively coupled with each other and with the data sources 202, query system 214, indexing system 212, or other components. In other embodiments, some or all of the elements of the intake system 210 may be implemented as worker nodes as disclosed in U.S. patent application Ser. Nos. 15/665,159, 15/665,148, 15/665,187, 15/665,248, 15/665,197, 15/665,279, 15/665,302, and 15/665,339, each of which is incorporated by reference herein in its entirety (hereinafter referred to as "the Parent Applications").

As noted above, the intake system 210 can function to conduct preliminary processing of data ingested at the data intake and query system 108. As such, the intake system 210 illustratively includes a forwarder 302 that obtains data from a data source 202 and transmits the data to a data retrieval subsystem 304. The data retrieval subsystem 304 may be configured to convert or otherwise format data provided by the forwarder 302 into an appropriate format for inclusion at the intake ingestion buffer and transmit the message to the intake ingestion buffer 306 for processing. Thereafter, a streaming data processor 308 may obtain data from the intake ingestion buffer 306, process the data according to one or more rules, and republish the data to either the intake ingestion buffer 306 (e.g., for additional processing) or to the output ingestion buffer 310, such that the data is made available to downstream components or systems. In this manner, the intake system 210 may repeatedly or iteratively process data according to any of a variety of rules, such that the data is formatted for use on the data intake and query system 108 or any other system. As discussed below, the intake system 210 may be configured to conduct such processing rapidly (e.g., in "real-time" with little or no perceptible delay), while ensuring resiliency of the data.

3.1.1. Forwarder

The forwarder 302 can include or be executed on a computing device configured to obtain data from a data source 202 and transmit the data to the data retrieval subsystem 304. In some implementations the forwarder 302 can be installed on a computing device associated with the data source 202. While a single forwarder 302 is illustratively shown in FIG. 3A, the intake system 210 may include a number of different forwarders 302. Each forwarder 302 may illustratively be associated with a different data source 202. A forwarder 302 initially may receive the data as a raw data stream generated by the data source 202. For example, a forwarder 302 may receive a data stream from a log file generated by an application server, from a stream of network data from a network device, or from any other source of data. In some embodiments, a forwarder 202 receives the raw data and may segment the data stream into "blocks", possibly of a uniform data size, to facilitate subsequent processing steps. The forwarder 202 may additionally or alternatively modify data received, prior to forwarding the data to the data retrieval subsystem 304. Illustratively, the forwarder 202 may "tag" metadata for each data block, such as by specifying a source, source type, or host associated with the data, or by appending one or more timestamp or time ranges to each data block.

In some embodiments, a forwarder 302 may comprise a service accessible to data sources 202 via a network 206. For example, one type of forwarder 302 may be capable of consuming vast amounts of real-time data from a potentially large number of data sources 202. The forwarder 302 may, for example, comprise a computing device which implements multiple data pipelines or "queues" to handle forwarding of network data to data retrieval subsystems 304.

3.1.2. Data Retrieval Subsystem

The data retrieval subsystem 304 illustratively corresponds to a computing device which obtains data (e.g., from the forwarder 302), and transforms the data into a format suitable for publication on the intake ingestion buffer 306. Illustratively, where the forwarder 302 segments input data into discrete blocks, the data retrieval subsystem 304 may generate a message for each block, and publish the message to the intake ingestion buffer 306. Generation of a message for each block may include, for example, formatting the data of the message in accordance with the requirements of a streaming data system implementing the intake ingestion buffer 306, the requirements of which may vary according to the streaming data system. In one embodiment, the intake ingestion buffer 306 formats messages according to the protocol buffers method of serializing structured data. Thus, the intake ingestion buffer 306 may be configured to convert data from an input format into a protocol buffer format. Where a forwarder 302 does not segment input data into discrete blocks, the data retrieval subsystem 304 may itself segment the data. Similarly, the data retrieval subsystem 304 may append metadata to the input data, such as a source, source type, or host associated with the data.

Generation of the message may include "tagging" the message with various information, which may be included as metadata for the data provided by the forwarder 302, and determining a "topic" for the message, under which the message should be published to the intake ingestion buffer 306. In general, the "topic" of a message may reflect a categorization of the message on a streaming data system. Illustratively, each topic may be associated with a logically distinct queue of messages, such that a downstream device or system may "subscribe" to the topic in order to be provided with messages published to the topic on the streaming data system.

In one embodiment, the data retrieval subsystem 304 may obtain a set of topic rules (e.g., provided by a user of the data intake and query system 108 or based on automatic inspection or identification of the various upstream and downstream components of the data intake and query system 108) that determine a topic for a message as a function of the received data or metadata regarding the received data. For example, the topic of a message may be determined as a function of the data source 202 from which the data stems. After generation of a message based on input data, the data retrieval subsystem can publish the message to the intake ingestion buffer 306 under the determined topic.

While the data retrieval and subsystem 304 is depicted in FIG. 3A as obtaining data from the forwarder 302, the data retrieval and subsystem 304 may additionally or alternatively obtain data from other sources. In some instances, the data retrieval and subsystem 304 may be implemented as a plurality of intake points, each functioning to obtain data from one or more corresponding data sources (e.g., the forwarder 302, data sources 202, or any other data source), generate messages corresponding to the data, determine topics to which the messages should be published, and to publish the messages to one or more topics of the intake ingestion buffer 306.

Figure 3B:
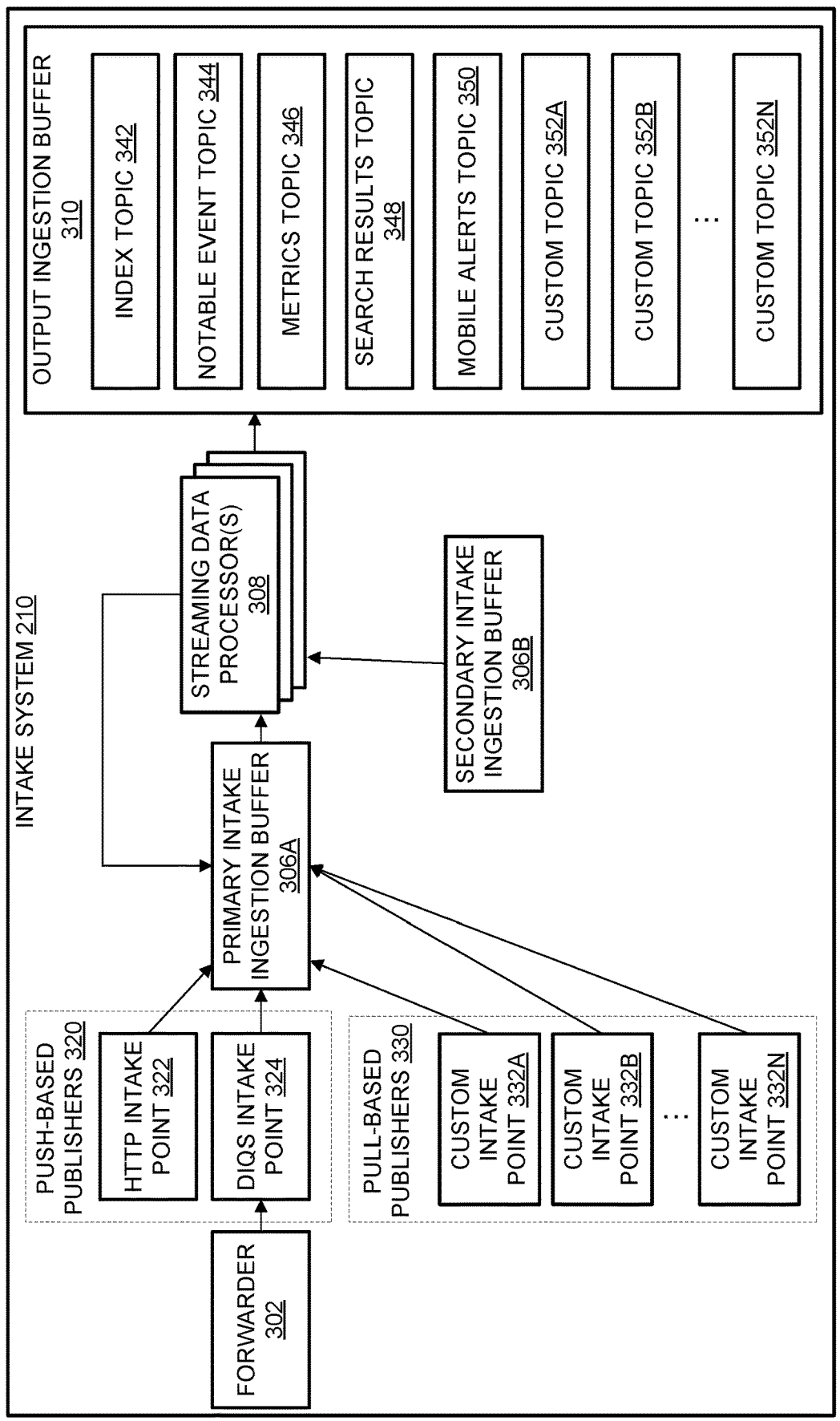
FIG. 3B is a block diagram of another embodiment of an intake system.

One illustrative set of intake points implementing the data retrieval and subsystem 304 is shown in FIG. 3B. Specifically, as shown in FIG. 3B, the data retrieval and subsystem 304 of FIG. 3A may be implemented as a set of push-based publishers 320 or a set of pull-based publishers 330. The illustrative push-based publishers 320 operate on a "push" model, such that messages are generated at the push-based publishers 320 and transmitted to an intake ingestion buffer 306 (shown in FIG. 3B as primary and secondary intake ingestion buffers 306A and 306B, which are discussed in more detail below). As will be appreciated by one skilled in the art, "push" data transmission models generally correspond to models in which a data source determines when data should be transmitted to a data target. A variety of mechanisms exist to provide "push" functionality, including "true push" mechanisms (e.g., where a data source independently initiates transmission of information) and "emulated push" mechanisms, such as "long polling" (a mechanism whereby a data target initiates a connection with a data source, but allows the data source to determine within a timeframe when data is to be transmitted to the data source).

As shown in FIG. 3B, the push-based publishers 320 illustratively include an HTTP intake point 322 and a data intake and query system (DIQS) intake point 324. The HTTP intake point 322 can include a computing device configured to obtain HTTP-based data (e.g., as JavaScript Object Notation, or JSON messages) to format the HTTP-based data as a message, to determine a topic for the message (e.g., based on fields within the HTTP-based data), and to publish the message to the primary intake ingestion buffer 306A. Similarly, the DIQS intake point 324 can be configured to obtain data from a forwarder 324, to format the forwarder data as a message, to determine a topic for the message, and to publish the message to the primary intake ingestion buffer 306A. In this manner, the DIQS intake point 324 can function in a similar manner to the operations described with respect to the data retrieval subsystem 304 of FIG. 3A.

In addition to the push-based publishers 320, one or more pull-based publishers 330 may be used to implement the data retrieval subsystem 304. The pull-based publishers 330 may function on a "pull" model, whereby a data target (e.g., the primary intake ingestion buffer 306A) functions to continuously or periodically (e.g., each n seconds) query the pull-based publishers 330 for new messages to be placed on the primary intake ingestion buffer 306A. In some instances, development of pull-based systems may require less coordination of functionality between a pull-based publisher 330 and the primary intake ingestion buffer 306A. Thus, for example, pull-based publishers 330 may be more readily developed by third parties (e.g., other than a developer of the data intake a query system 108), and enable the data intake and query system 108 to ingest data associated with third party data sources 202. Accordingly, FIG. 3B includes a set of custom intake points 332A through 332N, each of which functions to obtain data from a third-party data source 202, format the data as a message for inclusion in the primary intake ingestion buffer 306A, determine a topic for the message, and make the message available to the primary intake ingestion buffer 306A in response to a request (a "pull") for such messages.

While the pull-based publishers 330 are illustratively described as developed by third parties, push-based publishers 320 may also in some instances be developed by third parties. Additionally or alternatively, pull-based publishers may be developed by the developer of the data intake and query system 108. To facilitate integration of systems potentially developed by disparate entities, the primary intake ingestion buffer 306A may provide an API through which an intake point may publish messages to the primary intake ingestion buffer 306A. Illustratively, the API may enable an intake point to "push" messages to the primary intake ingestion buffer 306A, or request that the primary intake ingestion buffer 306A "pull" messages from the intake point. Similarly, the streaming data processors 308 may provide an API through which ingestions buffers may register with the streaming data processors 308 to facilitate pre-processing of messages on the ingestion buffers, and the output ingestion buffer 310 may provide an API through which the streaming data processors 308 may publish messages or through which downstream devices or systems may subscribe to topics on the output ingestion buffer 310. Furthermore, any one or more of the intake points 322 through 332N may provide an API through which data sources 202 may submit data to the intake points. Thus, any one or more of the components of FIGS. 3A and 3B may be made available via APIs to enable integration of systems potentially provided by disparate parties.

The specific configuration of publishers 320 and 330 shown in FIG. 3B is intended to be illustrative in nature. For example, the specific number and configuration of intake points may vary according to embodiments of the present application. In some instances, one or more components of the intake system 210 may be omitted. For example, a data source 202 may in some embodiments publish messages to an intake ingestion buffer 306, and thus an intake point 332 may be unnecessary. Other configurations of the intake system 210 are possible.

3.1.3. Ingestion Buffer

The intake system 210 is illustratively configured to ensure message resiliency, such that data is persisted in the event of failures within the intake system 310. Specifically, the intake system 210 may utilize one or more ingestion buffers, which operate to resiliently maintain data received at the intake system 210 until the data is acknowledged by downstream systems or components. In one embodiment, resiliency is provided at the intake system 210 by use of ingestion buffers that operate according to a publish-subscribe ("pub-sub") message model. In accordance with the pub-sub model, data ingested into the data intake and query system 108 may be atomized as "messages," each of which is categorized into one or more "topics." An ingestion buffer can maintain a queue for each such topic, and enable devices to "subscribe" to a given topic. As messages are published to the topic, the ingestion buffer can function to transmit the messages to each subscriber, and ensure message resiliency until at least each subscriber has acknowledged receipt of the message (e.g., at which point the ingestion buffer may delete the message). In this manner, the ingestion buffer may function as a "broker" within the pub-sub model. A variety of techniques to ensure resiliency at a pub-sub broker are known in the art, and thus will not be described in detail herein. In one embodiment, an ingestion buffer is implemented by a streaming data source. As noted above, examples of streaming data sources include (but are not limited to) Amazon's Simple Queue Service ("SQS") or Kinesis™ services, devices executing Apache Kafka™ software, or devices implementing the Message Queue Telemetry Transport (MQTT) protocol. Any one or more of these example streaming data sources may be utilized to implement an ingestion buffer in accordance with embodiments of the present disclosure.

With reference to FIG. 3A, the intake system 210 may include at least two logical ingestion buffers: an intake ingestion buffer 306 and an output ingestion buffer 310. As noted above, the intake ingestion buffer 306 can be configured to receive messages from the data retrieval subsystem 304 and resiliently store the message. The intake ingestion buffer 306 can further be configured to transmit the message to the streaming data processors 308 for processing. As further described below, the streaming data processors 308 can be configured with one or more data transformation rules to transform the messages, and republish the messages to one or both of the intake ingestion buffer 306 and the output ingestion buffer 310. The output ingestion buffer 310, in turn, may make the messages available to various subscribers to the output ingestion buffer 310, which subscribers may include the query system 214, the indexing system 212, or other third-party devices (e.g., client devices 102, host devices 106, etc.).

Both the input ingestion buffer 306 and output ingestion buffer 310 may be implemented on a streaming data source, as noted above. In one embodiment, the intake ingestion buffer 306 operates to maintain source-oriented topics, such as topics for each data source 202 from which data is obtained, while the output ingestion buffer operates to maintain content-oriented topics, such as topics to which the data of an individual message pertains. As discussed in more detail below, the streaming data processors 308 can be configured to transform messages from the intake ingestion buffer 306 (e.g., arranged according to source-oriented topics) and publish the transformed messages to the output ingestion buffer 310 (e.g., arranged according to content-oriented topics). In some instances, the streaming data processors 308 may additionally or alternatively republish transformed messages to the intake ingestion buffer 306, enabling iterative or repeated processing of the data within the message by the streaming data processors 308.

While shown in FIG. 3A as distinct, these ingestion buffers 306 and 310 may be implemented as a common ingestion buffer. However, use of distinct ingestion buffers may be beneficial, for example, where a geographic region in which data is received differs from a region in which the data is desired. For example, use of distinct ingestion buffers may beneficially allow the intake ingestion buffer 306 to operate in a first geographic region associated with a first set of data privacy restrictions, while the output ingestion buffer 308 operates in a second geographic region associated with a second set of data privacy restrictions. In this manner, the intake system 210 can be configured to comply with all relevant data privacy restrictions, ensuring privacy of data processed at the data intake and query system 108.

Moreover, either or both of the ingestion buffers 306 and 310 may be implemented across multiple distinct devices, as either a single or multiple ingestion buffers. Illustratively, as shown in FIG. 3B, the intake system 210 may include both a primary intake ingestion buffer 306A and a secondary intake ingestion buffer 306B. The primary intake ingestion buffer 306A is illustratively configured to obtain messages from the data retrieval subsystem 304 (e.g., implemented as a set of intake points 322 through 332N). The secondary intake ingestion buffer 306B is illustratively configured to provide an additional set of messages (e.g., from other data sources 202). In one embodiment, the primary intake ingestion buffer 306A is provided by an administrator or developer of the data intake and query system 108, while the secondary intake ingestion buffer 306B is a user-supplied ingestion buffer (e.g., implemented externally to the data intake and query system 108).

As noted above, an intake ingestion buffer 306 may in some embodiments categorize messages according to source-oriented topics (e.g., denoting a data source 202 from which the message was obtained). In other embodiments, an intake ingestion buffer 306 may in some embodiments categorize messages according to intake-oriented topics (e.g., denoting the intake point from which the message was obtained). The number and variety of such topics may vary, and thus are not shown in FIG. 3B. In one embodiment, the intake ingestion buffer 306 maintains only a single topic (e.g., all data to be ingested at the data intake and query system 108).

The output ingestion buffer 310 may in one embodiment categorize messages according to content-centric topics (e.g., determined based on the content of a message). Additionally or alternatively, the output ingestion buffer 310 may categorize messages according to consumer-centric topics (e.g., topics intended to store messages for consumption by a downstream device or system). An illustrative number of topics are shown in FIG. 3B, as topics 342 through 352N. Each topic may correspond to a queue of messages (e.g., in accordance with the pub-sub model) relevant to the corresponding topic. As described in more detail below, the streaming data processors 308 may be configured to process messages from the intake ingestion buffer 306 and determine which topics of the topics 342 through 352N into which to place the messages. For example, the index topic 342 may be intended to store messages holding data that should be consumed and indexed by the indexing system 212. The notable event topic 344 may be intended to store messages holding data that indicates a notable event at a data source 202 (e.g., the occurrence of an error or other notable event). The metrics topic 346 may be intended to store messages holding metrics data for data sources 202. The search results topic 348 may be intended to store messages holding data responsive to a search query. The mobile alerts topic 350 may be intended to store messages holding data for which an end user has requested alerts on a mobile device. A variety of custom topics 352A through 352N may be intended to hold data relevant to end-user-created topics.

As will be described below, by application of message transformation rules at the streaming data processors 308, the intake system 210 may divide and categorize messages from the intake ingestion buffer 306, partitioning the message into output topics relevant to a specific downstream consumer. In this manner, specific portions of data input to the data intake and query system 108 may be "divided out" and handled separately, enabling different types of data to be handled differently, and potentially at different speeds. Illustratively, the index topic 342 may be configured to include all or substantially all data included in the intake ingestion buffer 306. Given the volume of data, there may be a significant delay (e.g., minutes or hours) before a downstream consumer (e.g., the indexing system 212) processes a message in the index topic 342. Thus, for example, searching data processed by the indexing system 212 may incur significant delay.

Conversely, the search results topic 348 may be configured to hold only messages corresponding to data relevant to a current query. Illustratively, on receiving a query from a client device 204, the query system 214 may transmit to the intake system 210 a rule that detects, within messages from the intake ingestion buffer 306A, data potentially relevant to the query. The streaming data processors 308 may republish these messages within the search results topic 348, and the query system 214 may subscribe to the search results topic 348 in order to obtain the data within the messages. In this manner, the query system 214 can "bypass" the indexing system 212 and avoid delay that may be caused by that system, thus enabling faster (and potentially real time) display of search results.

While shown in FIGS. 3A and 3B as a single output ingestion buffer 310, the intake system 210 may in some instances utilize multiple output ingestion buffers 310.

3.1.4. Streaming Data Processors

As noted above, the streaming data processors 308 may apply one or more rules to process messages from the intake ingestion buffer 306A into messages on the output ingestion buffer 310. These rules may be specified, for example, by an end user of the data intake and query system 108 or may be automatically generated by the data intake and query system 108 (e.g., in response to a user query).

Illustratively, each rule may correspond to a set of selection criteria indicating messages to which the rule applies, as well as one or more processing sub-rules indicating an action to be taken by the streaming data processors 308 with respect to the message. The selection criteria may include any number or combination of criteria based on the data included within a message or metadata of the message (e.g., a topic to which the message is published). In one embodiment, the selection criteria are formatted in the same manner or similarly to extraction rules, discussed in more detail below. For example, selection criteria may include regular expressions that derive one or more values or a sub-portion of text from the portion of machine data in each message to produce a value for the field for that message. When a message is located within the intake ingestion buffer 308 that matches the selection criteria, the streaming data processors 308 may apply the processing rules to the message. Processing sub-rules may indicate, for example, a topic of the output ingestion buffer 310 into which the message should be placed. Processing sub-rules may further indicate transformations, such as field or unit normalization operations, to be performed on the message. Illustratively, a transformation may include modifying data within the message, such as altering a format in which the data is conveyed (e.g., converting millisecond timestamps values to microsecond timestamp values, converting imperial units to metric units, etc.), or supplementing the data with additional information (e.g., appending an error descriptor to an error code). In some instances, the streaming data processors 308 may be in communication with one or more external data stores (the locations of which may be specified within a rule) that provide information used to supplement or enrich messages processed at the streaming data processors 308. For example, a specific rule may include selection criteria identifying an error code within a message of the primary ingestion buffer 306A, and specifying that when the error code is detected within a message, that the streaming data processors 308 should conduct a lookup in an external data source (e.g., a database) to retrieve the human-readable descriptor for that error code, and inject the descriptor into the message. In this manner, rules may be used to process, transform, or enrich messages.

The streaming data processors 308 may include a set of computing devices configured to process messages from the intake ingestion buffer 306 at a speed commensurate with a rate at which messages are placed into the intake ingestion buffer 306. In one embodiment, the number of streaming data processors 308 used to process messages may vary based on a number of messages on the intake ingestion buffer 306 awaiting processing. Thus, as additional messages are queued into the intake ingestion buffer 306, the number of streaming data processors 308 may be increased to ensure that such messages are rapidly processed. In some instances, the streaming data processors 308 may be extensible on a per topic basis. Thus, individual devices implementing the streaming data processors 308 may subscribe to different topics on the intake ingestion buffer 306, and the number of devices subscribed to an individual topic may vary according to a rate of publication of messages to that topic (e.g., as measured by a backlog of messages in the topic). In this way, the intake system 210 can support ingestion of massive amounts of data from numerous data sources 202.

In some embodiments, an intake system may comprise a service accessible to client devices 102 and host devices 106 via a network 104. For example, one type of forwarder may be capable of consuming vast amounts of real-time data from a potentially large number of client devices 102 and/or host devices 106. The forwarder may, for example, comprise a computing device which implements multiple data pipelines or "queues" to handle forwarding of network data to indexers. A forwarder may also perform many of the functions that are performed by an indexer. For example, a forwarder may perform keyword extractions on raw data or parse raw data to create events. A forwarder may generate time stamps for events. Additionally or alternatively, a forwarder may perform routing of events to indexers. Data store 212 may contain events derived from machine data from a variety of sources all pertaining to the same component in an IT environment, and this data may be produced by the machine in question or by other components in the IT environment.

3.2. Indexing System

Figure 4:
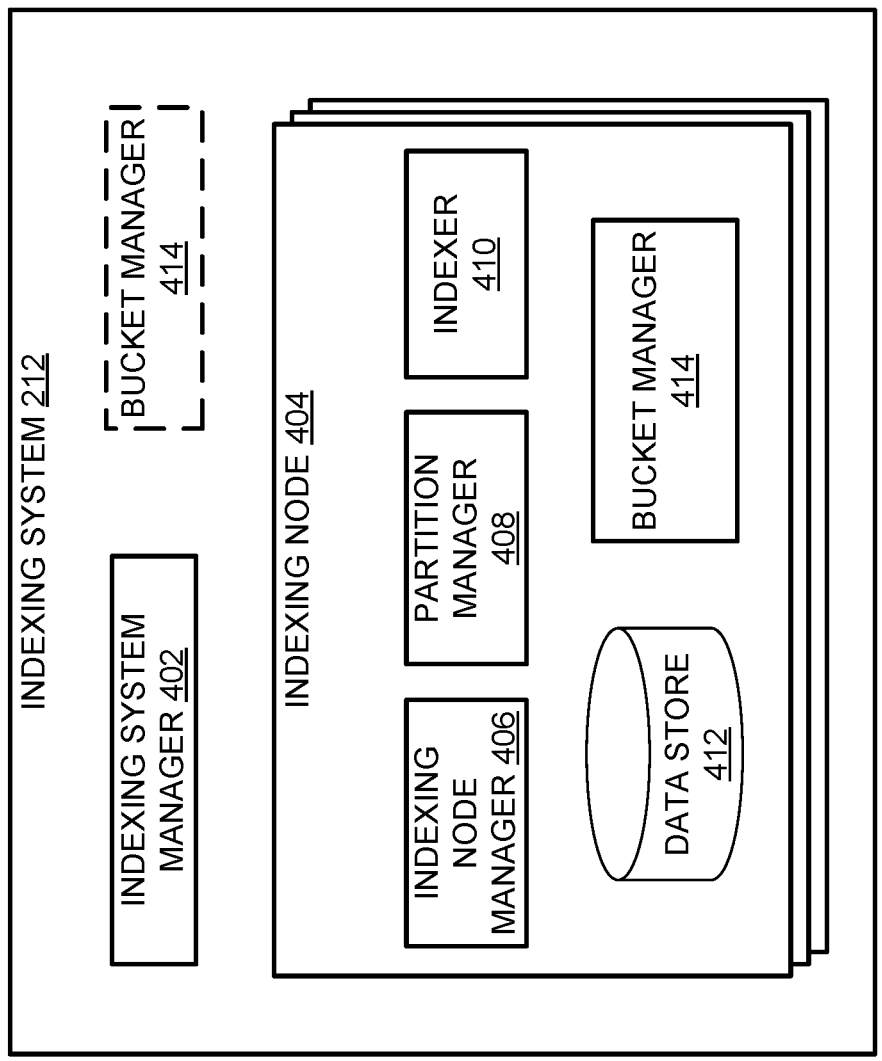
FIG. 4 is a block diagram illustrating an embodiment of an indexing system of the data intake and query system.

FIG. 4 is a block diagram illustrating an embodiment of an indexing system 212 of the data intake and query system 108. The indexing system 212 can receive, process, and store data from multiple data sources 202, which may be associated with different tenants, users, etc. Using the received data, the indexing system can generate events that include a portion of machine data associated with a timestamp and store the events in buckets based on one or more of the timestamps, tenants, indexes, etc., associated with the data. Moreover, the indexing system 212 can include various components that enable it to provide a stateless indexing service, or indexing service that is able to rapidly recover without data loss if one or more components of the indexing system 212 become unresponsive or unavailable.

In the illustrated embodiment, the indexing system 212 includes an indexing system manager 402 and one or more indexing nodes 404. However, it will be understood that the indexing system 212 can include fewer or more components. For example, in some embodiments, the common storage 216 or data store catalog 220 can form part of the indexing system 212, etc.

As described herein, each of the components of the indexing system 212 can be implemented using one or more computing devices as distinct computing devices or as one or more container instances or virtual machines across one or more computing devices. For example, in some embodiments, the indexing system manager 402 and indexing nodes 404 can be implemented as distinct computing devices with separate hardware, memory, and processors. In certain embodiments, the indexing system manager 402 and indexing nodes 404 can be implemented on the same or across different computing devices as distinct container instances, with each container having access to a subset of the resources of a host computing device (e.g., a subset of the memory or processing time of the processors of the host computing device), but sharing a similar operating system. In some cases, the components can be implemented as distinct virtual machines across one or more computing devices, where each virtual machine can have its own unshared operating system but shares the underlying hardware with other virtual machines on the same host computing device.

3.2.1 Indexing System Manager

As mentioned, the indexing system manager 402 can monitor and manage the indexing nodes 404, and can be implemented as a distinct computing device, virtual machine, container, container of a pod, or a process or thread associated with a container. In certain embodiments, the indexing system 212 can include one indexing system manager 402 to manage all indexing nodes 404 of the indexing system 212. In some embodiments, the indexing system 212 can include multiple indexing system managers 402. For example, an indexing system manager 402 can be instantiated for each computing device (or group of computing devices) configured as a host computing device for multiple indexing nodes 404.

The indexing system manager 402 can handle resource management, creation/destruction of indexing nodes 404, high availability, load balancing, application upgrades/rollbacks, logging and monitoring, storage, networking, service discovery, and performance and scalability, and otherwise handle containerization management of the containers of the indexing system 212. In certain embodiments, the indexing system manager 402 can be implemented using Kubernetes or Swarm.

In some cases, the indexing system manager 402 can monitor the available resources of a host computing device and request additional resources in a shared resource environment, based on workload of the indexing nodes 404 or create, destroy, or reassign indexing nodes 404 based on workload. Further, the indexing system manager 402 system can assign indexing nodes 404 to handle data streams based on workload, system resources, etc.

3.2.2. Indexing Nodes

The indexing nodes 404 can include one or more components to implement various functions of the indexing system 212. In the illustrated embodiment, the indexing node 404 includes an indexing node manager 406, partition manager 408, indexer 410, data store 412, and bucket manager 414. As described herein, the indexing nodes 404 can be implemented on separate computing devices or as containers or virtual machines in a virtualization environment.

In some embodiments, an indexing node 404, and can be implemented as a distinct computing device, virtual machine, container, container of a pod, or a process or thread associated with a container, or using multiple-related containers. In certain embodiments, such as in a Kubernetes deployment, each indexing node 404 can be implemented as a separate container or pod. For example, one or more of the components of the indexing node 404 can be implemented as different containers of a single pod, e.g., on a containerization platform, such as Docker, the one or more components of the indexing node can be implemented as different Docker containers managed by synchronization platforms such as Kubernetes or Swarm. Accordingly, reference to a containerized indexing node 404 can refer to the indexing node 404 as being a single container or as one or more components of the indexing node 404 being implemented as different, related containers or virtual machines.

3.2.2.1. Indexing Node Manager

The indexing node manager 406 can manage the processing of the various streams or partitions of data by the indexing node 404, and can be implemented as a distinct computing device, virtual machine, container, container of a pod, or a process or thread associated with a container. For example, in certain embodiments, as partitions or data streams are assigned to the indexing node 404, the indexing node manager 406 can generate one or more partition manager(s) 408 to manage each partition or data stream. In some cases, the indexing node manager 406 generates a separate partition manager 408 for each partition or shard that is processed by the indexing node 404. In certain embodiments, the partition can correspond to a topic of a data stream of the ingestion buffer 310. Each topic can be configured in a variety of ways. For example, in some embodiments, a topic may correspond to data from a particular data source 202, tenant, index/partition, or sourcetype. In this way, in certain embodiments, the indexing system 212 can discriminate between data from different sources or associated with different tenants, or indexes/partitions. For example, the indexing system 212 can assign more indexing nodes 404 to process data from one topic (associated with one tenant) than another topic (associated with another tenant), or store the data from one topic more frequently to common storage 216 than the data from a different topic, etc.

In some embodiments, the indexing node manager 406 monitors the various shards of data being processed by the indexing node 404 and the read pointers or location markers for those shards. In some embodiments, the indexing node manager 406 stores the read pointers or location marker in one or more data stores, such as but not limited to, common storage 216, DynamoDB, S3, or another type of storage system, shared storage system, or networked storage system, etc. As the indexing node 404 processes the data and the markers for the shards are updated by the intake system 210, the indexing node manager 406 can be updated to reflect the changes to the read pointers or location markers. In this way, if a particular partition manager 408 becomes unresponsive or unavailable, the indexing node manager 406 can generate a new partition manager 408 to handle the data stream without losing context of what data is to be read from the intake system 210. Accordingly, in some embodiments, by using the ingestion buffer 310 and tracking the location of the location markers in the shards of the ingestion buffer, the indexing system 212 can aid in providing a stateless indexing service.

In some embodiments, the indexing node manager 406 is implemented as a background process, or daemon, on the indexing node 404 and the partition manager(s) 408 are implemented as threads, copies, or forks of the background process. In some cases, an indexing node manager 406 can copy itself, or fork, to create a partition manager 408 or cause a template process to copy itself, or fork, to create each new partition manager 408, etc. This may be done for multithreading efficiency or for other reasons related to containerization and efficiency of managing indexers 410. In certain embodiments, the indexing node manager 406 generates a new process for each partition manager 408. In some cases, by generating a new process for each partition manager 408, the indexing node manager 408 can support multiple language implementations and be language agnostic. For example, the indexing node manager 408 can generate a process for a partition manager 408 in python and create a second process for a partition manager 408 in golang, etc.

3.2.2.2. Partition Manager

As mentioned, the partition manager(s) 408 can manage the processing of one or more of the partitions or shards of a data stream processed by an indexing node 404 or the indexer 410 of the indexing node 404, and can be implemented as a distinct computing device, virtual machine, container, container of a pod, or a process or thread associated with a container.

In some cases, managing the processing of a partition or shard can include, but it not limited to, communicating data from a particular shard to the indexer 410 for processing, monitoring the indexer 410 and the size of the data being processed by the indexer 410, instructing the indexer 410 to move the data to common storage 216, and reporting the storage of the data to the intake system 210. For a particular shard or partition of data from the intake system 210, the indexing node manager 406 can assign a particular partition manager 408. The partition manager 408 for that partition can receive the data from the intake system 210 and forward or communicate that data to the indexer 410 for processing.

In some embodiments, the partition manager 408 receives data from a pub-sub messaging system, such as the ingestion buffer 310. As described herein, the ingestion buffer 310 can have one or more streams of data and one or more shards or partitions associated with each stream of data. Each stream of data can be separated into shards and/or other partitions or types of organization of data. In certain cases, each shard can include data from multiple tenants, indexes/partition, etc. In some cases, each shard can correspond to data associated with a particular tenant, index/partition, source, sourcetype, etc. Accordingly, the indexing system 212 can include a partition manager 408 for individual tenants, indexes/partitions, sources, sourcetypes, etc. In this way, the indexing system 212 can manage and process the data differently. For example, the indexing system 212 can assign more indexing nodes 404 to process data from one tenant than another tenant, or store buckets associated with one tenant or partition/index more frequently to common storage 216 than buckets associated with a different tenant or partition/index, etc.

Accordingly, in some embodiments, a partition manager 408 receives data from one or more of the shards or partitions of the ingestion buffer 310. The partition manager 408 can forward the data from the shard to the indexer 410 for processing. In some cases, the amount of data coming into a shard may exceed the shard's throughput. For example, 4 MB/s of data may be sent to an ingestion buffer 310 for a particular shard, but the ingestion buffer 310 may be able to process only 2 MB/s of data per shard. Accordingly, in some embodiments, the data in the shard can include a reference to a location in storage where the indexing system 212 can retrieve the data. For example, a reference pointer to data can be placed in the ingestion buffer 310 rather than putting the data itself into the ingestion buffer. The reference pointer can reference a chunk of data that is larger than the throughput of the ingestion buffer 310 for that shard. In this way, the data intake and query system 108 can increase the throughput of individual shards of the ingestion buffer 310. In such embodiments, the partition manager 408 can obtain the reference pointer from the ingestion buffer 310 and retrieve the data from the referenced storage for processing. In some cases, the referenced storage to which reference pointers in the ingestion buffer 310 may point can correspond to the common storage 216 or other cloud or local storage. In some implementations, the chunks of data to which the reference pointers refer may be directed to common storage 216 from intake system 210, e.g., streaming data processor 308 or ingestion buffer 310.

As the indexer 410 processes the data, stores the data in buckets, and generates indexes of the data, the partition manager 408 can monitor the indexer 410 and the size of the data on the indexer 410 (inclusive of the data store 412) associated with the partition. The size of the data on the indexer 410 can correspond to the data that is actually received from the particular partition of the intake system 210, as well as data generated by the indexer 410 based on the received data (e.g., inverted indexes, summaries, etc.), and may correspond to one or more buckets. For instance, the indexer 410 may have generated one or more buckets for each tenant and/or partition associated with data being processed in the indexer 410.

Based on a bucket roll-over policy, the partition manager 408 can instruct the indexer 410 to convert editable groups of data or buckets to non-editable groups or buckets and/or copy the data associated with the partition to common storage 216. In some embodiments, the bucket roll-over policy can indicate that the data associated with the particular partition, which may have been indexed by the indexer 410 and stored in the data store 412 in various buckets, is to be copied to common storage 216 based on a determination that the size of the data associated with the particular partition satisfies a threshold size. In some cases, the bucket roll-over policy can include different threshold sizes for different partitions. In other implementations the bucket roll-over policy may be modified by other factors, such as an identity of a tenant associated with indexing node 404, system resource usage, which could be based on the pod or other container that contains indexing node 404, or one of the physical hardware layers with which the indexing node 404 is running, or any other appropriate factor for scaling and system performance of indexing nodes 404 or any other system component.

In certain embodiments, the bucket roll-over policy can indicate data is to be copied to common storage 216 based on a determination that the amount of data associated with all partitions (or a subset thereof) of the indexing node 404 satisfies a threshold amount. Further, the bucket roll-over policy can indicate that the one or more partition managers 408 of an indexing node 404 are to communicate with each other or with the indexing node manager 406 to monitor the amount of data on the indexer 410 associated with all of the partitions (or a subset thereof) assigned to the indexing node 404 and determine that the amount of data on the indexer 410 (or data store 412) associated with all the partitions (or a subset thereof) satisfies a threshold amount. Accordingly, based on the bucket roll-over policy, one or more of the partition managers 408 or the indexing node manager 406 can instruct the indexer 410 to convert editable buckets associated with the partitions (or subsets thereof) to non-editable buckets and/or store the data associated with the partitions (or subset thereof) in common storage 216.

In certain embodiments, the bucket roll-over policy can indicate that buckets are to be converted to non-editable buckets and stored in common storage based on a collective size of buckets satisfying a threshold size. In some cases, the bucket roll-over policy can use different threshold sizes for conversion and storage. For example, the bucket roll-over policy can use a first threshold size to indicate when editable buckets are to be converted to non-editable buckets (e.g., stop writing to the buckets) and a second threshold size to indicate when the data (or buckets) are to be stored in common storage 216. In certain cases, the bucket roll-over policy can indicate that the partition manager(s) 408 are to send a single command to the indexer 410 that causes the indexer 410 to convert editable buckets to non-editable buckets and store the buckets in common storage 216.

Based on an acknowledgement that the data associated with a partition (or multiple partitions as the case may be) has been stored in common storage 216, the partition manager 408 can communicate to the intake system 210, either directly, or through the indexing node manager 406, that the data has been stored and/or that the location marker or read pointer can be moved or updated. In some cases, the partition manager 408 receives the acknowledgement that the data has been stored from common storage 216 and/or from the indexer 410. In certain embodiments, which will be described in more detail herein, the intake system 210 does not receive communication that the data stored in intake system 210 has been read and processed until after that data has been stored in common storage 216.

The acknowledgement that the data has been stored in common storage 216 can also include location information about the data within the common storage 216. For example, the acknowledgement can provide a link, map, or path to the copied data in the common storage 216. Using the information about the data stored in common storage 216, the partition manager 408 can update the data store catalog 220. For example, the partition manager 408 can update the data store catalog 220 with an identifier of the data (e.g., bucket identifier, tenant identifier, partition identifier, etc.), the location of the data in common storage 216, a time range associated with the data, etc. In this way, the data store catalog 220 can be kept up-to-date with the contents of the common storage 216.

Moreover, as additional data is received from the intake system 210, the partition manager 408 can continue to communicate the data to the indexer 410, monitor the size or amount of data on the indexer 410, instruct the indexer 410 to copy the data to common storage 216, communicate the successful storage of the data to the intake system 210, and update the data store catalog 220.

As a non-limiting example, consider the scenario in which the intake system 210 communicates data from a particular shard or partition to the indexing system 212. The intake system 210 can track which data it has sent and a location marker for the data in the intake system 210 (e.g., a marker that identifies data that has been sent to the indexing system 212 for processing).

As described herein, the intake system 210 can retain or persistently make available the sent data until the intake system 210 receives an acknowledgement from the indexing system 212 that the sent data has been processed, stored in persistent storage (e.g., common storage 216), or is safe to be deleted. In this way, if an indexing node 404 assigned to process the sent data becomes unresponsive or is lost, e.g., due to a hardware failure or a crash of the indexing node manager 406 or other component, process, or daemon, the data that was sent to the unresponsive indexing node 404 will not be lost. Rather, a different indexing node 404 can obtain and process the data from the intake system 210.

As the indexing system 212 stores the data in common storage 216, it can report the storage to the intake system 210. In response, the intake system 210 can update its marker to identify different data that has been sent to the indexing system 212 for processing, but has not yet been stored. By moving the marker, the intake system 210 can indicate that the previously-identified data has been stored in common storage 216, can be deleted from the intake system 210 or, otherwise, can be allowed to be overwritten, lost, etc.

With reference to the example above, in some embodiments, the indexing node manager 406 can track the marker used by the ingestion buffer 310, and the partition manager 408 can receive the data from the ingestion buffer 310 and forward it to an indexer 410 for processing (or use the data in the ingestion buffer to obtain data from a referenced storage location and forward the obtained data to the indexer). The partition manager 408 can monitor the amount of data being processed and instruct the indexer 410 to copy the data to common storage 216. Once the data is stored in common storage 216, the partition manager 408 can report the storage to the ingestion buffer 310, so that the ingestion buffer 310 can update its marker. In addition, the indexing node manager 406 can update its records with the location of the updated marker. In this way, if partition manager 408 become unresponsive or fails, the indexing node manager 406 can assign a different partition manager 408 to obtain the data from the data stream without losing the location information, or if the indexer 410 becomes unavailable or fails, the indexing node manager 406 can assign a different indexer 410 to process and store the data.

3.2.2.3. Indexer and Data Store

As described herein, the indexer 410 can be the primary indexing execution engine, and can be implemented as a distinct computing device, container, container within a pod, etc. For example, the indexer 410 can tasked with parsing, processing, indexing, and storing the data received from the intake system 210 via the partition manager(s) 408. Specifically, in some embodiments, the indexer 410 can parse the incoming data to identify timestamps, generate events from the incoming data, group and save events into buckets, generate summaries or indexes (e.g., time series index, inverted index, keyword index, etc.) of the events in the buckets, and store the buckets in common storage 216.

In some cases, one indexer 410 can be assigned to each partition manager 408, and in certain embodiments, one indexer 410 can receive and process the data from multiple (or all) partition mangers 408 on the same indexing node 404 or from multiple indexing nodes 404.

In some embodiments, the indexer 410 can store the events and buckets in the data store 412 according to a bucket creation policy. The bucket creation policy can indicate how many buckets the indexer 410 is to generate for the data that it processes. In some cases, based on the bucket creation policy, the indexer 410 generates at least one bucket for each tenant and index (also referred to as a partition) associated with the data that it processes. For example, if the indexer 410 receives data associated with three tenants A, B, C, each with two indexes X, Y, then the indexer 410 can generate at least six buckets: at least one bucket for each of Tenant A::Index X, Tenant A::Index Y, Tenant B::Index X, Tenant B::Index Y, Tenant C::Index X, and Tenant C::Index Y. Additional buckets may be generated for a tenant/partition pair based on the amount of data received that is associated with the tenant/partition pair. However, it will be understood that the indexer 410 can generate buckets using a variety of policies. For example, the indexer 410 can generate one or more buckets for each tenant, partition, source, sourcetype, etc.

In some cases, if the indexer 410 receives data that it determines to be "old," e.g., based on a timestamp of the data or other temporal determination regarding the data, then it can generate a bucket for the "old" data. In some embodiments, the indexer 410 can determine that data is "old," if the data is associated with a timestamp that is earlier in time by a threshold amount than timestamps of other data in the corresponding bucket (e.g., depending on the bucket creation policy, data from the same partition and/or tenant) being processed by the indexer 410. For example, if the indexer 410 is processing data for the bucket for Tenant A::Index X having timestamps on 4/23 between 16:23:56 and 16:46:32 and receives data for the Tenant A::Index X bucket having a timestamp on 4/22 or on 4/23 at 08:05:32, then it can determine that the data with the earlier timestamps is "old" data and generate a new bucket for that data. In this way, the indexer 410 can avoid placing data in the same bucket that creates a time range that is significantly larger than the time range of other buckets, which can decrease the performance of the system as the bucket could be identified as relevant for a search more often than it otherwise would.

The threshold amount of time used to determine if received data is "old," can be predetermined or dynamically determined based on a number of factors, such as, but not limited to, time ranges of other buckets, amount of data being processed, timestamps of the data being processed, etc. For example, the indexer 410 can determine an average time range of buckets that it processes for different tenants and indexes. If incoming data would cause the time range of a bucket to be significantly larger (e.g., 25%, 50%, 75%, double, or other amount) than the average time range, then the indexer 410 can determine that the data is "old" data, and generate a separate bucket for it. By placing the "old" bucket in a separate bucket, the indexer 410 can reduce the instances in which the bucket is identified as storing data that may be relevant to a query. For example, by having a smaller time range, the query system 214 may identify the bucket less frequently as a relevant bucket then if the bucket had the large time range due to the "old" data. Additionally, in a process that will be described in more detail herein, time-restricted searches and search queries may be executed more quickly because there may be fewer buckets to search for a particular time range. In this manner, computational efficiency of searching large amounts of data can be improved. Although described with respect detecting "old" data, the indexer 410 can use similar techniques to determine that "new" data should be placed in a new bucket or that a time gap between data in a bucket and "new" data is larger than a threshold amount such that the "new" data should be stored in a separate bucket.

Once a particular bucket satisfies a size threshold, the indexer 410 can store the bucket in or copy the bucket to common storage 216. In certain embodiments, the partition manager 408 can monitor the size of the buckets and instruct the indexer 410 to copy the bucket to common storage 216. The threshold size can be predetermined or dynamically determined.

In certain embodiments, the partition manager 408 can monitor the size of multiple, or all, buckets associated with the partition being managed by the partition manager 408, and based on the collective size of the buckets satisfying a threshold size, instruct the indexer 410 to copy the buckets associated with the partition to common storage 216. In certain cases, one or more partition managers 408 or the indexing node manager 406 can monitor the size of buckets across multiple, or all partitions, associated with the indexing node 404, and instruct the indexer to copy the buckets to common storage 216 based on the size of the buckets satisfying a threshold size.

As described herein, buckets in the data store 412 that are being edited by the indexer 410 can be referred to as hot buckets or editable buckets. For example, the indexer 410 can add data, events, and indexes to editable buckets in the data store 412, etc. Buckets in the data store 412 that are no longer edited by the indexer 410 can be referred to as warm buckets or non-editable buckets. In some embodiments, once the indexer 410 determines that a hot bucket is to be copied to common storage 216, it can convert the hot (editable) bucket to a warm (non-editable) bucket, and then move or copy the warm bucket to the common storage 216. Once the warm bucket is moved or copied to common storage 216, the indexer 410 can notify the partition manager 408 that the data associated with the warm bucket has been processed and stored. As mentioned, the partition manager 408 can relay the information to the intake system 210. In addition, the indexer 410 can provide the partition manager 408 with information about the buckets stored in common storage 216, such as, but not limited to, location information, tenant identifier, index identifier, time range, etc. As described herein, the partition manager 408 can use this information to update the data store catalog 220.

3.2.3. Bucket Manager

The bucket manager 414 can manage the buckets stored in the data store 412, and can be implemented as a distinct computing device, virtual machine, container, container of a pod, or a process or thread associated with a container. In some cases, the bucket manager 414 can be implemented as part of the indexer 410, indexing node 404, or as a separate component of the indexing system 212.

As described herein, the indexer 410 stores data in the data store 412 as one or more buckets associated with different tenants, indexes, etc. In some cases, the contents of the buckets are not searchable by the query system 214 until they are stored in common storage 216. For example, the query system 214 may be unable to identify data responsive to a query that is located in hot (editable) buckets in the data store 412 and/or the warm (non-editable) buckets in the data store 412 that have not been copied to common storage 216. Thus, query results may be incomplete or inaccurate, or slowed as the data in the buckets of the data store 412 are copied to common storage 216.

To decrease the delay between processing and/or indexing the data and making that data searchable, the indexing system 212 can use a bucket roll-over policy that instructs the indexer 410 to convert hot buckets to warm buckets more frequently (or convert based on a smaller threshold size) and/or copy the warm buckets to common storage 216. While converting hot buckets to warm buckets more frequently or based on a smaller storage size can decrease the lag between processing the data and making it searchable, it can increase the storage size and overhead of buckets in common storage 216. For example, each bucket may have overhead associated with it, in terms of storage space required, processor power required, or other resource requirement. Thus, more buckets in common storage 216 can result in more storage used for overhead than for storing data, which can lead to increased storage size and costs. In addition, a larger number of buckets in common storage 216 can increase query times, as the opening of each bucket as part of a query can have certain processing overhead or time delay associated with it.

To decrease search times and reduce overhead and storage associated with the buckets (while maintaining a reduced delay between processing the data and making it searchable), the bucket manager 414 can monitor the buckets stored in the data store 412 and/or common storage 216 and merge buckets according to a bucket merge policy. For example, the bucket manager 414 can monitor and merge warm buckets stored in the data store 412 before, after, or concurrently with the indexer copying warm buckets to common storage 216.

The bucket merge policy can indicate which buckets are candidates for a merge or which bucket to merge (e.g., based on time ranges, size, tenant/partition or other identifiers), the number of buckets to merge, size or time range parameters for the merged buckets, and/or a frequency for creating the merged buckets. For example, the bucket merge policy can indicate that a certain number of buckets are to be merged, regardless of size of the buckets. As another non-limiting example, the bucket merge policy can indicate that multiple buckets are to be merged until a threshold bucket size is reached (e.g., 750 MB, or 1 GB, or more). As yet another non-limiting example, the bucket merge policy can indicate that buckets having a time range within a set period of time (e.g., 30 sec, 1 min., etc.) are to be merged, regardless of the number or size of the buckets being merged.

In addition, the bucket merge policy can indicate which buckets are to be merged or include additional criteria for merging buckets. For example, the bucket merge policy can indicate that only buckets having the same tenant identifier and/or partition are to be merged, or set constraints on the size of the time range for a merged bucket (e.g., the time range of the merged bucket is not to exceed an average time range of buckets associated with the same source, tenant, partition, etc.). In certain embodiments, the bucket merge policy can indicate that buckets that are older than a threshold amount (e.g., one hour, one day, etc.) are candidates for a merge or that a bucket merge is to take place once an hour, once a day, etc. In certain embodiments, the bucket merge policy can indicate that buckets are to be merged based on a determination that the number or size of warm buckets in the data store 412 of the indexing node 404 satisfies a threshold number or size, or the number or size of warm buckets associated with the same tenant identifier and/or partition satisfies the threshold number or size. It will be understood, that the bucket manager 414 can use any one or any combination of the aforementioned or other criteria for the bucket merge policy to determine when, how, and which buckets to merge.

Once a group of buckets are merged into one or more merged buckets, the bucket manager 414 can copy or instruct the indexer 406 to copy the merged buckets to common storage 216. Based on a determination that the merged buckets are successfully copied to the common storage 216, the bucket manager 414 can delete the merged buckets and the buckets used to generate the merged buckets (also referred to herein as unmerged buckets or pre-merged buckets) from the data store 412.

In some cases, the bucket manager 414 can also remove or instruct the common storage 216 to remove corresponding pre-merged buckets from the common storage 216 according to a bucket management policy. The bucket management policy can indicate when the pre-merged buckets are to be deleted or designated as able to be overwritten from common storage 216.

In some cases, the bucket management policy can indicate that the pre-merged buckets are to be deleted immediately, once any queries relying on the pre-merged buckets are completed, after a predetermined amount of time, etc. In some cases, the pre-merged buckets may be in use or identified for use by one or more queries. Removing the pre-merged buckets from common storage 216 in the middle of a query may cause one or more failures in the query system 214 or result in query responses that are incomplete or erroneous. Accordingly, the bucket management policy, in some cases, can indicate to the common storage 216 that queries that arrive before a merged bucket is stored in common storage 216 are to use the corresponding pre-merged buckets and queries that arrive after the merged bucket is stored in common storage 216 are to use the merged bucket.

Further, the bucket management policy can indicate that once queries using the pre-merged buckets are completed, the buckets are to be removed from common storage 216. However, it will be understood that the bucket management policy can indicate removal of the buckets in a variety of ways. For example, per the bucket management policy, the common storage 216 can remove the buckets after on one or more hours, one day, one week, etc., with or without regard to queries that may be relying on the pre-merged buckets. In some embodiments, the bucket management policy can indicate that the pre-merged buckets are to be removed without regard to queries relying on the pre-merged buckets and that any queries relying on the pre-merged buckets are to be redirected to the merged bucket.

In addition to removing the pre-merged buckets and merged bucket from the data store 412 and removing or instructing common storage 216 to remove the pre-merged buckets from the data store(s) 218, the bucket manger 414 can update the data store catalog 220 or cause the indexer 410 or partition manager 408 to update the data store catalog 220 with the relevant changes. These changes can include removing reference to the pre-merged buckets in the data store catalog 220 and/or adding information about the merged bucket, including, but not limited to, a bucket, tenant, and/or partition identifier associated with the merged bucket, a time range of the merged bucket, location information of the merged bucket in common storage 216, etc. In this way, the data store catalog 220 can be kept up-to-date with the contents of the common storage 216.

3.3. Query System

Figure 5:
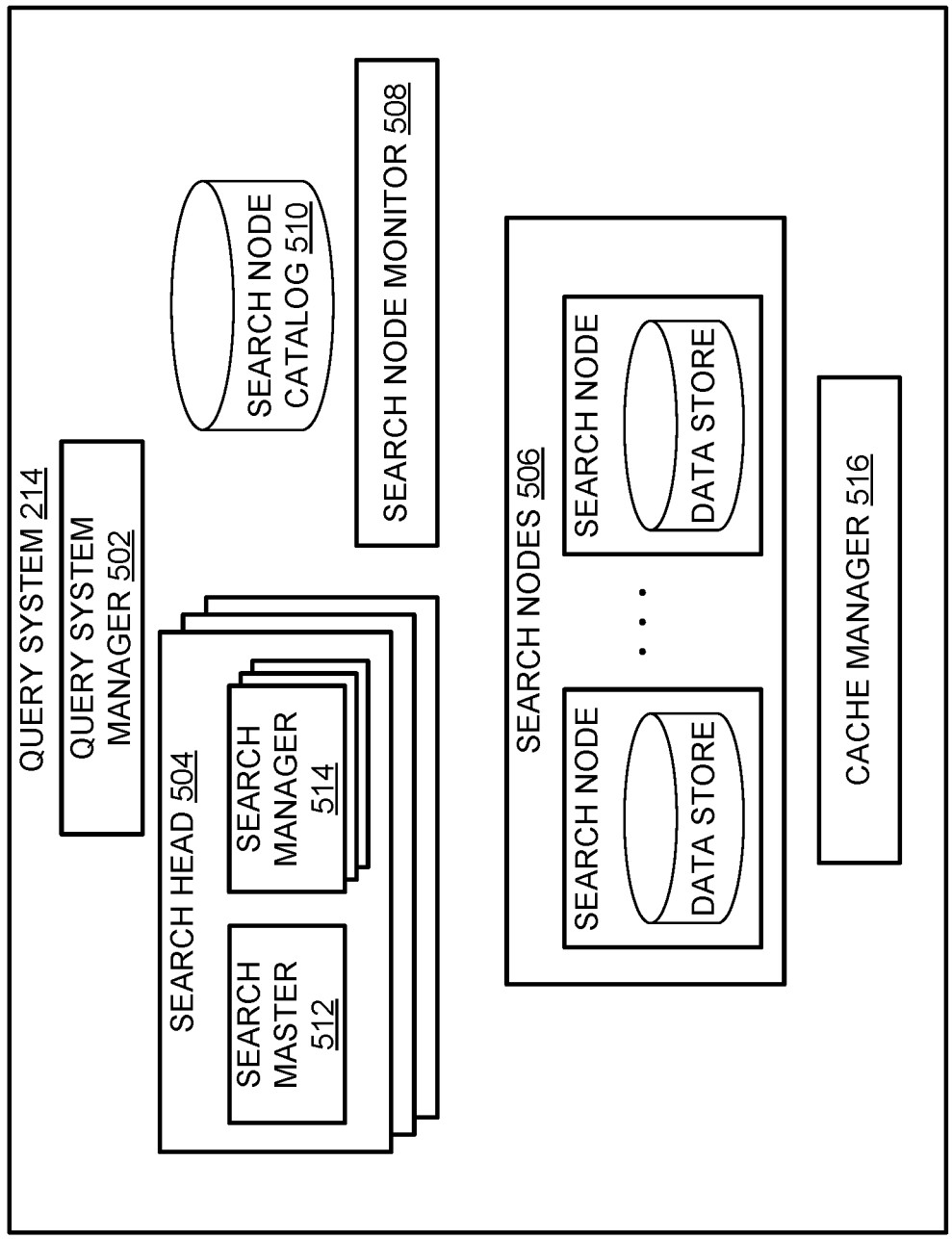
FIG. 5 is a block diagram illustrating an embodiment of a query system of the data intake and query system.

FIG. 5 is a block diagram illustrating an embodiment of a query system 214 of the data intake and query system 108. The query system 214 can receive, process, and execute queries from multiple client devices 204, which may be associated with different tenants, users, etc. Moreover, the query system 214 can include various components that enable it to provide a stateless or state-free search service, or search service that is able to rapidly recover without data loss if one or more components of the query system 214 become unresponsive or unavailable.

In the illustrated embodiment, the query system 214 includes one or more query system managers 502 (collectively or individually referred to as query system manager 502), one or more search heads 504 (collectively or individually referred to as search head 504 or search heads 504), one or more search nodes 506 (collectively or individually referred to as search node 506 or search nodes 506), a search node monitor 508, and a search node catalog 510. However, it will be understood that the query system 214 can include fewer or more components as desired. For example, in some embodiments, the common storage 216, data store catalog 220, or query acceleration data store 222 can form part of the query system 214, etc.

As described herein, each of the components of the query system 214 can be implemented using one or more computing devices as distinct computing devices or as one or more container instances or virtual machines across one or more computing devices. For example, in some embodiments, the query system manager 502, search heads 504, and search nodes 506 can be implemented as distinct computing devices with separate hardware, memory, and processors. In certain embodiments, the query system manager 502, search heads 504, and search nodes 506 can be implemented on the same or across different computing devices as distinct container instances, with each container having access to a subset of the resources of a host computing device (e.g., a subset of the memory or processing time of the processors of the host computing device), but sharing a similar operating system. In some cases, the components can be implemented as distinct virtual machines across one or more computing devices, where each virtual machine can have its own unshared operating system but shares the underlying hardware with other virtual machines on the same host computing device.

3.3.1. Query System Manager

As mentioned, the query system manager 502 can monitor and manage the search heads 504 and search nodes 506, and can be implemented as a distinct computing device, virtual machine, container, container of a pod, or a process or thread associated with a container. For example, the query system manager 502 can determine which search head 504 is to handle an incoming query or determine whether to generate an additional search node 506 based on the number of queries received by the query system 214 or based on another search node 506 becoming unavailable or unresponsive. Similarly, the query system manager 502 can determine that additional search heads 504 should be generated to handle an influx of queries or that some search heads 504 can be de-allocated or terminated based on a reduction in the number of queries received.

In certain embodiments, the query system 214 can include one query system manager 502 to manage all search heads 504 and search nodes 506 of the query system 214. In some embodiments, the query system 214 can include multiple query system managers 502. For example, a query system manager 502 can be instantiated for each computing device (or group of computing devices) configured as a host computing device for multiple search heads 504 and/or search nodes 506.

Moreover, the query system manager 502 can handle resource management, creation, assignment, or destruction of search heads 504 and/or search nodes 506, high availability, load balancing, application upgrades/rollbacks, logging and monitoring, storage, networking, service discovery, and performance and scalability, and otherwise handle containerization management of the containers of the query system 214. In certain embodiments, the query system manager 502 can be implemented using Kubernetes or Swarm. For example, in certain embodiments, the query system manager 502 may be part of a sidecar or sidecar container, that allows communication between various search nodes 506, various search heads 504, and/or combinations thereof.

In some cases, the query system manager 502 can monitor the available resources of a host computing device and/or request additional resources in a shared resource environment, based on workload of the search heads 504 and/or search nodes 506 or create, destroy, or reassign search heads 504 and/or search nodes 506 based on workload. Further, the query system manager 502 system can assign search heads 504 to handle incoming queries and/or assign search nodes 506 to handle query processing based on workload, system resources, etc.

3.3.2. Search Head

As described herein, the search heads 504 can manage the execution of queries received by the query system 214. For example, the search heads 504 can parse the queries to identify the set of data to be processed and the manner of processing the set of data, identify the location of the data, identify tasks to be performed by the search head and tasks to be performed by the search nodes 506, distribute the query (or sub-queries corresponding to the query) to the search nodes 506, apply extraction rules to the set of data to be processed, aggregate search results from the search nodes 506, store the search results in the query acceleration data store 222, etc.

As described herein, the search heads 504 can be implemented on separate computing devices or as containers or virtual machines in a virtualization environment. In some embodiments, the search heads 504 may be implemented using multiple-related containers. In certain embodiments, such as in a Kubernetes deployment, each search head 504 can be implemented as a separate container or pod. For example, one or more of the components of the search head 504 can be implemented as different containers of a single pod, e.g., on a containerization platform, such as Docker, the one or more components of the indexing node can be implemented as different Docker containers managed by synchronization platforms such as Kubernetes or Swarm. Accordingly, reference to a containerized search head 504 can refer to the search head 504 as being a single container or as one or more components of the search head 504 being implemented as different, related containers.

In the illustrated embodiment, the search head 504 includes a search master 512 and one or more search managers 514 to carry out its various functions. However, it will be understood that the search head 504 can include fewer or more components as desired. For example, the search head 504 can include multiple search masters 512.

3.3.2.1. Search Master

The search master 512 can manage the execution of the various queries assigned to the search head 504, and can be implemented as a distinct computing device, virtual machine, container, container of a pod, or a process or thread associated with a container. For example, in certain embodiments, as the search head 504 is assigned a query, the search master 512 can generate one or more search manager(s) 514 to manage the query. In some cases, the search master 512 generates a separate search manager 514 for each query that is received by the search head 504. In addition, once a query is completed, the search master 512 can handle the termination of the corresponding search manager 514.

In certain embodiments, the search master 512 can track and store the queries assigned to the different search managers 514. Accordingly, if a search manager 514 becomes unavailable or unresponsive, the search master 512 can generate a new search manager 514 and assign the query to the new search manager 514. In this way, the search head 504 can increase the resiliency of the query system 214, reduce delay caused by an unresponsive component, and can aid in providing a stateless searching service.

In some embodiments, the search master 512 is implemented as a background process, or daemon, on the search head 504 and the search manager(s) 514 are implemented as threads, copies, or forks of the background process. In some cases, a search master 512 can copy itself, or fork, to create a search manager 514 or cause a template process to copy itself, or fork, to create each new search manager 514, etc., in order to support efficient multithreaded implementations

3.3.2.2. Search Manager

As mentioned, the search managers 514 can manage the processing and execution of the queries assigned to the search head 504, and can be implemented as a distinct computing device, virtual machine, container, container of a pod, or a process or thread associated with a container. In some embodiments, one search manager 514 manages the processing and execution of one query at a time. In such embodiments, if the search head 504 is processing one hundred queries, the search master 512 can generate one hundred search managers 514 to manage the one hundred queries. Upon completing an assigned query, the search manager 514 can await assignment to a new query or be terminated.

As part of managing the processing and execution of a query, and as described herein, a search manager 514 can parse the query to identify the set of data and the manner in which the set of data is to be processed (e.g., the transformations that are to be applied to the set of data), determine tasks to be performed by the search manager 514 and tasks to be performed by the search nodes 506, identify search nodes 506 that are available to execute the query, map search nodes 506 to the set of data that is to be processed, instruct the search nodes 506 to execute the query and return results, aggregate and/or transform the search results from the various search nodes 506, and provide the search results to a user and/or to the query acceleration data store 222.

In some cases, to aid in identifying the set of data to be processed, the search manager 514 can consult the data store catalog 220 (depicted in FIG. 2). As described herein, the data store catalog 220 can include information regarding the data stored in common storage 216. In some cases, the data store catalog 220 can include bucket identifiers, a time range, and a location of the buckets in common storage 216. In addition, the data store catalog 220 can include a tenant identifier and partition identifier for the buckets. This information can be used to identify buckets that include data that satisfies at least a portion of the query.

As a non-limiting example, consider a search manager 514 that has parsed a query to identify the following filter criteria that is used to identify the data to be processed: time range: past hour, partition: sales, tenant: ABC, Inc., keyword: Error. Using the received filter criteria, the search manager 514 can consult the data store catalog 220. Specifically, the search manager 514 can use the data store catalog 220 to identify buckets associated with the _sales partition and the tenant ABC, Inc. and that include data from the past hour. In some cases, the search manager 514 can obtain bucket identifiers and location information from the data store catalog 220 for the buckets storing data that satisfies at least the aforementioned filter criteria. In certain embodiments, if the data store catalog 220 includes keyword pairs, it can use the keyword: Error to identify buckets that have at least one event that include the keyword Error.

Using the bucket identifiers and/or the location information, the search manager 514 can assign one or more search nodes 506 to search the corresponding buckets. Accordingly, the data store catalog 220 can be used to identify relevant buckets and reduce the number of buckets that are to be searched by the search nodes 506. In this way, the data store catalog 220 can decrease the query response time of the data intake and query system 108.

In some embodiments, the use of the data store catalog 220 to identify buckets for searching can contribute to the statelessness of the query system 214 and search head 504. For example, if a search head 504 or search manager 514 becomes unresponsive or unavailable, the query system manager 502 or search master 512, as the case may be, can spin up or assign an additional resource (new search head 504 or new search manager 514) to execute the query. As the bucket information is persistently stored in the data store catalog 220, data lost due to the unavailability or unresponsiveness of a component of the query system 214 can be recovered by using the bucket information in the data store catalog 220.

In certain embodiments, to identify search nodes 506 that are available to execute the query, the search manager 514 can consult the search node catalog 510. As described herein, the search node catalog 510 can include information regarding the search nodes 506. In some cases, the search node catalog 510 can include an identifier for each search node 506, as well as utilization and availability information. For example, the search node catalog 510 can identify search nodes 506 that are instantiated but are unavailable or unresponsive. In addition, the search node catalog 510 can identify the utilization rate of the search nodes 506. For example, the search node catalog 510 can identify search nodes 506 that are working at maximum capacity or at a utilization rate that satisfies utilization threshold, such that the search node 506 should not be used to execute additional queries for a time.

In addition, the search node catalog 510 can include architectural information about the search nodes 506. For example, the search node catalog 510 can identify search nodes 506 that share a data store and/or are located on the same computing device, or on computing devices that are co-located.

Accordingly, in some embodiments, based on the receipt of a query, a search manager 514 can consult the search node catalog 510 for search nodes 506 that are available to execute the received query. Based on the consultation of the search node catalog 510, the search manager 514 can determine which search nodes 506 to assign to execute the query.

The search manager 514 can map the search nodes 506 to the data that is to be processed according to a search node mapping policy. The search node mapping policy can indicate how search nodes 506 are to be assigned to data (e.g., buckets) and when search nodes 506 are to be assigned to (and instructed to search) the data or buckets.

In some cases, the search manager 514 can map the search nodes 506 to buckets that include data that satisfies at least a portion of the query. For example, in some cases, the search manager 514 can consult the data store catalog 220 to obtain bucket identifiers of buckets that include data that satisfies at least a portion of the query, e.g., as a non-limiting example, to obtain bucket identifiers of buckets that include data associated with a particular time range. Based on the identified buckets and search nodes 506, the search manager 514 can dynamically assign (or map) search nodes 506 to individual buckets according to a search node mapping policy.

In some embodiments, the search node mapping policy can indicate that the search manager 514 is to assign all buckets to search nodes 506 as a single operation. For example, where ten buckets are to be searched by five search nodes 506, the search manager 514 can assign two buckets to a first search node 506, two buckets to a second search node 506, etc. In another embodiment, the search node mapping policy can indicate that the search manager 514 is to assign buckets iteratively. For example, where ten buckets are to be searched by five search nodes 506, the search manager 514 can initially assign five buckets (e.g., one buckets to each search node 506), and assign additional buckets to each search node 506 as the respective search nodes 506 complete the execution on the assigned buckets.

Retrieving buckets from common storage 216 to be searched by the search nodes 506 can cause delay or may use a relatively high amount of network bandwidth or disk read/write bandwidth. In some cases, a local or shared data store associated with the search nodes 506 may include a copy of a bucket that was previously retrieved from common storage 216. Accordingly, to reduce delay caused by retrieving buckets from common storage 216, the search node mapping policy can indicate that the search manager 514 is to assign, preferably assign, or attempt to assign the same search node 506 to search the same bucket over time. In this way, the assigned search node 506 can keep a local copy of the bucket on its data store (or a data store shared between multiple search nodes 506) and avoid the processing delays associated with obtaining the bucket from the common storage 216.

In certain embodiments, the search node mapping policy can indicate that the search manager 514 is to use a consistent hash function or other function to consistently map a bucket to a particular search node 506. The search manager 514 can perform the hash using the bucket identifier obtained from the data store catalog 220, and the output of the hash can be used to identify the search node 506 assigned to the bucket. In some cases, the consistent hash function can be configured such that even with a different number of search nodes 506 being assigned to execute the query, the output will consistently identify the same search node 506, or have an increased probability of identifying the same search node 506.

In some embodiments, the query system 214 can store a mapping of search nodes 506 to bucket identifiers. The search node mapping policy can indicate that the search manager 514 is to use the mapping to determine whether a particular bucket has been assigned to a search node 506. If the bucket has been assigned to a particular search node 506 and that search node 506 is available, then the search manager 514 can assign the bucket to the search node 506. If the bucket has not been assigned to a particular search node 506, the search manager 514 can use a hash function to identify a search node 506 for assignment. Once assigned, the search manager 514 can store the mapping for future use.

In certain cases, the search node mapping policy can indicate that the search manager 514 is to use architectural information about the search nodes 506 to assign buckets. For example, if the identified search node 506 is unavailable or its utilization rate satisfies a threshold utilization rate, the search manager 514 can determine whether an available search node 506 shares a data store with the unavailable search node 506. If it does, the search manager 514 can assign the bucket to the available search node 506 that shares the data store with the unavailable search node 506. In this way, the search manager 514 can reduce the likelihood that the bucket will be obtained from common storage 216, which can introduce additional delay to the query while the bucket is retrieved from common storage 216 to the data store shared by the available search node 506.

In some instances, the search node mapping policy can indicate that the search manager 514 is to assign buckets to search nodes 506 randomly, or in a simple sequence (e.g., a first search nodes 506 is assigned a first bucket, a second search node 506 is assigned a second bucket, etc.). In other instances, as discussed, the search node mapping policy can indicate that the search manager 514 is to assign buckets to search nodes 506 based on buckets previously assigned to a search nodes 506, in a prior or current search. As mentioned above, in some embodiments each search node 506 may be associated with a local data store or cache of information (e.g., in memory of the search nodes 506, such as random access memory ["RAM"], disk-based cache, a data store, or other form of storage). Each search node 506 can store copies of one or more buckets from the common storage 216 within the local cache, such that the buckets may be more rapidly searched by search nodes 506. The search manager 514 (or cache manager 516) can maintain or retrieve from search nodes 506 information identifying, for each relevant search node 506, what buckets are copied within local cache of the respective search nodes 506. In the event that the search manager 514 determines that a search node 506 assigned to execute a search has within its data store or local cache a copy of an identified bucket, the search manager 514 can preferentially assign the search node 506 to search that locally-cached bucket.

In still more embodiments, according to the search node mapping policy, search nodes 506 may be assigned based on overlaps of computing resources of the search nodes 506. For example, where a containerized search node 506 is to retrieve a bucket from common storage 216 (e.g., where a local cached copy of the bucket does not exist on the search node 506), such retrieval may use a relatively high amount of network bandwidth or disk read/write bandwidth. Thus, assigning a second containerized search node 506 instantiated on the same host computing device might be expected to strain or exceed the network or disk read/write bandwidth of the host computing device. For this reason, in some embodiments, according to the search node mapping policy, the search manager 514 can assign buckets to search nodes 506 such that two containerized search nodes 506 on a common host computing device do not both retrieve buckets from common storage 216 at the same time.

Further, in certain embodiments, where a data store that is shared between multiple search nodes 506 includes two buckets identified for the search, the search manager 514 can, according to the search node mapping policy, assign both such buckets to the same search node 506 or to two different search nodes 506 that share the data store, such that both buckets can be searched in parallel by the respective search nodes 506.

The search node mapping policy can indicate that the search manager 514 is to use any one or any combination of the above-described mechanisms to assign buckets to search nodes 506. Furthermore, the search node mapping policy can indicate that the search manager 514 is to prioritize assigning search nodes 506 to buckets based on any one or any combination of: assigning search nodes 506 to process buckets that are in a local or shared data store of the search nodes 506, maximizing parallelization (e.g., assigning as many different search nodes 506 to execute the query as are available), assigning search nodes 506 to process buckets with overlapping timestamps, maximizing individual search node 506 utilization (e.g., ensuring that each search node 506 is searching at least one bucket at any given time, etc.), or assigning search nodes 506 to process buckets associated with a particular tenant, user, or other known feature of data stored within the bucket (e.g., buckets holding data known to be used in time-sensitive searches may be prioritized). Thus, according to the search node mapping policy, the search manager 514 can dynamically alter the assignment of buckets to search nodes 506 to increase the parallelization of a search, and to increase the speed and efficiency with which the search is executed.

It will be understood that the search manager 514 can assign any search node 506 to search any bucket. This flexibility can decrease query response time as the search manager can dynamically determine which search nodes 506 are best suited or available to execute the query on different buckets. Further, if one bucket is being used by multiple queries, the search manager 515 can assign multiple search nodes 506 to search the bucket. In addition, in the event a search node 506 becomes unavailable or unresponsive, the search manager 514 can assign a different search node 506 to search the buckets assigned to the unavailable search node 506.

As part of the query execution, the search manager 514 can instruct the search nodes 506 to execute the query (or sub-query) on the assigned buckets. As described herein, the search manager 514 can generate specific queries or sub-queries for the individual search nodes 506. The search nodes 506 can use the queries to execute the query on the buckets assigned thereto.

In some embodiments, the search manager 514 stores the sub-queries and bucket assignments for the different search nodes 506. Storing the sub-queries and bucket assignments can contribute to the statelessness of the query system 214. For example, in the event an assigned search node 506 becomes unresponsive or unavailable during the query execution, the search manager 514 can re-assign the sub-query and bucket assignments of the unavailable search node 506 to one or more available search nodes 506 or identify a different available search node 506 from the search node catalog 510 to execute the sub-query. In certain embodiments, the query system manager 502 can generate an additional search node 506 to execute the sub-query of the unavailable search node 506. Accordingly, the query system 214 can quickly recover from an unavailable or unresponsive component without data loss and while reducing or minimizing delay.

During the query execution, the search manager 514 can monitor the status of the assigned search nodes 506. In some cases, the search manager 514 can ping or set up a communication link between it and the search nodes 506 assigned to execute the query. As mentioned, the search manager 514 can store the mapping of the buckets to the search nodes 506. Accordingly, in the event a particular search node 506 becomes unavailable for his unresponsive, the search manager 514 can assign a different search node 506 to complete the execution of the query for the buckets assigned to the unresponsive search node 506.

In some cases, as part of the status updates to the search manager 514, the search nodes 506 can provide the search manager with partial results and information regarding the buckets that have been searched. In response, the search manager 514 can store the partial results and bucket information in persistent storage. Accordingly, if a search node 506 partially executes the query and becomes unresponsive or unavailable, the search manager 514 can assign a different search node 506 to complete the execution, as described above. For example, the search manager 514 can assign a search node 506 to execute the query on the buckets that were not searched by the unavailable search node 506. In this way, the search manager 514 can more quickly recover from an unavailable or unresponsive search node 506 without data loss and while reducing or minimizing delay.

As the search manager 514 receives query results from the different search nodes 506, it can process the data. In some cases, the search manager 514 processes the partial results as it receives them. For example, if the query includes a count, the search manager 514 can increment the count as it receives the results from the different search nodes 506. In certain cases, the search manager 514 waits for the complete results from the search nodes before processing them. For example, if the query includes a command that operates on a result set, or a partial result set, e.g., a stats command (e.g., a command that calculates one or more aggregate statistics over the results set, e.g., average, count, or standard deviation, as examples), the search manager 514 can wait for the results from all the search nodes 506 before executing the stats command.

As the search manager 514 processes the results or completes processing the results, it can store the results in the query acceleration data store 222 or communicate the results to a client device 204. As described herein, results stored in the query acceleration data store 222 can be combined with other results over time. For example, if the query system 212 receives an open-ended query (e.g., no set end time), the search manager 515 can store the query results over time in the query acceleration data store 222. Query results in the query acceleration data store 222 can be updated as additional query results are obtained. In this manner, if an open-ended query is run at time B, query results may be stored from initial time A to time B. If the same open-ended query is run at time C, then the query results from the prior open-ended query can be obtained from the query acceleration data store 222 (which gives the results from time A to time B), and the query can be run from time B to time C and combined with the prior results, rather than running the entire query from time A to time C. In this manner, the computational efficiency of ongoing search queries can be improved.

3.3.3. Search Nodes

As described herein, the search nodes 506 can be the primary query execution engines for the query system 214, and can be implemented as distinct computing devices, virtual machines, containers, container of a pods, or processes or threads associated with one or more containers. Accordingly, each search node 506 can include a processing device and a data store, as depicted at a high level in FIG. 5. Depending on the embodiment, the processing device and data store can be dedicated to the search node (e.g., embodiments where each search node is a distinct computing device) or can be shared with other search nodes or components of the data intake and query system 108 (e.g., embodiments where the search nodes are implemented as containers or virtual machines or where the shared data store is a networked data store, etc.).

In some embodiments, the search nodes 506 can obtain and search buckets identified by the search manager 514 that include data that satisfies at least a portion of the query, identify the set of data within the buckets that satisfies the query, perform one or more transformations on the set of data, and communicate the set of data to the search manager 514. Individually, a search node 506 can obtain the buckets assigned to it by the search manager 514 for a particular query, search the assigned buckets for a subset of the set of data, perform one or more transformation on the subset of data, and communicate partial search results to the search manager 514 for additional processing and combination with the partial results from other search nodes 506.

In some cases, the buckets to be searched may be located in a local data store of the search node 506 or a data store that is shared between multiple search nodes 506. In such cases, the search nodes 506 can identify the location of the buckets and search the buckets for the set of data that satisfies the query.

In certain cases, the buckets may be located in the common storage 216. In such cases, the search nodes 506 can search the buckets in the common storage 216 and/or copy the buckets from the common storage 216 to a local or shared data store and search the locally stored copy for the set of data. As described herein, the cache manager 516 can coordinate with the search nodes 506 to identify the location of the buckets (whether in a local or shared data store or in common storage 216) and/or obtain buckets stored in common storage 216.

Once the relevant buckets (or relevant files of the buckets) are obtained, the search nodes 506 can search their contents to identify the set of data to be processed. In some cases, upon obtaining a bucket from the common storage 216, a search node 306 can decompress the bucket from a compressed format, and accessing one or more files stored within the bucket. In some cases, the search node 306 references a bucket summary or manifest to locate one or more portions (e.g., records or individual files) of the bucket that potentially contain information relevant to the search.

In some cases, the search nodes 506 can use all of the files of a bucket to identify the set of data. In certain embodiments, the search nodes 506 use a subset of the files of a bucket to identify the set of data. For example, in some cases, a search node 506 can use an inverted index, bloom filter, or bucket summary or manifest to identify a subset of the set of data without searching the raw machine data of the bucket. In certain cases, the search node 506 uses the inverted index, bloom filter, bucket summary, and raw machine data to identify the subset of the set of data that satisfies the query.

In some embodiments, depending on the query, the search nodes 506 can perform one or more transformations on the data from the buckets. For example, the search nodes 506 may perform various data transformations, scripts, and processes, e.g., a count of the set of data, etc.

As the search nodes 506 execute the query, they can provide the search manager 514 with search results. In some cases, a search node 506 provides the search manager 514 results as they are identified by the search node 506, and updates the results over time. In certain embodiments, a search node 506 waits until all of its partial results are gathered before sending the results to the search manager 504.

In some embodiments, the search nodes 506 provide a status of the query to the search manager 514. For example, an individual search node 506 can inform the search manager 514 of which buckets it has searched and/or provide the search manager 514 with the results from the searched buckets. As mentioned, the search manager 514 can track or store the status and the results as they are received from the search node 506. In the event the search node 506 becomes unresponsive or unavailable, the tracked information can be used to generate and assign a new search node 506 to execute the remaining portions of the query assigned to the unavailable search node 506.

3.3.4. Cache Manager

As mentioned, the cache manager 516 can communicate with the search nodes 506 to obtain or identify the location of the buckets assigned to the search nodes 506, and can be implemented as a distinct computing device, virtual machine, container, container of a pod, or a process or thread associated with a container.

In some embodiments, based on the receipt of a bucket assignment, a search node 506 can provide the cache manager 516 with an identifier of the bucket that it is to search, a file associated with the bucket that it is to search, and/or a location of the bucket. In response, the cache manager 516 can determine whether the identified bucket or file is located in a local or shared data store or is to be retrieved from the common storage 216.

As mentioned, in some cases, multiple search nodes 506 can share a data store. Accordingly, if the cache manager 516 determines that the requested bucket is located in a local or shared data store, the cache manager 516 can provide the search node 506 with the location of the requested bucket or file. In certain cases, if the cache manager 516 determines that the requested bucket or file is not located in the local or shared data store, the cache manager 516 can request the bucket or file from the common storage 216, and inform the search node 506 that the requested bucket or file is being retrieved from common storage 216.

In some cases, the cache manager 516 can request one or more files associated with the requested bucket prior to, or in place of, requesting all contents of the bucket from the common storage 216. For example, a search node 506 may request a subset of files from a particular bucket. Based on the request and a determination that the files are located in common storage 216, the cache manager 516 can download or obtain the identified files from the common storage 216.

In some cases, based on the information provided from the search node 506, the cache manager 516 may be unable to uniquely identify a requested file or files within the common storage 216. Accordingly, in certain embodiments, the cache manager 516 can retrieve a bucket summary or manifest file from the common storage 216 and provide the bucket summary to the search node 506. In some cases, the cache manager 516 can provide the bucket summary to the search node 506 while concurrently informing the search node 506 that the requested files are not located in a local or shared data store and are to be retrieved from common storage 216.

Using the bucket summary, the search node 506 can uniquely identify the files to be used to execute the query. Using the unique identification, the cache manager 516 can request the files from the common storage 216. Accordingly, rather than downloading the entire contents of the bucket from common storage 216, the cache manager 516 can download those portions of the bucket that are to be used by the search node 506 to execute the query. In this way, the cache manager 516 can decrease the amount of data sent over the network and decrease the search time.

As a non-limiting example, a search node 506 may determine that an inverted index of a bucket is to be used to execute a query. For example, the search node 506 may determine that all the information that it needs to execute the query on the bucket can be found in an inverted index associated with the bucket. Accordingly, the search node 506 can request the file associated with the inverted index of the bucket from the cache manager 516. Based on a determination that the requested file is not located in a local or shared data store, the cache manager 516 can determine that the file is located in the common storage 216.

As the bucket may have multiple inverted indexes associated with it, the information provided by the search node 506 may be insufficient to uniquely identify the inverted index within the bucket. To address this issue, the cache manager 516 can request a bucket summary or manifest from the common storage 216, and forward it to the search node 506. The search node 506 can analyze the bucket summary to identify the particular inverted index that is to be used to execute the query, and request the identified particular inverted index from the cache manager 516 (e.g., by name and/or location). Using the bucket manifest and/or the information received from the search node 506, the cache manager 516 can obtain the identified particular inverted index from the common storage 216. By obtaining the bucket manifest and downloading the requested inverted index instead of all inverted indexes or files of the bucket, the cache manager 516 can reduce the amount of data communicated over the network and reduce the search time for the query.

In some cases, when requesting a particular file, the search node 506 can include a priority level for the file. For example, the files of a bucket may be of different sizes and may be used more or less frequently when executing queries. For example, the bucket manifest may be a relatively small file. However, if the bucket is searched, the bucket manifest can be a relatively valuable file (and frequently used) because it includes a list or index of the various files of the bucket. Similarly, a bloom filter of a bucket may be a relatively small file but frequently used as it can relatively quickly identify the contents of the bucket. In addition, an inverted index may be used more frequently than raw data of a bucket to satisfy a query.

Accordingly, to improve retention of files that are commonly used in a search of a bucket, the search node 506 can include a priority level for the requested file. The cache manager 516 can use the priority level received from the search node 506 to determine how long to keep or when to evict the file from the local or shared data store. For example, files identified by the search node 506 as having a higher priority level can be stored for a greater period of time than files identified as having a lower priority level.

Furthermore, the cache manager 516 can determine what data and how long to retain the data in the local or shared data stores of the search nodes 506 based on a bucket caching policy. In some cases, the bucket caching policy can rely on any one or any combination of the priority level received from the search nodes 506 for a particular file, least recently used, most recent in time, or other policies to indicate how long to retain files in the local or shared data store.

In some instances, according to the bucket caching policy, the cache manager 516 or other component of the query system 214 (e.g., the search master 512 or search manager 514) can instruct search nodes 506 to retrieve and locally cache copies of various buckets from the common storage 216, independently of processing queries. In certain embodiments, the query system 214 is configured, according to the bucket caching policy, such that one or more buckets from the common storage 216 (e.g., buckets associated with a tenant or partition of a tenant) or each bucket from the common storage 216 is locally cached on at least one search node 506.

In some embodiments, according to the bucket caching policy, the query system 214 is configured such that at least one bucket from the common storage 216 is locally cached on at least two search nodes 506. Caching a bucket on at least two search nodes 506 may be beneficial, for example, in instances where different queries both require searching the bucket (e.g., because the at least search nodes 506 may process their respective local copies in parallel). In still other embodiments, the query system 214 is configured, according to the bucket caching policy, such that one or more buckets from the common storage 216 or all buckets from the common storage 216 are locally cached on at least a given number n of search nodes 506, wherein n is defined by a replication factor on the system 108. For example, a replication factor of five may be established to ensure that five copies of a bucket are locally cached across different search nodes 506.

In certain embodiments, the search manager 514 (or search master 512) can assign buckets to different search nodes 506 based on time. For example, buckets that are less than one day old can be assigned to a first group of search nodes 506 for caching, buckets that are more than one day but less than one week old can be assigned to a different group of search nodes 506 for caching, and buckets that are more than one week old can be assigned to a third group of search nodes 506 for caching. In certain cases, the first group can be larger than the second group, and the second group can be larger than the third group. In this way, the query system 214 can provide better/faster results for queries searching data that is less than one day old, and so on, etc. It will be understood that the search nodes can be grouped and assigned buckets in a variety of ways. For example, search nodes 506 can be grouped based on a tenant identifier, index, etc. In this way, the query system 212 can dynamically provide faster results based any one or any number of factors.

In some embodiments, when a search node 506 is added to the query system 214, the cache manager 516 can, based on the bucket caching policy, instruct the search node 506 to download one or more buckets from common storage 216 prior to receiving a query. In certain embodiments, the cache manager 516 can instruct the search node 506 to download specific buckets, such as most recent in time buckets, buckets associated with a particular tenant or partition, etc. In some cases, the cache manager 516 can instruct the search node 506 to download the buckets before the search node 506 reports to the search node monitor 508 that it is available for executing queries. It will be understood that other components of the query system 214 can implement this functionality, such as, but not limited to the query system manager 502, search node monitor 508, search manager 514, or the search nodes 506 themselves.

In certain embodiments, when a search node 506 is removed from the query system 214 or becomes unresponsive or unavailable, the cache manager 516 can identify the buckets that the removed search node 506 was responsible for and instruct the remaining search nodes 506 that they will be responsible for the identified buckets. In some cases, the remaining search nodes 506 can download the identified buckets from common storage 516 or retrieve them from the data store associated with the removed search node 506.

In some cases, the cache manager 516 can change the bucket-search node 506 assignments, such as when a search node 506 is removed or added. In certain embodiments, based on a reassignment, the cache manager 516 can inform a particular search node 506 to remove buckets to which it is no longer assigned, reduce the priority level of the buckets, etc. In this way, the cache manager 516 can make it so the reassigned bucket will be removed more quickly from the search node 506 than it otherwise would without the reassignment. In certain embodiments, the search node 506 that receives the new for the bucket can retrieve the bucket from the now unassigned search node 506 and/or retrieve the bucket from common storage 216.

3.3.5. Search Node Monitor and Catalog

The search node monitor 508 can monitor search nodes and populate the search node catalog 510 with relevant information, and can be implemented as a distinct computing device, virtual machine, container, container of a pod, or a process or thread associated with a container.

In some cases, the search node monitor 508 can ping the search nodes 506 over time to determine their availability, responsiveness, and/or utilization rate. In certain embodiments, each search node 506 can include a monitoring module that provides performance metrics or status updates about the search node 506 to the search node monitor 508. For example, the monitoring module can indicate the amount of processing resources in use by the search node 506, the utilization rate of the search node 506, the amount of memory used by the search node 506, etc. In certain embodiments, the search node monitor 508 can determine that a search node 506 is unavailable or failing based on the data in the status update or absence of a state update from the monitoring module of the search node 506.

Using the information obtained from the search nodes 506, the search node monitor 508 can populate the search node catalog 510 and update it over time. As described herein, the search manager 514 can use the search node catalog 510 to identify search nodes 506 available to execute a query. In some embodiments, the search manager 214 can communicate with the search node catalog 510 using an API.

As the availability, responsiveness, and/or utilization change for the different search nodes 506, the search node monitor 508 can update the search node catalog 510. In this way, the search node catalog 510 can retain an up-to-date list of search nodes 506 available to execute a query.

Furthermore, as search nodes 506 are instantiated (or at other times), the search node monitor 508 can update the search node catalog 510 with information about the search node 506, such as, but not limited to its computing resources, utilization, network architecture (identification of machine where it is instantiated, location with reference to other search nodes 506, computing resources shared with other search nodes 506, such as data stores, processors, I/O, etc.), etc.

3.4. Common Storage

Returning to FIG. 2, the common storage 216 can be used to store data indexed by the indexing system 212, and can be implemented using one or more data stores 218.

In some systems, the same computing devices (e.g., indexers) operate both to ingest, index, store, and search data. The use of an indexer to both ingest and search information may be beneficial, for example, because an indexer may have ready access to information that it has ingested, and can quickly access that information for searching purposes. However, use of an indexer to both ingest and search information may not be desirable in all instances. As an illustrative example, consider an instance in which ingested data is organized into buckets, and each indexer is responsible for maintaining buckets within a data store corresponding to the indexer. Illustratively, a set of ten indexers may maintain 100 buckets, distributed evenly across ten data stores (each of which is managed by a corresponding indexer). Information may be distributed throughout the buckets according to a load-balancing mechanism used to distribute information to the indexers during data ingestion. In an idealized scenario, information responsive to a query would be spread across the 100 buckets, such that each indexer may search their corresponding ten buckets in parallel, and provide search results to a search head. However, it is expected that this idealized scenario may not always occur, and that there will be at least some instances in which information responsive to a query is unevenly distributed across data stores. As one example, consider a query in which responsive information exists within ten buckets, all of which are included in a single data store associated with a single indexer. In such an instance, a bottleneck may be created at the single indexer, and the effects of parallelized searching across the indexers may be minimized. To increase the speed of operation of search queries in such cases, it may therefore be desirable to store data indexed by the indexing system 212 in common storage 216 that can be accessible to any one or multiple components of the indexing system 212 or the query system 214.

Common storage 216 may correspond to any data storage system accessible to the indexing system 212 and the query system 214. For example, common storage 216 may correspond to a storage area network (SAN), network attached storage (NAS), other network-accessible storage system (e.g., a hosted storage system, such as Amazon S3 or EBS provided by Amazon, Inc., Google Cloud Storage, Microsoft Azure Storage, etc., which may also be referred to as "cloud" storage), or combination thereof. The common storage 216 may include, for example, hard disk drives (HDDs), solid state storage devices (SSDs), or other substantially persistent or non-transitory media. Data stores 218 within common storage 216 may correspond to physical data storage devices (e.g., an individual HDD) or a logical storage device, such as a grouping of physical data storage devices or a containerized or virtualized storage device hosted by an underlying physical storage device. In some embodiments, the common storage 216 may also be referred to as a shared storage system or shared storage environment as the data stores 218 may store data associated with multiple customers, tenants, etc., or across different data intake and query systems 108 or other systems unrelated to the data intake and query systems 108.

The common storage 216 can be configured to provide high availability, highly resilient, low loss data storage. In some cases, to provide the high availability, highly resilient, low loss data storage, the common storage 216 can store multiple copies of the data in the same and different geographic locations and across different types of data stores (e.g., solid state, hard drive, tape, etc.). Further, as data is received at the common storage 216 it can be automatically replicated multiple times according to a replication factor to different data stores across the same and/or different geographic locations.

In one embodiment, common storage 216 may be multi-tiered, with each tier providing more rapid access to information stored in that tier. For example, a first tier of the common storage 216 may be physically co-located with the indexing system 212 or the query system 214 and provide rapid access to information of the first tier, while a second tier may be located in a different physical location (e.g., in a hosted or "cloud" computing environment) and provide less rapid access to information of the second tier.

Distribution of data between tiers may be controlled by any number of algorithms or mechanisms. In one embodiment, a first tier may include data generated or including timestamps within a threshold period of time (e.g., the past seven days), while a second tier or subsequent tiers includes data older than that time period. In another embodiment, a first tier may include a threshold amount (e.g., n terabytes) or recently accessed data, while a second tier stores the remaining less recently accessed data.

In one embodiment, data within the data stores 218 is grouped into buckets, each of which is commonly accessible to the indexing system 212 and query system 214. The size of each bucket may be selected according to the computational resources of the common storage 216 or the data intake and query system 108 overall. For example, the size of each bucket may be selected to enable an individual bucket to be relatively quickly transmitted via a network, without introducing excessive additional data storage requirements due to metadata or other overhead associated with an individual bucket. In one embodiment, each bucket is 750 megabytes in size. Further, as mentioned, in some embodiments, some buckets can be merged to create larger buckets.

As described herein, each bucket can include one or more files, such as, but not limited to, one or more compressed or uncompressed raw machine data files, metadata files, filter files, indexes files, bucket summary or manifest files, etc. In addition, each bucket can store events including raw machine data associated with a timestamp.

As described herein, the indexing nodes 404 can generate buckets during indexing and communicate with common storage 216 to store the buckets. For example, data may be provided to the indexing nodes 404 from one or more ingestion buffers of the intake system 210 The indexing nodes 404 can process the information and store it as buckets in common storage 216, rather than in a data store maintained by an individual indexer or indexing node. Thus, the common storage 216 can render information of the data intake and query system 108 commonly accessible to elements of the system 108. As described herein, the common storage 216 can enable parallelized searching of buckets to occur independently of the operation of indexing system 212.

As noted above, it may be beneficial in some instances to separate data indexing and searching. Accordingly, as described herein, the search nodes 506 of the query system 214 can search for data stored within common storage 216. The search nodes 506 may therefore be communicatively attached (e.g., via a communication network) with the common storage 216, and be enabled to access buckets within the common storage 216.

Further, as described herein, because the search nodes 506 in some instances are not statically assigned to individual data stores 218 (and thus to buckets within such a data store 218), the buckets searched by an individual search node 506 may be selected dynamically, to increase the parallelization with which the buckets can be searched. For example, consider an instance where information is stored within 100 buckets, and a query is received at the data intake and query system 108 for information within ten buckets. Unlike a scenario in which buckets are statically assigned to an indexer, which could result in a bottleneck if the ten relevant buckets are associated with the same indexer, the ten buckets holding relevant information may be dynamically distributed across multiple search nodes 506. Thus, if ten search nodes 506 are available to process a query, each search node 506 may be assigned to retrieve and search within one bucket greatly increasing parallelization when compared to the low-parallelization scenarios (e.g., where a single indexer 206 is required to search all ten buckets).

Moreover, because searching occurs at the search nodes 506 rather than at the indexing system 212, indexing resources can be allocated independently to searching operations. For example, search nodes 506 may be executed by a separate processor or computing device than indexing nodes 404, enabling computing resources available to search nodes 506 to scale independently of resources available to indexing nodes 404. Additionally, the impact on data ingestion and indexing due to above-average volumes of search query requests is reduced or eliminated, and similarly, the impact of data ingestion on search query result generation time also is reduced or eliminated.

As will be appreciated in view of the above description, the use of a common storage 216 can provide many advantages within the data intake and query system 108. Specifically, use of a common storage 216 can enable the system 108 to decouple functionality of data indexing by indexing nodes 404 with functionality of searching by search nodes 506. Moreover, because buckets containing data are accessible by each search node 506, a search manager 514 can dynamically allocate search nodes 506 to buckets at the time of a search in order to increase parallelization. Thus, use of a common storage 216 can substantially improve the speed and efficiency of operation of the system 108.

3.5. Data Store Catalog

The data store catalog 220 can store information about the data stored in common storage 216, and can be implemented using one or more data stores. In some embodiments, the data store catalog 220 can be implemented as a portion of the common storage 216 and/or using similar data storage techniques (e.g., local or cloud storage, multi-tiered storage, etc.). In another implementation, the data store catalog 22—may utilize a database, e.g., a relational database engine, such as commercially-provided relational database services, e.g., Amazon's Aurora. In some implementations, the data store catalog 220 may use an API to allow access to register buckets, and to allow query system 214 to access buckets. In other implementations, data store catalog 220 may be implemented through other means, and maybe stored as part of common storage 216, or another type of common storage, as previously described. In various implementations, requests for buckets may include a tenant identifier and some form of user authentication, e.g., a user access token that can be authenticated by authentication service. In various implementations, the data store catalog 220 may store one data structure, e.g., table, per tenant, for the buckets associated with that tenant, one data structure per partition of each tenant, etc. In other implementations, a single data structure, e.g., a single table, may be used for all tenants, and unique tenant IDs may be used to identify buckets associated with the different tenants.

As described herein, the data store catalog 220 can be updated by the indexing system 212 with information about the buckets or data stored in common storage 216. For example, the data store catalog can store an identifier for a sets of data in common storage 216, a location of the sets of data in common storage 216, tenant or indexes associated with the sets of data, timing information about the sets of data, etc. In embodiments where the data in common storage 216 is stored as buckets, the data store catalog 220 can include a bucket identifier for the buckets in common storage 216, a location of or path to the buckets in common storage 216, a time range of the data in the bucket (e.g., range of time between the first-in-time event of the bucket and the last-in-time event of the bucket), a tenant identifier identifying a customer or computing device associated with the bucket, and/or an index or partition associated with the bucket, etc.

In certain embodiments, the data store catalog 220 can include an indication of a location of a copy of a bucket found in one or more search nodes 506. For example, as buckets are copied to search nodes 506, the query system 214 can update the data store catalog 220 with information about which search nodes 506 include a copy of the buckets. This information can be used by the query system 214 to assign search nodes 506 to buckets as part of a query.

In certain embodiments, the data store catalog 220 can function as an index or inverted index of the buckets stored in common storage 216. For example, the data store catalog 220 can provide location and other information about the buckets stored in common storage 216. In some embodiments, the data store catalog 220 can provide additional information about the contents of the buckets. For example, the data store catalog 220 can provide a list of sources, sourcetypes, or hosts associated with the data in the buckets.

In certain embodiments, the data store catalog 220 can include one or more keywords found within the data of the buckets. In such embodiments, the data store catalog can be similar to an inverted index, except rather than identifying specific events associated with a particular host, source, sourcetype, or keyword, it can identify buckets with data associated with the particular host, source, sourcetype, or keyword.

In some embodiments, the query system 214 (e.g., search head 504, search master 512, search manager 514, etc.) can communicate with the data store catalog 220 as part of processing and executing a query. In certain cases, the query system 214 communicates with the data store catalog 220 using an API. As a non-limiting example, the query system 214 can provide the data store catalog 220 with at least a portion of the query or one or more filter criteria associated with the query. In response, the data store catalog 220 can provide the query system 214 with an identification of buckets that store data that satisfies at least a portion of the query. In addition, the data store catalog 220 can provide the query system 214 with an indication of the location of the identified buckets in common storage 216 and/or in one or more local or shared data stores of the search nodes 506.

Accordingly, using the information from the data store catalog 220, the query system 214 can reduce (or filter) the amount of data or number of buckets to be searched. For example, using tenant or partition information in the data store catalog 220, the query system 214 can exclude buckets associated with a tenant or a partition, respectively, that is not to be searched. Similarly, using time range information, the query system 214 can exclude buckets that do not satisfy a time range from a search. In this way, the data store catalog 220 can reduce the amount of data to be searched and decrease search times.

As mentioned, in some cases, as buckets are copied from common storage 216 to search nodes 506 as part of a query, the query system 214 can update the data store catalog 220 with the location information of the copy of the bucket. The query system 214 can use this information to assign search nodes 506 to buckets. For example, if the data store catalog 220 indicates that a copy of a bucket in common storage 216 is stored in a particular search node 506, the query system 214 can assign the particular search node to the bucket. In this way, the query system 214 can reduce the likelihood that the bucket will be retrieved from common storage 216. In certain embodiments, the data store catalog 220 can store an indication that a bucket was recently downloaded to a search node 506. The query system 214 for can use this information to assign search node 506 to that bucket.

3.6. Query Acceleration Data Store

With continued reference to FIG. 2, the query acceleration data store 222 can be used to store query results or datasets for accelerated access, and can be implemented as, a distributed in-memory database system, storage subsystem, local or networked storage (e.g., cloud storage), and so on, which can maintain (e.g., store) datasets in both low-latency memory (e.g., random access memory, such as volatile or non-volatile memory) and longer-latency memory (e.g., solid state storage, disk drives, and so on). In some embodiments, to increase efficiency and response times, the accelerated data store 222 can maintain particular datasets in the low-latency memory, and other datasets in the longer-latency memory. For example, in some embodiments, the datasets can be stored in-memory (non-limiting examples: RAM or volatile memory) with disk spillover (non-limiting examples: hard disks, disk drive, non-volatile memory, etc.). In this way, the query acceleration data store 222 can be used to serve interactive or iterative searches. In some cases, datasets which are determined to be frequently accessed by a user can be stored in the lower-latency memory. Similarly, datasets of less than a threshold size can be stored in the lower-latency memory.

In certain embodiments, the search manager 514 or search nodes 506 can store query results in the query acceleration data store 222. In some embodiments, the query results can correspond to partial results from one or more search nodes 506 or to aggregated results from all the search nodes 506 involved in a query or the search manager 514. In such embodiments, the results stored in the query acceleration data store 222 can be served at a later time to the search head 504, combined with additional results obtained from a later query, transformed or further processed by the search nodes 506 or search manager 514, etc. For example, in some cases, such as where a query does not include a termination date, the search manager 514 can store initial results in the acceleration data store 222 and update the initial results as additional results are received. At any time, the initial results, or iteratively updated results can be provided to a client device 204, transformed by the search nodes 506 or search manager 514, etc.

As described herein, a user can indicate in a query that particular datasets or results are to be stored in the query acceleration data store 222. The query can then indicate operations to be performed on the particular datasets. For subsequent queries directed to the particular datasets (e.g., queries that indicate other operations for the datasets stored in the acceleration data store 222), the search nodes 506 can obtain information directly from the query acceleration data store 222.

Additionally, since the query acceleration data store 222 can be utilized to service requests from different client devices 204, the query acceleration data store 222 can implement access controls (e.g., an access control list) with respect to the stored datasets. In this way, the stored datasets can optionally be accessible only to users associated with requests for the datasets. Optionally, a user who provides a query can indicate that one or more other users are authorized to access particular requested datasets. In this way, the other users can utilize the stored datasets, thus reducing latency associated with their queries.

In some cases, data from the intake system 210 (e.g., ingested data buffer 310, etc.) can be stored in the acceleration data store 222. In such embodiments, the data from the intake system 210 can be transformed by the search nodes 506 or combined with data in the common storage 216

Furthermore, in some cases, if the query system 214 receives a query that includes a request to process data in the query acceleration data store 222, as well as data in the common storage 216, the search manager 514 or search nodes 506 can begin processing the data in the query acceleration data store 222, while also obtaining and processing the other data from the common storage 216. In this way, the query system 214 can rapidly provide initial results for the query, while the search nodes 506 obtain and search the data from the common storage 216.

It will be understood that the data intake and query system 108 can include fewer or more components as desired. For example, in some embodiments, the system 108 does not include an acceleration data store 222. Further, it will be understood that in some embodiments, the functionality described herein for one component can be performed by another component. For example, the search master 512 and search manager 514 can be combined as one component, etc.

4.0. Data Intake and Query System Functions

As described herein, the various components of the data intake and query system 108 can perform a variety of functions associated with the intake, indexing, storage, and querying of data from a variety of sources. It will be understood that any one or any combination of the functions described herein can be combined as part of a single routine or method. For example, a routine can include any one or any combination of one or more data ingestion functions, one or more indexing functions, and/or one or more searching functions.

4.1 Ingestion

Figure 6:
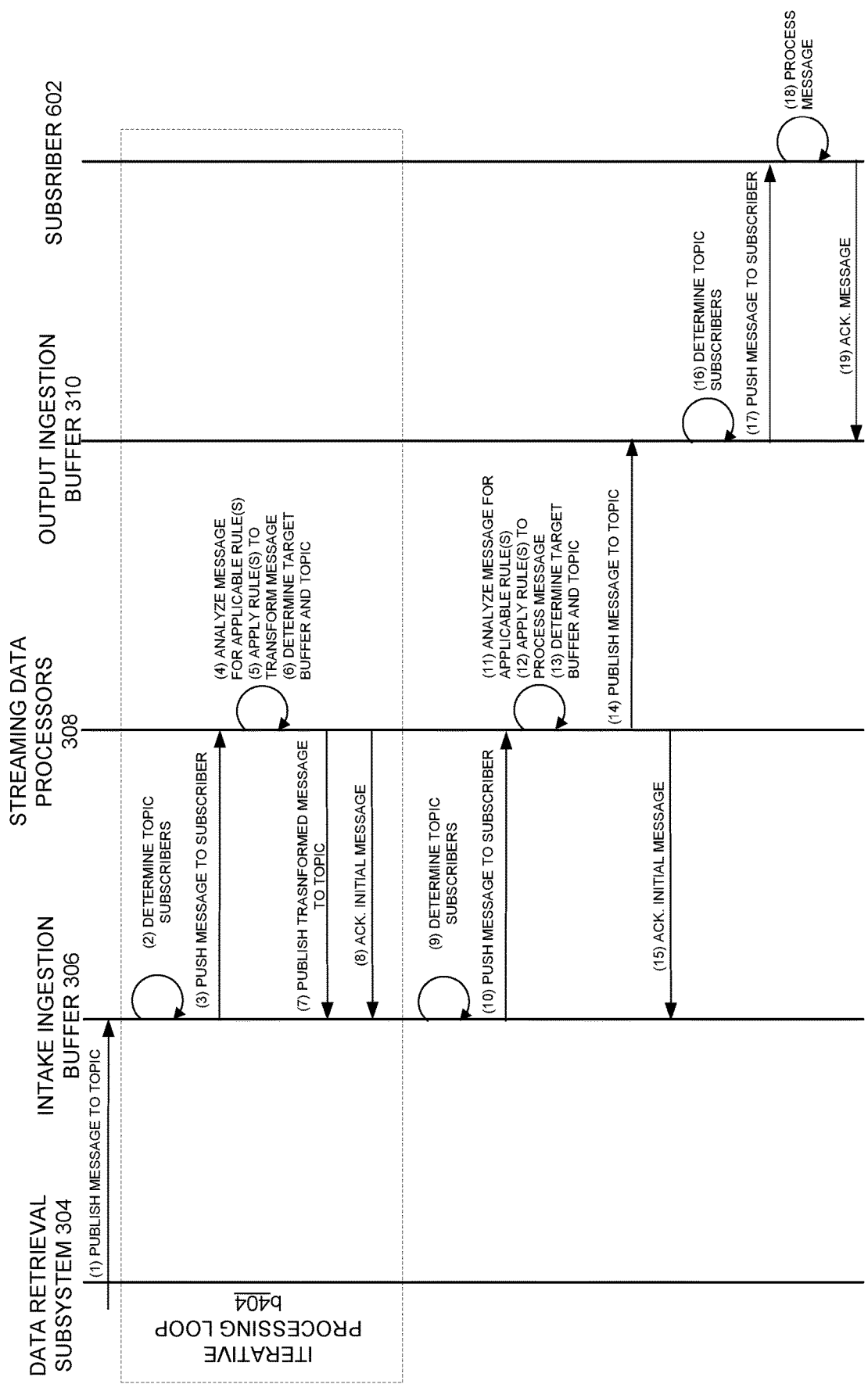
FIG. 6 is a flow diagram depicting illustrative interactions for processing data through an intake system, in accordance with example embodiments.

As discussed above, ingestion into the data intake and query system 108 can be facilitated by an intake system 210, which functions to process data according to a streaming data model, and make the data available as messages on an output ingestion buffer 310, categorized according to a number of potential topics. Messages may be published to the output ingestion buffer 310 by a streaming data processors 308, based on preliminary processing of messages published to an intake ingestion buffer 306. The intake ingestion buffer 304 is, in turn, populated with messages by one or more publishers, each of which may represent an intake point for the data intake and query system 108. The publishers may collectively implement a data retrieval subsystem 304 for the data intake and query system 108, which subsystem 304 functions to retrieve data from a data source 202 and publish the data in the form of a message on the intake ingestion buffer 304. A flow diagram depicting an illustrative embodiment for processing data at the intake system 210 is shown at FIG. 6. While the flow diagram is illustratively described with respect to a single message, the same or similar interactions may be used to process multiple messages at the intake system 210.

4.1.1 Publication to Intake Topic(s)

As shown in FIG. 6, processing of data at the intake system 210 can illustratively begin at (1), where a data retrieval subsystem 304 or a data source 202 publishes a message to a topic at the intake ingestion buffer 306. Generally described, the data retrieval subsystem 304 may include either or both push-based and pull-based publishers. Push-based publishers can illustratively correspond to publishers which independently initiate transmission of messages to the intake ingestion buffer 306. Pull-based publishes can illustratively correspond to publishers which await an inquiry by the intake ingestion buffer 306 for messages to be published to the buffer 306. The publication of a message at (1) is intended to include publication under either push- or pull-based models.

As discussed above, the data retrieval subsystem 304 may generate the message based on data received from a forwarder 302 and/or from one or more data sources 202. In some instances, generation of a message may include converting a format of the data into a format suitable for publishing on the intake ingestion buffer 306. Generation of a message may further include determining a topic for the message. In one embodiment, the data retrieval subsystem 304 selects a topic based on a data source 202 from which the data is received, or based on the specific publisher (e.g., intake point) on which the message is generated. For example, each data source 202 or specific publisher may be associated with a particular topic on the intake ingestion buffer 306 to which corresponding messages are published. In some instances, the same source data may be used to generate multiple messages to the intake ingestion buffer 306 (e.g., associated with different topics).

4.1.2 Transmission to Streaming Data Processors

After receiving a message from a publisher, the intake ingestion buffer 306, at (2), determines subscribers to the topic. For the purposes of example, it will be associated that at least one device of the streaming data processors 308 has subscribed to the topic (e.g., by previously transmitting to the intake ingestion buffer 306 a subscription request). As noted above, the streaming data processors 308 may be implemented by a number of (logically or physically) distinct devices. As such, the streaming data processors 308, at (2), may operate to determine which devices of the streaming data processors 308 have subscribed to the topic (or topics) to which the message was published.

Thereafter, at (3), the intake ingestion buffer 306 publishes the message to the streaming data processors 308 in accordance with the pub-sub model. This publication may correspond to a "push" model of communication, whereby an ingestion buffer determines topic subscribers and initiates transmission of messages within the topic to the subscribers. While interactions of FIG. 6 are described with reference to such a push model, in some embodiments a pull model of transmission may additionally or alternatively be used. Illustratively, rather than an ingestion buffer determining topic subscribers and initiating transmission of messages for the topic to a subscriber (e.g., the streaming data processors 308), an ingestion buffer may enable a subscriber to query for unread messages for a topic, and for the subscriber to initiate transmission of the messages from the ingestion buffer to the subscriber. Thus, an ingestion buffer (e.g., the intake ingestion buffer 306) may enable subscribers to "pull" messages from the buffer. As such, interactions of FIG. 6 (e.g., including interactions (2) and (3) as well as (9), (10), (16), and (17) described below) may be modified to include pull-based interactions (e.g., whereby a subscriber queries for unread messages and retrieves the messages from an appropriate ingestion buffer).

4.1.3 Messages Processing

On receiving a message, the streaming data processors 308, at (4), analyze the message to determine one or more rules applicable to the message. As noted above, rules maintained at the streaming data processors 308 can generally include selection criteria indicating messages to which the rule applies. This selection criteria may be formatted in the same manner or similarly to extraction rules, discussed in more detail below, and may include any number or combination of criteria based on the data included within a message or metadata of the message, such as regular expressions based on the data or metadata.

On determining that a rule is applicable to the message, the streaming data processors 308 can apply to the message one or more processing sub-rules indicated within the rule. Processing sub-rules may include modifying data or metadata of the message. Illustratively, processing sub-rules may edit or normalize data of the message (e.g., to convert a format of the data) or inject additional information into the message (e.g., retrieved based on the data of the message). For example, a processing sub-rule may specify that the data of the message be transformed according to a transformation algorithmically specified within the sub-rule. Thus, at (5), the streaming data processors 308 applies the sub-rule to transform the data of the message.

In addition or alternatively, processing sub-rules can specify a destination of the message after the message is processed at the streaming data processors 308. The destination may include, for example, a specific ingestion buffer (e.g., intake ingestion buffer 306, output ingestion buffer 310, etc.) to which the message should be published, as well as the topic on the ingestion buffer to which the message should be published. For example, a particular rule may state that messages including metrics within a first format (e.g., imperial units) should have their data transformed into a second format (e.g., metric units) and be republished to the intake ingestion buffer 306. At such, at (6), the streaming data processors 308 can determine a target ingestion buffer and topic for the transformed message based on the rule determined to apply to the message. Thereafter, the streaming data processors 308 publishes the message to the destination buffer and topic.

For the purposes of illustration, the interactions of FIG. 6 assume that, during an initial processing of a message, the streaming data processors 308 determines (e.g., according to a rule of the data processor) that the message should be republished to the intake ingestion buffer 306, as shown at (7). The streaming data processors 308 further acknowledges the initial message to the intake ingestion buffer 306, at (8), thus indicating to the intake ingestion buffer 306 that the streaming data processors 308 has processed the initial message or published it to an intake ingestion buffer. The intake ingestion buffer 306 may be configured to maintain a message until all subscribers have acknowledged receipt of the message. Thus, transmission of the acknowledgement at (8) may enable the intake ingestion buffer 306 to delete the initial message.

It is assumed for the purposes of these illustrative interactions that at least one device implementing the streaming data processors 308 has subscribed to the topic to which the transformed message is published. Thus, the streaming data processors 308 is expected to again receive the message (e.g., as previously transformed the streaming data processors 308), determine whether any rules apply to the message, and process the message in accordance with one or more applicable rules. In this manner, interactions (2) through (8) may occur repeatedly, as designated in FIG. 6 by the iterative processing loop 402. By use of iterative processing, the streaming data processors 308 may be configured to progressively transform or enrich messages obtained at data sources 202. Moreover, because each rule may specify only a portion of the total transformation or enrichment of a message, rules may be created without knowledge of the entire transformation. For example, a first rule may be provided by a first system to transform a message according to the knowledge of that system (e.g., transforming an error code into an error descriptor), while a second rule may process the message according to the transformation (e.g., by detecting that the error descriptor satisfies alert criteria). Thus, the streaming data processors 308 enable highly granulized processing of data without requiring an individual entity (e.g., user or system) to have knowledge of all permutations or transformations of the data.

After completion of the iterative processing loop 402, the interactions of FIG. 6 proceed to interaction (9), where the intake ingestion buffer 306 again determines subscribers of the message. The intake ingestion buffer 306, at (10), the transmits the message to the streaming data processors 308, and the streaming data processors 308 again analyze the message for applicable rules, process the message according to the rules, determine a target ingestion buffer and topic for the processed message, and acknowledge the message to the intake ingestion buffer 306, at interactions (11), (12), (13), and (15). These interactions are similar to interactions (4), (5), (6), and (8) discussed above, and therefore will not be re-described. However, in contrast to interaction (13), the streaming data processors 308 may determine that a target ingestion buffer for the message is the output ingestion buffer 310. Thus, the streaming data processors 308, at (14), publishes the message to the output ingestion buffer 310, making the data of the message available to a downstream system.

FIG. 6 illustrates one processing path for data at the streaming data processors 308. However, other processing paths may occur according to embodiments of the present disclosure. For example, in some instances, a rule applicable to an initially published message on the intake ingestion buffer 306 may cause the streaming data processors 308 to publish the message out ingestion buffer 310 on first processing the data of the message, without entering the iterative processing loop 402. Thus, interactions (2) through (8) may be omitted.

In other instances, a single message published to the intake ingestion buffer 306 may spawn multiple processing paths at the streaming data processors 308. Illustratively, the streaming data processors 308 may be configured to maintain a set of rules, and to independently apply to a message all rules applicable to the message. Each application of a rule may spawn an independent processing path, and potentially a new message for publication to a relevant ingestion buffer. In other instances, the streaming data processors 308 may maintain a ranking of rules to be applied to messages, and may be configured to process only a highest ranked rule which applies to the message. Thus, a single message on the intake ingestion buffer 306 may result in a single message or multiple messages published by the streaming data processors 308, according to the configuration of the streaming data processors 308 in applying rules.

As noted above, the rules applied by the streaming data processors 308 may vary during operation of those processors 308. For example, the rules may be updated as user queries are received (e.g., to identify messages whose data is relevant to those queries). In some instances, rules of the streaming data processors 308 may be altered during the processing of a message, and thus the interactions of FIG. 6 may be altered dynamically during operation of the streaming data processors 308.

While the rules above are described as making various illustrative alterations to messages, various other alterations are possible within the present disclosure. For example, rules in some instances be used to remove data from messages, or to alter the structure of the messages to conform to the format requirements of a downstream system or component. Removal of information may be beneficial, for example, where the messages include private, personal, or confidential information which is unneeded or should not be made available by a downstream system. In some instances, removal of information may include replacement of the information with a less confidential value. For example, a mailing address may be considered confidential information, whereas a postal code may not be. Thus, a rule may be implemented at the streaming data processors 308 to replace mailing addresses with a corresponding postal code, to ensure confidentiality. Various other alterations will be apparent in view of the present disclosure.

4.1.4 Transmission to Subscribers

As discussed above, the rules applied by the streaming data processors 308 may eventually cause a message containing data from a data source 202 to be published to a topic on an output ingestion buffer 310, which topic may be specified, for example, by the rule applied by the streaming data processors 308. The output ingestion buffer 310 may thereafter make the message available to downstream systems or components. These downstream systems or components are generally referred to herein as "subscribers." For example, the indexing system 212 may subscribe to an indexing topic 342, the query system 214 may subscribe to a search results topic 348, a client device 102 may subscribe to a custom topic 352A, etc. In accordance with the pub-sub model, the output ingestion buffer 310 may transmit each message published to a topic to each subscriber of that topic, and resiliently store the messages until acknowledged by each subscriber (or potentially until an error is logged with respect to a subscriber). As noted above, other models of communication are possible and contemplated within the present disclosure. For example, rather than subscribing to a topic on the output ingestion buffer 310 and allowing the output ingestion buffer 310 to initiate transmission of messages to the subscriber 602, the output ingestion buffer 310 may be configured to allow a subscriber 602 to query the buffer 310 for messages (e.g., unread messages, new messages since last transmission, etc.), and to initiate transmission of those messages form the buffer 310 to the subscriber 602. In some instances, such querying may remove the need for the subscriber 602 to separately "subscribe" to the topic.

Accordingly, at (16), after receiving a message to a topic, the output ingestion buffer 310 determines the subscribers to the topic (e.g., based on prior subscription requests transmitted to the output ingestion buffer 310). At (17), the output ingestion buffer 310 transmits the message to a subscriber 402. Thereafter, the subscriber may process the message at (18). Illustrative examples of such processing are described below, and may include (for example) preparation of search results for a client device 204, indexing of the data at the indexing system 212, and the like. After processing, the subscriber can acknowledge the message to the output ingestion buffer 310, thus confirming that the message has been processed at the subscriber.

4.1.5 Data Resiliency and Security

In accordance with embodiments of the present disclosure, the interactions of FIG. 6 may be ordered such that resiliency is maintained at the intake system 210. Specifically, as disclosed above, data streaming systems (which may be used to implement ingestion buffers) may implement a variety of techniques to ensure the resiliency of messages stored at such systems, absent systematic or catastrophic failures. Thus, the interactions of FIG. 6 may be ordered such that data from a data source 202 is expected or guaranteed to be included in at least one message on an ingestion system until confirmation is received that the data is no longer required.

For example, as shown in FIG. 6, interaction (8)—wherein the streaming data processors 308 acknowledges receipt of an initial message at the intake ingestion buffer 306—can illustratively occur after interaction (7)—wherein the streaming data processors 308 republishes the data to the intake ingestion buffer 306. Similarly, interaction (15)—wherein the streaming data processors 308 acknowledges receipt of an initial message at the intake ingestion buffer 306—can illustratively occur after interaction (14)—wherein the streaming data processors 308 republishes the data to the intake ingestion buffer 306. This ordering of interactions can ensure, for example, that the data being processed by the streaming data processors 308 is, during that processing, always stored at the ingestion buffer 306 in at least one message. Because an ingestion buffer 306 can be configured to maintain and potentially resend messages until acknowledgement is received from each subscriber, this ordering of interactions can ensure that, should a device of the streaming data processors 308 fail during processing, another device implementing the streaming data processors 308 can later obtain the data and continue the processing.

Similarly, as shown in FIG. 6, each subscriber 402 may be configured to acknowledge a message to the output ingestion buffer 310 after processing for the message is completed. In this manner, should a subscriber 402 fail after receiving a message but prior to completing processing of the message, the processing of the subscriber 402 can be restarted to successfully process the message. Thus, the interactions of FIG. 6 can maintain resiliency of data on the intake system 108 commensurate with the resiliency provided by an individual ingestion buffer 306.

While message acknowledgement is described herein as an illustrative mechanism to ensure data resiliency at an intake system 210, other mechanisms for ensuring data resiliency may additionally or alternatively be used.

As will be appreciated in view of the present disclosure, the configuration and operation of the intake system 210 can further provide high amounts of security to the messages of that system. Illustratively, the intake ingestion buffer 306 or output ingestion buffer 310 may maintain an authorization record indicating specific devices or systems with authorization to publish or subscribe to a specific topic on the ingestion buffer. As such, an ingestion buffer may ensure that only authorized parties are able to access sensitive data. In some instances, this security may enable multiple entities to utilize the intake system 210 to manage confidential information, with little or no risk of that information being shared between the entities. The managing of data or processing for multiple entities is in some instances referred to as "multi-tenancy."

Illustratively, a first entity may publish messages to a first topic on the intake ingestion buffer 306, and the intake ingestion buffer 306 may verify that any intake point or data source 202 publishing to that first topic be authorized by the first entity to do so. The streaming data processors 308 may maintain rules specific to the first entity, which the first entity may illustrative provide through authenticated session on an interface (e.g., GUI, API, command line interface (CLI), etc.). The rules of the first entity may specify one or more entity-specific topics on the output ingestion buffer 310 to which messages containing data of the first entity should be published by the streaming data processors 308. The output ingestion buffer 310 may maintain authorization records for such entity-specific topics, thus restricting messages of those topics to parties authorized by the first entity. In this manner, data security for the first entity can be ensured across the intake system 210. Similar operations may be performed for other entities, thus allowing multiple entities to separately and confidentially publish data to and retrieve data from the intake system.

4.1.6 Message Processing Algorithm

Figure 7:
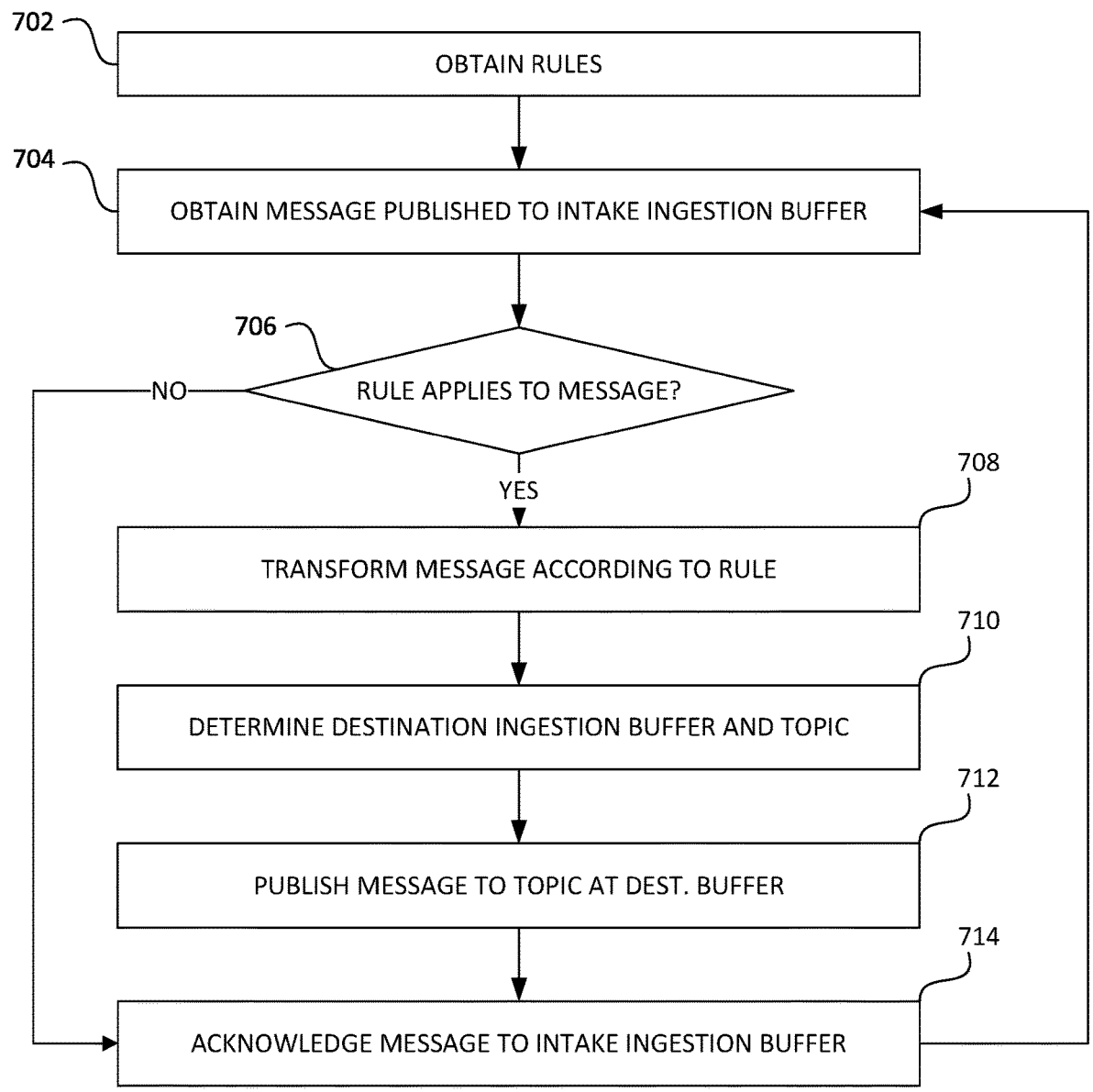
FIG. 7 is a flowchart depicting an illustrative routine for processing data at an intake system, according to example embodiments.

With reference to FIG. 7, an illustrative algorithm or routine for processing messages at the intake system 210 will be described in the form of a flowchart. The routine begins at block b102, where the intake system 210 obtains one or more rules for handling messages enqueued at an intake ingestion buffer 306. As noted above, the rules may, for example, be human-generated, or may be automatically generated based on operation of the data intake and query system 108 (e.g., in response to user submission of a query to the system 108).

At block 704, the intake system 210 obtains a message at the intake ingestion buffer 306. The message may be published to the intake ingestion buffer 306, for example, by the data retrieval subsystem 304 (e.g., working in conjunction with a forwarder 302) and reflect data obtained from a data source 202.

At block 706, the intake system 210 determines whether any obtained rule applies to the message. Illustratively, the intake system 210 (e.g., via the streaming data processors 308) may apply selection criteria of each rule to the message to determine whether the message satisfies the selection criteria. Thereafter, the routine varies according to whether a rule applies to the message. If no rule applies, the routine can continue to block 714, where the intake system 210 transmits an acknowledgement for the message to the intake ingestion buffer 306, thus enabling the buffer 306 to discard the message (e.g., once all other subscribers have acknowledged the message). In some variations of the routine, a "default rule" may be applied at the intake system 210, such that all messages are processed as least according to the default rule. The default rule may, for example, forward the message to an indexing topic 342 for processing by an indexing system 212. In such a configuration, block 706 may always evaluate as true.

In the instance that at least one rule is determined to apply to the message, the routine continues to block 708, where the intake system 210 (e.g., via the streaming data processors 308) transforms the message as specified by the applicable rule. For example, a processing sub-rule of the applicable rule may specify that data or metadata of the message be converted from one format to another via an algorithmic transformation. As such, the intake system 210 may apply the algorithmic transformation to the data or metadata of the message at block 708 to transform the data or metadata of the message. In some instances, no transformation may be specified within intake system 210, and thus block 708 may be omitted.

At block 710, the intake system 210 determines a destination ingestion buffer to which to publish the (potentially transformed) message, as well as a topic to which the message should be published. The destination ingestion buffer and topic may be specified, for example, in processing sub-rules of the rule determined to apply to the message. In one embodiment, the destination ingestion buffer and topic may vary according to the data or metadata of the message. In another embodiment, the destination ingestion buffer and topic may be fixed with respect to a particular rule.

At block 712, the intake system 210 publishes the (potentially transformed) message to the determined destination ingestion buffer and topic. The determined destination ingestion buffer may be, for example, the intake ingestion buffer 306 or the output ingestion buffer 310. Thereafter, at block 714, the intake system 210 acknowledges the initial message on the intake ingestion buffer 306, thus enabling the intake ingestion buffer 306 to delete the message.

Thereafter, the routine returns to block 704, where the intake system 210 continues to process messages from the intake ingestion buffer 306. Because the destination ingestion buffer determined during a prior implementation of the routine may be the intake ingestion buffer 306, the routine may continue to process the same underlying data within multiple messages published on that buffer 306 (thus implementing an iterative processing loop with respect to that data). The routine may then continue to be implemented during operation of the intake system 210, such that data published to the intake ingestion buffer 306 is processed by the intake system 210 and made available on an output ingestion buffer 310 to downstream systems or components.

While the routine of FIG. 7 is described linearly, various implementations may involve concurrent or at least partially parallel processing. For example, in one embodiment, the intake system 210 is configured to process a message according to all rules determined to apply to that message. Thus for example if at block 706 five rules are determined to apply to the message, the intake system 210 may implement five instances of blocks 708 through 714, each of which may transform the message in different ways or publish the message to different ingestion buffers or topics. These five instances may be implemented in serial, parallel, or a combination thereof. Thus, the linear description of FIG. 7 is intended simply for illustrative purposes.

While the routine of FIG. 7 is described with respect to a single message, in some embodiments streaming data processors 308 may be configured to process multiple messages concurrently or as a batch. Similarly, all or a portion of the rules used by the streaming data processors 308 may apply to sets or batches of messages. Illustratively, the streaming data processors 308 may obtain a batch of messages from the intake ingestion buffer 306 and process those messages according to a set of "batch" rules, whose criteria and/or processing sub-rules apply to the messages of the batch collectively. Such rules may, for example, determine aggregate attributes of the messages within the batch, sort messages within the batch, group subsets of messages within the batch, and the like. In some instances, such rules may further alter messages based on aggregate attributes, sorting, or groupings. For example, a rule may select the third messages within a batch, and perform a specific operation on that message. As another example, a rule may determine how many messages within a batch are contained within a specific group of messages. Various other examples for batch-based rules will be apparent in view of the present disclosure. Batches of messages may be determined based on a variety of criteria. For example, the streaming data processors 308 may batch messages based on a threshold number of messages (e.g., each thousand messages), based on timing (e.g., all messages received over a ten minute window), or based on other criteria (e.g., the lack of new messages posted to a topic within a threshold period of time).

4.2. Indexing

Figure 8:
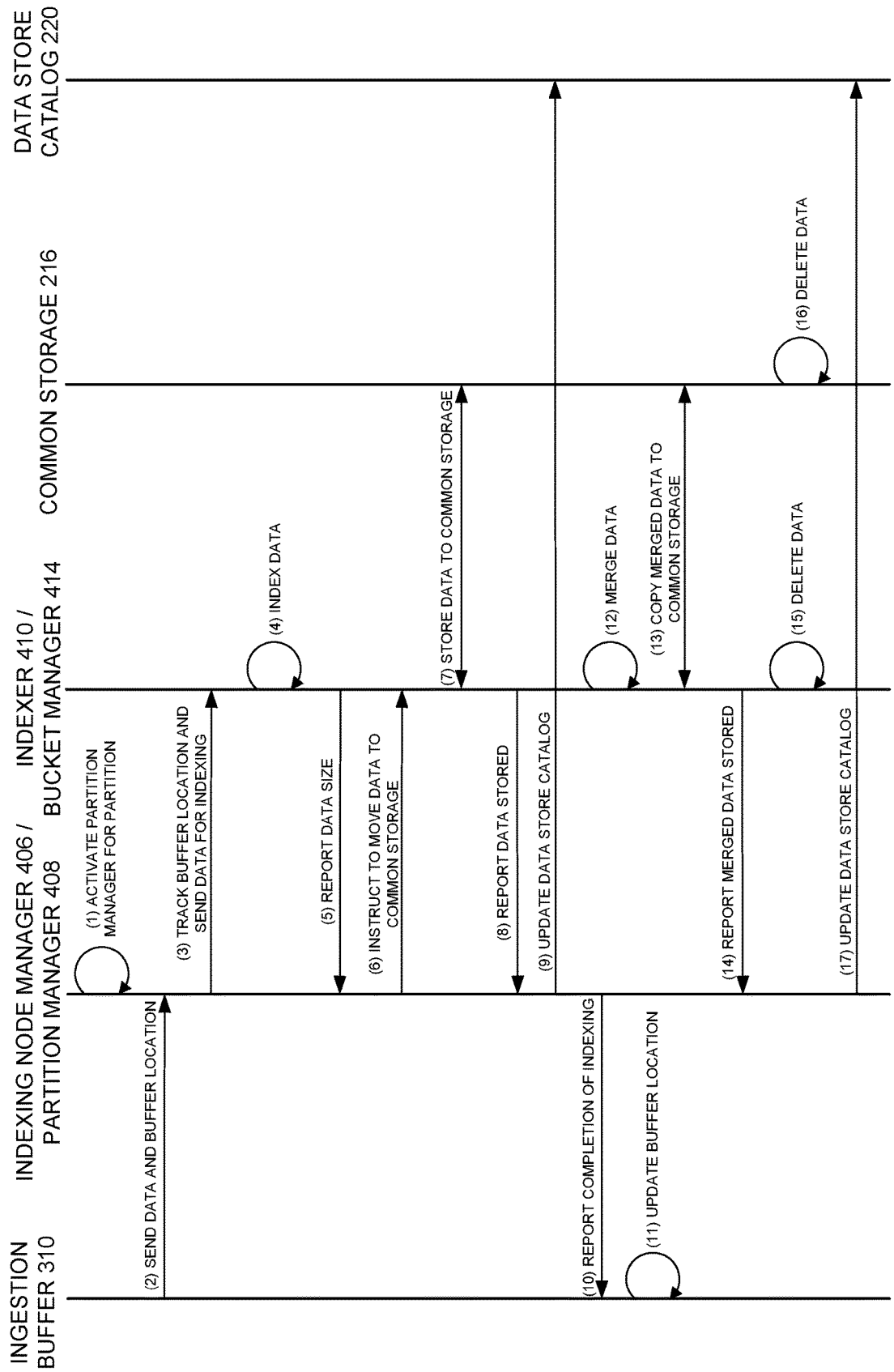
FIG. 8 is a data flow diagram illustrating an embodiment of the data flow and communications between a variety of the components of the data intake and query system during indexing.

FIG. 8 is a data flow diagram illustrating an embodiment of the data flow and communications between a variety of the components of the data intake and query system 108 during indexing. Specifically, FIG. 8 is a data flow diagram illustrating an embodiment of the data flow and communications between an ingestion buffer 310, an indexing node manager 406 or partition manager 408, an indexer 410, common storage 216, and the data store catalog 220. However, it will be understood, that in some of embodiments, one or more of the functions described herein with respect to FIG. 8 can be omitted, performed in a different order and/or performed by a different component of the data intake and query system 108. Accordingly, the illustrated embodiment and description should not be construed as limiting.

At (1), the indexing node manager 406 activates a partition manager 408 for a partition. As described herein, the indexing node manager 406 can activate a partition manager 408 for each partition or shard that is processed by an indexing node 404. In some embodiments, the indexing node manager 406 can activate the partition manager 408 based on an assignment of a new partition to the indexing node 404 or a partition manager 408 becoming unresponsive or unavailable, etc.

In some embodiments, the partition manager 408 can be a copy of the indexing node manager 406 or a copy of a template process. In certain embodiments, the partition manager 408 can be instantiated in a separate container from the indexing node manager 406.

At (2), the ingestion buffer 310 sends data and a buffer location to the indexing node 212. As described herein, the data can be raw machine data, performance metrics data, correlation data, JSON blobs, XML data, data in a datamodel, report data, tabular data, streaming data, data exposed in an API, data in a relational database, etc. The buffer location can correspond to a marker in the ingestion buffer 310 that indicates the point at which the data within a partition has been communicated to the indexing node 404. For example, data before the marker can correspond to data that has not been communicated to the indexing node 404, and data after the marker can correspond to data that has been communicated to the indexing node. In some cases, the marker can correspond to a set of data that has been communicated to the indexing node 404, but for which no indication has been received that the data has been stored. Accordingly, based on the marker, the ingestion buffer 310 can retain a portion of its data persistently until it receives confirmation that the data can be deleted or has been stored in common storage 216.

At (3), the indexing node manager 406 tracks the buffer location and the partition manager 408 communicates the data to the indexer 410. As described herein, the indexing node manager 406 can track (and/or store) the buffer location for the various partitions received from the ingestion buffer 310. In addition, as described herein, the partition manager 408 can forward the data received from the ingestion buffer 310 to the indexer 410 for processing. In various implementations, as previously described, the data from ingestion buffer 310 that is sent to the indexer 410 may include a path to stored data, e.g., data stored in common store 216 or another common store, which is then retrieved by the indexer 410 or another component of the indexing node 404.

At (4), the indexer 410 processes the data. As described herein, the indexer 410 can perform a variety of functions, enrichments, or transformations on the data as it is indexed. For example, the indexer 410 can parse the data, identify events from the data, identify and associate timestamps with the events, associate metadata or one or more field values with the events, group events (e.g., based on time, partition, and/or tenant ID, etc.), etc. Furthermore, the indexer 410 can generate buckets based on a bucket creation policy and store the events in the hot buckets, which may be stored in data store 412 of the indexing node 404 associated with that indexer 410 (see FIG. 4).

At (5), the indexer 410 reports the size of the data being indexed to the partition manager 408. In some cases, the indexer 410 can routinely provide a status update to the partition manager 408 regarding the data that is being processed by the indexer 410.

The status update can include, but is not limited to the size of the data, the number of buckets being created, the amount of time since the buckets have been created, etc. In some embodiments, the indexer 410 can provide the status update based on one or more thresholds being satisfied (e.g., one or more threshold sizes being satisfied by the amount of data being processed, one or more timing thresholds being satisfied based on the amount of time the buckets have been created, one or more bucket number thresholds based on the number of buckets created, the number of hot or warm buckets, number of buckets that have not been stored in common storage 216, etc.).

In certain cases, the indexer 410 can provide an update to the partition manager 408 regarding the size of the data that is being processed by the indexer 410 in response to one or more threshold sizes being satisfied. For example, each time a certain amount of data is added to the indexer 410 (e.g., 5 MB, 10 MB, etc.), the indexer 410 can report the updated size to the partition manager 408. In some cases, the indexer 410 can report the size of the data stored thereon to the partition manager 408 once a threshold size is satisfied.

In certain embodiments, the indexer 408 reports the size of the date being indexed to the partition manager 408 based on a query by the partition manager 408. In certain embodiments, the indexer 410 and partition manager 408 maintain an open communication link such that the partition manager 408 is persistently aware of the amount of data on the indexer 410.

In some cases, a partition manager 408 monitors the data processed by the indexer 410. For example, the partition manager 408 can track the size of the data on the indexer 410 that is associated with the partition being managed by the partition manager 408. In certain cases, one or more partition managers 408 can track the amount or size of the data on the indexer 410 that is associated with any partition being managed by the indexing node manager 406 or that is associated with the indexing node 404.

At (6), the partition manager 408 instructs the indexer 410 to copy the data to common storage 216. As described herein, the partition manager 408 can instruct the indexer 410 to copy the data to common storage 216 based on a bucket roll-over policy. As described herein, in some cases, the bucket roll-over policy can indicate that one or more buckets are to be rolled over based on size. Accordingly, in some embodiments, the partition manager 408 can instruct the indexer 410 to copy the data to common storage 216 based on a determination that the amount of data stored on the indexer 410 satisfies a threshold amount. The threshold amount can correspond to the amount of data associated with the partition that is managed by the partition manager 408 or the amount of data being processed by the indexer 410 for any partition.

In some cases, the partition manager 408 can instruct the indexer 410 to copy the data that corresponds to the partition being managed by the partition manager 408 to common storage 216 based on the size of the data that corresponds to the partition satisfying the threshold amount. In certain embodiments, the partition manager 408 can instruct the indexer 410 to copy the data associated with any partition being processed by the indexer 410 to common storage 216 based on the amount of the data from the partitions that are being processed by the indexer 410 satisfying the threshold amount.

In some embodiments, (5) and/or (6) can be omitted. For example, the indexer 410 can monitor the data stored thereon. Based on the bucket roll-over policy, the indexer 410 can determine that the data is to be copied to common storage 216. Accordingly, in some embodiments, the indexer 410 can determine that the data is to be copied to common storage 216 without communication with the partition manager 408.

At (7), the indexer 410 copies and/or stores the data to common storage 216. As described herein, in some cases, as the indexer 410 processes the data, it generates events and stores the events in hot buckets. In response to receiving the instruction to move the data to common storage 216, the indexer 410 can convert the hot buckets to warm buckets, and copy or move the warm buckets to the common storage 216.

As part of storing the data to common storage 216, the indexer 410 can verify or obtain acknowledgements that the data is stored successfully. In some embodiments, the indexer 410 can determine information regarding the data stored in the common storage 216. For example, the information can include location information regarding the data that was stored to the common storage 216, bucket identifiers of the buckets that were copied to common storage 216, as well as additional information, e.g., in implementations in which the ingestion buffer 310 uses sequences of records as the form for data storage, the list of record sequence numbers that were used as part of those buckets that were copied to common storage 216.

At (8), the indexer 410 reports or acknowledges to the partition manager 408 that the data is stored in the common storage 216. In various implementations, this can be in response to periodic requests from the partition manager 408 to the indexer 410 regarding which buckets and/or data have been stored to common storage 216. The indexer 410 can provide the partition manager 408 with information regarding the data stored in common storage 216 similar to the data that is provided to the indexer 410 by the common storage 216. In some cases, (8) can be replaced with the common storage 216 acknowledging or reporting the storage of the data to the partition manager 408.

At (9), the partition manager 408 updates the data store catalog 220. As described herein, the partition manager 408 can update the data store catalog 220 with information regarding the data or buckets stored in common storage 216. For example, the partition manager 408 can update the data store catalog 220 to include location information, a bucket identifier, a time range, and tenant and partition information regarding the buckets copied to common storage 216, etc. In this way, the data store catalog 220 can include up-to-date information regarding the buckets stored in common storage 216.

At (10), the partition manager 408 reports the completion of the storage to the ingestion buffer 310, and at (11), the ingestion buffer 310 updates the buffer location or marker. Accordingly, in some embodiments, the ingestion buffer 310 can maintain its marker until it receives an acknowledgement that the data that it sent to the indexing node 404 has been indexed by the indexing node 404 and stored to common storage 216. In addition, the updated buffer location or marker can be communicated to and stored by the indexing node manager 406. In this way, a data intake and query system 108 can use the ingestion buffer 310 to provide a stateless environment for the indexing system 212. For example, as described herein, if an indexing node 404 or one of its components (e.g., indexing node manager 486, partition manager 408, indexer) becomes unavailable or unresponsive before data from the ingestion buffer 310 is copied to common storage 216, the indexing system 212 can generate or assign a new indexing node 404 (or component), to process the data that was assigned to the now unavailable indexing node 404 (or component) while reducing, minimizing, or eliminating data loss.

At (12), a bucket manager 414, which may form part of the indexer 410, the indexing node 404, or indexing system 212, merges multiple buckets into one or more merged buckets. As described herein, to reduce delay between processing data and making that data available for searching, the indexer 410 can convert smaller hot buckets to warm buckets and copy the warm buckets to common storage 216. However, as smaller buckets in common storage 216 can result in increased overhead and storage costs, the bucket manager 414 can monitor warm buckets in the indexer 410 and merge the warm buckets into one or more merged buckets.

In some cases, the bucket manager 414 can merge the buckets according to a bucket merge policy. As described herein, the bucket merge policy can indicate which buckets are candidates for a merge (e.g., based on time ranges, size, tenant/partition or other identifiers, etc.), the number of buckets to merge, size or time range parameters for the merged buckets, a frequency for creating the merged buckets, etc.

At (13), the bucket manager 414 stores and/or copies the merged data or buckets to common storage 216, and obtains information about the merged buckets stored in common storage 216. Similar to (7), the obtained information can include information regarding the storage of the merged buckets, such as, but not limited to, the location of the buckets, one or more bucket identifiers, tenant or partition identifiers, etc. At (14), the bucket manager 414 reports the storage of the merged data to the partition manager 408, similar to the reporting of the data storage at (8).

At (15), the indexer 410 deletes data from the data store (e.g., data store 412). As described herein, once the merged buckets have been stored in common storage 216, the indexer 410 can delete corresponding buckets that it has stored locally. For example, the indexer 410 can delete the merged buckets from the data store 412, as well as the pre-merged buckets (buckets used to generate the merged buckets). By removing the data from the data store 412, the indexer 410 can free up additional space for additional hot buckets, warm buckets, and/or merged buckets.

At (16), the common storage 216 deletes data according to a bucket management policy. As described herein, once the merged buckets have been stored in common storage 216, the common storage 216 can delete the pre-merged buckets stored therein. In some cases, as described herein, the common storage 216 can delete the pre-merged buckets immediately, after a predetermined amount of time, after one or more queries relying on the pre-merged buckets have completed, or based on other criteria in the bucket management policy, etc. In certain embodiments, a controller at the common storage 216 handles the deletion of the data in common storage 216 according to the bucket management policy. In certain embodiments, one or more components of the indexing node 404 delete the data from common storage 216 according to the bucket management policy. However, for simplicity, reference is made to common storage 216 performing the deletion.

At (17), the partition manager 408 updates the data store catalog 220 with the information about the merged buckets. Similar to (9), the partition manager 408 can update the data store catalog 220 with the merged bucket information. The information can include, but is not limited to, the time range of the merged buckets, location of the merged buckets in common storage 216, a bucket identifier for the merged buckets, tenant and partition information of the merged buckets, etc. In addition, as part of updating the data store catalog 220, the partition manager 408 can remove reference to the pre-merged buckets. Accordingly, the data store catalog 220 can be revised to include information about the merged buckets and omit information about the pre-merged buckets. In this way, as the search managers 514 request information about buckets in common storage 216 from the data store catalog 220, the data store catalog 220 can provide the search managers 514 with the merged bucket information.

As mentioned previously, in some of embodiments, one or more of the functions described herein with respect to FIG. 8 can be omitted, performed in a variety of orders and/or performed by a different component of the data intake and query system 108. For example, the partition manager 408 can (9) update the data store catalog 220 before, after, or concurrently with the deletion of the data in the (15) indexer 410 or (16) common storage 216. Similarly, in certain embodiments, the indexer 410 can (12) merge buckets before, after, or concurrently with (7)-(11), etc.

4.2.1. Containerized Indexing Nodes

Figure 9:
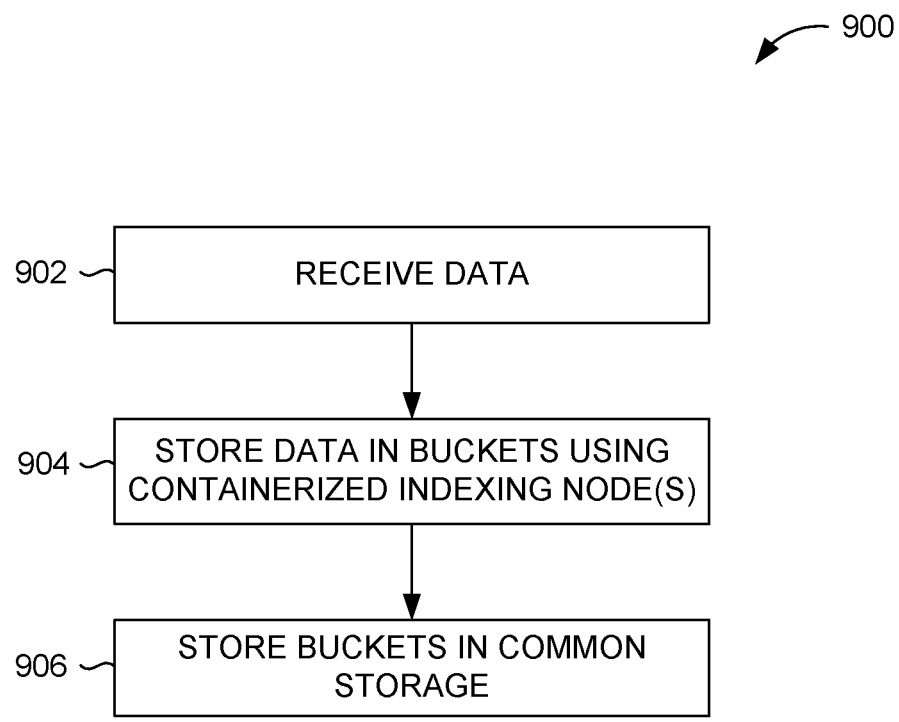
FIG. 9 is a flow diagram illustrative of an embodiment of a routine implemented by an indexing system to store data in common storage.

FIG. 9 is a flow diagram illustrative of an embodiment of a routine 900 implemented by the indexing system 212 to store data in common storage 216. Although described as being implemented by the indexing system 212, it will be understood that the elements outlined for routine 900 can be implemented by one or more computing devices/components that are associated with the data intake and query system 108, such as, but not limited to, the indexing manager 402, the indexing node 404, indexing node manager 406, the partition manager 408, the indexer 410, the bucket manager 414, etc. Thus, the following illustrative embodiment should not be construed as limiting.

At block 902, the indexing system 212 receives data. As described herein, the system 312 can receive data from a variety of sources in various formats. For example, as described herein, the data received can be machine data, performance metrics, correlated data, etc.

At block 904, the indexing system 212 stores the data in buckets using one or more containerized indexing nodes 404. As described herein, the indexing system 212 can include multiple containerized indexing nodes 404 to receive and process the data. The containerized indexing nodes 404 can enable the indexing system 212 to provide a highly extensible and dynamic indexing service. For example, based on resource availability and/or workload, the indexing system 212 can instantiate additional containerized indexing nodes 404 or terminate containerized indexing nodes 404. Further, multiple containerized indexing nodes 404 can be instantiated on the same computing device, and share the resources of the computing device.

As described herein, each indexing node 404 can be implemented using containerization or operating-system-level virtualization, or other virtualization technique. For example, the indexing node 404, or one or more components of the indexing node 404 can be implemented as separate containers or container instances. Each container instance can have certain resources (e.g., memory, processor, etc.) of the underlying computing system assigned to it, but may share the same operating system and may use the operating system's system call interface. Further, each container may run the same or different computer applications concurrently or separately, and may interact with each other. It will be understood that other virtualization techniques can be used. For example, the containerized indexing nodes 404 can be implemented using virtual machines using full virtualization or paravirtualization, etc.

In some embodiments, the indexing node 404 can be implemented as a group of related containers or a pod, and the various components of the indexing node 404 can be implemented as related containers of a pod. Further, the indexing node 404 can assign different containers to execute different tasks. For example, one container of a containerized indexing node 404 can receive the incoming data and forward it to a second container for processing, etc. The second container can generate buckets for the data, store the data in buckets, and communicate the buckets to common storage 216. A third container of the containerized indexing node 404 can merge the buckets into merged buckets and store the merged buckets in common storage. However, it will be understood that the containerized indexing node 404 can be implemented in a variety of configurations. For example, in some cases, the containerized indexing node 404 can be implemented as a single container and can include multiple processes to implement the tasks described above by the three containers. Any combination of containerization and processed can be used to implement the containerized indexing node 404 as desired.

In some embodiments, the containerized indexing node 404 processes the received data (or the data obtained using the received data) and stores it in buckets. As part of the processing, the containerized indexing node 404 can determine information about the data (e.g., host, source, sourcetype), extract or identify timestamps, associated metadata fields with the data, extract keywords, transform the data, identify and organize the data into events having raw machine data associated with a timestamp, etc. In some embodiments, the containerized indexing node 404 uses one or more configuration files and/or extraction rules to extract information from the data or events.

In addition, as part of processing and storing the data, the containerized indexing node 404 can generate buckets for the data according to a bucket creation policy. As described herein, the containerized indexing node 404 can concurrently generate and fill multiple buckets with the data that it processes. In some embodiments, the containerized indexing node 404 generates buckets for each partition or tenant associated with the data that is being processed. In certain embodiments, the indexing node 404 stores the data or events in the buckets based on the identified timestamps.

Furthermore, containerized indexing node 404 can generate one or more indexes associated with the buckets, such as, but not limited to, one or more inverted indexes, TSIDXs, keyword indexes, etc. The data and the indexes can be stored in one or more files of the buckets. In addition, the indexing node 404 can generate additional files for the buckets, such as, but not limited to, one or more filter files, a bucket summary, or manifest, etc.

At block 906, the indexing node 404 stores buckets in common storage 216. As described herein, in certain embodiments, the indexing node 404 stores the buckets in common storage 216 according to a bucket roll-over policy. In some cases, the buckets are stored in common storage 216 in one or more directories based on an index/partition or tenant associated with the buckets. Further, the buckets can be stored in a time series manner to facilitate time series searching as described herein. Additionally, as described herein, the common storage 216 can replicate the buckets across multiple tiers and data stores across one or more geographical locations.

Fewer, more, or different blocks can be used as part of the routine 900. In some cases, one or more blocks can be omitted. For example, in some embodiments, the containerized indexing node 404 or a indexing system manager 402 can monitor the amount of data received by the indexing system 212. Based on the amount of data received and/or a workload or utilization of the containerized indexing node 404, the indexing system 212 can instantiate an additional containerized indexing node 404 to process the data.

In some cases, the containerized indexing node 404 can instantiate a container or process to manage the processing and storage of data from an additional shard or partition of data received from the intake system. For example, as described herein, the containerized indexing node 404 can instantiate a partition manager 408 for each partition or shard of data that is processed by the containerized indexing node 404.

In certain embodiments, the indexing node 404 can delete locally stored buckets. For example, once the buckets are stored in common storage 216, the indexing node 404 can delete the locally stored buckets. In this way, the indexing node 404 can reduce the amount of data stored thereon.

As described herein, the indexing node 404 can merge buckets and store merged buckets in the common storage 216. In some cases, as part of merging and storing buckets in common storage 216, the indexing node 404 can delete locally storage pre-merged buckets (buckets used to generate the merged buckets) and/or the merged buckets or can instruct the common storage 216 to delete the pre-merged buckets. In this way, the indexing node 404 can reduce the amount of data stored in the indexing node 404 and/or the amount of data stored in common storage 216.

In some embodiments, the indexing node 404 can update a data store catalog 220 with information about pre-merged or merged buckets stored in common storage 216. As described herein, the information can identify the location of the buckets in common storage 216 and other information, such as, but not limited to, a partition or tenant associated with the bucket, time range of the bucket, etc. As described herein, the information stored in the data store catalog 220 can be used by the query system 214 to identify buckets to be searched as part of a query.

Furthermore, it will be understood that the various blocks described herein with reference to FIG. 9 can be implemented in a variety of orders, or can be performed concurrently. For example, the indexing node 404 can concurrently convert buckets and store them in common storage 216, or concurrently receive data from a data source and process data from the data source, etc.

4.2.2. Moving Buckets to Common Storage

Figure 10:
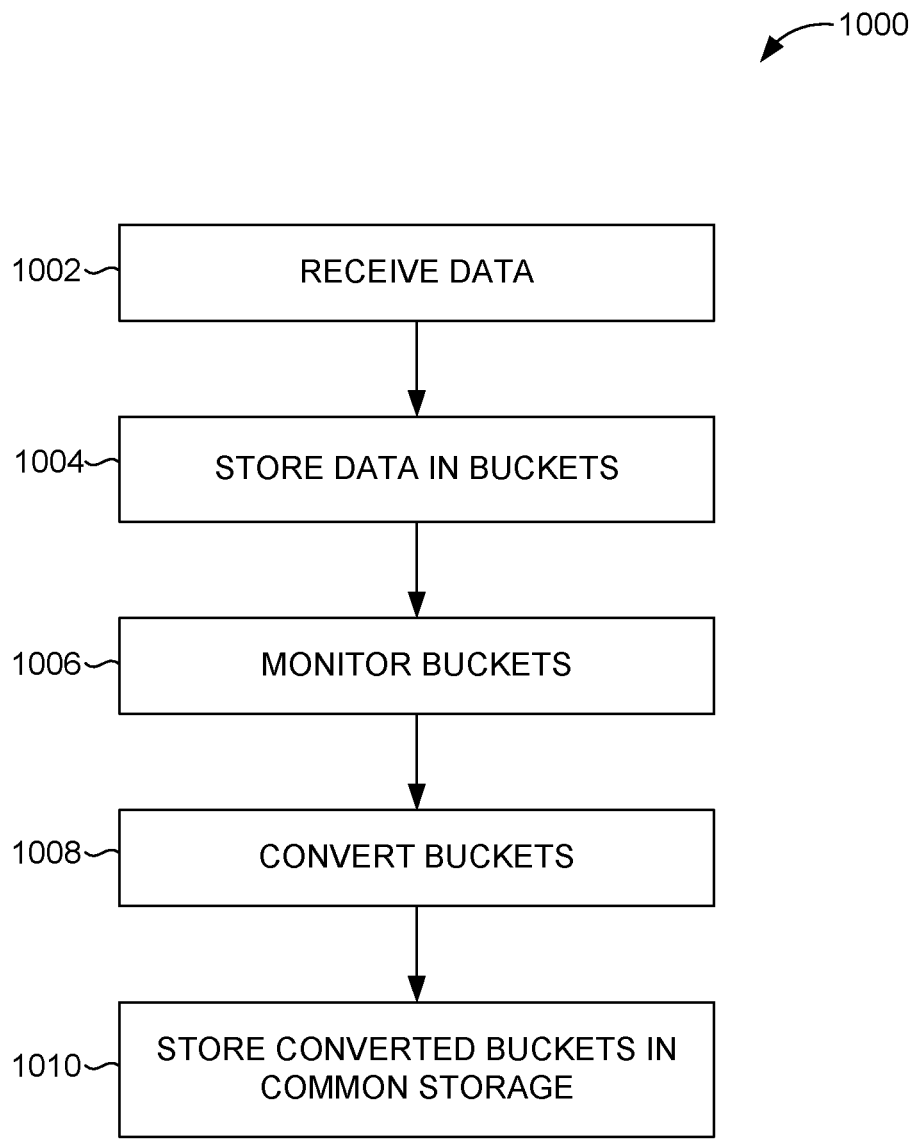
FIG. 10 is a flow diagram illustrative of an embodiment of a routine implemented by an indexing system to store data in common storage.

FIG. 10 is a flow diagram illustrative of an embodiment of a routine 1000 implemented by the indexing node 404 to store data in common storage 216. Although described as being implemented by the indexing node 404, it will be understood that the elements outlined for routine 1000 can be implemented by one or more computing devices/components that are associated with the data intake and query system 108, such as, but not limited to, the indexing manager 402, the indexing node manager 406, the partition manager 408, the indexer 410, the bucket manager 414, etc. Thus, the following illustrative embodiment should not be construed as limiting.

At block 1002, the indexing node 404 receives data. As described herein, the indexing node 404 can receive data from a variety of sources in various formats. For example, as described herein, the data received can be machine data, performance metrics, correlated data, etc.

Further, as described herein, the indexing node 404 can receive data from one or more components of the intake system 210 (e.g., the ingesting buffer 310, forwarder 302, etc.) or other data sources 202. In some embodiments, the indexing node 404 can receive data from a shard or partition of the ingestion buffer 310. Further, in certain cases, the indexing node 404 can generate a partition manager 408 for each shard or partition of a data stream. In some cases, the indexing node 404 receives data from the ingestion buffer 310 that references or points to data stored in one or more data stores, such as a data store 218 of common storage 216, or other network accessible data store or cloud storage. In such embodiments, the indexing node 404 can obtain the data from the referenced data store using the information received from the ingestion buffer 310.

At block 1004, the indexing node 404 stores data in buckets. In some embodiments, the indexing node 404 processes the received data (or the data obtained using the received data) and stores it in buckets. As part of the processing, the indexing node 404 can determine information about the data (e.g., host, source, sourcetype), extract or identify timestamps, associated metadata fields with the data, extract keywords, transform the data, identify and organize the data into events having raw machine data associated with a timestamp, etc. In some embodiments, the indexing node 404 uses one or more configuration files and/or extraction rules to extract information from the data or events.

In addition, as part of processing and storing the data, the indexing node 404 can generate buckets for the data according to a bucket creation policy. As described herein, the indexing node 404 can concurrently generate and fill multiple buckets with the data that it processes. In some embodiments, the indexing node 404 generates buckets for each partition or tenant associated with the data that is being processed. In certain embodiments, the indexing node 404 stores the data or events in the buckets based on the identified timestamps.

Furthermore, indexing node 404 can generate one or more indexes associated with the buckets, such as, but not limited to, one or more inverted indexes, TSIDXs, keyword indexes, bloom filter files, etc. The data and the indexes can be stored in one or more files of the buckets. In addition, the indexing node 404 can generate additional files for the buckets, such as, but not limited to, one or more filter files, a buckets summary, or manifest, etc.

At block 1006, the indexing node 404 monitors the buckets. As described herein, the indexing node 404 can process significant amounts of data across a multitude of buckets, and can monitor the size or amount of data stored in individual buckets, groups of buckets or all the buckets that it is generating and filling. In certain embodiments, one component of the indexing node 404 can monitor the buckets (e.g., partition manager 408), while another component fills the buckets (e.g., indexer 410).

In some embodiments, as part of monitoring the buckets, the indexing node 404 can compare the individual size of the buckets or the collective size of multiple buckets with a threshold size. Once the threshold size is satisfied, the indexing node 404 can determine that the buckets are to be stored in common storage 216. In certain embodiments, the indexing node 404 can monitor the amount of time that has passed since the buckets have been stored in common storage 216. Based on a determination that a threshold amount of time has passed, the indexing node 404 can determine that the buckets are to be stored in common storage 216. Further, it will be understood that the indexing node 404 can use a bucket roll-over policy and/or a variety of techniques to determine when to store buckets in common storage 216.

At block 1008, the indexing node 404 converts the buckets. In some cases, as part of preparing the buckets for storage in common storage 216, the indexing node 404 can convert the buckets from editable buckets to non-editable buckets. In some cases, the indexing node 404 convert hot buckets to warm buckets based on the bucket roll-over policy. The bucket roll-over policy can indicate that buckets are to be converted from hot to warm buckets based on a predetermined period of time, one or more buckets satisfying a threshold size, the number of hot buckets, etc. In some cases, based on the bucket roll-over policy, the indexing node 404 converts hot buckets to warm buckets based on a collective size of multiple hot buckets satisfying a threshold size. The multiple hot buckets can correspond to any one or any combination of randomly selected hot buckets, hot buckets associated with a particular partition or shard (or partition manager 408), hot buckets associated with a particular tenant or partition, all hot buckets in the data store 412 or being processed by the indexer 410, etc.

At block 1010, the indexing node 404 stores the converted buckets in a data store. As described herein, the indexing node 404 can store the buckets in common storage 216 or other location accessible to the query system 214. In some cases, the indexing node 404 stores a copy of the buckets in common storage 416 and retains the original bucket in its data store 412. In certain embodiments, the indexing node 404 stores a copy of the buckets in common storage and deletes any reference to the original buckets in its data store 412.

Furthermore, as described herein, in some cases, the indexing node 404 can store the one or more buckets based on the bucket roll-over policy. In addition to indicating when buckets are to be converted from hot buckets to warm buckets, the bucket roll-over policy can indicate when buckets are to be stored in common storage 216. In some cases, the bucket roll-over policy can use the same or different policies or thresholds to indicate when hot buckets are to be converted to warm and when buckets are to be stored in common storage 216.

In certain embodiments, the bucket roll-over policy can indicate that buckets are to be stored in common storage 216 based on a collective size of buckets satisfying a threshold size. As mentioned, the threshold size used to determine that the buckets are to be stored in common storage 216 can be the same as or different from the threshold size used to determine that editable buckets should be converted to non-editable buckets. Accordingly, in certain embodiments, based on a determination that the size of the one or more buckets have satisfied a threshold size, the indexing node 404 can convert the buckets to non-editable buckets and store the buckets in common storage 216.

Other thresholds and/or other factors or combinations of thresholds and factors can be used as part of the bucket roll-over policy. For example, the bucket roll-over policy can indicate that buckets are to be stored in common storage 216 based on the passage of a threshold amount of time. As yet another example, bucket roll-over policy can indicate that buckets are to be stored in common storage 216 based on the number of buckets satisfying a threshold number.

It will be understood that the bucket roll-over policy can use a variety of techniques or thresholds to indicate when to store the buckets in common storage 216. For example, in some cases, the bucket roll-over policy can use any one or any combination of a threshold time period, threshold number of buckets, user information, tenant or partition information, query frequency, amount of data being received, time of day or schedules, etc., to indicate when buckets are to be stored in common storage 216 (and/or converted to non-editable buckets). In some cases, the bucket roll-over policy can use different priorities to determine how to store the buckets, such as, but not limited to, minimizing or reducing time between processing and storage to common storage 216, maximizing or increasing individual bucket size, etc. Furthermore, the bucket roll-over policy can use dynamic thresholds to indicate when buckets are to be stored in common storage 216.

As mentioned, in some cases, based on an increased query frequency, the bucket roll-over policy can indicate that buckets are to be moved to common storage 216 more frequently by adjusting one more thresholds used to determine when the buckets are to be stored to common storage 216 (e.g., threshold size, threshold number, threshold time, etc.).

In addition, the bucket roll-over policy can indicate that different sets of buckets are to be rolled-over differently or at different rates or frequencies. For example, the bucket roll-over policy can indicate that buckets associated with a first tenant or partition are to be rolled over according to one policy and buckets associated with a second tenant or partition are to be rolled over according to a different policy. The different policies may indicate that the buckets associated with the first tenant or partition are to be stored more frequently to common storage 216 than the buckets associated with the second tenant or partition. Accordingly, the bucket roll-over policy can use one set of thresholds (e.g., threshold size, threshold number, and/or threshold time, etc.) to indicate when the buckets associated with the first tenant or partition are to be stored in common storage 216 and a different set of thresholds for the buckets associated with the second tenant or partition.

As another non-limiting example, consider a scenario in which buckets from a partition _main are being queried more frequently than bucket from the partition _test. The bucket roll-over policy can indicate that based on the increased frequency of queries for buckets from partition _main, buckets associated with partition _main should be moved more frequently to common storage 216, for example, by adjusting the threshold size used to determine when to store the buckets in common storage 216. In this way, the query system 214 can obtain relevant search results more quickly for data associated with the _main partition. Further, if the frequency of queries for buckets from the _main partition decreases, the data intake and query system 108 can adjust the threshold accordingly. In addition, the bucket roll-over policy may indicate that the changes are only for buckets associated with the partition _main or that the changes are to be made for all buckets, or all buckets associated with a particular tenant that is associated with the partition _main, etc.

Furthermore, as mentioned, the bucket roll-over policy can indicate that buckets are to be stored in common storage 216 at different rates or frequencies based on time of day. For example, the data intake and query system 108 can adjust the thresholds so that the buckets are moved to common storage 216 more frequently during working hours and less frequently during non-working hours. In this way, the delay between processing and making the data available for searching during working hours can be reduced, and can decrease the amount of merging performed on buckets generated during non-working hours. In other cases, the data intake and query system 108 can adjust the thresholds so that the buckets are moved to common storage 216 less frequently during working hours and more frequently during non-working hours.

As mentioned, the bucket roll-over policy can indicate that based on an increased rate at which data is received, buckets are to be moved to common storage more (or less) frequently. For example, if the bucket roll-over policy initially indicates that the buckets are to be stored every millisecond, as the rate of data received by the indexing node 404 increases, the amount of data received during each millisecond can increase, resulting in more data waiting to be stored. As such, in some cases, the bucket roll-over policy can indicate that the buckets are to be stored more frequently in common storage 216. Further, in some cases, such as when a collective bucket size threshold is used, an increased rate at which data is received may overburden the indexing node 404 due to the overhead associated with copying each bucket to common storage 216. As such, in certain cases, the bucket roll-over policy can use a larger collective bucket size threshold to indicate that the buckets are to be stored in common storage 216. In this way, the bucket roll-over policy can reduce the ratio of overhead to data being stored.

Similarly, the bucket roll-over policy can indicate that certain users are to be treated differently. For example, if a particular user is logged in, the bucket roll-over policy can indicate that the buckets in an indexing node 404 are to be moved to common storage 216 more or less frequently to accommodate the user's preferences, etc. Further, as mentioned, in some embodiments, the data intake and query system 108 may indicate that only those buckets associated with the user (e.g., based on tenant information, indexing information, user information, etc.) are to be stored more or less frequently.

Furthermore, the bucket roll-over policy can indicate whether, after copying buckets to common storage 216, the locally stored buckets are to be retained or discarded. In some cases, the bucket roll-over policy can indicate that the buckets are to be retained for merging. In certain cases, the bucket roll-over policy can indicate that the buckets are to be discarded.

Fewer, more, or different blocks can be used as part of the routine 1000. In some cases, one or more blocks can be omitted. For example, in certain embodiments, the indexing node 404 may not convert the buckets before storing them. As another example, the routine 1000 can include notifying the data source, such as the intake system, that the buckets have been uploaded to common storage, merging buckets and uploading merged buckets to common storage, receiving identifying information about the buckets in common storage 216 and updating a data store catalog 220 with the received information, etc.

Furthermore, it will be understood that the various blocks described herein with reference to FIG. 10 can be implemented in a variety of orders, or can be performed concurrently. For example, the indexing node 404 can concurrently convert buckets and store them in common storage 216, or concurrently receive data from a data source and process data from the data source, etc.

4.2.3. Updating Location Marker in Ingestion Buffer

Figure 11:
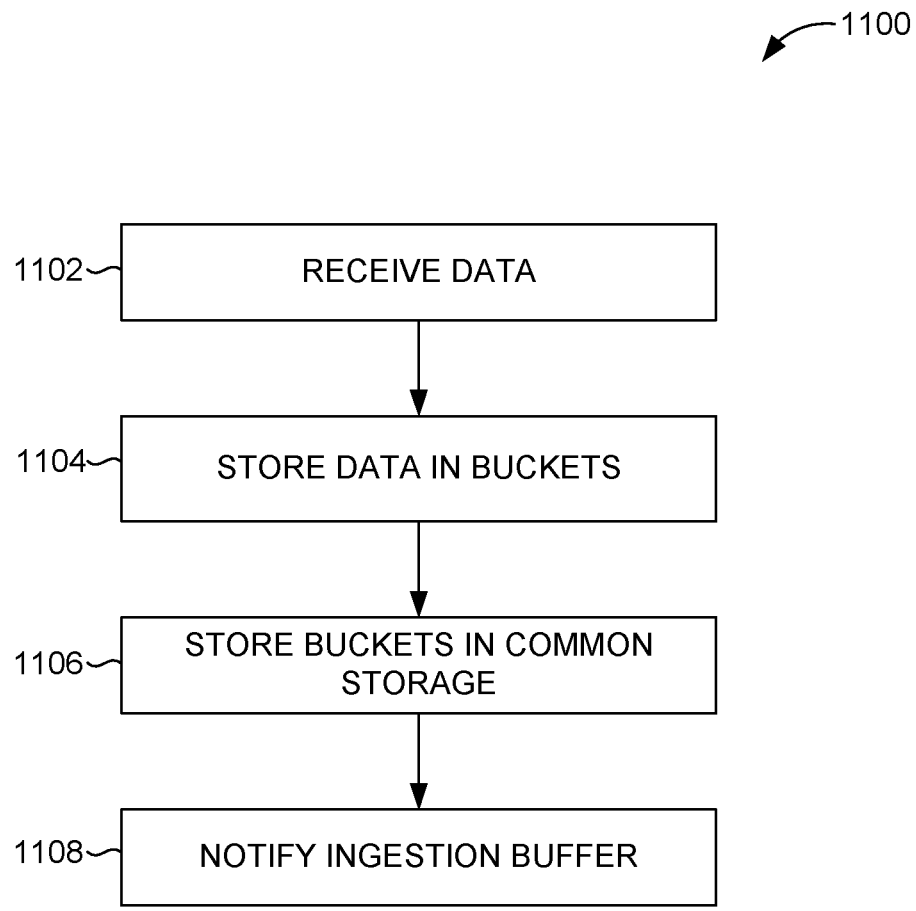
FIG. 11 is a flow diagram illustrative of an embodiment of a routine implemented by an indexing node to update a location marker in an ingestion buffer.

FIG. 11 is a flow diagram illustrative of an embodiment of a routine 1100 implemented by the indexing node 404 to update a location marker in an ingestion buffer, e.g., ingestion buffer 310. Although described as being implemented by the indexing node 404, it will be understood that the elements outlined for routine 1100 can be implemented by one or more computing devices/components that are associated with the data intake and query system 108, such as, but not limited to, the indexing manager 402, the indexing node manager 406, the partition manager 408, the indexer 410, the bucket manager 414, etc. Thus, the following illustrative embodiment should not be construed as limiting. Moreover, although the example refers to updating a location marker in ingestion buffer 310, other implementations can include other ingestion components with other types of location tracking that can be updated in a similar manner as the location marker.

At block 1102, the indexing node 404 receives data. As described in greater detail above with reference to block 1002, the indexing node 404 can receive a variety of types of data from a variety of sources.

In some embodiments, the indexing node 404 receives data from an ingestion buffer 310. As described herein, the ingestion buffer 310 can operate according to a pub-sub messaging service. As such, the ingestion buffer 310 can communicate data to the indexing node 404, and also ensure that the data is available for additional reads until it receives an acknowledgement from the indexing node 404 that the data can be removed.

In some cases, the ingestion buffer 310 can use one or more read pointers or location markers to track the data that has been communicated to the indexing node 404 but that has not been acknowledged for removal. As the ingestion buffer 310 receives acknowledgments from the indexing node 404, it can update the location markers. In some cases, such as where the ingestion buffer 310 uses multiple partitions or shards to provide the data to the indexing node 404, the ingestion buffer 310 can include at least one location marker for each partition or shard. In this way, the ingestion buffer 310 can separately track the progress of the data reads in the different shards.

In certain embodiments, the indexing node 404 can receive (and/or store) the location markers in addition to or as part of the data received from the ingestion buffer 310. Accordingly, the indexing node 404 can track the location of the data in the ingestion buffer 310 that the indexing node 404 has received from the ingestion buffer 310. In this way, if an indexer 410 or partition manager 408 becomes unavailable or fails, the indexing node 404 can assign a different indexer 410 or partition manager 408 to process or manage the data from the ingestion buffer 310 and provide the indexer 410 or partition manager 408 with a location from which the indexer 410 or partition manager 408 can obtain the data.

At block 1104, the indexing node 404 stores the data in buckets. As described in greater detail above with reference to block 1004 of FIG. 10, as part of storing the data in buckets, the indexing node 404 can parse the data, generate events, generate indexes of the data, compress the data, etc. In some cases, the indexing node 404 can store the data in hot or warm buckets and/or convert hot buckets to warm buckets based on the bucket roll-over policy.

At block 1106, the indexing node 404 stores buckets in common storage 216. As described herein, in certain embodiments, the indexing node 404 stores the buckets in common storage 216 according to the bucket roll-over policy. In some cases, the buckets are stored in common storage 216 in one or more directories based on an index/partition or tenant associated with the buckets. Further, the buckets can be stored in a time series manner to facilitate time series searching as described herein. Additionally, as described herein, the common storage 216 can replicate the buckets across multiple tiers and data stores across one or more geographical locations. In some cases, in response to the storage, the indexing node 404 receives an acknowledgement that the data was stored. Further, the indexing node 404 can receive information about the location of the data in common storage, one or more identifiers of the stored data, etc. The indexing node 404 can use this information to update the data store catalog 220.

At block 1108, the indexing node 404 notifies an ingestion buffer 310 that the data has been stored in common storage 216. As described herein, in some cases, the ingestion buffer 310 can retain location markers for the data that it sends to the indexing node 404. The ingestion buffer 310 can use the location markers to indicate that the data sent to the indexing node 404 is to be made persistently available to the indexing system 212 until the ingestion buffer 310 receives an acknowledgement from the indexing node 404 that the data has been stored successfully. In response to the acknowledgement, the ingestion buffer 310 can update the location marker(s) and communicate the updated location markers to the indexing node 404. The indexing node 404 can store updated location markers for use in the event one or more components of the indexing node 404 (e.g., partition manager 408, indexer 410) become unavailable or fail. In this way, the ingestion buffer 310 and the location markers can aid in providing a stateless indexing service.

Fewer, more, or different blocks can be used as part of the routine 1100. In some cases, one or more blocks can be omitted. For example, in certain embodiments, the indexing node 404 can update the data store catalog 220 with information about the buckets created by the indexing node 404 and/or stored in common storage 215, as described herein.

Furthermore, it will be understood that the various blocks described herein with reference to FIG. 11 can be implemented in a variety of orders. In some cases, the indexing node 404 can implement some blocks concurrently or change the order as desired. For example, the indexing node 404 can concurrently receive data, store other data in buckets, and store buckets in common storage.

4.2.4. Merging Buckets

Figure 12:
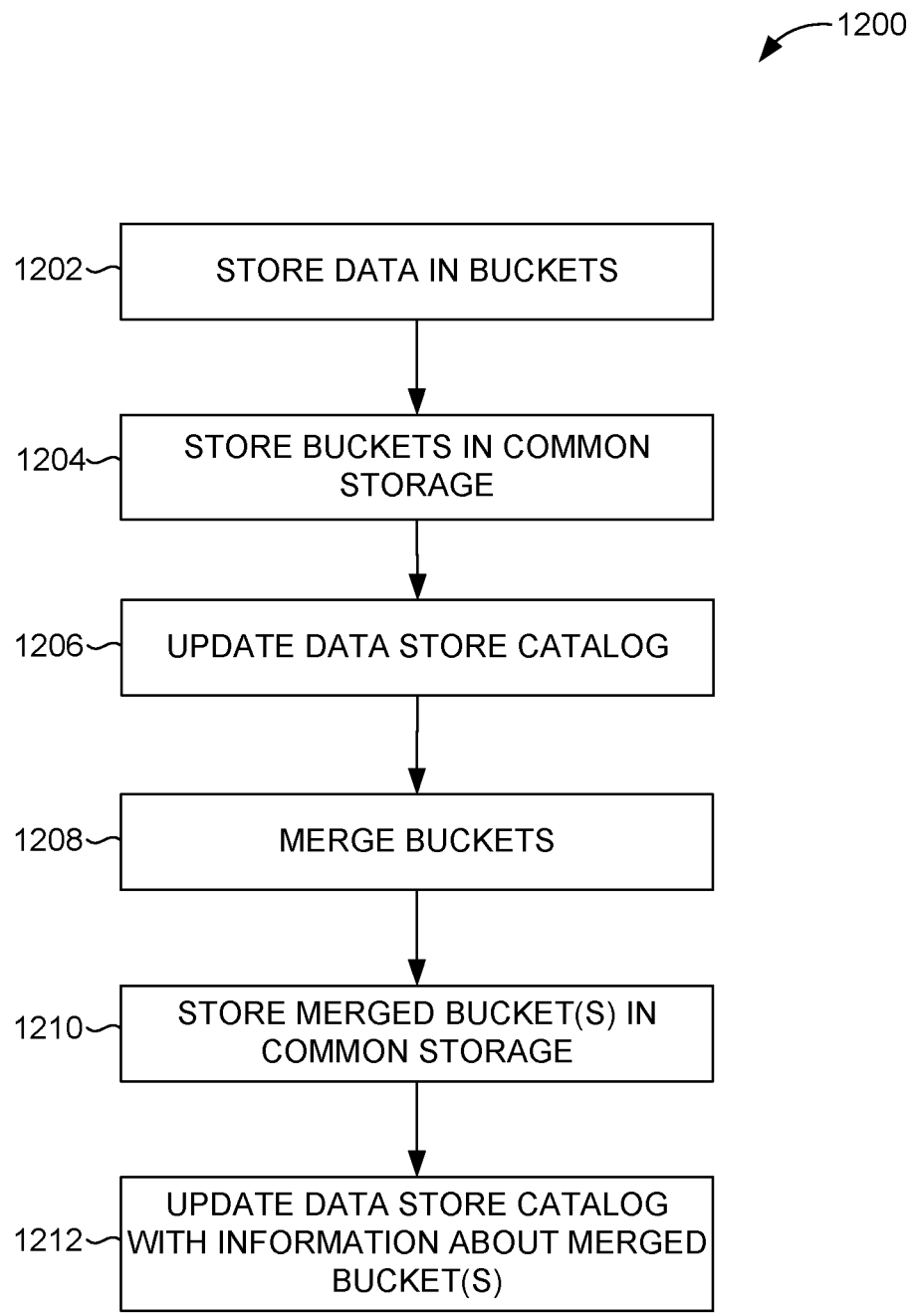
FIG. 12 is a flow diagram illustrative of an embodiment of a routine implemented by an indexing node to merge buckets.

FIG. 12 is a flow diagram illustrative of an embodiment of a routine 1200 implemented by the indexing node 404 to merge buckets. Although described as being implemented by the indexing node 404, it will be understood that the elements outlined for routine 1200 can be implemented by one or more computing devices/components that are associated with the data intake and query system 108, such as, but not limited to, the indexing manager 402, the indexing node manager 406, the partition manager 408, the indexer 410, the bucket manager 414, etc. Thus, the following illustrative embodiment should not be construed as limiting.

At block 1202, the indexing node 404 stores data in buckets. As described herein, the indexing node 404 can process various types of data from a variety of sources. Further, the indexing node 404 can create one or more buckets according to a bucket creation policy and store the data in the store the data in one or more buckets. In addition, in certain embodiments, the indexing node 404 can convert hot or editable buckets to warm or non-editable buckets according to a bucket roll-over policy.

At block 1204, the indexing node 404 stores buckets in common storage 216. As described herein, the indexing node 404 can store the buckets in common storage 216 according to the bucket roll-over policy. In some cases, the buckets are stored in common storage 216 in one or more directories based on an index/partition or tenant associated with the buckets. Further, the buckets can be stored in a time series manner to facilitate time series searching as described herein. Additionally, as described herein, the common storage 216 can replicate the buckets across multiple tiers and data stores across one or more geographical locations.

At block 1206, the indexing node 404 updates the data store catalog 220. As described herein, in some cases, in response to the storage, the indexing node 404 receives an acknowledgement that the data was stored. Further, the indexing node 404 can receive information about the location of the data in common storage, one or more identifiers of the stored data, etc. The received information can be used by the indexing node 404 to update the data store catalog 220. In addition, the indexing node 404 can provide the data store catalog 220 with any one or any combination of the tenant or partition associated with the bucket, a time range of the events in the bucket, one or more metadata fields of the bucket (e.g., host, source, sourcetype, etc.), etc. In this way, the data store catalog 220 can store up-to-date information about the buckets in common storage 216. Further, this information can be used by the query system 214 to identify relevant buckets for a query.

In some cases, the indexing node 404 can update the data store catalog 220 before, after, or concurrently with storing the data to common storage 216. For example, as buckets are created by the indexing node 404, the indexing node 404 can update the data store catalog 220 with information about the created buckets, such as, but not limited to, an partition or tenant associated with the bucket, a time range or initial time (e.g., time of earliest-in-time timestamp), etc. In addition, the indexing node 404 can include an indication that the bucket is a hot bucket or editable bucket and that the contents of the bucket are not (yet) available for searching or in the common storage 216.

As the bucket is filled with events or data, the indexing node 404 can update the data store catalog 220 with additional information about the bucket (e.g., updated time range based on additional events, size of the bucket, number of events in the bucket, certain keywords or metadata from the bucket, such as, but not limited to a host, source, or sourcetype associated with different events in the bucket, etc.). Further, once the bucket is uploaded to common storage 216, the indexing node 404 can complete the entry for the bucket, such as, by providing a completed time range, location information of the bucket in common storage 216, completed keyword or metadata information as desired, etc.

The information in the data store catalog 220 can be used by the query system 214 to execute queries. In some cases, based on the information in the data store catalog 220 about buckets that are not yet available for searching, the query system 214 can wait until the data is available for searching before completing the query or inform a user that some data that may be relevant has not been processed or that the results will be updated. Further, in some cases, the query system 214 can inform the indexing system 212 about the bucket, and the indexing system 212 can cause the indexing node 404 to store the bucket in common storage 216 sooner than it otherwise would without the communication from the query system 214.

In addition, the indexing node 404 can update the data store catalog 220 with information about buckets to be merged. For example, once one or more buckets are identified for merging, the indexing node 404 can update an entry for the buckets in the data store catalog 220 indicating that they are part of a merge operation and/or will be replaced. In some cases, as part of the identification, the data store catalog 220 can provide information about the entries to the indexing node 404 for merging. As the entries may have summary information about the buckets, the indexing node 404 can use the summary information to generate a merged entry for the data store catalog 220 as opposed to generating the summary information from the merged data itself. In this way, the information from the data store catalog 220 can increase the efficiency of a merge operation by the indexing node 404.

At block 1208, the indexing node 404 merges buckets. In some embodiments, the indexing node 404 can merge buckets according to a bucket merge policy. As described herein, the bucket merge policy can indicate which buckets to merge, when to merge buckets and one or more parameters for the merged buckets (e.g., time range for the merged buckets, size of the merged buckets, etc.). For example, the bucket merge policy can indicate that only buckets associated with the same tenant identifier and/or partition can be merged. As another example, the bucket merge policy can indicate that only buckets that satisfy a threshold age (e.g., have existed or been converted to warm buckets for more than a set period of time) are eligible for a merge. Similarly, the bucket merge policy can indicate that each merged bucket must be at least 750 MB or no greater than 1 GB, or cannot have a time range that exceeds a predetermined amount or is larger than 75% of other buckets. The other buckets can refer to one or more buckets in common storage 216 or similar buckets (e.g., buckets associated with the same tenant, partition, host, source, or sourcetype, etc.). In certain cases, the bucket merge policy can indicate that buckets are to be merged based on a schedule (e.g., during non-working hours) or user login (e.g., when a particular user is not logged in), etc. In certain embodiments, the bucket merge policy can indicate that bucket merges can be adjusted dynamically. For example, based on the rate of incoming data or queries, the bucket merge policy can indicate that buckets are to be merged more or less frequently, etc. In some cases, the bucket merge policy can indicate that due to increased processing demands by other indexing nodes 404 or other components of an indexing node 404, such as processing and storing buckets, that bucket merges are to occur less frequently so that the computing resources used to merge buckets can be redirected to other tasks. It will be understood that a variety of priorities and policies can be used as part of the bucket merge policy.

At block 1210, the indexing node 404 stores the merged buckets in common storage 216. In certain embodiments, the indexing node 404 can store the merged buckets based on the bucket merge policy. For example, based on the bucket merge policy indicating that merged buckets are to satisfy a size threshold, the indexing node 404 can store a merged bucket once it satisfies the size threshold. Similarly, the indexing node 404 can store the merged buckets after a predetermined amount of time or during non-working hours, etc., per the bucket merge policy.

In response to the storage of the merged buckets in common storage 216, the indexing node 404 can receive an acknowledgement that the merged buckets have been stored. In some cases, the acknowledgement can include information about the merged buckets, including, but not limited to, a storage location in common storage 216, identifier, etc.

At block 1212, the indexing node 404 updates the data store catalog 220. As described herein, the indexing node 404 can store information about the merged buckets in the data store catalog. 220. The information can be similar to the information stored in the data store catalog 220 for the pre-merged buckets (buckets used to create the merged buckets). For example, in some cases, the indexing node 404 can store any one or any combination of the following in the data store catalog: the tenant or partition associated with the merged buckets, a time range of the merged bucket, the location information of the merged bucket in common storage 216, metadata fields associated with the bucket (e.g., host, source, sourcetype), etc. As mentioned, the information about the merged buckets in the data store catalog 220 can be used by the query system 214 to identify relevant buckets for a search. Accordingly, in some embodiments, the data store catalog 220 can be used in a similar fashion as an inverted index, and can include similar information (e.g., time ranges, field-value pairs, keyword pairs, location information, etc.). However, instead of providing information about individual events in a bucket, the data store catalog 220 can provide information about individual buckets in common storage 216.

In some cases, the indexing node 404 can retrieve information from the data store catalog 220 about the pre-merged buckets and use that information to generate information about the merged bucket(s) for storage in the data store catalog 220. For example, the indexing node 404 can use the time ranges of the pre-merged buckets to generate a merged time range, identify metadata fields associated with the different events in the pre-merged buckets, etc. In certain embodiments, the indexing node 404 can generate the information about the merged buckets for the data store catalog 220 from the merged data itself without retrieving information about the pre-merged buckets from the data store catalog 220.

In certain embodiments, as part of updating the data store catalog 220 with information about the merged buckets, the indexing node 404 can delete the information in the data store catalog 220 about the pre-merged buckets. For example, once the merged bucket is stored in common storage 216, the merged bucket can be used for queries. As such, the information about the pre-merged buckets can be removed so that the query system 214 does not use the pre-merged buckets to execute a query.

Fewer, more, or different blocks can be used as part of the routine 1200. In some cases, one or more blocks can be omitted. For example, in certain embodiments, the indexing node 404 can delete locally stored buckets. In some cases, the indexing node 404 deletes any buckets used to form merged buckets and/or the merged buckets. In this way, the indexing node 404 can reduce the amount of data stored in the indexing node 404.

In certain embodiments, the indexing node 404 can instruct the common storage 216 to delete buckets or delete the buckets in common storage according to a bucket management policy. For example, the indexing node 404 can instruct the common storage 216 to delete any buckets used to generate the merged buckets. Based on the bucket management policy, the common storage 216 can remove the buckets. As described herein, the bucket management policy can indicate when buckets are to be removed from common storage 216. For example, the bucket management policy can indicate that buckets are to be removed from common storage 216 after a predetermined amount of time, once any queries relying on the pre-merged buckets are completed, etc.

By removing buckets from common storage 216, the indexing node 404 can reduce the size or amount of data stored in common storage 216 and improve search times. For example, in some cases, large buckets can increase search times as there are fewer buckets for the query system 214 to search. By another example, merging buckets after indexing allows optimal or near-optimal bucket sizes for search (e.g., performed by query system 214) and index (e.g., performed by indexing system 212) to be determined independently or near-independently.

Furthermore, it will be understood that the various blocks described herein with reference to FIG. 12 can be implemented in a variety of orders. In some cases, the indexing node 404 can implement some blocks concurrently or change the order as desired. For example, the indexing node 404 can concurrently merge buckets while updating an ingestion buffer 310 about the data stored in common storage 216 or updating the data store catalog 220. As another example, the indexing node 404 can delete data about the pre-merged buckets locally and instruct the common storage 216 to delete the data about the pre-merged buckets while concurrently updating the data store catalog 220 about the merged buckets. In some embodiments, the indexing node 404 deletes the pre-merged bucket data entries in the data store catalog 220 prior to instructing the common storage 216 to delete the buckets. In this way, the data indexing node 404 can reduce the risk that a query relies on information in the data store catalog 220 that does not reflect the data stored in the common storage 216.

4.3. Querying

Figure 13:
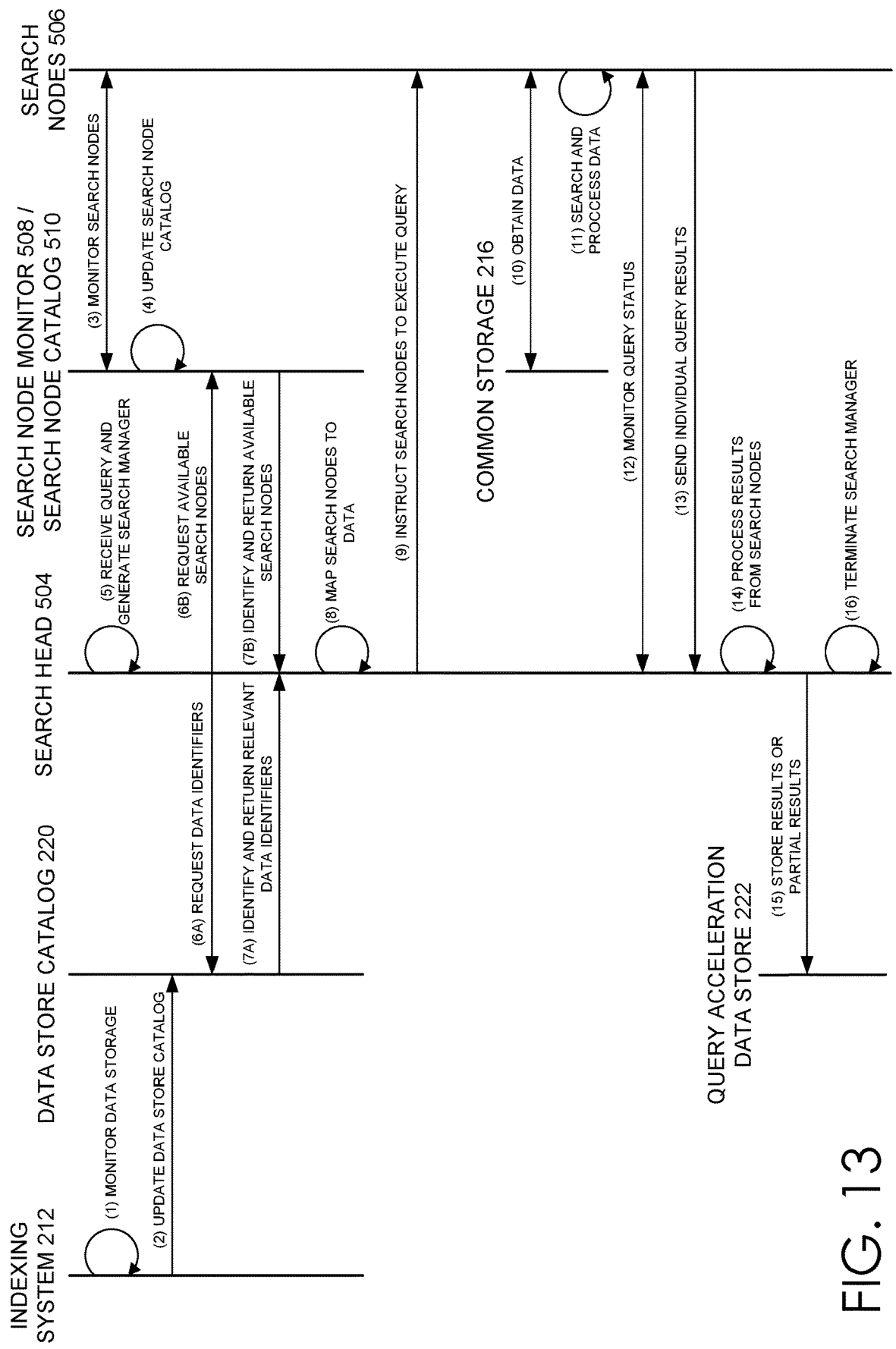
FIG. 13 is a data flow diagram illustrating an embodiment of the data flow and communications between a variety of the components of the data intake and query system during execution of a query.

FIG. 13 is a data flow diagram illustrating an embodiment of the data flow and communications between a variety of the components of the data intake and query system 108 during execution of a query. Specifically, FIG. 13 is a data flow diagram illustrating an embodiment of the data flow and communications between the indexing system 212, the data store catalog 220, a search head 504, a search node monitor 508, search node catalog 510, search nodes 506, common storage 216, and the query acceleration data store 222. However, it will be understood, that in some of embodiments, one or more of the functions described herein with respect to FIG. 13 can be omitted, performed in a different order and/or performed by a different component of the data intake and query system 108. Accordingly, the illustrated embodiment and description should not be construed as limiting.

Further, it will be understood that the various functions described herein with respect to FIG. 13 can be performed by one or more distinct components of the data intake and query system 108. For example, for simplicity, reference is made to a search head 504 performing one or more functions. However, it will be understood that these functions can be performed by one or more components of the search head 504, such as, but not limited to, the search master 512 and/or the search manager 514. Similarly, reference is made to the indexing system 212 performing one or more functions. However, it will be understood that the functions identified as being performed by the indexing system 212 can be performed by one or more components of the indexing system 212.

At (1) and (2), the indexing system 212 monitors the storage of processed data and updates the data store catalog 220 based on the monitoring. As described herein, one or more components of the indexing system 212, such as the partition manager 408 and/or the indexer 410 can monitor the storage of data or buckets to common storage 216. As the data is stored in common storage 216, the indexing system 212 can obtain information about the data stored in the common storage 216, such as, but not limited to, location information, bucket identifiers, tenant identifier (e.g., for buckets that are single tenant) etc. The indexing system 212 can use the received information about the data stored in common storage 216 to update the data store catalog 220.

Furthermore, as described herein, in some embodiments, the indexing system 212 can merge buckets into one or more merged buckets, store the merged buckets in common storage 216, and update the data store catalog to 220 with the information about the merged buckets stored in common storage 216.

At (3) and (4), the search node monitor 508 monitors the search nodes 506 and updates the search node catalog 510. As described herein, the search node monitor 508 can monitor the availability, responsiveness, and/or utilization rate of the search nodes 506. Based on the status of the search nodes 506, the search node monitor 508 can update the search node catalog 510. In this way, the search node catalog 510 can retain information regarding a current status of each of the search nodes 506 in the query system 214.

At (5), the search head 504 receives a query and generates a search manager 514. As described herein, in some cases, a search master 512 can generate the search manager 514. For example, the search master 512 can spin up or instantiate a new process, container, or virtual machine, or copy itself to generate the search manager 514, etc. As described herein, in some embodiments, the search manager 514 can perform one or more of functions described herein with reference to FIG. 13 as being performed by the search head 504 to process and execute the query.

The search head 504 (6A) requests data identifiers from the data store catalog 220 and (6B) requests an identification of available search nodes from the search node catalog 510. As described, the data store catalog 220 can include information regarding the data stored in common storage 216 and the search node catalog 510 can include information regarding the search nodes 506 of the query system 214. Accordingly, the search head 504 can query the respective catalogs to identify data or buckets that include data that satisfies at least a portion of the query and search nodes available to execute the query. In some cases, these requests can be done concurrently or in any order.

At (7A), the data store catalog 220 provides the search head 504 with an identification of data that satisfies at least a portion of the query. As described herein, in response to the request from the search head 504, the data store catalog 220 can be used to identify and return identifiers of buckets in common storage 216 and/or location information of data in common storage 216 that satisfy at least a portion of the query or at least some filter criteria (e.g., buckets associated with an identified tenant or partition or that satisfy an identified time range, etc.).

In some cases, as the data store catalog 220 can routinely receive updates by the indexing system 212, it can implement a read-write lock while it is being queried by the search head 504. Furthermore, the data store catalog 220 can store information regarding which buckets were identified for the search. In this way, the data store catalog 220 can be used by the indexing system 212 to determine which buckets in common storage 216 can be removed or deleted as part of a merge operation.

At (7B), the search node catalog 510 provides the search head 504 with an identification of available search nodes 506. As described herein, in response to the request from the search head 504, the search node catalog 510 can be used to identify and return identifiers for search nodes 506 that are available to execute the query.

At (8) the search head 504 maps the identified search nodes 506 to the data according to a search node mapping policy. In some cases, per the search node mapping policy, the search head 504 can dynamically map search nodes 506 to the identified data or buckets. As described herein, the search head 504 can map the identified search nodes 506 to the identified data or buckets at one time or iteratively as the buckets are searched according to the search node mapping policy. In certain embodiments, per the search node mapping policy, the search head 504 can map the identified search nodes 506 to the identified data based on previous assignments, data stored in a local or shared data store of one or more search heads 506, network architecture of the search nodes 506, a hashing algorithm, etc.

In some cases, as some of the data may reside in a local or shared data store between the search nodes 506, the search head 504 can attempt to map that was previously assigned to a search node 506 to the same search node 506. In certain embodiments, to map the data to the search nodes 506, the search head 504 uses the identifiers, such as bucket identifiers, received from the data store catalog 220. In some embodiments, the search head 504 performs a hash function to map a bucket identifier to a search node 506. In some cases, the search head 504 uses a consistent hash algorithm to increase the probability of mapping a bucket identifier to the same search node 506.

In certain embodiments, the search head 504 or query system 214 can maintain a table or list of bucket mappings to search nodes 506. In such embodiments, per the search node mapping policy, the search head 504 can use the mapping to identify previous assignments between search nodes and buckets. If a particular bucket identifier has not been assigned to a search node 506, the search head 504 can use a hash algorithm to assign it to a search node 506. In certain embodiments, prior to using the mapping for a particular bucket, the search head 504 can confirm that the search node 506 that was previously assigned to the particular bucket is available for the query. In some embodiments, if the search node 506 is not available for the query, the search head 504 can determine whether another search node 506 that shares a data store with the unavailable search node 506 is available for the query. If the search head 504 determines that an available search node 506 shares a data store with the unavailable search node 506, the search head 504 can assign the identified available search node 506 to the bucket identifier that was previously assigned to the now unavailable search node 506.

At (9), the search head 504 instructs the search nodes 506 to execute the query. As described herein, based on the assignment of buckets to the search nodes 506, the search head 504 can generate search instructions for each of the assigned search nodes 506. These instructions can be in various forms, including, but not limited to, JSON, DAG, etc. In some cases, the search head 504 can generate sub-queries for the search nodes 506. Each sub-query or instructions for a particular search node 506 generated for the search nodes 506 can identify the buckets that are to be searched, the filter criteria to identify a subset of the set of data to be processed, and the manner of processing the subset of data. Accordingly, the instructions can provide the search nodes 506 with the relevant information to execute their particular portion of the query.

At (10), the search nodes 506 obtain the data to be searched. As described herein, in some cases the data to be searched can be stored on one or more local or shared data stores of the search nodes 506. In certain embodiments, the data to be searched is located in the common storage 216. In such embodiments, the search nodes 506 or a cache manager 516 can obtain the data from the common storage 216.

In some cases, the cache manager 516 can identify or obtain the data requested by the search nodes 506. For example, if the requested data is stored on the local or shared data store of the search nodes 506, the cache manager 516 can identify the location of the data for the search nodes 506. If the requested data is stored in common storage 216, the cache manager 516 can obtain the data from the common storage 216.

As described herein, in some embodiments, the cache manager 516 can obtain a subset of the files associated with the bucket to be searched by the search nodes 506. For example, based on the query, the search node 506 can determine that a subset of the files of a bucket are to be used to execute the query. Accordingly, the search node 506 can request the subset of files, as opposed to all files of the bucket. The cache manager 516 can download the subset of files from common storage 216 and provide them to the search node 506 for searching.

In some embodiments, such as when a search node 506 cannot uniquely identify the file of a bucket to be searched, the cache manager 516 can download a bucket summary or manifest that identifies the files associated with the bucket. The search node 506 can use the bucket summary or manifest to uniquely identify the file to be used in the query. The common storage 216 can then obtain that uniquely identified file from common storage 216.

At (11), the search nodes 506 search and process the data. As described herein, the sub-queries or instructions received from the search head 504 can instruct the search nodes 506 to identify data within one or more buckets and perform one or more transformations on the data. Accordingly, each search node 506 can identify a subset of the set of data to be processed and process the subset of data according to the received instructions. This can include searching the contents of one or more inverted indexes of a bucket or the raw machine data or events of a bucket, etc. In some embodiments, based on the query or sub-query, a search node 506 can perform one or more transformations on the data received from each bucket or on aggregate data from the different buckets that are searched by the search node 506.

At (12), the search head 504 monitors the status of the query of the search nodes 506. As described herein, the search nodes 506 can become unresponsive or fail for a variety of reasons (e.g., network failure, error, high utilization rate, etc.). Accordingly, during execution of the query, the search head 504 can monitor the responsiveness and availability of the search nodes 506. In some cases, this can be done by pinging or querying the search nodes 506, establishing a persistent communication link with the search nodes 506, or receiving status updates from the search nodes 506. In some cases, the status can indicate the buckets that have been searched by the search nodes 506, the number or percentage of remaining buckets to be searched, the percentage of the query that has been executed by the search node 506, etc. In some cases, based on a determination that a search node 506 has become unresponsive, the search head 504 can assign a different search node 506 to complete the portion of the query assigned to the unresponsive search node 506.

In certain embodiments, depending on the status of the search nodes 506, the search manager 514 can dynamically assign or re-assign buckets to search nodes 506. For example, as search nodes 506 complete their search of buckets assigned to them, the search manager 514 can assign additional buckets for search. As yet another example, if one search node 506 is 95% complete with its search while another search node 506 is less than 50% complete, the query manager can dynamically assign additional buckets to the search node 506 that is 95% complete or re-assign buckets from the search node 506 that is less than 50% complete to the search node that is 95% complete. In this way, the search manager 514 can improve the efficiency of how a computing system performs searches through the search manager 514 increasing parallelization of searching and decreasing the search time.

At (13), the search nodes 506 send individual query results to the search head 504. As described herein, the search nodes 506 can send the query results as they are obtained from the buckets and/or send the results once they are completed by a search node 506. In some embodiments, as the search head 504 receives results from individual search nodes 506, it can track the progress of the query. For example, the search head 504 can track which buckets have been searched by the search nodes 506. Accordingly, in the event a search node 506 becomes unresponsive or fails, the search head 504 can assign a different search node 506 to complete the portion of the query assigned to the unresponsive search node 506. By tracking the buckets that have been searched by the search nodes and instructing different search node 506 to continue searching where the unresponsive search node 506 left off, the search head 504 can reduce the delay caused by a search node 506 becoming unresponsive, and can aid in providing a stateless searching service.

At (14), the search head 504 processes the results from the search nodes 506. As described herein, the search head 504 can perform one or more transformations on the data received from the search nodes 506. For example, some queries can include transformations that cannot be completed until the data is aggregated from the different search nodes 506. In some embodiments, the search head 504 can perform these transformations.

At (15), the search head 504 stores results in the query acceleration data store 222. As described herein, in some cases some, all, or a copy of the results of the query can be stored in the query acceleration data store 222. The results stored in the query acceleration data store 222 can be combined with other results already stored in the query acceleration data store 222 and/or be combined with subsequent results. For example, in some cases, the query system 214 can receive ongoing queries, or queries that do not have a predetermined end time. In such cases, as the search head 504 receives a first set of results, it can store the first set of results in the query acceleration data store 222. As subsequent results are received, the search head 504 can add them to the first set of results, and so forth. In this way, rather than executing the same or similar query data across increasingly larger time ranges, the query system 214 can execute the query across a first time range and then aggregate the results of the query with the results of the query across the second time range. In this way, the query system can reduce the amount of queries and the size of queries being executed and can provide query results in a more time efficient manner.

At (16), the search head 504 terminates the search manager 514. As described herein, in some embodiments a search head 504 or a search master 512 can generate a search manager 514 for each query assigned to the search head 504. Accordingly, in some embodiments, upon completion of a search, the search head 504 or search master 512 can terminate the search manager 514. In certain embodiments, rather than terminating the search manager 514 upon completion of a query, the search head 504 can assign the search manager 514 to a new query.

As mentioned previously, in some of embodiments, one or more of the functions described herein with respect to FIG. 13 can be omitted, performed in a variety of orders and/or performed by a different component of the data intake and query system 108. For example, the search head 504 can monitor the status of the query throughout its execution by the search nodes 506 (e.g., during (10), (11), and (13)). Similarly, (1) and (2) can be performed concurrently, (3) and (4) can be performed concurrently, and all can be performed before, after, or concurrently with (5). Similarly, steps (6A) and (6B) and steps (7A) and (7B) can be performed before, after, or concurrently with each other. Further, (6A) and (7A) can be performed before, after, or concurrently with (7A) and (7B). As yet another example, (10), (11), and (13) can be performed concurrently. For example, a search node 506 can concurrently receive one or more files for one bucket, while searching the content of one or more files of a second bucket and sending query results for a third bucket to the search head 504. Similarly, the search head 504 can (8) map search nodes 506 to buckets while concurrently (9) generating instructions for and instructing other search nodes 506 to begin execution of the query.

4.3.1. Containerized Search Nodes

Figure 14:
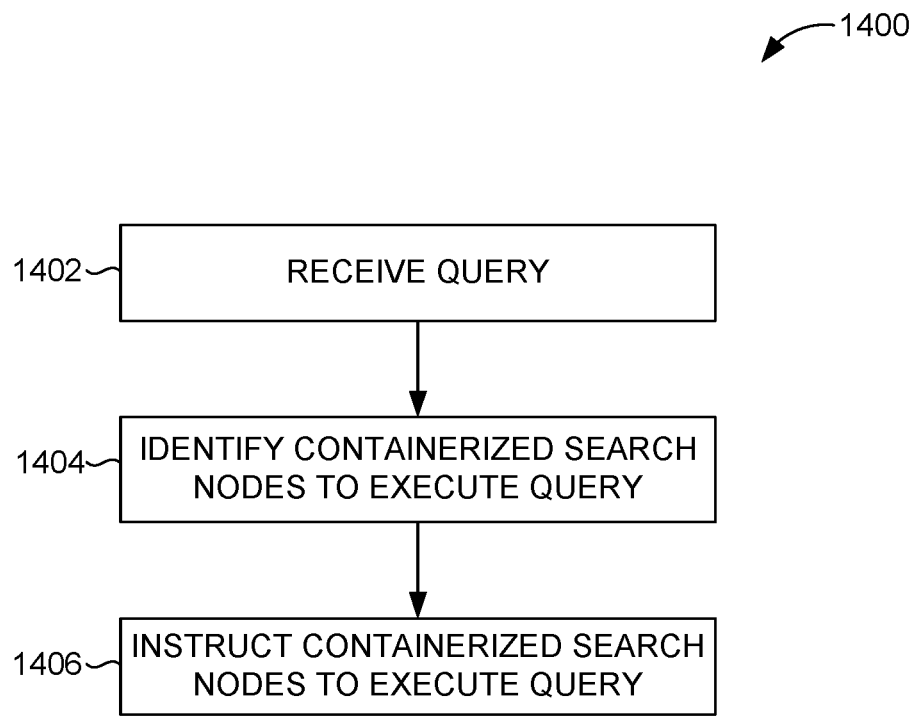
FIG. 14 is a flow diagram illustrative of an embodiment of a routine implemented by a query system to execute a query.

FIG. 14 is a flow diagram illustrative of an embodiment of a routine 1400 implemented by the query system 214 to execute a query. Although described as being implemented by the search head 504, it will be understood that the elements outlined for routine 1400 can be implemented by one or more computing devices/components that are associated with the data intake and query system 108, such as, but not limited to, the query system manager 502, the search head 504, the search master 512, the search manager 514, the search nodes 506, etc. Thus, the following illustrative embodiment should not be construed as limiting.

At block 1402, the search manager 514 receives a query. As described in greater detail above, the search manager 514 can receive the query from the search head 504, search master 512, etc. In some cases, the search manager 514 can receive the query from a client device 204. The query can be in a query language as described in greater detail above. In some cases, the query received by the search manager 514 can correspond to a query received and reviewed by the search head 504. For example, the search head 504 can determine whether the query was submitted by an authenticated user and/or review the query to determine that it is in a proper format for the data intake and query system 108, has correct semantics and syntax, etc. In some cases, the search head 504 can use a search master 512 to receive search queries, and in some cases, spawn the search manager 514 to process and execute the query.

At block 1404, the search manager 514 identifies one or more containerized search nodes, e.g., search nodes 506, to execute the query. As described herein, the query system 214 can include multiple containerized search nodes 506 to execute queries. One or more of the containerized search nodes 506 can be instantiated on the same computing device, and share the resources of the computing device. In addition, the containerized search nodes 506 can enable the query system 214 to provide a highly extensible and dynamic searching service. For example, based on resource availability and/or workload, the query system 214 can instantiate additional containerized search nodes 506 or terminate containerized search nodes 506. Furthermore, the query system 214 can dynamically assign containerized search nodes 506 to execute queries on data in common storage 216 based on a search node mapping policy.

As described herein, each search node 506 can be implemented using containerization or operating-system-level virtualization, or other virtualization technique. For example, the containerized search node 506, or one or more components of the search node 506 can be implemented as separate containers or container instances. Each container instance can have certain resources (e.g., memory, processor, etc.) of the underlying computing system assigned to it, but may share the same operating system and may use the operating system's system call interface. Further, each container may run the same or different computer applications concurrently or separately, and may interact with each other. It will be understood that other virtualization techniques can be used. For example, the containerized search nodes 506 can be implemented using virtual machines using full virtualization or paravirtualization, etc.

In some embodiments, the search node 506 can be implemented as a group of related containers or a pod, and the various components of the search node 506 can be implemented as related containers of a pod. Further, the search node 506 can assign different containers to execute different tasks. For example one container of a containerized search node 506 can receive and query instructions, a second container can obtain the data or buckets to be searched, and a third container of the containerized search node 506 can search the buckets and/or perform one or more transformations on the data. However, it will be understood that the containerized search node 506 can be implemented in a variety of configurations. For example, in some cases, the containerized search node 506 can be implemented as a single container and can include multiple processes to implement the tasks described above by the three containers. Any combination of containerization and processed can be used to implement the containerized search node 506 as desired.

In some cases, the search manager 514 can identify the search nodes 506 using the search node catalog 510. For example, as described herein a search node monitor 508 can monitor the status of the search nodes 506 instantiated in the query system 514 and monitor their status. The search node monitor can store the status of the search nodes 506 in the search node catalog 510.

In certain embodiments, the search manager 514 can identify search nodes 506 using a search node mapping policy, previous mappings, previous searches, or the contents of a data store associated with the search nodes 506. For example, based on the previous assignment of a search node 506 to search data as part of a query, the search manager 514 can assign the search node 506 to search the same data for a different query. As another example, as search nodes 506 search data, it can cache the data in a local or shared data store. Based on the data in the cache, the search manager 514 can assign the search node 506 to search the again as part of a different query.

In certain embodiments, the search manager 514 can identify search nodes 506 based on shared resources. For example, if the search manager 514 determines that a search node 506 shares a data store with a search node 506 that previously performed a search on data and cached the data in the shared data store, the search manager 514 can assign the search node 506 that share the data store to search the data stored therein as part of a different query.

In some embodiments, the search manager 514 can identify search nodes 506 using a hashing algorithm. For example, as described herein, the search manager 514 based can perform a hash on a bucket identifier of a bucket that is to be searched to identify a search node to search the bucket. In some implementations, that hash may be a consistent hash, to increase the chance that the same search node will be selected to search that bucket as was previously used, thereby reducing the chance that the bucket must be retrieved from common storage 216.

It will be understood that the search manger 514 can identify search nodes 506 based on any one or any combination of the aforementioned methods. Furthermore, it will be understood that the search manager 514 can identify search nodes 506 in a variety of ways.

At 1406, the search manager 514 instructs the search nodes 506 to execute the query. As described herein, the search manager 514 can process the query to determine portions of the query that it will execute and portions of the query to be executed by the search nodes 506. Furthermore, the search manager 514 can generate instructions or sub-queries for each search node 506 that is to execute a portion of the query. In some cases, the search manager 514 generates a DAG for execution by the search nodes 506. The instructions or sub-queries can identify the data or buckets to be searched by the search nodes 506. In addition, the instructions or sub-queries may identify one or more transformations that the search nodes 506 are to perform on the data.

Fewer, more, or different blocks can be used as part of the routine 1400. In some cases, one or more blocks can be omitted. For example, in certain embodiments, the search manager 514 can receive partial results from the search nodes 506, process the partial results, perform one or more transformation on the partial results or aggregated results, etc. Further, in some embodiments, the search manager 514 provide the results to a client device 204. In some embodiments, the search manager 514 can combine the results with results stored in the accelerated data store 222 or store the results in the accelerated data store 222 for combination with additional search results.

In some cases, the search manager 514 can identify the data or buckets to be searched by, for example, using the data store catalog 220, and map the buckets to the search nodes 506 according to a search node mapping policy. As described herein, the data store catalog 220 can receive updates from the indexing system 212 about the data that is stored in common storage 216. The information in the data store catalog 220 can include, but is not limited to, information about the location of the buckets in common storage 216, and other information that can be used by the search manager 514 to identify buckets that include data that satisfies at least a portion of the query.

In certain cases, as part of executing the query, the search nodes 506 can obtain the data to be searched from common storage 216 using the cache manager 516. The obtained data can be stored on a local or shared data store and searched as part of the query. In addition, the data can be retained on the local or shared data store based on a bucket caching policy as described herein.

Furthermore, it will be understood that the various blocks described herein with reference to FIG. 14 can be implemented in a variety of orders. In some cases, the search manager 514 can implement some blocks concurrently or change the order as desired. For example, the search manager 514 an concurrently identify search nodes 506 to execute the query and instruct the search nodes 506 to execute the query. As described herein, in some embodiments, the search manager 514 can instruct the search nodes 506 to execute the query at once. In certain embodiments, the search manager 514 can assign a first group of buckets for searching, and dynamically assign additional groups of buckets to search nodes 506 depending on which search nodes 506 complete their searching first or based on an updated status of the search nodes 506, etc.

4.3.2. Identifying Buckets and Search Nodes for Query

Figure 15:
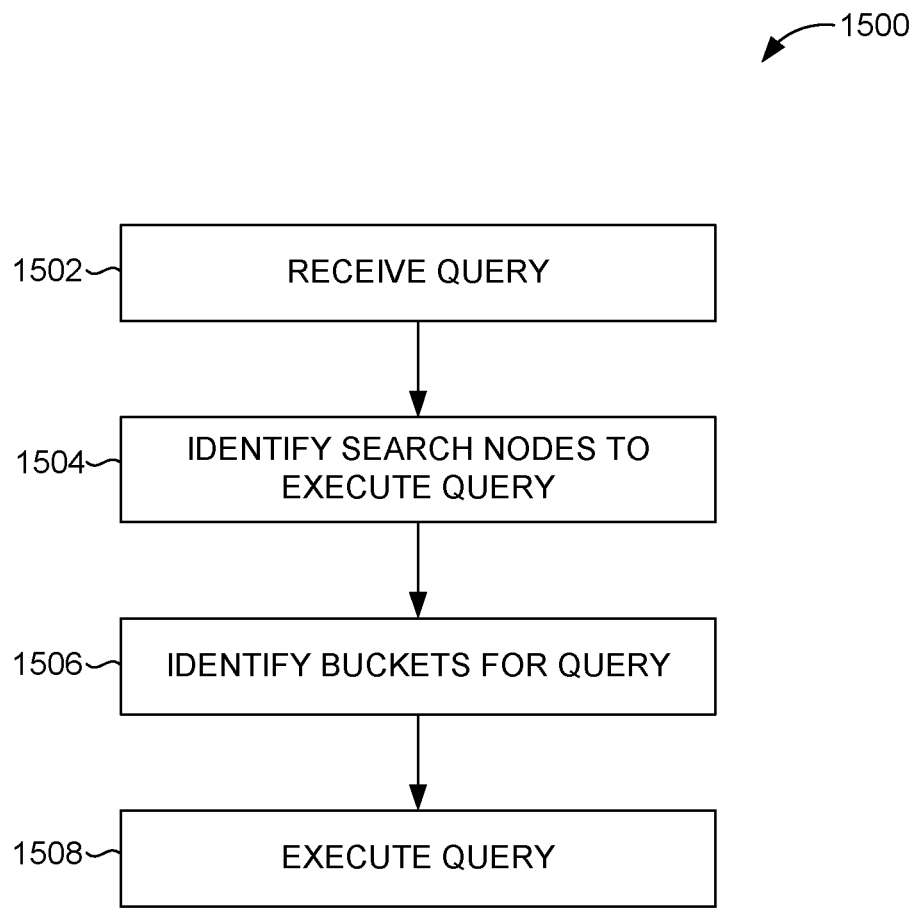
FIG. 15 is a flow diagram illustrative of an embodiment of a routine implemented by a query system to execute a query.

FIG. 15 is a flow diagram illustrative of an embodiment of a routine 1500 implemented by the query system 214 to execute a query. Although described as being implemented by the search manager 514, it will be understood that the elements outlined for routine 1500 can be implemented by one or more computing devices/components that are associated with the data intake and query system 108, such as, but not limited to, the query system manager 502, the search head 504, the search master 512, the search manager 514, the search nodes 506, etc. Thus, the following illustrative embodiment should not be construed as limiting.

At block 1502, the search manager 514 receives a query, as described in greater detail herein at least with reference to block 1402 of FIG. 14.

At block 1504, the search manager 514 identifies search nodes to execute the query, as described in greater detail herein at least with reference to block 1404 of FIG. 14. However, it will be noted, that in certain embodiments, the search nodes 506 may not be containerized.

At block 1506, the search manager 514 identifies buckets to query. As described herein, in some cases, the search manager 514 can consult the data store catalog 220 to identify buckets to be searched. In certain embodiments, the search manager 514 can use metadata of the buckets stored in common storage 216 to identify the buckets for the query. For example, the search manager 514 can compare a tenant identifier and/or partition identifier associated with the query with the tenant identifier and/or partition identifier of the buckets. The search manager 514 can exclude buckets that have a tenant identifier and/or partition identifier that does not match the tenant identifier and/or partition identifier associated with the query. Similarly, the search manager can compare a time range associate with the query with the time range associated with the buckets in common storage 216. Based on the comparison, the search manager 514 can identify buckets that satisfy the time range associated with the query (e.g., at least partly overlap with the time range from the query).

At 1508, the search manager 514 executes the query. As described herein, at least with reference to 1406 of FIG. 14, in some embodiments, as part of executing the query, the search manager 514 can process the search query, identify tasks for it to complete and tasks for the search nodes 506, generate instructions or sub-queries for the search nodes 506 and instruct the search nodes 506 to execute the query. Further, the search manager 514 can aggregate the results from the search nodes 506 and perform one or more transformations on the data.

Fewer, more, or different blocks can be used as part of the routine 1500. In some cases, one or more blocks can be omitted. For example, as described herein, the search manager 514 can map the search nodes 506 to certain data or buckets for the search according to a search node mapping policy. Based on the search node mapping policy, search manager 514 can instruct the search nodes to search the buckets to which they are mapped. Further, as described herein, in some cases, the search node mapping policy can indicate that the search manager 514 is to use a hashing algorithm, previous assignment, network architecture, cache information, etc., to map the search nodes 506 to the buckets.

As another example, the routine 1500 can include storing the search results in the accelerated data store 222. Furthermore, as described herein, the search nodes 506 can store buckets from common storage 216 to a local or shared data store for searching, etc.

In addition, it will be understood that the various blocks described herein with reference to FIG. 15 can be implemented in a variety of orders, or implemented concurrently. For example, the search manager 514 can identify search nodes to execute the query and identify bucket for the query concurrently or in any order.

4.3.3. Identifying Buckets for Query Execution

Figure 16:
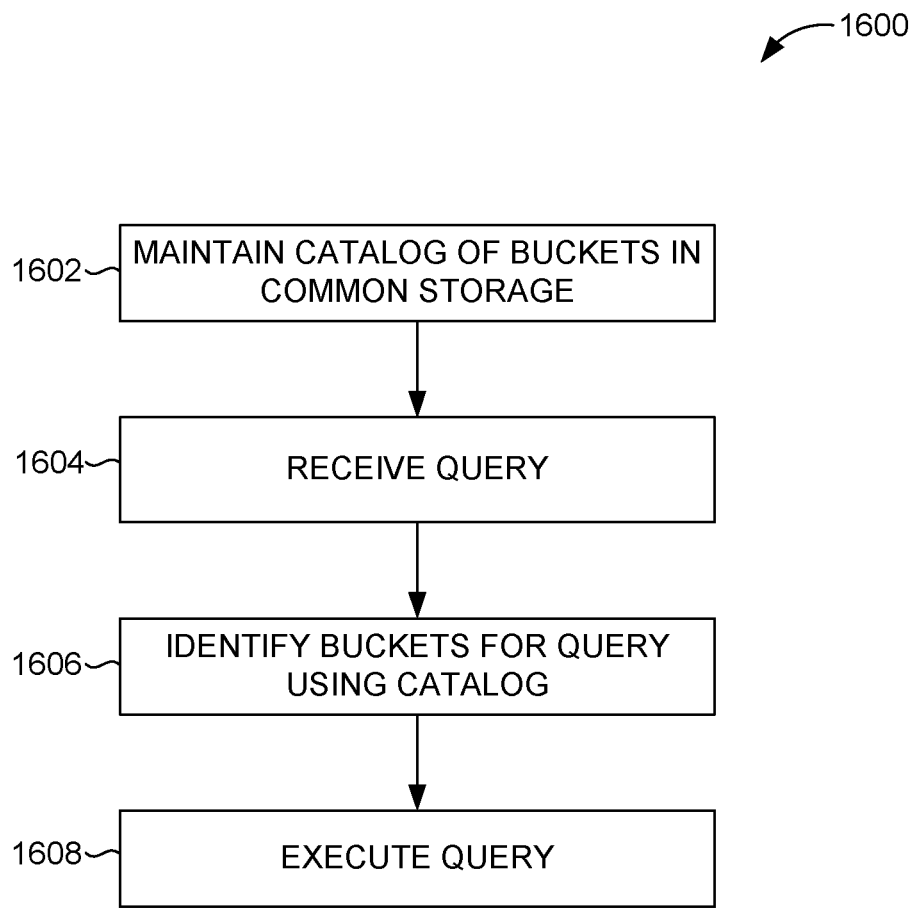
FIG. 16 is a flow diagram illustrative of an embodiment of a routine implemented by a query system to identify buckets for query execution.

FIG. 16 is a flow diagram illustrative of an embodiment of a routine 1600 implemented by the query system 214 to identify buckets for query execution. Although described as being implemented by the search manager 514, it will be understood that the elements outlined for routine 1600 can be implemented by one or more computing devices/components that are associated with the data intake and query system 108, such as, but not limited to, the query system manager 502, the search head 504, the search master 512, the search manager 514, the search nodes 506, etc. Thus, the following illustrative embodiment should not be construed as limiting.

At block 1602, the data intake and query system 108 maintains a catalog of bucket in common storage 216. As described herein, the catalog can also be referred to as the data store catalog 220, and can include information about the buckets in common storage 216, such as, but not limited to, location information, metadata fields, tenant and partition information, time range information, etc. Further, the data store catalog 220 can be kept up-to-date based on information received from the indexing system 212 as the indexing system 212 processes and stores data in the common storage 216.

At block 1604, the search manager 514 receives a query, as described in greater detail herein at least with reference to block 1402 of FIG. 14.

At block 1606, the search manager 514 identifies buckets to be searched as part of the query using the data store catalog 220. As described herein, the search manager 514 can use the data store catalog 220 to filter the universe of buckets in the common storage 216 to buckets that include data that satisfies at least a portion of the query. For example, if a query includes a time range of 4/23/18 from 03:30:50 to 04:53:32, the search manager 514 can use the time range information in the data store catalog to identify buckets with a time range that overlaps with the time range provided in the query. In addition, if the query indicates that only a _main partition is to be searched, the search manager 514 can use the information in the data store catalog to identify buckets that satisfy the time range and are associated with the _main partition. Accordingly, depending on the information in the query and the information stored in the data store catalog 220 about the buckets, the search manager 514 can reduce the number of buckets to be searched. In this way, the data store catalog 220 can reduce search time and the processing resources used to execute a query.

At block 1608, the search manager 514 executes the query, as described in greater detail herein at least with reference to block 1508 of FIG. 15.

Fewer, more, or different blocks can be used as part of the routine 1600. In some cases, one or more blocks can be omitted. For example, as described herein, the search manager 514 can identify and map search nodes 306 to the buckets for searching or store the search results in the accelerated data store 222. Furthermore, as described herein, the search nodes 506 can store buckets from common storage 216 to a local or shared data store for searching, etc. In addition, it will be understood that the various blocks described herein with reference to FIG. 15 can be implemented in a variety of orders, or implemented concurrently.

4.3.4. Identifying Search Nodes for Query Execution

Figure 17:
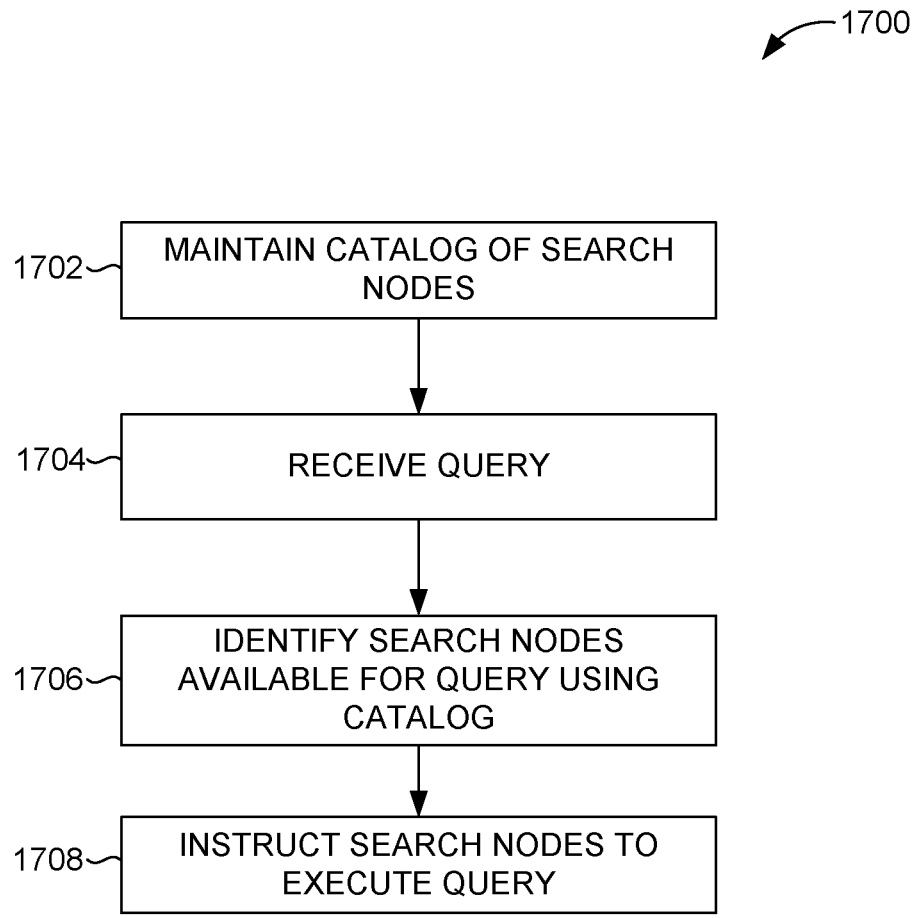
FIG. 17 is a flow diagram illustrative of an embodiment of a routine implemented by a query system to identify search nodes for query execution.

FIG. 17 is a flow diagram illustrative of an embodiment of a routine 1700 implemented by the query system 214 to identify search nodes for query execution. Although described as being implemented by the search manager 514, it will be understood that the elements outlined for routine 1700 can be implemented by one or more computing devices/components that are associated with the data intake and query system 108, such as, but not limited to, the query system manager 502, the search head 504, the search master 512, the search manager 514, the search nodes 506, etc. Thus, the following illustrative embodiment should not be construed as limiting.

At block 1702, the query system 214 maintains a catalog of instantiated search nodes 506. As described herein, the catalog can also be referred to as the search node catalog 510, and can include information about the search nodes 506, such as, but not limited to, availability, utilization, responsiveness, network architecture, etc. Further, the search node catalog 510 can be kept up-to-date based on information received by the search node monitor 508 from the search nodes 506.

At block 1704, the search manager 514 receives a query, as described in greater detail herein at least with reference to block 1402 of FIG. 14. At block 1706, the search manager 514 identifies available search nodes using the search node catalog 220.

At block 1708, the search manager 514 instructs the search nodes 506 to execute the query, as described in greater detail herein at least with reference to block 1406 of FIG. 14 and block 1508 of FIG. 15.

Fewer, more, or different blocks can be used as part of the routine 1700. In some cases, one or more blocks can be omitted. For example, in certain embodiments, the search manager can identify buckets in common storage 216 for searching. In addition, it will be understood that the various blocks described herein with reference to FIG. 17 can be implemented in a variety of orders, or implemented concurrently.

4.3.5. Hashing Bucket Identifiers for Query Execution

Figure 18:
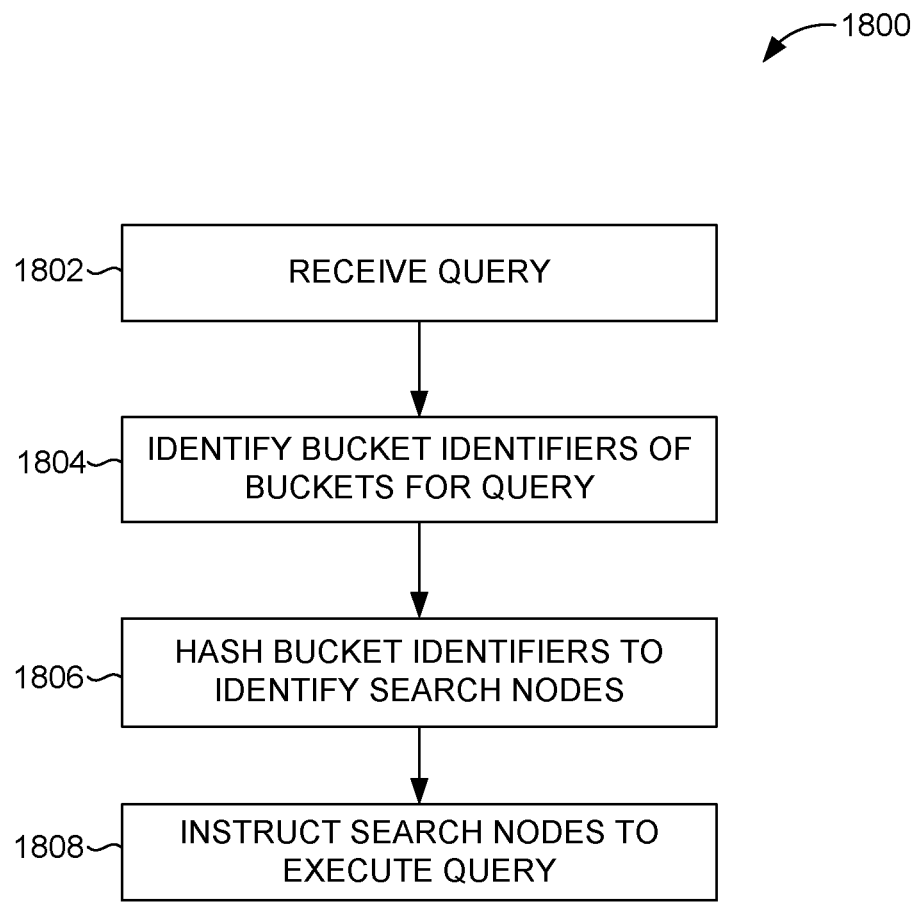
FIG. 18 is a flow diagram illustrative of an embodiment of a routine implemented by a query system to hash bucket identifiers for query execution.

FIG. 18 is a flow diagram illustrative of an embodiment of a routine 1800 implemented by the query system 214 to hash bucket identifiers for query execution. Although described as being implemented by the search manager 514, it will be understood that the elements outlined for routine 1800 can be implemented by one or more computing devices/components that are associated with the data intake and query system 108, such as, but not limited to, the query system manager 502, the search head 504, the search master 512, the search manager 514, the search nodes 506, etc. Thus, the following illustrative embodiment should not be construed as limiting.

At block 1802, the search manager 514 receives a query, as described in greater detail herein at least with reference to block 1402 of FIG. 14.

At block 1804, the search manager 514 identifies bucket identifiers associated with buckets to be searched as part of the query. The bucket identifiers can correspond to an alphanumeric identifier or other identifier that can be used to uniquely identify the bucket from other buckets stored in common storage 216. In some embodiments, the unique identifier may incorporate one or more portions of a tenant identifier, partition identifier, or time range of the bucket or a random or sequential (e.g., based on time of storage, creation, etc.) alphanumeric string, etc. As described herein, the search manager 514 can parse the query to identify buckets to be searched. In some cases, the search manager 514 can identify buckets to be searched and an associated bucket identifier based on metadata of the buckets and/or using a data store catalog 220. However, it will be understood that the search manager 514 can use a variety of techniques to identify buckets to be searched.

At block 1806, the search manager 514 performs a hash function on the bucket identifiers. The search manager can, in some embodiments, use the output of the hash function to identify a search node 506 to search the bucket. For example, as a non-limiting example, consider a scenario in which a bucket identifier is 4149 and the search manager 514 identified ten search nodes to process the query. The search manager 514 could perform a modulo ten operation on the bucket identifier to determine which search node 506 is to search the bucket. Based on this example, the search manager 514 would assign the ninth search node 506 to search the bucket, e.g., because the value 4149 modulo ten is 9, so the bucket having the identifier 4149 is assigned to the ninth search node. In some cases, the search manager can use a consistent hash to increase the likelihood that the same search node 506 is repeatedly assigned to the same bucket for searching. In this way, the search manager 514 can increase the likelihood that the bucket to be searched is already located in a local or shared data store of the search node 506, and reduce the likelihood that the bucket will be downloaded from common storage 216. It will be understood that the search manager can use a variety of techniques to map the bucket to a search node 506 according to a search node mapping policy. For example, the search manager 514 can use previous assignments, network architecture, etc., to assign buckets to search nodes 506 according to the search node mapping policy.

At block 1808, the search manager 514 instructs the search nodes 506 to execute the query, as described in greater detail herein at least with reference to block 4906 of FIG. 49 and block 1508 of FIG. 15.

Fewer, more, or different blocks can be used as part of the routine 1800. In some cases, one or more blocks can be omitted. In addition, it will be understood that the various blocks described herein with reference to FIG. 18 can be implemented in a variety of orders, or implemented concurrently.

4.3.6. Obtaining Data for Query Execution

Figure 19:
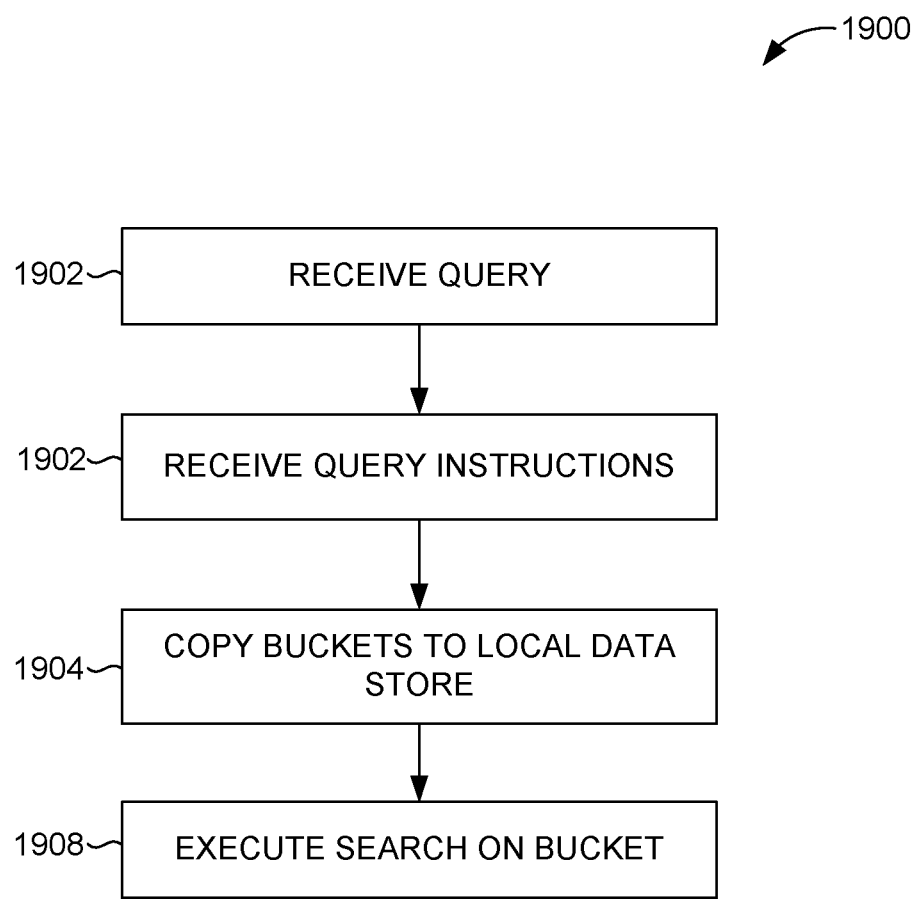
FIG. 19 is a flow diagram illustrative of an embodiment of a routine implemented by a search node to execute a search on a bucket.

FIG. 19 is a flow diagram illustrative of an embodiment of a routine 1900 implemented by a search node 506 to execute a search on a bucket. Although reference is made to downloading and searching a bucket, it will be understood that this can refer to downloading and searching one or more files associated within a bucket and does not necessarily refer to downloading all files associated with the bucket.

Further, although described as being implemented by the search node 506, it will be understood that the elements outlined for routine 1900 can be implemented by one or more computing devices/components that are associated with the data intake and query system 108, such as, but not limited to, the query system manager 502, the search head 504, the search master 512, search manager 514, cache manager 516, etc. Thus, the following illustrative embodiment should not be construed as limiting.

At block 1902, the search node 506 receives instructions for a query or sub-query. As described herein, a search manager 514 can receive and parse a query to determine the tasks to be assigned to the search nodes 506, such as, but not limited to, the searching of one or more buckets in common storage 216, etc. The search node 506 can parse the instructions and identify the buckets that are to be searched. In some cases, the search node 506 can determine that a bucket that is to be searched is not located in the search nodes local or shared data store.

At block 1904, the search node 506 obtains the bucket from common storage 216. As described herein, in some embodiments, the search node 506 obtains the bucket from common storage 216 in conjunction with a cache manager 516. For example, the search node 506 can request the cache manager 516 to identify the location of the bucket. The cache manager 516 can review the data stored in the local or shared data store for the bucket. If the cache manager 516 cannot locate the bucket in the local or shared data store, it can inform the search node 506 that the bucket is not stored locally and that it will be retrieved from common storage 216. As described herein, in some cases, the cache manager 516 can download a portion of the bucket (e.g., one or more files) and provide the portion of the bucket to the search node 506 as part of informing the search node 506 that the bucket is not found locally. The search node 506 can use the downloaded portion of the bucket to identify any other portions of the bucket that are to be retrieved from common storage 216.

Accordingly, as described herein, the search node 506 can retrieve all or portions of the bucket from common storage 216 and store the retrieved portions to a local or shared data store.

At block 1906, the search node 506 executes the search on the portions of the bucket stored in the local data store. As described herein, the search node 506 can review one or more files of the bucket to identify data that satisfies the query. In some cases, the search nodes 506 searches an inverted index to identify the data. In certain embodiments, the search node 506 searches the raw machine data, uses one or more configuration files, regex rules, and/or late binding schema to identify data in the bucket that satisfies the query.

Fewer, more, or different blocks can be used as part of the routine 1900. For example, in certain embodiments, the routine 1900 includes blocks for requesting a cache manager 516 to search for the bucket in the local or shared storage, and a block for informing the search node 506 that the requested bucket is not available in the local or shared data store. As another example, the routine 1900 can include performing one or more transformations on the data, and providing partial search results to a search manager 514, etc. In addition, it will be understood that the various blocks described herein with reference to FIG. 19 can be implemented in a variety of orders, or implemented concurrently.

4.3.7. Caching Search Results

Figure 20:
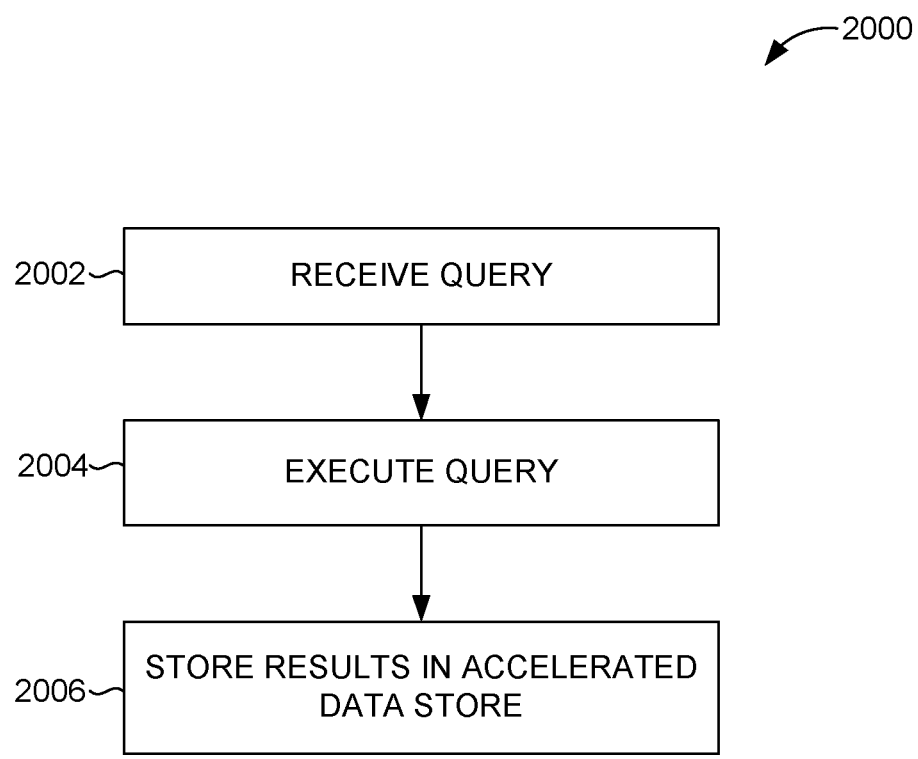
FIG. 20 is a flow diagram illustrative of an embodiment of a routine implemented by the query system to store search results.

FIG. 20 is a flow diagram illustrative of an embodiment of a routine 2000 implemented by the query system 212 to store search results. Although described as being implemented by the search manager 514, it will be understood that the elements outlined for routine 2000 can be implemented by one or more computing devices/components that are associated with the data intake and query system 108, such as, but not limited to, the query system manager 502, the search head 504, the search master 512, the search nodes 506, etc. Thus, the following illustrative embodiment should not be construed as limiting.

At block 2002, the search manager 514 receives a query, as described in greater detail herein at least with reference to block 4902 of FIG. 49, and at block 2004, the search manager 514 executes the query, as described in greater detail herein at least with reference to block 1508 of FIG. 15. For example, as described herein, the search manager 514 can identify buckets for searching assign the buckets to search nodes 506, and instruct the search nodes 506 to search the buckets. Furthermore, the search manager can receive partial results from each of the buckets, and perform one or more transformations on the received data.

At block 2006, the search manager 514 stores the results in the accelerated data store 222. As described herein, the results can be combined with results previously stored in the accelerated data store 222 and/or can be stored for combination with results to be obtained later in time. In some cases, the search manager 514 can receive queries and determine that at least a portion of the results are stored in the accelerated data store 222. Based on the identification, the search manager 514 can generate instructions for the search nodes 506 to obtain results to the query that are not stored in the accelerated data store 222, combine the results in the accelerated data store 222 with results obtained by the search nodes 506, and provide the aggregated search results to the client device 204, or store the aggregated search results in the accelerated data store 222 for further aggregation. By storing results in the accelerated data store 222, the search manager 514 can reduce the search time and computing resources used for future searches that rely on the query results.

Fewer, more, or different blocks can be used as part of the routine 2000. In some cases, one or more blocks can be omitted. For example, in certain embodiments, the search manager 514 can consult a data store catalog 220 to identify buckets, consult a search node catalog 510 to identify available search nodes, map buckets to search nodes 506, etc. Further, in some cases, the search nodes 506 can retrieve buckets from common storage 216. In addition, it will be understood that the various blocks described herein with reference to FIG. 20 can be implemented in a variety of orders, or implemented concurrently.

4.4. Data Ingestion, Indexing, and Storage Flow

Figure 21A:
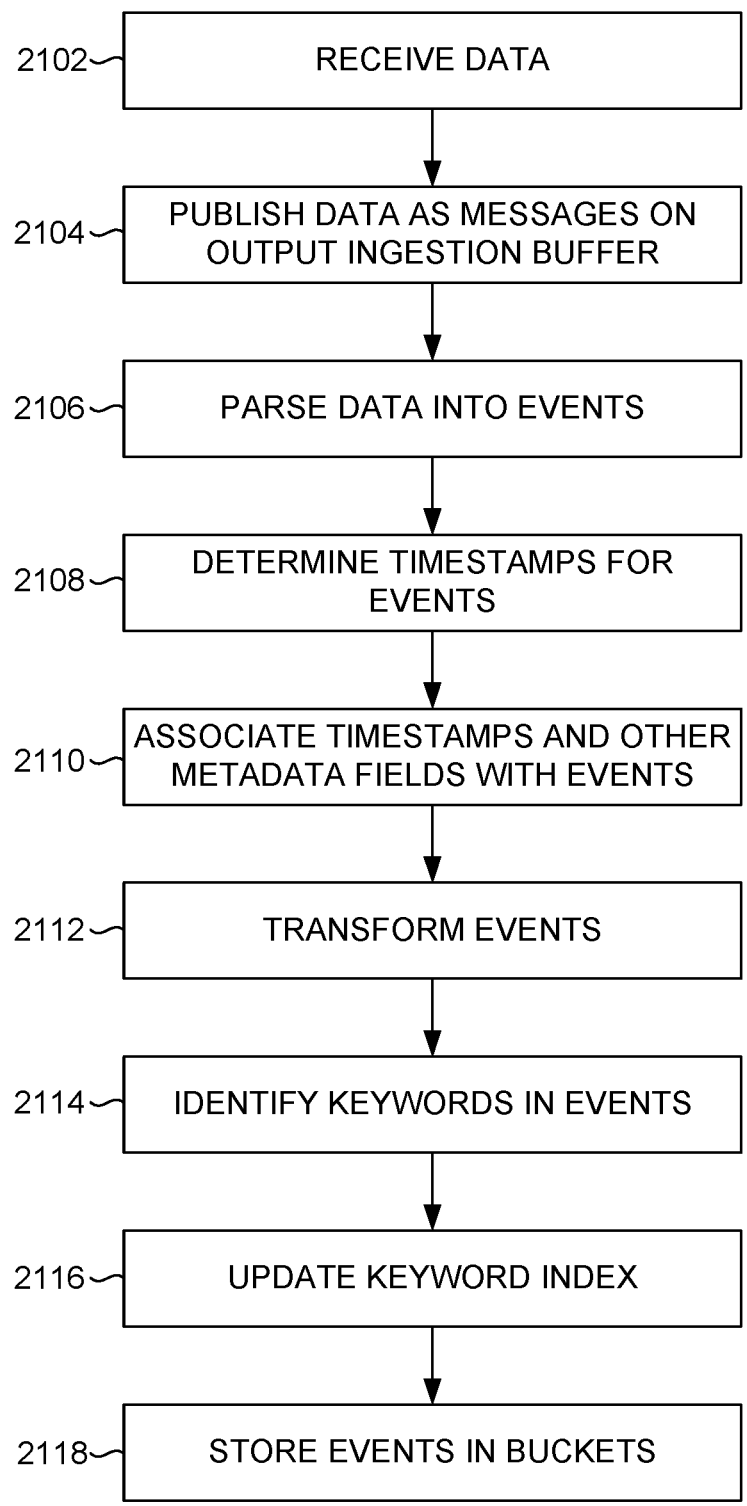
FIG. 21A is a flowchart of an example method that illustrates how indexers process, index, and store data received from intake system, in accordance with example embodiments.

FIG. 21A is a flow diagram of an example method that illustrates how a data intake and query system 108 processes, indexes, and stores data received from data sources 202, in accordance with example embodiments. The data flow illustrated in FIG. 21A is provided for illustrative purposes only; it will be understood that one or more of the steps of the processes illustrated in FIG. 21A may be removed or that the ordering of the steps may be changed. Furthermore, for the purposes of illustrating a clear example, one or more particular system components are described in the context of performing various operations during each of the data flow stages. For example, the intake system 210 is described as receiving and processing machine data during an input phase; the indexing system 212 is described as parsing and indexing machine data during parsing and indexing phases; and a query system 214 is described as performing a search query during a search phase. However, other system arrangements and distributions of the processing steps across system components may be used.

4.4.1. Input

At block 2102, the intake system 210 receives data from an input source, such as a data source 202 shown in FIG. 2. The intake system 210 initially may receive the data as a raw data stream generated by the input source. For example, the intake system 210 may receive a data stream from a log file generated by an application server, from a stream of network data from a network device, or from any other source of data. In some embodiments, the intake system 210 receives the raw data and may segment the data stream into messages, possibly of a uniform data size, to facilitate subsequent processing steps. The intake system 210 may thereafter process the messages in accordance with one or more rules, as discussed above for example with reference to FIGS. 6 and 7, to conduct preliminary processing of the data. In one embodiment, the processing conducted by the intake system 210 may be used to indicate one or more metadata fields applicable to each message. For example, the intake system 210 may include metadata fields within the messages, or publish the messages to topics indicative of a metadata field. These metadata fields may, for example, provide information related to a message as a whole and may apply to each event that is subsequently derived from the data in the message. For example, the metadata fields may include separate fields specifying each of a host, a source, and a source type related to the message. A host field may contain a value identifying a host name or IP address of a device that generated the data. A source field may contain a value identifying a source of the data, such as a pathname of a file or a protocol and port related to received network data. A source type field may contain a value specifying a particular source type label for the data. Additional metadata fields may also be included during the input phase, such as a character encoding of the data, if known, and possibly other values that provide information relevant to later processing steps.

At block 504, the intake system 210 publishes the data as messages on an output ingestion buffer 310. Illustratively, other components of the data intake and query system 108 may be configured to subscribe to various topics on the output ingestion buffer 310, thus receiving the data of the messages when published to the buffer 310.

4.4.2. Parsing

At block 2106, the indexing system 212 receives messages from the intake system 210 (e.g., by obtaining the messages from the output ingestion buffer 310) and parses the data of the message to organize the data into events. In some embodiments, to organize the data into events, the indexing system 212 may determine a source type associated with each message (e.g., by extracting a source type label from the metadata fields associated with the message, etc.) and refer to a source type configuration corresponding to the identified source type. The source type definition may include one or more properties that indicate to the indexing system 212 to automatically determine the boundaries within the received data that indicate the portions of machine data for events. In general, these properties may include regular expression-based rules or delimiter rules where, for example, event boundaries may be indicated by predefined characters or character strings. These predefined characters may include punctuation marks or other special characters including, for example, carriage returns, tabs, spaces, line breaks, etc. If a source type for the data is unknown to the indexing system 212, the indexing system 212 may infer a source type for the data by examining the structure of the data. Then, the indexing system 212 can apply an inferred source type definition to the data to create the events.

At block 2108, the indexing system 212 determines a timestamp for each event. Similar to the process for parsing machine data, an indexing system 212 may again refer to a source type definition associated with the data to locate one or more properties that indicate instructions for determining a timestamp for each event. The properties may, for example, instruct the indexing system 212 to extract a time value from a portion of data for the event, to interpolate time values based on timestamps associated with temporally proximate events, to create a timestamp based on a time the portion of machine data was received or generated, to use the timestamp of a previous event, or use any other rules for determining timestamps.

At block 2110, the indexing system 212 associates with each event one or more metadata fields including a field containing the timestamp determined for the event. In some embodiments, a timestamp may be included in the metadata fields. These metadata fields may include any number of "default fields" that are associated with all events, and may also include one more custom fields as defined by a user. Similar to the metadata fields associated with the data blocks at block 2104, the default metadata fields associated with each event may include a host, source, and source type field including or in addition to a field storing the timestamp.

At block 2112, the indexing system 212 may optionally apply one or more transformations to data included in the events created at block 2106. For example, such transformations can include removing a portion of an event (e.g., a portion used to define event boundaries, extraneous characters from the event, other extraneous text, etc.), masking a portion of an event (e.g., masking a credit card number), removing redundant portions of an event, etc. The transformations applied to events may, for example, be specified in one or more configuration files and referenced by one or more source type definitions.

FIG. 21C illustrates an illustrative example of how machine data can be stored in a data store in accordance with various disclosed embodiments. In other embodiments, machine data can be stored in a flat file in a corresponding bucket with an associated index file, such as a time series index or "TSIDX." As such, the depiction of machine data and associated metadata as rows and columns in the table of FIG. 21C is merely illustrative and is not intended to limit the data format in which the machine data and metadata is stored in various embodiments described herein. In one particular embodiment, machine data can be stored in a compressed or encrypted formatted. In such embodiments, the machine data can be stored with or be associated with data that describes the compression or encryption scheme with which the machine data is stored. The information about the compression or encryption scheme can be used to decompress or decrypt the machine data, and any metadata with which it is stored, at search time.

As mentioned above, certain metadata, e.g., host 2136, source 2137, source type 2138 and timestamps 2135 can be generated for each event, and associated with a corresponding portion of machine data 2139 when storing the event data in a data store, e.g., data store 212. Any of the metadata can be extracted from the corresponding machine data, or supplied or defined by an entity, such as a user or computer system. The metadata fields can become part of or stored with the event. Note that while the time-stamp metadata field can be extracted from the raw data of each event, the values for the other metadata fields may be determined by the indexing system 212 or indexing node 404 based on information it receives pertaining to the source of the data separate from the machine data.

While certain default or user-defined metadata fields can be extracted from the machine data for indexing purposes, all the machine data within an event can be maintained in its original condition. As such, in embodiments in which the portion of machine data included in an event is unprocessed or otherwise unaltered, it is referred to herein as a portion of raw machine data. In other embodiments, the port of machine data in an event can be processed or otherwise altered. As such, unless certain information needs to be removed for some reasons (e.g. extraneous information, confidential information), all the raw machine data contained in an event can be preserved and saved in its original form. Accordingly, the data store in which the event records are stored is sometimes referred to as a "raw record data store." The raw record data store contains a record of the raw event data tagged with the various default fields.

In FIG. 21C, the first three rows of the table represent events 2131, 2132, and 2133 and are related to a server access log that records requests from multiple clients processed by a server, as indicated by entry of "access.log" in the source column 2136.

In the example shown in FIG. 21C, each of the events 2131-2133 is associated with a discrete request made from a client device. The raw machine data generated by the server and extracted from a server access log can include the IP address of the client 2140, the user id of the person requesting the document 2141, the time the server finished processing the request 2142, the request line from the client 2143, the status code returned by the server to the client 2145, the size of the object returned to the client (in this case, the gif file requested by the client) 2146 and the time spent to serve the request in microseconds 2144. As seen in FIG. 21C, all the raw machine data retrieved from the server access log is retained and stored as part of the corresponding events, 2131-2133 in the data store.

Event 2134 is associated with an entry in a server error log, as indicated by "error.log" in the source column 2137 that records errors that the server encountered when processing a client request. Similar to the events related to the server access log, all the raw machine data in the error log file pertaining to event 2134 can be preserved and stored as part of the event 2134.

Saving minimally processed or unprocessed machine data in a data store associated with metadata fields in the manner similar to that shown in FIG. 21C is advantageous because it allows search of all the machine data at search time instead of searching only previously specified and identified fields or field-value pairs. As mentioned above, because data structures used by various embodiments of the present disclosure maintain the underlying raw machine data and use a late-binding schema for searching the raw machines data, it enables a user to continue investigating and learn valuable insights about the raw data. In other words, the user is not compelled to know about all the fields of information that will be needed at data ingestion time. As a user learns more about the data in the events, the user can continue to refine the late-binding schema by defining new extraction rules, or modifying or deleting existing extraction rules used by the system.

4.4.3. Indexing

At blocks 2114 and 2116, the indexing system 212 can optionally generate a keyword index to facilitate fast keyword searching for events. To build a keyword index, at block 2114, the indexing system 212 identifies a set of keywords in each event. At block 2116, the indexing system 212 includes the identified keywords in an index, which associates each stored keyword with reference pointers to events containing that keyword (or to locations within events where that keyword is located, other location identifiers, etc.). When the data intake and query system 108 subsequently receives a keyword-based query, the query system 214 can access the keyword index to quickly identify events containing the keyword.

In some embodiments, the keyword index may include entries for field name-value pairs found in events, where a field name-value pair can include a pair of keywords connected by a symbol, such as an equals sign or colon. This way, events containing these field name-value pairs can be quickly located. In some embodiments, fields can automatically be generated for some or all of the field names of the field name-value pairs at the time of indexing. For example, if the string "dest=10.0.1.2" is found in an event, a field named "dest" may be created for the event, and assigned a value of "10.0.1.2".

At block 2118, the indexing system 212 stores the events with an associated timestamp in a local data store 212 and/or common storage 216. Timestamps enable a user to search for events based on a time range. In some embodiments, the stored events are organized into "buckets," where each bucket stores events associated with a specific time range based on the timestamps associated with each event. This improves time-based searching, as well as allows for events with recent timestamps, which may have a higher likelihood of being accessed, to be stored in a faster memory to facilitate faster retrieval. For example, buckets containing the most recent events can be stored in flash memory rather than on a hard disk. In some embodiments, each bucket may be associated with an identifier, a time range, and a size constraint.

The indexing system 212 may be responsible for storing the events contained in various data stores 218 of common storage 216. By distributing events among the data stores in common storage 216, the query system 214 can analyze events for a query in parallel. For example, using map-reduce techniques, each search node 506 can return partial responses for a subset of events to a search head that combines the results to produce an answer for the query. By storing events in buckets for specific time ranges, the indexing system 212 may further optimize the data retrieval process by enabling search nodes 506 to search buckets corresponding to time ranges that are relevant to a query.

In some embodiments, each indexing node 404 (e.g., the indexer 410 or data store 412) of the indexing system 212 has a home directory and a cold directory. The home directory stores hot buckets and warm buckets, and the cold directory stores cold buckets. A hot bucket is a bucket that is capable of receiving and storing events. A warm bucket is a bucket that can no longer receive events for storage but has not yet been moved to the cold directory. A cold bucket is a bucket that can no longer receive events and may be a bucket that was previously stored in the home directory. The home directory may be stored in faster memory, such as flash memory, as events may be actively written to the home directory, and the home directory may typically store events that are more frequently searched and thus are accessed more frequently. The cold directory may be stored in slower and/or larger memory, such as a hard disk, as events are no longer being written to the cold directory, and the cold directory may typically store events that are not as frequently searched and thus are accessed less frequently. In some embodiments, an indexing node 404 may also have a quarantine bucket that contains events having potentially inaccurate information, such as an incorrect time stamp associated with the event or a time stamp that appears to be an unreasonable time stamp for the corresponding event. The quarantine bucket may have events from any time range; as such, the quarantine bucket may always be searched at search time. Additionally, an indexing node 404 may store old, archived data in a frozen bucket that is not capable of being searched at search time. In some embodiments, a frozen bucket may be stored in slower and/or larger memory, such as a hard disk, and may be stored in offline and/or remote storage.

In some embodiments, an indexing node 404 may not include a cold directory and/or cold or frozen buckets. For example, as warm buckets and/or merged buckets are copied to common storage 216, they can be deleted from the indexing node 404. In certain embodiments, one or more data stores 218 of the common storage 216 can include a home directory that includes warm buckets copied from the indexing nodes 404 and a cold directory of cold or frozen buckets as described above.

Moreover, events and buckets can also be replicated across different indexing nodes 404 and data stores 218 of the common storage 216.

Figure 21B:
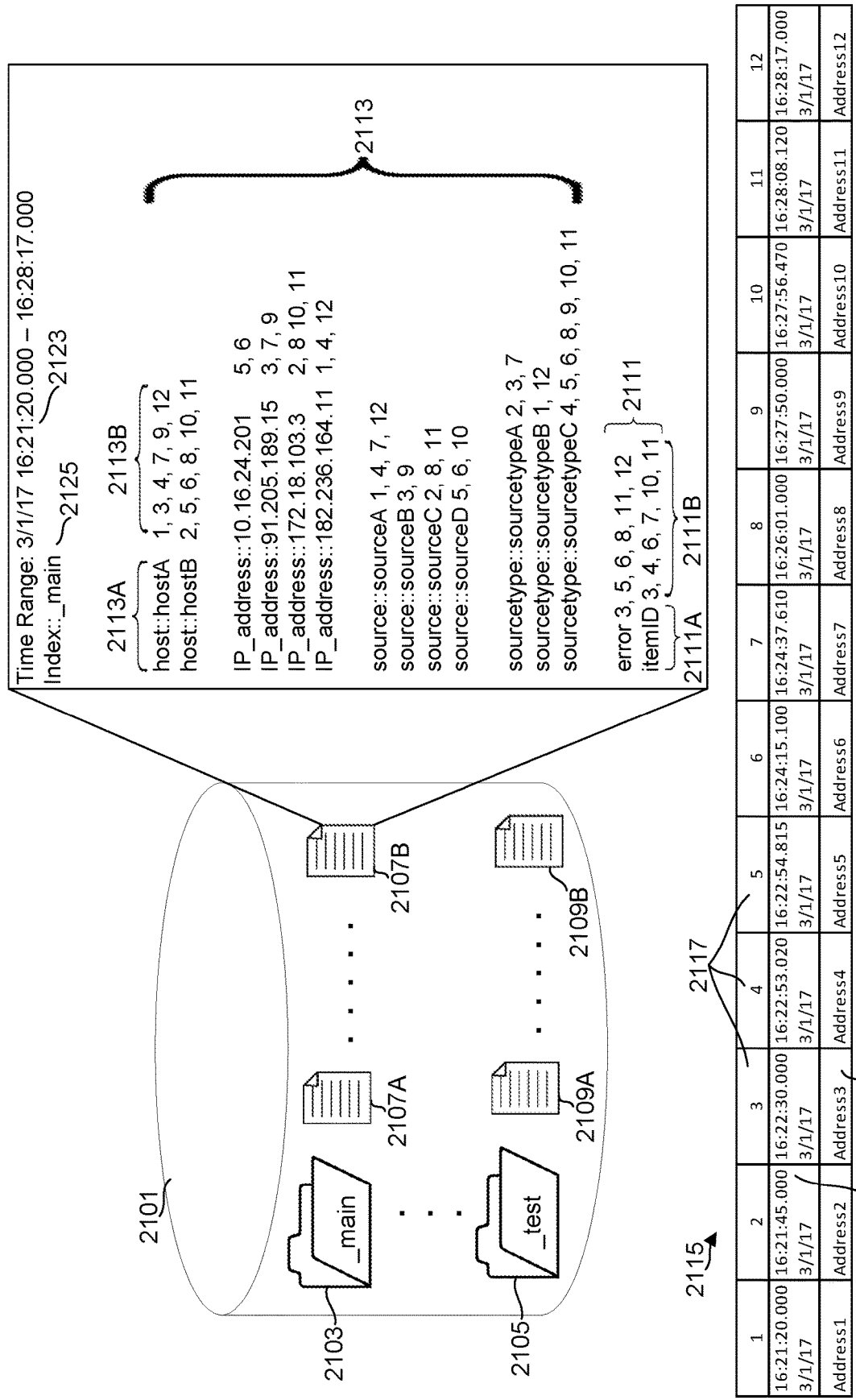
FIG. 21B is a block diagram of a data structure in which time-stamped event data can be stored in a data store, in accordance with example embodiments.

FIG. 21B is a block diagram of an example data store 2101 that includes a directory for each index (or partition) that contains a portion of data stored in the data store 2101. FIG. 21B further illustrates details of an embodiment of an inverted index 2107B and an event reference array 2115 associated with inverted index 2107B.

The data store 2101 can correspond to a data store 218 that stores events in common storage 216, a data store 412 associated with an indexing node 404, or a data store associated with a search peer 506. In the illustrated embodiment, the data store 2101 includes a _main directory 2103 associated with a _main partition and a _test directory 2105 associated with a _test partition. However, the data store 2101 can include fewer or more directories. In some embodiments, multiple indexes can share a single directory or all indexes can share a common directory. Additionally, although illustrated as a single data store 2101, it will be understood that the data store 2101 can be implemented as multiple data stores storing different portions of the information shown in FIG. 21B. For example, a single index or partition can span multiple directories or multiple data stores, and can be indexed or searched by multiple search nodes 506.

Furthermore, although not illustrated in FIG. 21B, it will be understood that, in some embodiments, the data store 2101 can include directories for each tenant and sub-directories for each partition of each tenant, or vice versa. Accordingly, the directories 2101 and 2103 illustrated in FIG. 21B can, in certain embodiments, correspond to sub-directories of a tenant or include sub-directories for different tenants.

In the illustrated embodiment of FIG. 21B, the partition-specific directories 2103 and 2105 include inverted indexes 2107A, 2107B and 2109A, 2109B, respectively. The inverted indexes 2107A . . . 2107B, and 2109A . . . 2109B can be keyword indexes or field-value pair indexes described herein and can include less or more information than depicted in FIG. 21B.

In some embodiments, the inverted index 2107A . . . 2107B, and 2109A . . . 2109B can correspond to a distinct time-series bucket stored in common storage 216, a search node 506, or an indexing node 404 and that contains events corresponding to the relevant partition (e.g., _main partition, _test partition). As such, each inverted index can correspond to a particular range of time for an partition. Additional files, such as high performance indexes for each time-series bucket of an partition, can also be stored in the same directory as the inverted indexes 2107A . . . 2107B, and 2109A . . . 2109B. In some embodiments inverted index 2107A . . . 2107B, and 2109A . . . 2109B can correspond to multiple time-series buckets or inverted indexes 2107A . . . 2107B, and 2109A . . . 2109B can correspond to a single time-series bucket.

Each inverted index 2107A . . . 2107B, and 2109A . . . 2109B can include one or more entries, such as keyword (or token) entries or field-value pair entries. Furthermore, in certain embodiments, the inverted indexes 2107A . . . 2107B, and 2109A . . . 2109B can include additional information, such as a time range 2123 associated with the inverted index or an partition identifier 2125 identifying the partition associated with the inverted index 2107A . . . 2107B, and 2109A . . . 2109B. However, each inverted index 2107A . . . 2107B, and 2109A . . . 2109B can include less or more information than depicted.

Token entries, such as token entries 2111 illustrated in inverted index 2107B, can include a token 2111A (e.g., "error," "itemID," etc.) and event references 2111B indicative of events that include the token. For example, for the token "error," the corresponding token entry includes the token "error" and an event reference, or unique identifier, for each event stored in the corresponding time-series bucket that includes the token "error." In the illustrated embodiment of FIG. 21B, the error token entry includes the identifiers 3, 5, 6, 8, 11, and 12 corresponding to events located in the time-series bucket associated with the inverted index 2107B that is stored in common storage 216, a search node 506, or an indexing node 404 and is associated with the partition _main 2103.

In some cases, some token entries can be default entries, automatically determined entries, or user specified entries. In some embodiments, the indexing system 212 can identify each word or string in an event as a distinct token and generate a token entry for the identified word or string. In some cases, the indexing system 212 can identify the beginning and ending of tokens based on punctuation, spaces, as described in greater detail herein. In certain cases, the indexing system 212 can rely on user input or a configuration file to identify tokens for token entries 2111, etc. It will be understood that any combination of token entries can be included as a default, automatically determined, a or included based on user-specified criteria.

Similarly, field-value pair entries, such as field-value pair entries 2113 shown in inverted index 2107B, can include a field-value pair 2113A and event references 2113B indicative of events that include a field value that corresponds to the field-value pair. For example, for a field-value pair sourcetype::sendmail, a field-value pair entry can include the field-value pair sourcetype::sendmail and a unique identifier, or event reference, for each event stored in the corresponding time-series bucket that includes a sendmail sourcetype.

In some cases, the field-value pair entries 2113 can be default entries, automatically determined entries, or user specified entries. As a non-limiting example, the field-value pair entries for the fields host, source, sourcetype can be included in the inverted indexes 2107A . . . 2107B, and 2109A . . . 2109B as a default. As such, all of the inverted indexes 2107A . . . 2107B, and 2109A . . . 2109B can include field-value pair entries for the fields host, source, source-type. As yet another non-limiting example, the field-value pair entries for the IP_address field can be user specified and may only appear in the inverted index 2107B based on user-specified criteria. As another non-limiting example, as the indexing system 212 indexes the events, it can automatically identify field-value pairs and create field-value pair entries. For example, based on the indexing system's 212 review of events, it can identify IP_address as a field in each event and add the IP_address field-value pair entries to the inverted index 2107B. It will be understood that any combination of field-value pair entries can be included as a default, automatically determined, or included based on user-specified criteria.

Each unique identifier 2117, or event reference, can correspond to a unique event located in the time series bucket. However, the same event reference can be located in multiple entries. For example if an event has a sourcetype splunkd, host www1 and token "warning," then the unique identifier for the event will appear in the field-value pair entries sourcetype::splunkd and host::www1, as well as the token entry "warning." With reference to the illustrated embodiment of FIG. 21B and the event that corresponds to the event reference 3, the event reference 3 is found in the field-value pair entries 2113 host::hostA, source::sourceB, sourcetype::sourcetypeA, and IP_address::91.205.189.15 indicating that the event corresponding to the event references is from hostA, sourceB, of sourcetypeA, and includes 91.205.189.15 in the event data.

For some fields, the unique identifier is located in only one field-value pair entry for a particular field. For example, the inverted index may include four sourcetype field-value pair entries corresponding to four different sourcetypes of the events stored in a bucket (e.g., sourcetypes: sendmail, splunkd, web_access, and web_service). Within those four sourcetype field-value pair entries, an identifier for a particular event may appear in only one of the field-value pair entries. With continued reference to the example illustrated embodiment of FIG. 21B, since the event reference 7 appears in the field-value pair entry sourcetype::sourcetypeA, then it does not appear in the other field-value pair entries for the sourcetype field, including sourcetype::sourcetypeB, sourcetype::sourcetypeC, and sourcetype::sourcetypeD.

The event references 2117 can be used to locate the events in the corresponding bucket. For example, the inverted index can include, or be associated with, an event reference array 2115. The event reference array 2115 can include an array entry 2117 for each event reference in the inverted index 2107B. Each array entry 2117 can include location information 2119 of the event corresponding to the unique identifier (non-limiting example: seek address of the event), a timestamp 2121 associated with the event, or additional information regarding the event associated with the event reference, etc.

For each token entry 2111 or field-value pair entry 2113, the event reference 2101B or unique identifiers can be listed in chronological order or the value of the event reference can be assigned based on chronological data, such as a timestamp associated with the event referenced by the event reference. For example, the event reference 1 in the illustrated embodiment of FIG. 21B can correspond to the first-in-time event for the bucket, and the event reference 12 can correspond to the last-in-time event for the bucket. However, the event references can be listed in any order, such as reverse chronological order, ascending order, descending order, or some other order, etc. Further, the entries can be sorted. For example, the entries can be sorted alphabetically (collectively or within a particular group), by entry origin (e.g., default, automatically generated, user-specified, etc.), by entry type (e.g., field-value pair entry, token entry, etc.), or chronologically by when added to the inverted index, etc. In the illustrated embodiment of FIG. 21B, the entries are sorted first by entry type and then alphabetically.

As a non-limiting example of how the inverted indexes 2107A . . . 2107B, and 2109A . . . 2109B can be used during a data categorization request command, the query system 214 can receive filter criteria indicating data that is to be categorized and categorization criteria indicating how the data is to be categorized. Example filter criteria can include, but is not limited to, indexes (or partitions), hosts, sources, sourcetypes, time ranges, field identifier, tenant and/or user identifiers, keywords, etc.

Using the filter criteria, the query system 214 identifies relevant inverted indexes to be searched. For example, if the filter criteria includes a set of partitions (also referred to as indexes), the query system 214 can identify the inverted indexes stored in the directory corresponding to the particular partition as relevant inverted indexes. Other means can be used to identify inverted indexes associated with a partition of interest. For example, in some embodiments, the query system 214 can review an entry in the inverted indexes, such as an partition-value pair entry 2113 to determine if a particular inverted index is relevant. If the filter criteria does not identify any partition, then the query system 214 can identify all inverted indexes managed by the query system 214 as relevant inverted indexes.

Similarly, if the filter criteria includes a time range, the query system 214 can identify inverted indexes corresponding to buckets that satisfy at least a portion of the time range as relevant inverted indexes. For example, if the time range is last hour then the query system 214 can identify all inverted indexes that correspond to buckets storing events associated with timestamps within the last hour as relevant inverted indexes.

When used in combination, an index filter criterion specifying one or more partitions and a time range filter criterion specifying a particular time range can be used to identify a subset of inverted indexes within a particular directory (or otherwise associated with a particular partition) as relevant inverted indexes. As such, the query system 214 can focus the processing to only a subset of the total number of inverted indexes in the data intake and query system 108.

Once the relevant inverted indexes are identified, the query system 214 can review them using any additional filter criteria to identify events that satisfy the filter criteria. In some cases, using the known location of the directory in which the relevant inverted indexes are located, the query system 214 can determine that any events identified using the relevant inverted indexes satisfy an index filter criterion. For example, if the filter criteria includes a partition main, then the query system 214 can determine that any events identified using inverted indexes within the partition main directory (or otherwise associated with the partition main) satisfy the index filter criterion.

Furthermore, based on the time range associated with each inverted index, the query system 214 can determine that that any events identified using a particular inverted index satisfies a time range filter criterion. For example, if a time range filter criterion is for the last hour and a particular inverted index corresponds to events within a time range of 50 minutes ago to 35 minutes ago, the query system 214 can determine that any events identified using the particular inverted index satisfy the time range filter criterion. Conversely, if the particular inverted index corresponds to events within a time range of 59 minutes ago to 62 minutes ago, the query system 214 can determine that some events identified using the particular inverted index may not satisfy the time range filter criterion.

Using the inverted indexes, the query system 214 can identify event references (and therefore events) that satisfy the filter criteria. For example, if the token "error" is a filter criterion, the query system 214 can track all event references within the token entry "error." Similarly, the query system 214 can identify other event references located in other token entries or field-value pair entries that match the filter criteria. The system can identify event references located in all of the entries identified by the filter criteria. For example, if the filter criteria include the token "error" and field-value pair sourcetype::web_ui, the query system 214 can track the event references found in both the token entry "error" and the field-value pair entry sourcetype::web_ui. As mentioned previously, in some cases, such as when multiple values are identified for a particular filter criterion (e.g., multiple sources for a source filter criterion), the system can identify event references located in at least one of the entries corresponding to the multiple values and in all other entries identified by the filter criteria. The query system 214 can determine that the events associated with the identified event references satisfy the filter criteria.

In some cases, the query system 214 can further consult a timestamp associated with the event reference to determine whether an event satisfies the filter criteria. For example, if an inverted index corresponds to a time range that is partially outside of a time range filter criterion, then the query system 214 can consult a timestamp associated with the event reference to determine whether the corresponding event satisfies the time range criterion. In some embodiments, to identify events that satisfy a time range, the query system 214 can review an array, such as the event reference array 2115 that identifies the time associated with the events. Furthermore, as mentioned above using the known location of the directory in which the relevant inverted indexes are located (or other partition identifier), the query system 214 can determine that any events identified using the relevant inverted indexes satisfy the index filter criterion.

In some cases, based on the filter criteria, the query system 214 reviews an extraction rule. In certain embodiments, if the filter criteria includes a field name that does not correspond to a field-value pair entry in an inverted index, the query system 214 can review an extraction rule, which may be located in a configuration file, to identify a field that corresponds to a field-value pair entry in the inverted index.

For example, the filter criteria includes a field name "sessionID" and the query system 214 determines that at least one relevant inverted index does not include a field-value pair entry corresponding to the field name sessionID, the query system 214 can review an extraction rule that identifies how the sessionID field is to be extracted from a particular host, source, or sourcetype (implicitly identifying the particular host, source, or sourcetype that includes a sessionID field). The query system 214 can replace the field name "sessionID" in the filter criteria with the identified host, source, or sourcetype. In some cases, the field name "sessionID" may be associated with multiples hosts, sources, or sourcetypes, in which case, all identified hosts, sources, and sourcetypes can be added as filter criteria. In some cases, the identified host, source, or sourcetype can replace or be appended to a filter criterion, or be excluded. For example, if the filter criteria includes a criterion for source S1 and the "sessionID" field is found in source S2, the source S2 can replace S1 in the filter criteria, be appended such that the filter criteria includes source S1 and source S2, or be excluded based on the presence of the filter criterion source S1. If the identified host, source, or sourcetype is included in the filter criteria, the query system 214 can then identify a field-value pair entry in the inverted index that includes a field value corresponding to the identity of the particular host, source, or sourcetype identified using the extraction rule.

Once the events that satisfy the filter criteria are identified, the query system 214 can categorize the results based on the categorization criteria. The categorization criteria can include categories for grouping the results, such as any combination of partition, source, sourcetype, or host, or other categories or fields as desired.

The query system 214 can use the categorization criteria to identify categorization criteria-value pairs or categorization criteria values by which to categorize or group the results. The categorization criteria-value pairs can correspond to one or more field-value pair entries stored in a relevant inverted index, one or more partition-value pairs based on a directory in which the inverted index is located or an entry in the inverted index (or other means by which an inverted index can be associated with a partition), or other criteria-value pair that identifies a general category and a particular value for that category. The categorization criteria values can correspond to the value portion of the categorization criteria-value pair.

As mentioned, in some cases, the categorization criteria-value pairs can correspond to one or more field-value pair entries stored in the relevant inverted indexes. For example, the categorization criteria-value pairs can correspond to field-value pair entries of host, source, and sourcetype (or other field-value pair entry as desired). For instance, if there are ten different hosts, four different sources, and five different sourcetypes for an inverted index, then the inverted index can include ten host field-value pair entries, four source field-value pair entries, and five sourcetype field-value pair entries. The query system 214 can use the nineteen distinct field-value pair entries as categorization criteria-value pairs to group the results.

Specifically, the query system 214 can identify the location of the event references associated with the events that satisfy the filter criteria within the field-value pairs, and group the event references based on their location. As such, the query system 214 can identify the particular field value associated with the event corresponding to the event reference. For example, if the categorization criteria include host and sourcetype, the host field-value pair entries and sourcetype field-value pair entries can be used as categorization criteria-value pairs to identify the specific host and sourcetype associated with the events that satisfy the filter criteria.

In addition, as mentioned, categorization criteria-value pairs can correspond to data other than the field-value pair entries in the relevant inverted indexes. For example, if partition or index is used as a categorization criterion, the inverted indexes may not include partition field-value pair entries. Rather, the query system 214 can identify the categorization criteria-value pair associated with the partition based on the directory in which an inverted index is located, information in the inverted index, or other information that associates the inverted index with the partition, etc. As such a variety of methods can be used to identify the categorization criteria-value pairs from the categorization criteria.

Accordingly based on the categorization criteria (and categorization criteria-value pairs), the query system 214 can generate groupings based on the events that satisfy the filter criteria. As a non-limiting example, if the categorization criteria includes a partition and sourcetype, then the groupings can correspond to events that are associated with each unique combination of partition and sourcetype. For instance, if there are three different partitions and two different sourcetypes associated with the identified events, then the six different groups can be formed, each with a unique partition value-sourcetype value combination. Similarly, if the categorization criteria includes partition, sourcetype, and host and there are two different partitions, three sourcetypes, and five hosts associated with the identified events, then the query system 214 can generate up to thirty groups for the results that satisfy the filter criteria. Each group can be associated with a unique combination of categorization criteria-value pairs (e.g., unique combinations of partition value sourcetype value, and host value).

In addition, the query system 214 can count the number of events associated with each group based on the number of events that meet the unique combination of categorization criteria for a particular group (or match the categorization criteria-value pairs for the particular group). With continued reference to the example above, the query system 214 can count the number of events that meet the unique combination of partition, sourcetype, and host for a particular group.

The query system 214, such as the search head 504 can aggregate the groupings from the buckets, or search nodes 506, and provide the groupings for display. In some cases, the groups are displayed based on at least one of the host, source, sourcetype, or partition associated with the groupings. In some embodiments, the query system 214 can further display the groups based on display criteria, such as a display order or a sort order as described in greater detail above.

As a non-limiting example and with reference to FIG. 21B, consider a request received by the query system 214 that includes the following filter criteria: keyword=error, partition=main, time range=3/1/17 16:22.00.000-16:28.00.000, sourcetype=sourcetypeC, host=hostB, and the following categorization criteria: source.

Based on the above criteria, a search node 506 of the query system 214 that is associated with the data store 2101 identifies _main directory 2103 and can ignore _test directory 2105 and any other partition-specific directories. The search node 506 determines that inverted index 2107B is a relevant index based on its location within the _main directory 2103 and the time range associated with it. For sake of simplicity in this example, the search node 506 determines that no other inverted indexes in the _main directory 2103, such as inverted index 2107A satisfy the time range criterion.

Having identified the relevant inverted index 2107B, the search node 506 reviews the token entries 2111 and the field-value pair entries 2113 to identify event references, or events, that satisfy all of the filter criteria.

With respect to the token entries 2111, the search node 506 can review the error token entry and identify event references 3, 5, 6, 8, 11, 12, indicating that the term "error" is found in the corresponding events. Similarly, the search node 506 can identify event references 4, 5, 6, 8, 9, 10, 11 in the field-value pair entry sourcetype::sourcetypeC and event references 2, 5, 6, 8, 10, 11 in the field-value pair entry host::hostB. As the filter criteria did not include a source or an IP_address field-value pair, the search node 506 can ignore those field-value pair entries.

In addition to identifying event references found in at least one token entry or field-value pair entry (e.g., event references 3, 4, 5, 6, 8, 9, 10, 11, 12), the search node 506 can identify events (and corresponding event references) that satisfy the time range criterion using the event reference array 2115 (e.g., event references 2, 3, 4, 5, 6, 7, 8, 9, 10). Using the information obtained from the inverted index 2107B (including the event reference array 2115), the search node 506 can identify the event references that satisfy all of the filter criteria (e.g., event references 5, 6, 8).

Having identified the events (and event references) that satisfy all of the filter criteria, the search node 506 can group the event references using the received categorization criteria (source). In doing so, the search node 506 can determine that event references 5 and 6 are located in the field-value pair entry source::sourceD (or have matching categorization criteria-value pairs) and event reference 8 is located in the field-value pair entry source::sourceC. Accordingly, the search node 506 can generate a sourceC group having a count of one corresponding to reference 8 and a sourceD group having a count of two corresponding to references 5 and 6. This information can be communicated to the search head 504. In turn the search head 504 can aggregate the results from the various search nodes 506 and display the groupings. As mentioned above, in some embodiments, the groupings can be displayed based at least in part on the categorization criteria, including at least one of host, source, sourcetype, or partition.

It will be understood that a change to any of the filter criteria or categorization criteria can result in different groupings. As a one non-limiting example, consider a request received by a search node 506 that includes the following filter criteria: partition=main, time range=3/1/17 3/1/17 16:21:20.000-16:28:17.000, and the following categorization criteria: host, source, sourcetype can result in the search node 506 identifying event references 1-12 as satisfying the filter criteria. The search node 506 can generate up to 24 groupings corresponding to the 24 different combinations of the categorization criteria-value pairs, including host (hostA, hostB), source (sourceA, sourceB, sourceC, sourceD), and sourcetype (sourcetypeA, sourcetypeB, sourcetypeC). However, as there are only twelve events identifiers in the illustrated embodiment and some fall into the same grouping, the search node 506 generates eight groups and counts as follows:

Group 1 (hostA, sourceA, sourcetypeA): 1 (event reference 7)
Group 2 (hostA, sourceA, sourcetypeB): 2 (event references 1, 12)
Group 3 (hostA, sourceA, sourcetypeC): 1 (event reference 4)
Group 4 (hostA, sourceB, sourcetypeA): 1 (event reference 3)
Group 5 (hostA, sourceB, sourcetypeC): 1 (event reference 9)
Group 6 (hostB, sourceC, sourcetypeA): 1 (event reference 2)
Group 7 (hostB, sourceC, sourcetypeC): 2 (event references 8, 11)
Group 8 (hostB, sourceD, sourcetypeC): 3 (event references 5, 6, 10)

As noted, each group has a unique combination of categorization criteria-value pairs or categorization criteria values. The search node 506 communicates the groups to the search head 504 for aggregation with results received from other search nodes 506. In communicating the groups to the search head 504, the search node 506 can include the categorization criteria-value pairs for each group and the count. In some embodiments, the search node 506 can include more or less information. For example, the search node 506 can include the event references associated with each group and other identifying information, such as the search node 506 or inverted index used to identify the groups.

As another non-limiting example, consider a request received by an search node 506 that includes the following filter criteria: partition=main, time range=3/1/17 3/1/17 16:21:20.000-16:28:17.000, source=sourceA, sourceD, and keyword=itemID and the following categorization criteria: host, source, sourcetype can result in the search node identifying event references 4, 7, and 10 as satisfying the filter criteria, and generate the following groups:

Group 1 (hostA, sourceA, sourcetypeC): 1 (event reference 4)
Group 2 (hostA, sourceA, sourcetypeA): 1 (event reference 7)
Group 3 (hostB, sourceD, sourcetypeC): 1 (event references 10)

The search node 506 communicates the groups to the search head 504 for aggregation with results received from other search node 506s. As will be understand there are myriad ways for filtering and categorizing the events and event references. For example, the search node 506 can review multiple inverted indexes associated with an partition or review the inverted indexes of multiple partitions, and categorize the data using any one or any combination of partition, host, source, sourcetype, or other category, as desired.

Further, if a user interacts with a particular group, the search node 506 can provide additional information regarding the group. For example, the search node 506 can perform a targeted search or sampling of the events that satisfy the filter criteria and the categorization criteria for the selected group, also referred to as the filter criteria corresponding to the group or filter criteria associated with the group.

In some cases, to provide the additional information, the search node 506 relies on the inverted index. For example, the search node 506 can identify the event references associated with the events that satisfy the filter criteria and the categorization criteria for the selected group and then use the event reference array 2115 to access some or all of the identified events. In some cases, the categorization criteria values or categorization criteria-value pairs associated with the group become part of the filter criteria for the review.

With reference to FIG. 21B for instance, suppose a group is displayed with a count of six corresponding to event references 4, 5, 6, 8, 10, 11 (i.e., event references 4, 5, 6, 8, 10, 11 satisfy the filter criteria and are associated with matching categorization criteria values or categorization criteria-value pairs) and a user interacts with the group (e.g., selecting the group, clicking on the group, etc.). In response, the search head 504 communicates with the search node 506 to provide additional information regarding the group.

In some embodiments, the search node 506 identifies the event references associated with the group using the filter criteria and the categorization criteria for the group (e.g., categorization criteria values or categorization criteria-value pairs unique to the group). Together, the filter criteria and the categorization criteria for the group can be referred to as the filter criteria associated with the group. Using the filter criteria associated with the group, the search node 506 identifies event references 4, 5, 6, 8, 10, 11.

Based on a sampling criteria, discussed in greater detail above, the search node 506 can determine that it will analyze a sample of the events associated with the event references 4, 5, 6, 8, 10, 11. For example, the sample can include analyzing event data associated with the event references 5, 8, 10. In some embodiments, the search node 506 can use the event reference array 2115 to access the event data associated with the event references 5, 8, 10. Once accessed, the search node 506 can compile the relevant information and provide it to the search head 504 for aggregation with results from other search nodes. By identifying events and sampling event data using the inverted indexes, the search node can reduce the amount of actual data this is analyzed and the number of events that are accessed in order to generate the summary of the group and provide a response in less time.

4.5. Query Processing Flow

Figure 22A:
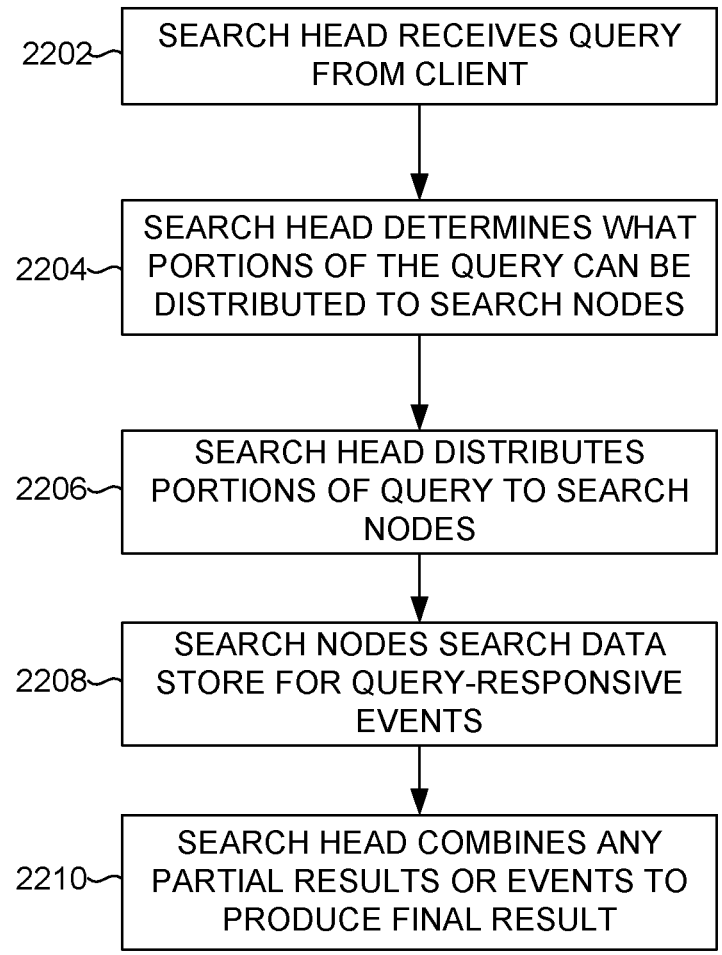
FIG. 22A is a flow diagram of an example method that illustrates how a search head and indexers perform a search query, in accordance with example embodiments.

FIG. 22A is a flow diagram illustrating an embodiment of a routine implemented by the query system 214 for executing a query. At block 2202, a search head 504 receives a search query. At block 2204, the search head 504 analyzes the search query to determine what portion(s) of the query to delegate to search nodes 506 and what portions of the query to execute locally by the search head 504. At block 2206, the search head distributes the determined portions of the query to the appropriate search nodes 506. In some embodiments, a search head cluster may take the place of an independent search head 504 where each search head 504 in the search head cluster coordinates with peer search heads 504 in the search head cluster to schedule jobs, replicate search results, update configurations, fulfill search requests, etc. In some embodiments, the search head 504 (or each search head) consults with a search node catalog 510 that provides the search head with a list of search nodes 506 to which the search head can distribute the determined portions of the query. A search head 504 may communicate with the search node catalog 510 to discover the addresses of active search nodes 506.

At block 2208, the search nodes 506 to which the query was distributed, search data stores associated with them for events that are responsive to the query. To determine which events are responsive to the query, the search node 506 searches for events that match the criteria specified in the query. These criteria can include matching keywords or specific values for certain fields. The searching operations at block 2208 may use the late-binding schema to extract values for specified fields from events at the time the query is processed. In some embodiments, one or more rules for extracting field values may be specified as part of a source type definition in a configuration file. The search nodes 506 may then either send the relevant events back to the search head 504, or use the events to determine a partial result, and send the partial result back to the search head 504.

At block 2210, the search head 504 combines the partial results and/or events received from the search nodes 506 to produce a final result for the query. In some examples, the results of the query are indicative of performance or security of the IT environment and may help improve the performance of components in the IT environment. This final result may comprise different types of data depending on what the query requested. For example, the results can include a listing of matching events returned by the query, or some type of visualization of the data from the returned events. In another example, the final result can include one or more calculated values derived from the matching events.

The results generated by the system 108 can be returned to a client using different techniques. For example, one technique streams results or relevant events back to a client in real-time as they are identified. Another technique waits to report the results to the client until a complete set of results (which may include a set of relevant events or a result based on relevant events) is ready to return to the client. Yet another technique streams interim results or relevant events back to the client in real-time until a complete set of results is ready, and then returns the complete set of results to the client. In another technique, certain results are stored as "search jobs" and the client may retrieve the results by referring the search jobs.

The search head 504 can also perform various operations to make the search more efficient. For example, before the search head 504 begins execution of a query, the search head 504 can determine a time range for the query and a set of common keywords that all matching events include. The search head 504 may then use these parameters to query the search nodes 506 to obtain a superset of the eventual results. Then, during a filtering stage, the search head 504 can perform field-extraction operations on the superset to produce a reduced set of search results. This speeds up queries, which may be particularly helpful for queries that are performed on a periodic basis.

4.6. Pipelined Search Language

Various embodiments of the present disclosure can be implemented using, or in conjunction with, a pipelined command language. A pipelined command language is a language in which a set of inputs or data is operated on by a first command in a sequence of commands, and then subsequent commands in the order they are arranged in the sequence. Such commands can include any type of functionality for operating on data, such as retrieving, searching, filtering, aggregating, processing, transmitting, and the like. As described herein, a query can thus be formulated in a pipelined command language and include any number of ordered or unordered commands for operating on data.

Splunk Processing Language (SPL) is an example of a pipelined command language in which a set of inputs or data is operated on by any number of commands in a particular sequence. A sequence of commands, or command sequence, can be formulated such that the order in which the commands are arranged defines the order in which the commands are applied to a set of data or the results of an earlier executed command. For example, a first command in a command sequence can operate to search or filter for specific data in particular set of data. The results of the first command can then be passed to another command listed later in the command sequence for further processing.

In various embodiments, a query can be formulated as a command sequence defined in a command line of a search UI. In some embodiments, a query can be formulated as a sequence of SPL commands. Some or all of the SPL commands in the sequence of SPL commands can be separated from one another by a pipe symbol "|". In such embodiments, a set of data, such as a set of events, can be operated on by a first SPL command in the sequence, and then a subsequent SPL command following a pipe symbol "|" after the first SPL command operates on the results produced by the first SPL command or other set of data, and so on for any additional SPL commands in the sequence. As such, a query formulated using SPL comprises a series of consecutive commands that are delimited by pipe "|" characters. The pipe character indicates to the system that the output or result of one command (to the left of the pipe) should be used as the input for one of the subsequent commands (to the right of the pipe). This enables formulation of queries defined by a pipeline of sequenced commands that refines or enhances the data at each step along the pipeline until the desired results are attained. Accordingly, various embodiments described herein can be implemented with Splunk Processing Language (SPL) used in conjunction with the SPLUNK® ENTERPRISE system.

While a query can be formulated in many ways, a query can start with a search command and one or more corresponding search terms at the beginning of the pipeline. Such search terms can include any combination of keywords, phrases, times, dates, Boolean expressions, fieldname-field value pairs, etc. that specify which results should be obtained from an index. The results can then be passed as inputs into subsequent commands in a sequence of commands by using, for example, a pipe character. The subsequent commands in a sequence can include directives for additional processing of the results once it has been obtained from one or more indexes. For example, commands may be used to filter unwanted information out of the results, extract more information, evaluate field values, calculate statistics, reorder the results, create an alert, create summary of the results, or perform some type of aggregation function. In some embodiments, the summary can include a graph, chart, metric, or other visualization of the data. An aggregation function can include analysis or calculations to return an aggregate value, such as an average value, a sum, a maximum value, a root mean square, statistical values, and the like.

Due to its flexible nature, use of a pipelined command language in various embodiments is advantageous because it can perform "filtering" as well as "processing" functions. In other words, a single query can include a search command and search term expressions, as well as data-analysis expressions. For example, a command at the beginning of a query can perform a "filtering" step by retrieving a set of data based on a condition (e.g., records associated with server response times of less than 1 microsecond). The results of the filtering step can then be passed to a subsequent command in the pipeline that performs a "processing" step (e.g. calculation of an aggregate value related to the filtered events such as the average response time of servers with response times of less than 1 microsecond). Furthermore, the search command can allow events to be filtered by keyword as well as field value criteria. For example, a search command can filter out all events containing the word "warning" or filter out all events where a field value associated with a field "clientip" is "10.0.1.2."

The results obtained or generated in response to a command in a query can be considered a set of results data. The set of results data can be passed from one command to another in any data format. In one embodiment, the set of result data can be in the form of a dynamically created table. Each command in a particular query can redefine the shape of the table. In some implementations, an event retrieved from an index in response to a query can be considered a row with a column for each field value. Columns contain basic information about the data and also may contain data that has been dynamically extracted at search time.

Figure 22B:
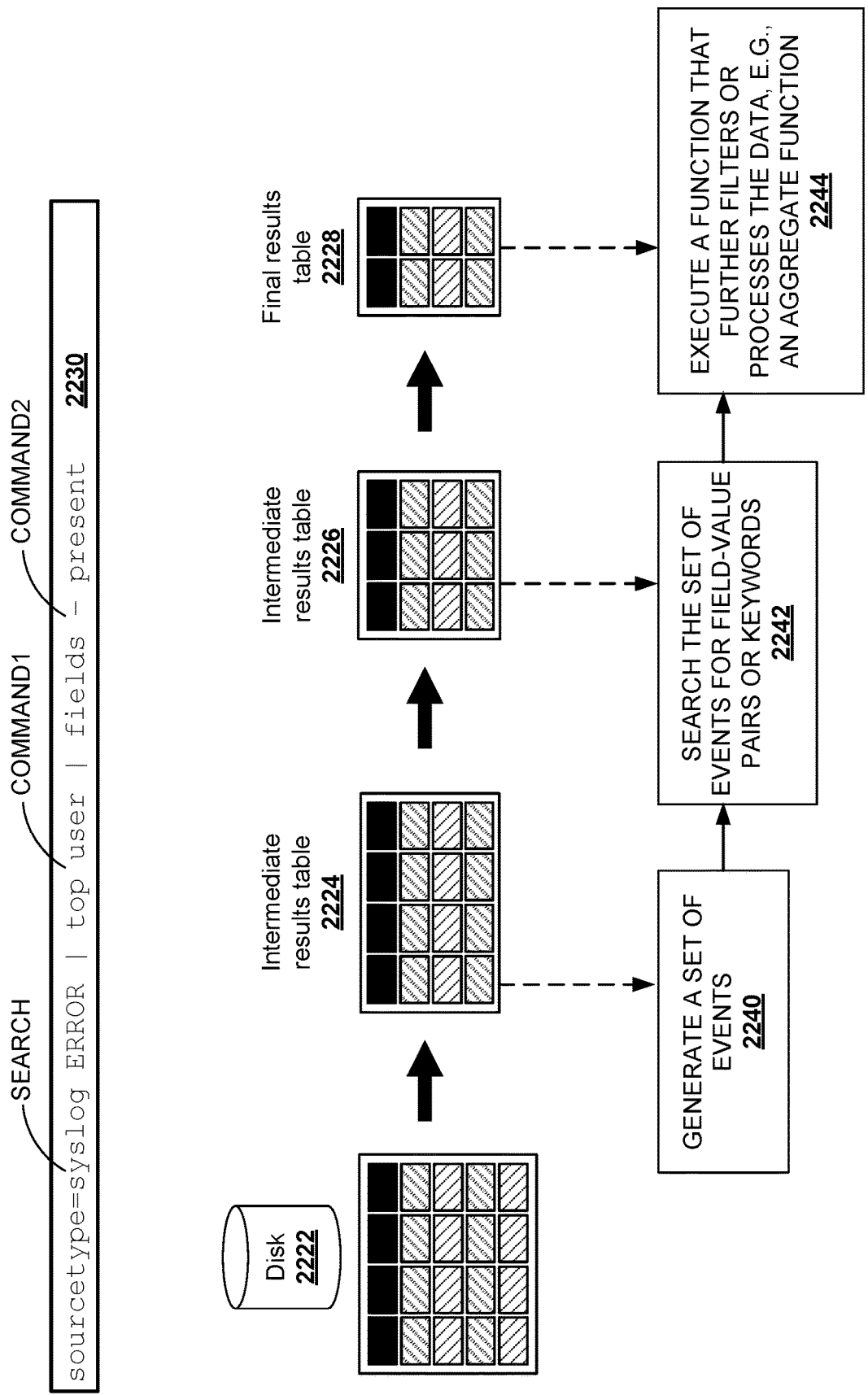
FIG. 22B provides a visual representation of an example manner in which a pipelined command language or query operates, in accordance with example embodiments.

FIG. 22B provides a visual representation of the manner in which a pipelined command language or query operates in accordance with the disclosed embodiments. The query 2230 can be inputted by the user into a search. The query comprises a search, the results of which are piped to two commands (namely, command 1 and command 2) that follow the search step.

Disk 2222 represents the event data in the raw record data store.

When a user query is processed, a search step will precede other queries in the pipeline in order to generate a set of events at block 2240. For example, the query can comprise search terms "sourcetype=syslog ERROR" at the front of the pipeline as shown in FIG. 22B. Intermediate results table 2224 shows fewer rows because it represents the subset of events retrieved from the index that matched the search terms "sourcetype=syslog ERROR" from search command 2230. By way of further example, instead of a search step, the set of events at the head of the pipeline may be generating by a call to a pre-existing inverted index (as will be explained later).

At block 2242, the set of events generated in the first part of the query may be piped to a query that searches the set of events for field-value pairs or for keywords. For example, the second intermediate results table 2226 shows fewer columns, representing the result of the top command, "top user" which summarizes the events into a list of the top 10 users and displays the user, count, and percentage.

Finally, at block 2244, the results of the prior stage can be pipelined to another stage where further filtering or processing of the data can be performed, e.g., preparing the data for display purposes, filtering the data based on a condition, performing a mathematical calculation with the data, etc. As shown in FIG. 22B, the "fields-percent" part of command 2230 removes the column that shows the percentage, thereby, leaving a final results table 2228 without a percentage column. In different embodiments, other query languages, such as the Structured Query Language ("SQL"), can be used to create a query.

4.7. Field Extraction

The query system 214 allows users to search and visualize events generated from machine data received from homogenous data sources. The query system 214 also allows users to search and visualize events generated from machine data received from heterogeneous data sources. The query system 214 includes various components for processing a query, such as, but not limited to a query system manager 502, one or more search heads 504 having one or more search masters 512 and search managers 514, and one or more search nodes 506. A query language may be used to create a query, such as any suitable pipelined query language. For example, Splunk Processing Language (SPL) can be utilized to make a query. SPL is a pipelined search language in which a set of inputs is operated on by a first command in a command line, and then a subsequent command following the pipe symbol "I" operates on the results produced by the first command, and so on for additional commands. Other query languages, such as the Structured Query Language ("SQL"), can be used to create a query.

In response to receiving the search query, a search head 504 (e.g., a search master 512 or search manager 514) can use extraction rules to extract values for fields in the events being searched. The search head 504 can obtain extraction rules that specify how to extract a value for fields from an event. Extraction rules can comprise regex rules that specify how to extract values for the fields corresponding to the extraction rules. In addition to specifying how to extract field values, the extraction rules may also include instructions for deriving a field value by performing a function on a character string or value retrieved by the extraction rule. For example, an extraction rule may truncate a character string or convert the character string into a different data format. In some cases, the query itself can specify one or more extraction rules.

The search head 504 can apply the extraction rules to events that it receives from search nodes 506. The search nodes 506 may apply the extraction rules to events in an associated data store or common storage 216. Extraction rules can be applied to all the events in a data store or common storage 216 or to a subset of the events that have been filtered based on some criteria (e.g., event time stamp values, etc.). Extraction rules can be used to extract one or more values for a field from events by parsing the portions of machine data in the events and examining the data for one or more patterns of characters, numbers, delimiters, etc., that indicate where the field begins and, optionally, ends.

Figure 23A:
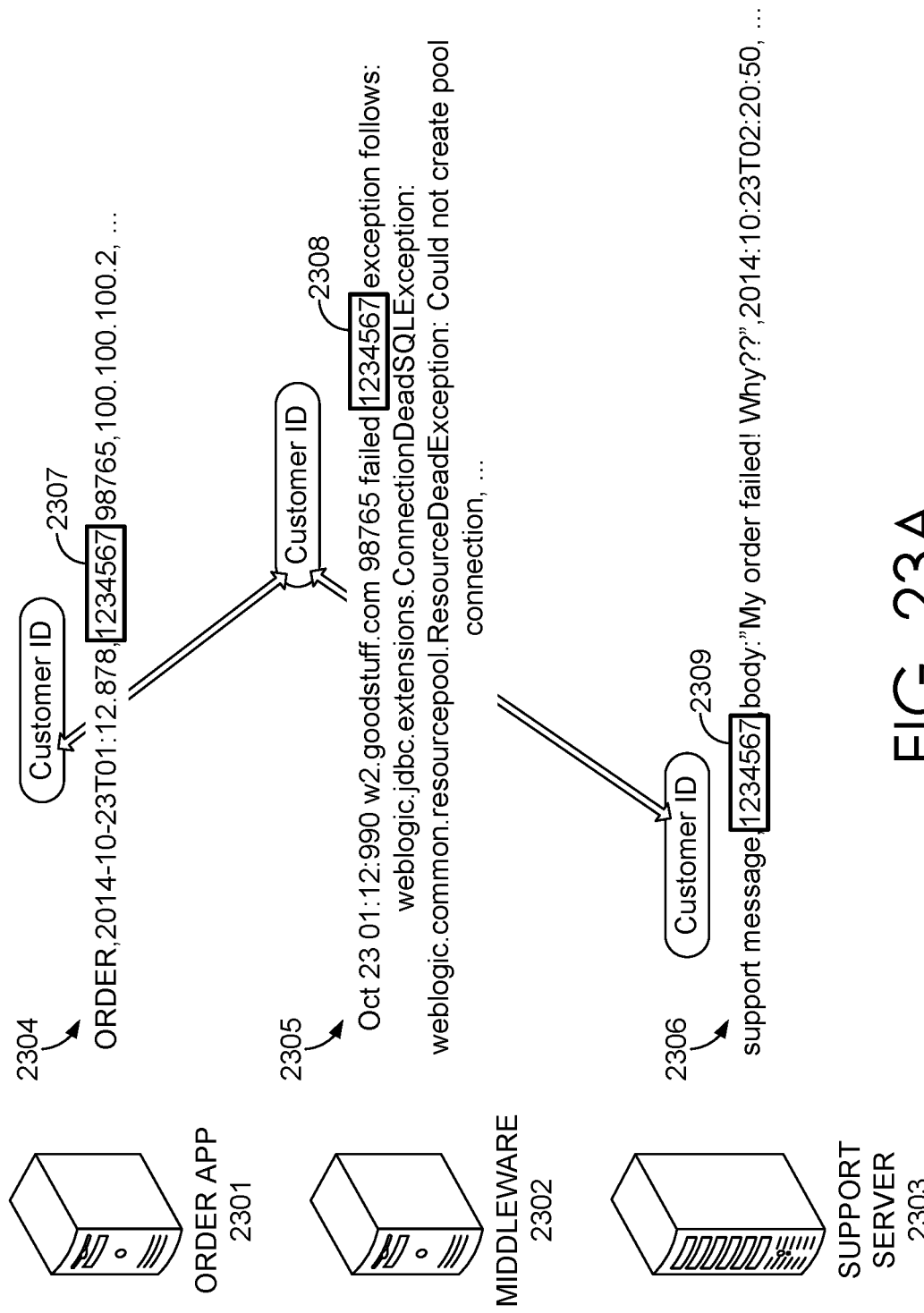
FIG. 23A is a diagram of an example scenario where a common customer identifier is found among log data received from three disparate data sources, in accordance with example embodiments.

FIG. 23A is a diagram of an example scenario where a common customer identifier is found among log data received from three disparate data sources, in accordance with example embodiments. In this example, a user submits an order for merchandise using a vendor's shopping application program 2301 running on the user's system. In this example, the order was not delivered to the vendor's server due to a resource exception at the destination server that is detected by the middleware code 2302. The user then sends a message to the customer support server 2303 to complain about the order failing to complete. The three systems 2301, 2302, and 2303 are disparate systems that do not have a common logging format. The order application 2301 sends log data 2304 to the data intake and query system 108 in one format, the middleware code 2302 sends error log data 2305 in a second format, and the support server 2303 sends log data 2306 in a third format.

Using the log data received at the data intake and query system 108 from the three systems, the vendor can uniquely obtain an insight into user activity, user experience, and system behavior. The query system 214 allows the vendor's administrator to search the log data from the three systems, thereby obtaining correlated information, such as the order number and corresponding customer ID number of the person placing the order. The system also allows the administrator to see a visualization of related events via a user interface. The administrator can query the query system 214 for customer ID field value matches across the log data from the three systems that are stored in common storage 216. The customer ID field value exists in the data gathered from the three systems, but the customer ID field value may be located in different areas of the data given differences in the architecture of the systems. There is a semantic relationship between the customer ID field values generated by the three systems. The query system 214 requests events from the one or more data stores 218 to gather relevant events from the three systems. The search head 504 then applies extraction rules to the events in order to extract field values that it can correlate. The search head 504 may apply a different extraction rule to each set of events from each system when the event format differs among systems. In this example, the user interface can display to the administrator the events corresponding to the common customer ID field values 2307, 2308, and 2309, thereby providing the administrator with insight into a customer's experience.

Note that query results can be returned to a client, a search head 504, or any other system component for further processing. In general, query results may include a set of one or more events, a set of one or more values obtained from the events, a subset of the values, statistics calculated based on the values, a report containing the values, a visualization (e.g., a graph or chart) generated from the values, and the like.

Figure 23B:
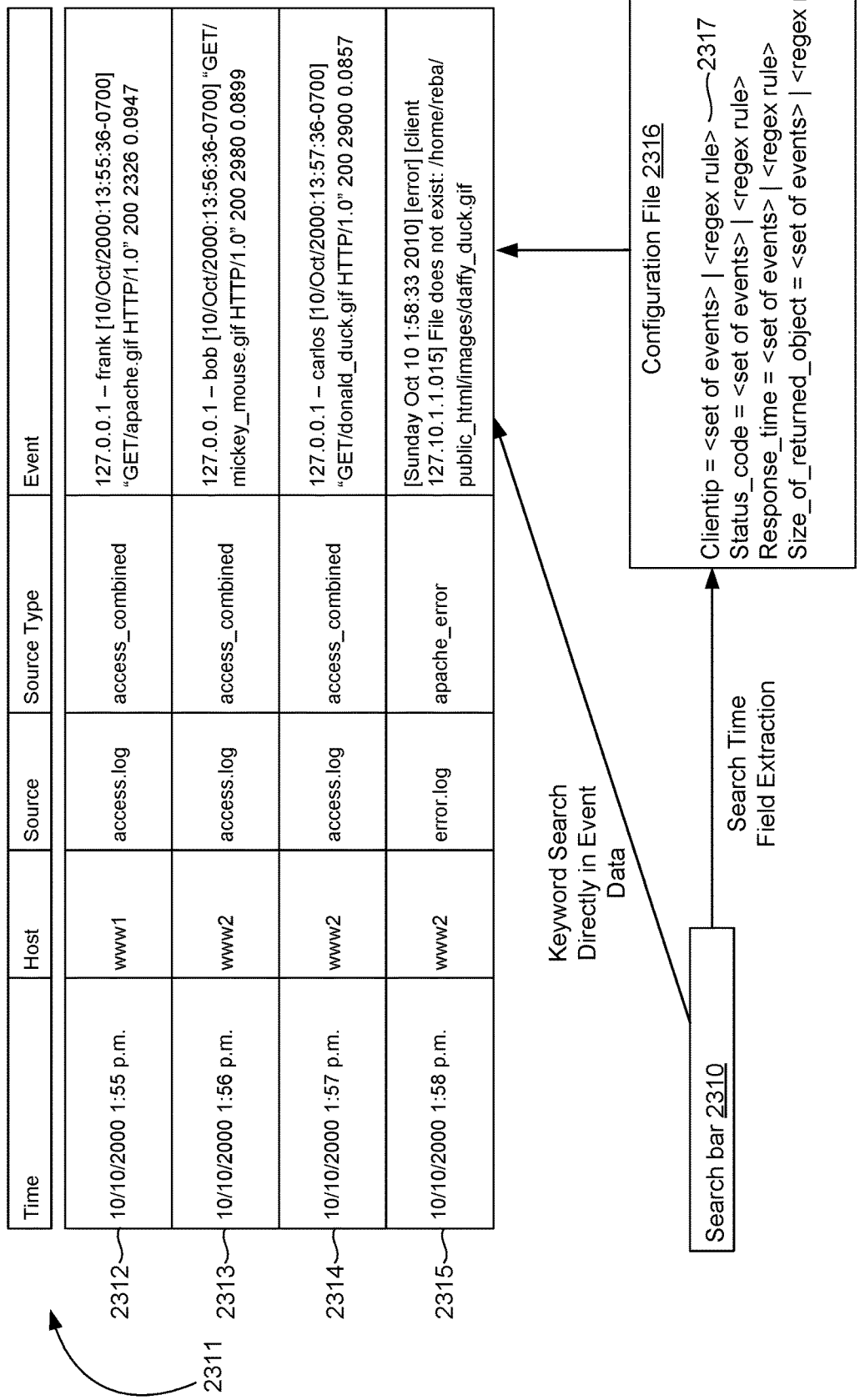
FIG. 23B illustrates an example of processing keyword searches and field searches, in accordance with disclosed embodiments.

The query system 214 enables users to run queries against the stored data to retrieve events that meet criteria specified in a query, such as containing certain keywords or having specific values in defined fields. FIG. 23B illustrates the manner in which keyword searches and field searches are processed in accordance with disclosed embodiments.

If a user inputs a search query into search bar 2310 that includes only keywords (also known as "tokens"), e.g., the keyword "error" or "warning", the query system 214 of the data intake and query system 108 can search for those keywords directly in the event data 2311 stored in the raw record data store. Note that while FIG. 23B only illustrates four events 2312, 2313, 2314, 2315, the raw record data store (corresponding to data store 212 in FIG. 2) may contain records for millions of events.

As disclosed above, the indexing system 212 can optionally generate a keyword index to facilitate fast keyword searching for event data. The indexing system 212 can include the identified keywords in an index, which associates each stored keyword with reference pointers to events containing that keyword (or to locations within events where that keyword is located, other location identifiers, etc.). When the query system 214 subsequently receives a keyword-based query, the query system 214 can access the keyword index to quickly identify events containing the keyword. For example, if the keyword "HTTP" was indexed by the indexing system 212 at index time, and the user searches for the keyword "HTTP", the events 2312, 2313, and 2314, will be identified based on the results returned from the keyword index. As noted above, the index contains reference pointers to the events containing the keyword, which allows for efficient retrieval of the relevant events from the raw record data store.

If a user searches for a keyword that has not been indexed by the indexing system 212, the data intake and query system 108 may nevertheless be able to retrieve the events by searching the event data for the keyword in the raw record data store directly as shown in FIG. 23B. For example, if a user searches for the keyword "frank", and the name "frank" has not been indexed at search time, the query system 214 can search the event data directly and return the first event 2312. Note that whether the keyword has been indexed at index time or search time or not, in both cases the raw data with the events 2311 is accessed from the raw data record store to service the keyword search. In the case where the keyword has been indexed, the index will contain a reference pointer that will allow for a more efficient retrieval of the event data from the data store. If the keyword has not been indexed, the query system 214 can search through the records in the data store to service the search.

In most cases, however, in addition to keywords, a user's search will also include fields. The term "field" refers to a location in the event data containing one or more values for a specific data item. Often, a field is a value with a fixed, delimited position on a line, or a name and value pair, where there is a single value to each field name. A field can also be multivalued, that is, it can appear more than once in an event and have a different value for each appearance, e.g., email address fields. Fields are searchable by the field name or field name-value pairs. Some examples of fields are "clientip" for IP addresses accessing a web server, or the "From" and "To" fields in email addresses.

By way of further example, consider the search, "status=404". This search query finds events with "status" fields that have a value of "404." When the search is run, the query system 214 does not look for events with any other "status" value. It also does not look for events containing other fields that share "404" as a value. As a result, the search returns a set of results that are more focused than if "404" had been used in the search string as part of a keyword search. Note also that fields can appear in events as "key=value" pairs such as "user_name=Bob." But in most cases, field values appear in fixed, delimited positions without identifying keys. For example, the data store may contain events where the "user_name" value always appears by itself after the timestamp as illustrated by the following string: "Nov 15 09:33:22 johnmedlock."

The data intake and query system 108 advantageously allows for search time field extraction. In other words, fields can be extracted from the event data at search time using late-binding schema as opposed to at data ingestion time, which was a major limitation of the prior art systems.

In response to receiving the search query, a search head 504 of the query system 214 can use extraction rules to extract values for the fields associated with a field or fields in the event data being searched. The search head 504 can obtain extraction rules that specify how to extract a value for certain fields from an event. Extraction rules can comprise regex rules that specify how to extract values for the relevant fields. In addition to specifying how to extract field values, the extraction rules may also include instructions for deriving a field value by performing a function on a character string or value retrieved by the extraction rule. For example, a transformation rule may truncate a character string, or convert the character string into a different data format. In some cases, the query itself can specify one or more extraction rules.

FIG. 23B illustrates the manner in which configuration files may be used to configure custom fields at search time in accordance with the disclosed embodiments. In response to receiving a search query, the data intake and query system 108 determines if the query references a "field." For example, a query may request a list of events where the "clientip" field equals "127.0.0.1." If the query itself does not specify an extraction rule and if the field is not a metadata field, e.g., time, host, source, source type, etc., then in order to determine an extraction rule, the query system 214 may, in one or more embodiments, need to locate configuration file 2316 during the execution of the search as shown in FIG. 23B.

Configuration file 2316 may contain extraction rules for all the various fields that are not metadata fields, e.g., the "clientip" field. The extraction rules may be inserted into the configuration file in a variety of ways. In some embodiments, the extraction rules can comprise regular expression rules that are manually entered in by the user. Regular expressions match patterns of characters in text and are used for extracting custom fields in text.

In one or more embodiments, as noted above, a field extractor may be configured to automatically generate extraction rules for certain field values in the events when the events are being created, indexed, or stored, or possibly at a later time. In one embodiment, a user may be able to dynamically create custom fields by highlighting portions of a sample event that should be extracted as fields using a graphical user interface. The system can then generate a regular expression that extracts those fields from similar events and store the regular expression as an extraction rule for the associated field in the configuration file 2316.

In some embodiments, the indexing system 212 can automatically discover certain custom fields at index time and the regular expressions for those fields will be automatically generated at index time and stored as part of extraction rules in configuration file 2316. For example, fields that appear in the event data as "key=value" pairs may be automatically extracted as part of an automatic field discovery process. Note that there may be several other ways of adding field definitions to configuration files in addition to the methods discussed herein.

The search head 504 can apply the extraction rules derived from configuration file 2316 to event data that it receives from search nodes 506. The search nodes 506 may apply the extraction rules from the configuration file to events in an associated data store or common storage 216. Extraction rules can be applied to all the events in a data store, or to a subset of the events that have been filtered based on some criteria (e.g., event time stamp values, etc.). Extraction rules can be used to extract one or more values for a field from events by parsing the event data and examining the event data for one or more patterns of characters, numbers, delimiters, etc., that indicate where the field begins and, optionally, ends.

In one more embodiments, the extraction rule in configuration file 2316 will also need to define the type or set of events that the rule applies to. Because the raw record data store will contain events from multiple heterogeneous sources, multiple events may contain the same fields in different locations because of discrepancies in the format of the data generated by the various sources. Furthermore, certain events may not contain a particular field at all. For example, event 2315 also contains "clientip" field, however, the "clientip" field is in a different format from events 2312, 2313, and 2314. To address the discrepancies in the format and content of the different types of events, the configuration file will also need to specify the set of events that an extraction rule applies to, e.g., extraction rule 2317 specifies a rule for filtering by the type of event and contains a regular expression for parsing out the field value. Accordingly, each extraction rule can pertain to only a particular type of event. If a particular field, e.g., "clientip" occurs in multiple types of events, each of those types of events can have its own corresponding extraction rule in the configuration file 2316 and each of the extraction rules would comprise a different regular expression to parse out the associated field value. The most common way to categorize events is by source type because events generated by a particular source can have the same format.

The field extraction rules stored in configuration file 2316 perform search-time field extractions. For example, for a query that requests a list of events with source type "access_combined" where the "clientip" field equals "127.0.0.1," the query system 214 can first locate the configuration file 2316 to retrieve extraction rule 2317 that allows it to extract values associated with the "clientip" field from the event data 2320 "where the source type is" access_combined. After the "clientip" field has been extracted from all the events comprising the "clientip" field where the source type is "access_combined," the query system 214 can then execute the field criteria by performing the compare operation to filter out the events where the "clientip" field equals "127.0.0.1." In the example shown in FIG. 23B, the events 2312, 2313, and 2314 would be returned in response to the user query. In this manner, the query system 214 can service queries containing field criteria in addition to queries containing keyword criteria (as explained above).

In some embodiments, the configuration file 2316 can be created during indexing. It may either be manually created by the user or automatically generated with certain predetermined field extraction rules. As discussed above, the events may be distributed across several data stores in common storage 216, wherein various indexing nodes 404 may be responsible for storing the events in the common storage 216 and various search nodes 506 may be responsible for searching the events contained in common storage 216.

The ability to add schema to the configuration file at search time results in increased efficiency. A user can create new fields at search time and simply add field definitions to the configuration file. As a user learns more about the data in the events, the user can continue to refine the late-binding schema by adding new fields, deleting fields, or modifying the field extraction rules in the configuration file for use the next time the schema is used by the system. Because the data intake and query system 108 maintains the underlying raw data and uses late-binding schema for searching the raw data, it enables a user to continue investigating and learn valuable insights about the raw data long after data ingestion time.

The ability to add multiple field definitions to the configuration file at search time also results in increased flexibility. For example, multiple field definitions can be added to the configuration file to capture the same field across events generated by different source types. This allows the data intake and query system 108 to search and correlate data across heterogeneous sources flexibly and efficiently.

Further, by providing the field definitions for the queried fields at search time, the configuration file 2316 allows the record data store to be field searchable. In other words, the raw record data store can be searched using keywords as well as fields, wherein the fields are searchable name/value pairings that distinguish one event from another and can be defined in configuration file 2316 using extraction rules. In comparison to a search containing field names, a keyword search does not need the configuration file and can search the event data directly as shown in FIG. 23B.

It should also be noted that any events filtered out by performing a search-time field extraction using a configuration file 2316 can be further processed by directing the results of the filtering step to a processing step using a pipelined search language. Using the prior example, a user can pipeline the results of the compare step to an aggregate function by asking the query system 214 to count the number of events where the "clientip" field equals "127.0.0.1."

4.8. Example Search Screen

Figure 24A:
FIG. 24A is an interface diagram of an example user interface for a search screen, in accordance with example embodiments.

FIG. 24A is an interface diagram of an example user interface for a search screen 2400, in accordance with example embodiments. Search screen 2400 includes a search bar 2402 that accepts user input in the form of a search string. It also includes a time range picker 2412 that enables the user to specify a time range for the search. For historical searches (e.g., searches based on a particular historical time range), the user can select a specific time range, or alternatively a relative time range, such as "today," "yesterday" or "last week." For real-time searches (e.g., searches whose results are based on data received in real-time), the user can select the size of a preceding time window to search for real-time events. Search screen 2400 also initially displays a "data summary" dialog as is illustrated in FIG. 24B that enables the user to select different sources for the events, such as by selecting specific hosts and log files.

After the search is executed, the search screen 2400 in FIG. 24A can display the results through search results tabs 2404, wherein search results tabs 2404 includes: an "events tab" that displays various information about events returned by the search; a "statistics tab" that displays statistics about the search results; and a "visualization tab" that displays various visualizations of the search results. The events tab illustrated in FIG. 24A displays a timeline graph 2405 that graphically illustrates the number of events that occurred in one-hour intervals over the selected time range. The events tab also displays an events list 2408 that enables a user to view the machine data in each of the returned events.

The events tab additionally displays a sidebar that is an interactive field picker 2406. The field picker 2406 may be displayed to a user in response to the search being executed and allows the user to further analyze the search results based on the fields in the events of the search results. The field picker 2406 includes field names that reference fields present in the events in the search results. The field picker may display any Selected Fields 2420 that a user has pre-selected for display (e.g., host, source, sourcetype) and may also display any Interesting Fields 2422 that the system determines may be interesting to the user based on pre-specified criteria (e.g., action, bytes, categoryid, clientip, date_hour, date_mday, date_minute, etc.). The field picker also provides an option to display field names for all the fields present in the events of the search results using the All Fields control 2424.

Each field name in the field picker 2406 has a value type identifier to the left of the field name, such as value type identifier 2426. A value type identifier identifies the type of value for the respective field, such as an "a" for fields that include literal values or a "#" for fields that include numerical values.

Each field name in the field picker also has a unique value count to the right of the field name, such as unique value count 2428. The unique value count indicates the number of unique values for the respective field in the events of the search results.

Each field name is selectable to view the events in the search results that have the field referenced by that field name. For example, a user can select the "host" field name, and the events shown in the events list 2408 will be updated with events in the search results that have the field that is reference by the field name "host."

4.9. Data Models

A data model is a hierarchically structured search-time mapping of semantic knowledge about one or more datasets. It encodes the domain knowledge used to build a variety of specialized searches of those datasets. Those searches, in turn, can be used to generate reports.

A data model is composed of one or more "objects" (or "data model objects") that define or otherwise correspond to a specific set of data. An object is defined by constraints and attributes. An object's constraints are search criteria that define the set of events to be operated on by running a search having that search criteria at the time the data model is selected. An object's attributes are the set of fields to be exposed for operating on that set of events generated by the search criteria.

Objects in data models can be arranged hierarchically in parent/child relationships. Each child object represents a subset of the dataset covered by its parent object. The top-level objects in data models are collectively referred to as "root objects."

Child objects have inheritance. Child objects inherit constraints and attributes from their parent objects and may have additional constraints and attributes of their own. Child objects provide a way of filtering events from parent objects. Because a child object may provide an additional constraint in addition to the constraints it has inherited from its parent object, the dataset it represents may be a subset of the dataset that its parent represents. For example, a first data model object may define a broad set of data pertaining to e-mail activity generally, and another data model object may define specific datasets within the broad dataset, such as a subset of the e-mail data pertaining specifically to e-mails sent. For example, a user can simply select an "e-mail activity" data model object to access a dataset relating to e-mails generally (e.g., sent or received), or select an "e-mails sent" data model object (or data sub-model object) to access a dataset relating to e-mails sent.

Because a data model object is defined by its constraints (e.g., a set of search criteria) and attributes (e.g., a set of fields), a data model object can be used to quickly search data to identify a set of events and to identify a set of fields to be associated with the set of events. For example, an "e-mails sent" data model object may specify a search for events relating to e-mails that have been sent, and specify a set of fields that are associated with the events. Thus, a user can retrieve and use the "e-mails sent" data model object to quickly search source data for events relating to sent e-mails, and may be provided with a listing of the set of fields relevant to the events in a user interface screen.

Examples of data models can include electronic mail, authentication, databases, intrusion detection, malware, application state, alerts, compute inventory, network sessions, network traffic, performance, audits, updates, vulnerabilities, etc. Data models and their objects can be designed by knowledge managers in an organization, and they can enable downstream users to quickly focus on a specific set of data. A user iteratively applies a model development tool (not shown in FIG. 24A) to prepare a query that defines a subset of events and assigns an object name to that subset. A child subset is created by further limiting a query that generated a parent subset.

Data definitions in associated schemas can be taken from the common information model (CIM) or can be devised for a particular schema and optionally added to the CIM. Child objects inherit fields from parents and can include fields not present in parents. A model developer can select fewer extraction rules than are available for the sources returned by the query that defines events belonging to a model. Selecting a limited set of extraction rules can be a tool for simplifying and focusing the data model, while allowing a user flexibility to explore the data subset. Development of a data model is further explained in U.S. Pat. Nos. 8,788,525 and 8,788,526, both entitled "DATA MODEL FOR MACHINE DATA FOR SEMANTIC SEARCH", both issued on 22 Jul. 2014, U.S. Pat. No. 8,983,994, entitled "GENERATION OF A DATA MODEL FOR SEARCHING MACHINE DATA", issued on 17 Mar. 2015, U.S. Pat. No. 9,128,980, entitled "GENERATION OF A DATA MODEL APPLIED TO QUERIES", issued on 8 Sep. 2015, and U.S. Pat. No. 9,589,012, entitled "GENERATION OF A DATA MODEL APPLIED TO OBJECT QUERIES", issued on 7 Mar. 2017, each of which is hereby incorporated by reference in its entirety for all purposes.

A data model can also include reports. One or more report formats can be associated with a particular data model and be made available to run against the data model. A user can use child objects to design reports with object datasets that already have extraneous data pre-filtered out. In some embodiments, the data intake and query system 108 provides the user with the ability to produce reports (e.g., a table, chart, visualization, etc.) without having to enter SPL, SQL, or other query language terms into a search screen. Data models are used as the basis for the search feature.

Data models may be selected in a report generation interface. The report generator supports drag-and-drop organization of fields to be summarized in a report. When a model is selected, the fields with available extraction rules are made available for use in the report. The user may refine and/or filter search results to produce more precise reports. The user may select some fields for organizing the report and select other fields for providing detail according to the report organization. For example, "region" and "salesperson" are fields used for organizing the report and sales data can be summarized (subtotaled and totaled) within this organization. The report generator allows the user to specify one or more fields within events and apply statistical analysis on values extracted from the specified one or more fields. The report generator may aggregate search results across sets of events and generate statistics based on aggregated search results. Building reports using the report generation interface is further explained in U.S. patent application Ser. No. 14/503,335, entitled "GENERATING REPORTS FROM UNSTRUCTURED DATA", filed on 30 Sep. 2014, and which is hereby incorporated by reference in its entirety for all purposes. Data visualizations also can be generated in a variety of formats, by reference to the data model. Reports, data visualizations, and data model objects can be saved and associated with the data model for future use. The data model object may be used to perform searches of other data.

FIGS. 25-31 are interface diagrams of example report generation user interfaces, in accordance with example embodiments. The report generation process may be driven by a predefined data model object, such as a data model object defined and/or saved via a reporting application or a data model object obtained from another source. A user can load a saved data model object using a report editor. For example, the initial search query and fields used to drive the report editor may be obtained from a data model object. The data model object that is used to drive a report generation process may define a search and a set of fields. Upon loading of the data model object, the report generation process may enable a user to use the fields (e.g., the fields defined by the data model object) to define criteria for a report (e.g., filters, split rows/columns, aggregates, etc.) and the search may be used to identify events (e.g., to identify events responsive to the search) used to generate the report. That is, for example, if a data model object is selected to drive a report editor, the graphical user interface of the report editor may enable a user to define reporting criteria for the report using the fields associated with the selected data model object, and the events used to generate the report may be constrained to the events that match, or otherwise satisfy, the search constraints of the selected data model object.

Figure 25:
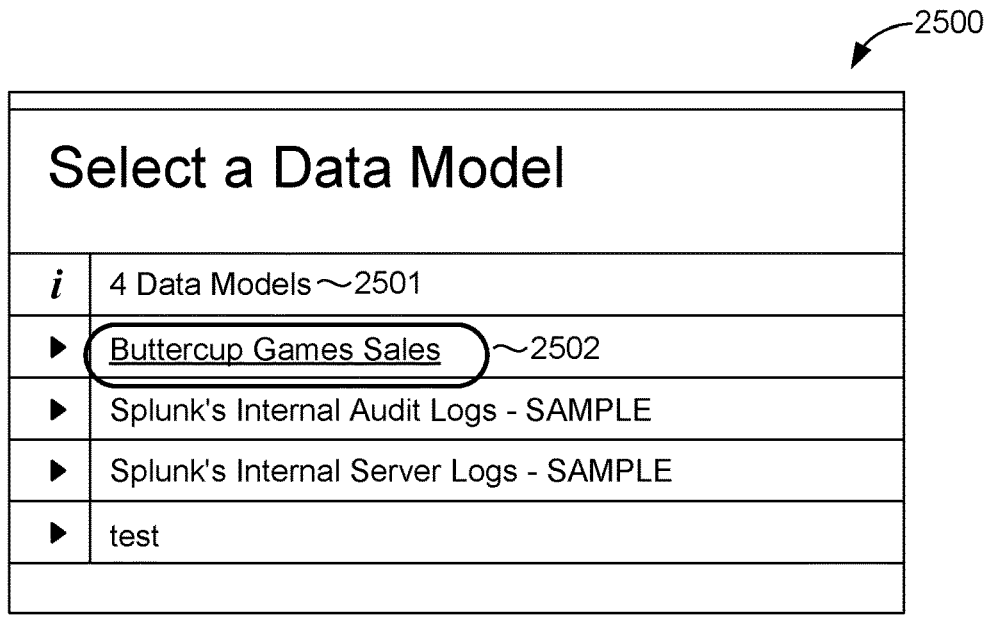

The selection of a data model object for use in driving a report generation may be facilitated by a data model object selection interface. FIG. 25 illustrates an example interactive data model selection graphical user interface 2500 of a report editor that displays a listing of available data models 2501. The user may select one of the data models 2502.

Figure 26:
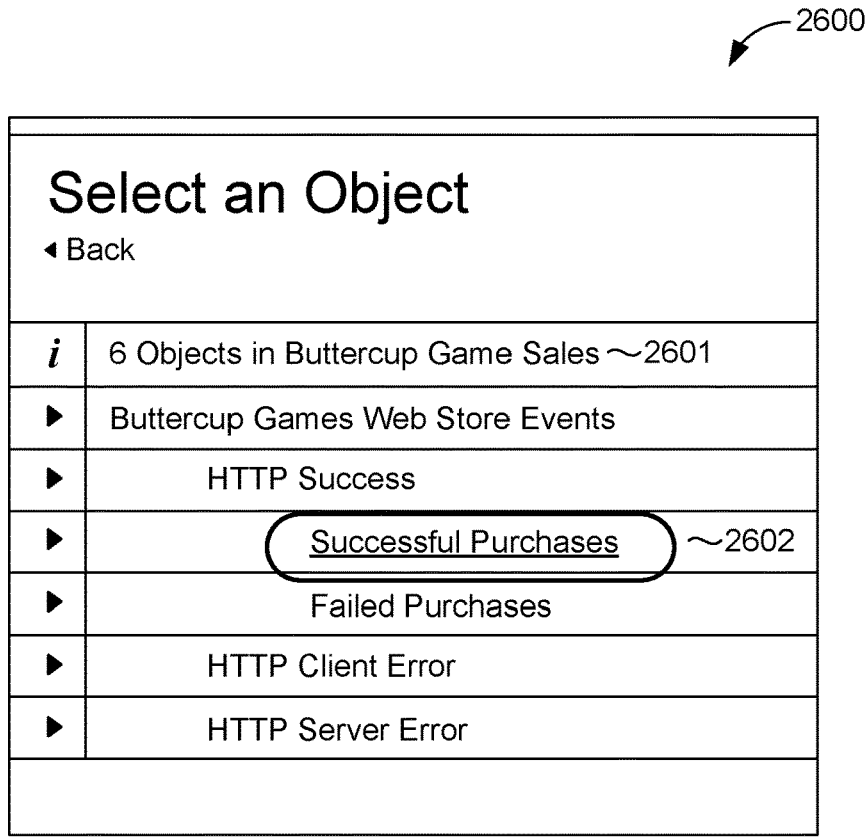

FIG. 26 illustrates an example data model object selection graphical user interface 2600 that displays available data objects 2601 for the selected data object model 2502. The user may select one of the displayed data model objects 2602 for use in driving the report generation process.

Figure 27A:
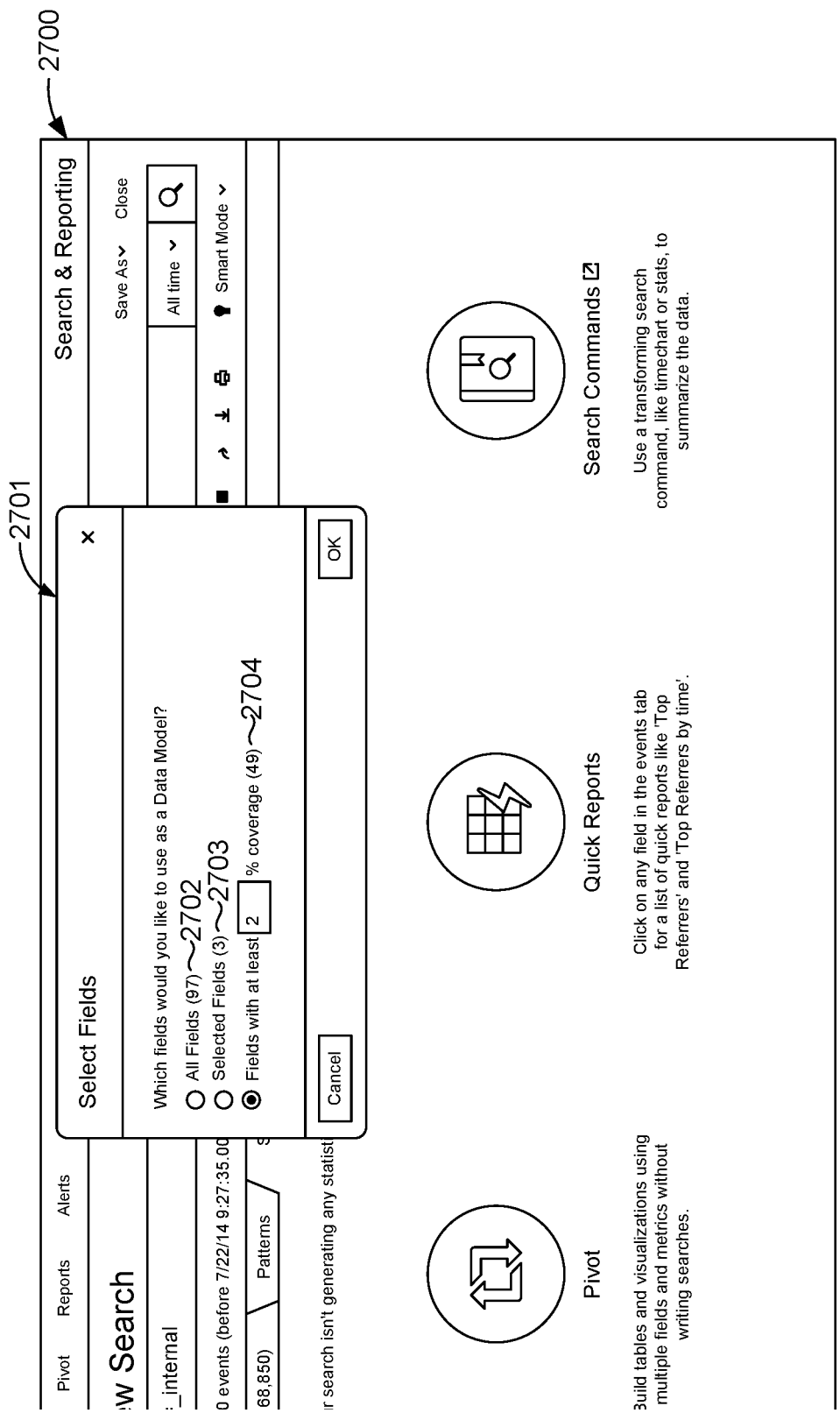

Once a data model object is selected by the user, a user interface screen 2700 shown in FIG. 27A may display an interactive listing of automatic field identification options 2701 based on the selected data model object. For example, a user may select one of the three illustrated options (e.g., the "All Fields" option 2702, the "Selected Fields" option 2703, or the "Coverage" option (e.g., fields with at least a specified % of coverage) 2704). If the user selects the "All Fields" option 2702, all of the fields identified from the events that were returned in response to an initial search query may be selected. That is, for example, all of the fields of the identified data model object fields may be selected. If the user selects the "Selected Fields" option 2703, only the fields from the fields of the identified data model object fields that are selected by the user may be used. If the user selects the "Coverage" option 2704, only the fields of the identified data model object fields meeting a specified coverage criteria may be selected. A percent coverage may refer to the percentage of events returned by the initial search query that a given field appears in. Thus, for example, if an object dataset includes 10,000 events returned in response to an initial search query, and the "avg_age" field appears in 854 of those 10,000 events, then the "avg_age" field would have a coverage of 8.54% for that object dataset. If, for example, the user selects the "Coverage" option and specifies a coverage value of 2%, only fields having a coverage value equal to or greater than 2% may be selected. The number of fields corresponding to each selectable option may be displayed in association with each option. For example, "97" displayed next to the "All Fields" option 2702 indicates that 97 fields will be selected if the "All Fields" option is selected. The "3" displayed next to the "Selected Fields" option 2703 indicates that 3 of the 97 fields will be selected if the "Selected Fields" option is selected. The "49" displayed next to the "Coverage" option 2704 indicates that 49 of the 97 fields (e.g., the 49 fields having a coverage of 2% or greater) will be selected if the "Coverage" option is selected. The number of fields corresponding to the "Coverage" option may be dynamically updated based on the specified percent of coverage.

Figure 27B:
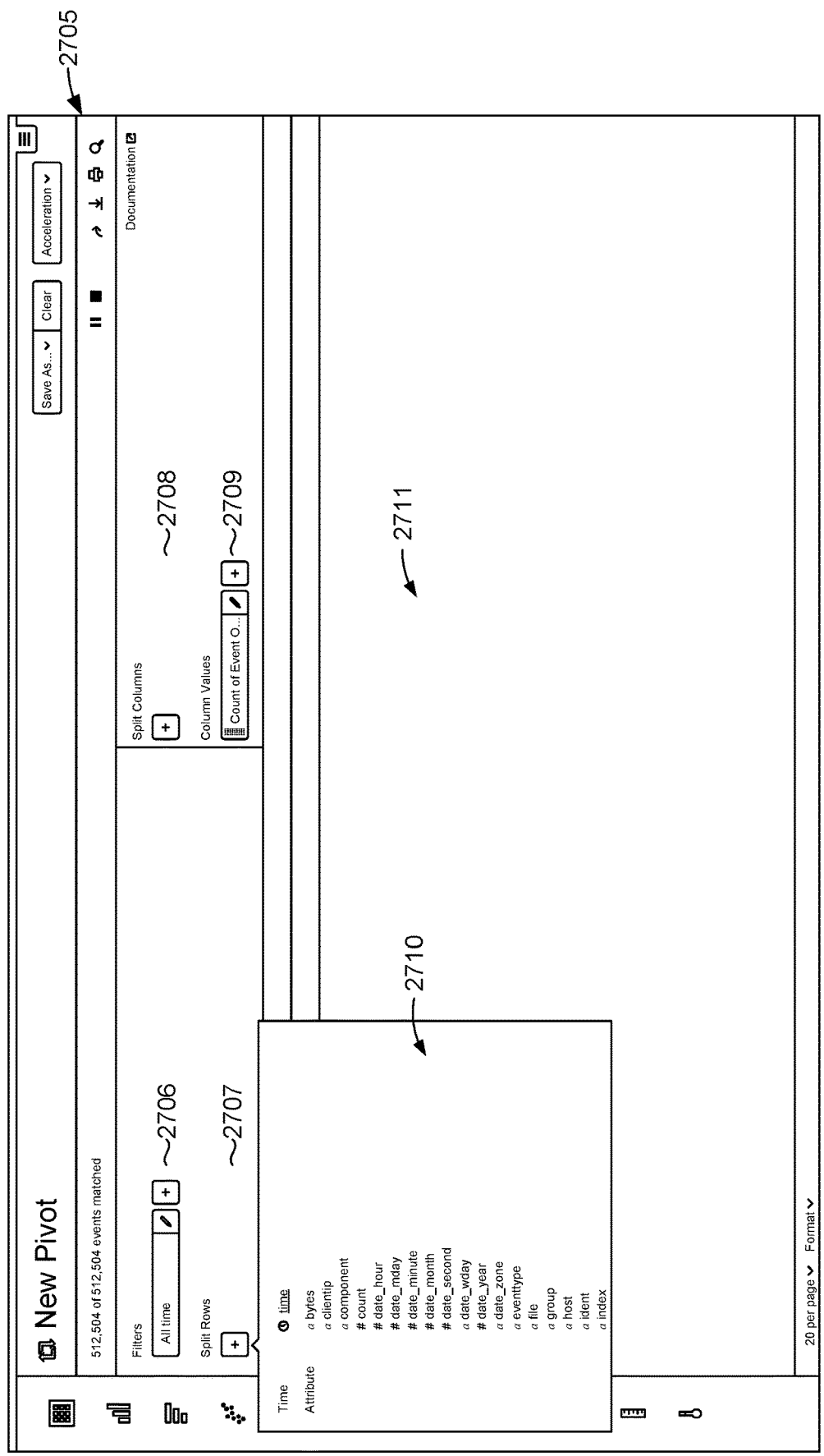
Figure 27C:
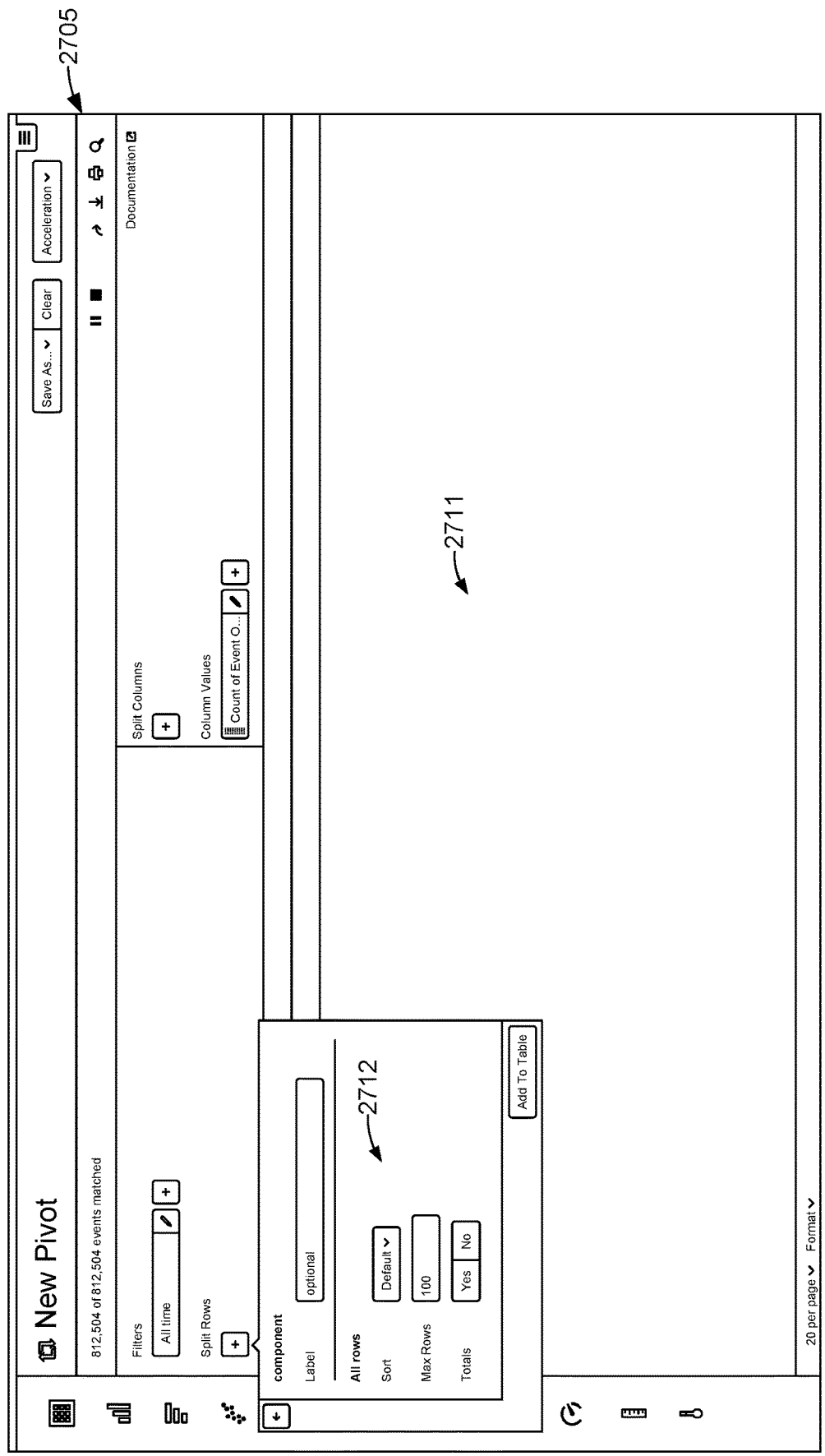

FIG. 27B illustrates an example graphical user interface screen 2705 displaying the reporting application's "Report Editor" page. The screen may display interactive elements for defining various elements of a report. For example, the page includes a "Filters" element 2706, a "Split Rows" element 2707, a "Split Columns" element 2708, and a "Column Values" element 2709. The page may include a list of search results 2711. In this example, the Split Rows element 2707 is expanded, revealing a listing of fields 2710 that can be used to define additional criteria (e.g., reporting criteria). The listing of fields 2710 may correspond to the selected fields. That is, the listing of fields 2710 may list only the fields previously selected, either automatically and/or manually by a user. FIG. 27C illustrates a formatting dialogue 2712 that may be displayed upon selecting a field from the listing of fields 2710. The dialogue can be used to format the display of the results of the selection (e.g., label the column for the selected field to be displayed as "component").

Figure 27D:
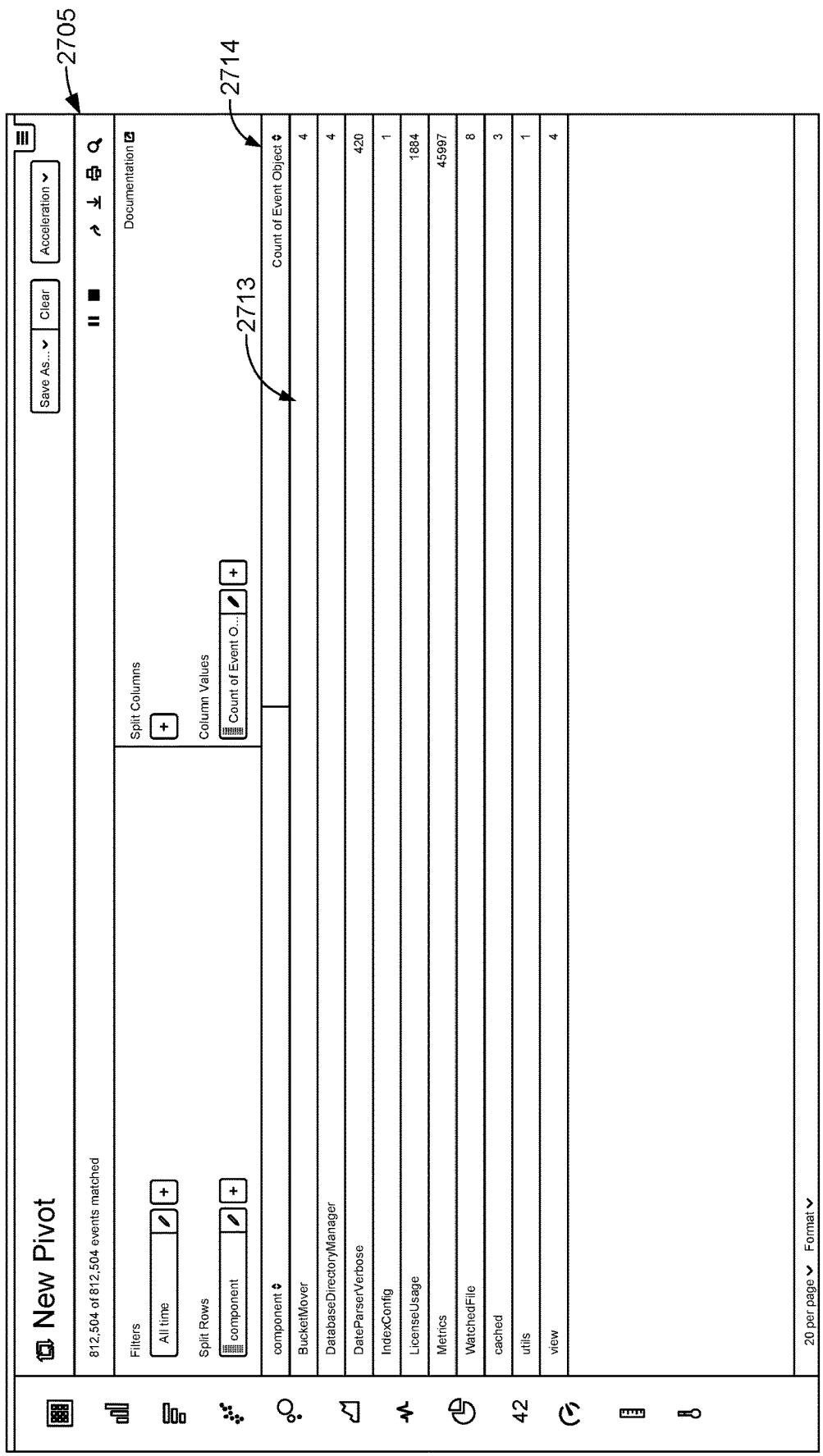

FIG. 27D illustrates an example graphical user interface screen 2705 including a table of results 2713 based on the selected criteria including splitting the rows by the "component" field. A column 2714 having an associated count for each component listed in the table may be displayed that indicates an aggregate count of the number of times that the particular field-value pair (e.g., the value in a row for a particular field, such as the value "BucketMover" for the field "component") occurs in the set of events responsive to the initial search query.

Figure 28:
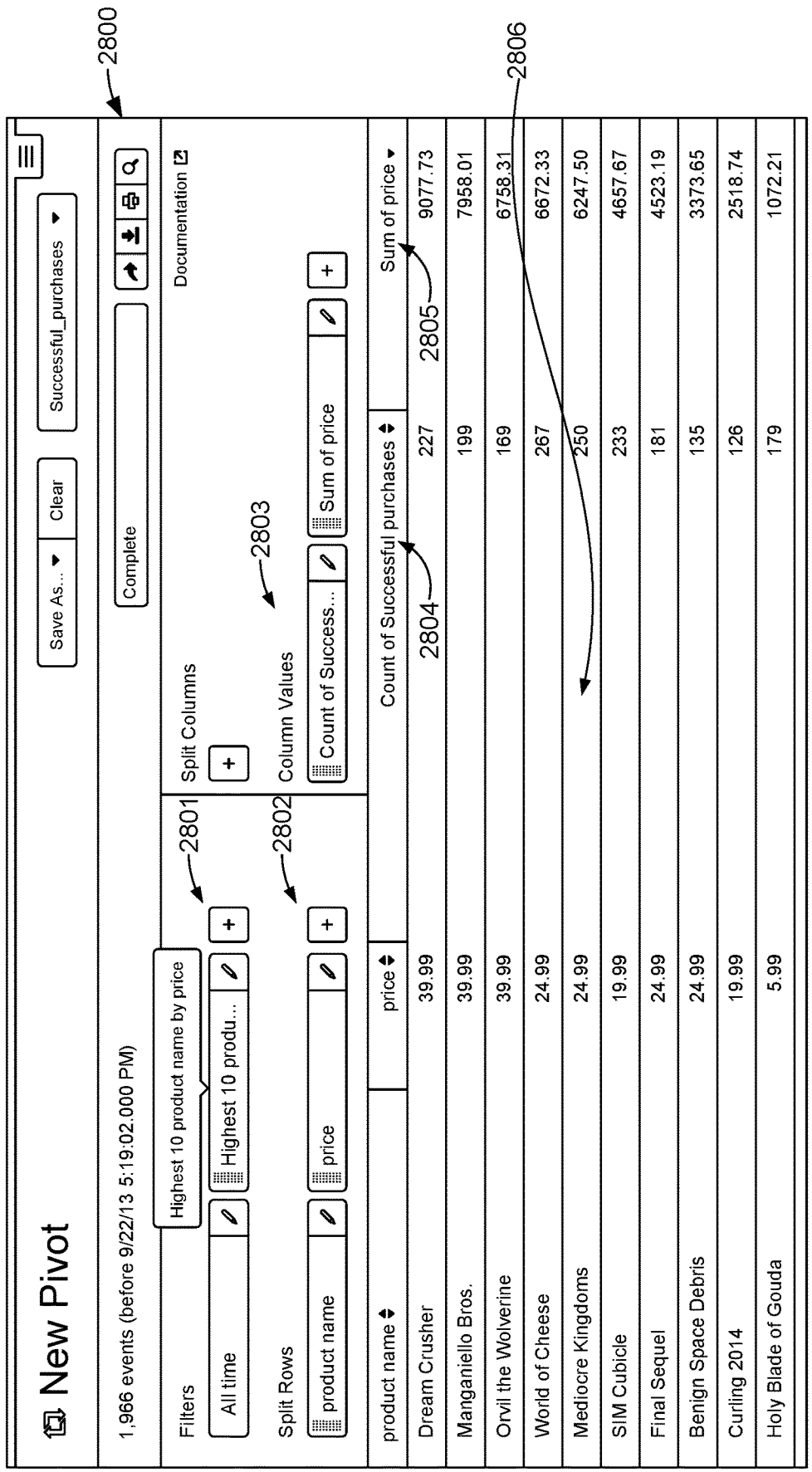

FIG. 28 illustrates an example graphical user interface screen 2800 that allows the user to filter search results and to perform statistical analysis on values extracted from specific fields in the set of events. In this example, the top ten product names ranked by price are selected as a filter 2801 that causes the display of the ten most popular products sorted by price. Each row is displayed by product name and price 2802. This results in each product displayed in a column labeled "product name" along with an associated price in a column labeled "price" 2806. Statistical analysis of other fields in the events associated with the ten most popular products have been specified as column values 2803. A count of the number of successful purchases for each product is displayed in column 2804. These statistics may be produced by filtering the search results by the product name, finding all occurrences of a successful purchase in a field within the events and generating a total of the number of occurrences. A sum of the total sales is displayed in column 2805, which is a result of the multiplication of the price and the number of successful purchases for each product.

Figure 30:
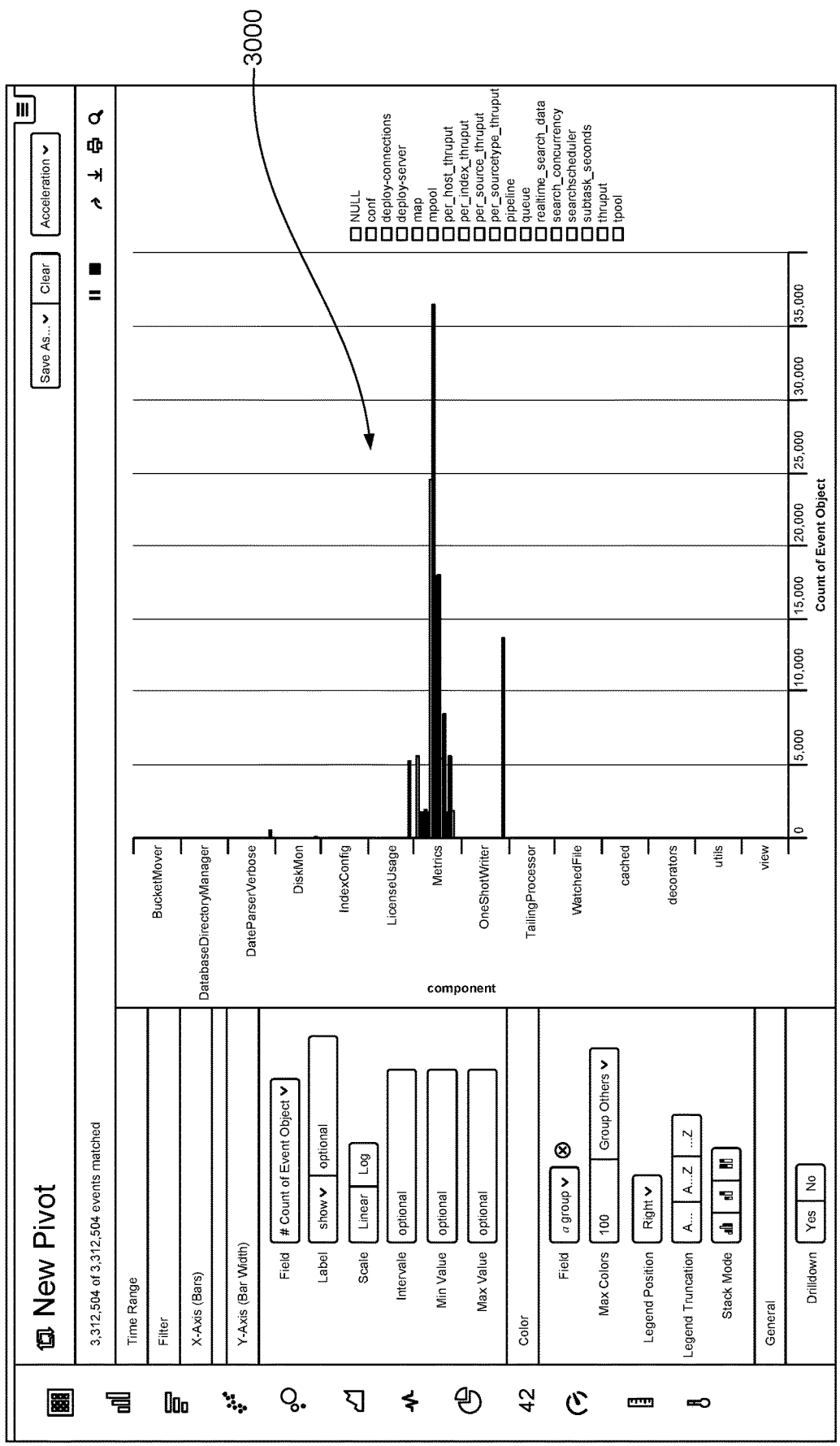
Figure 31:
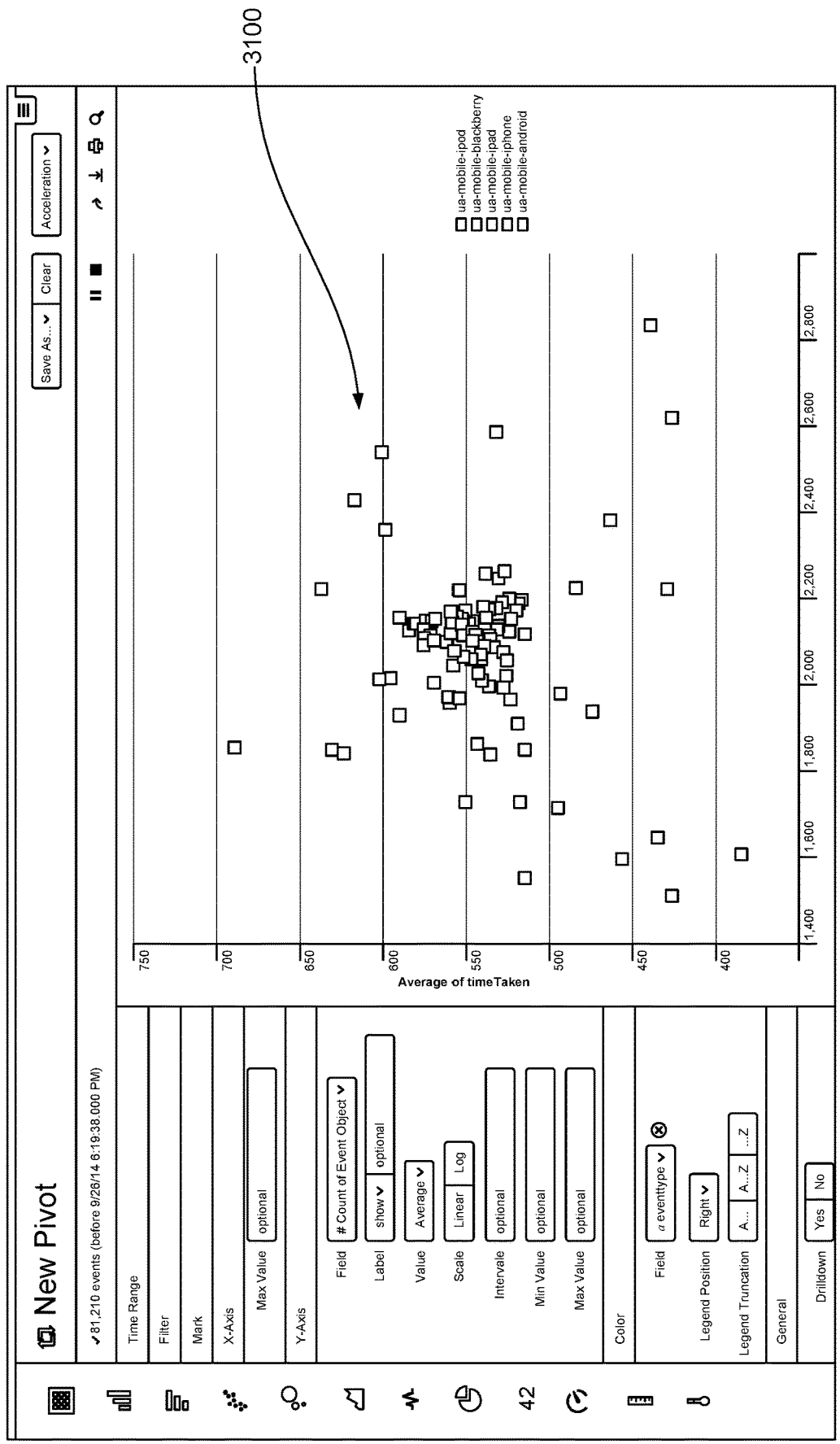

The reporting application allows the user to create graphical visualizations of the statistics generated for a report. For example, FIG. 29 illustrates an example graphical user interface 2900 that displays a set of components and associated statistics 2901. The reporting application allows the user to select a visualization of the statistics in a graph (e.g., bar chart, scatter plot, area chart, line chart, pie chart, radial gauge, marker gauge, filler gauge, etc.), where the format of the graph may be selected using the user interface controls 2902 along the left panel of the user interface 2900. FIG. 30 illustrates an example of a bar chart visualization 3000 of an aspect of the statistical data 2901. FIG. 31 illustrates a scatter plot visualization 3100 of an aspect of the statistical data 2901.

4.10. Acceleration Techniques

The above-described system provides significant flexibility by enabling a user to analyze massive quantities of minimally-processed data "on the fly" at search time using a late-binding schema, instead of storing pre-specified portions of the data in a database at ingestion time. This flexibility enables a user to see valuable insights, correlate data, and perform subsequent queries to examine interesting aspects of the data that may not have been apparent at ingestion time.

However, performing extraction and analysis operations at search time can involve a large amount of data and require a large number of computational operations, which can cause delays in processing the queries. Advantageously, the data intake and query system 108 also employs a number of unique acceleration techniques that have been developed to speed up analysis operations performed at search time. These techniques include: (1) performing search operations in parallel using multiple search nodes 506; (2) using a keyword index; (3) using a high performance analytics store; and (4) accelerating the process of generating reports. These novel techniques are described in more detail below.

4.10.1. Aggregation Technique

Figure 32:
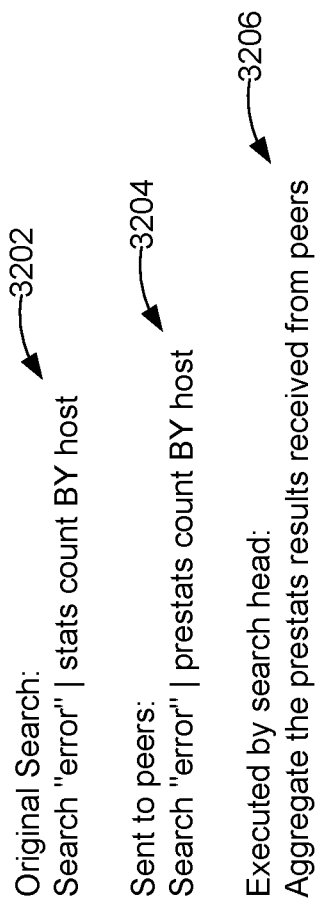
FIG. 32 is an example search query received from a client and executed by search peers, in accordance with example embodiments.

To facilitate faster query processing, a query can be structured such that multiple search nodes 506 perform the query in parallel, while aggregation of search results from the multiple search nodes 506 is performed at the search head 504. For example, FIG. 32 is an example search query received from a client and executed by search nodes 506, in accordance with example embodiments. FIG. 32 illustrates how a search query 3202 received from a client at a search head 504 can split into two phases, including: (1) subtasks 3204 (e.g., data retrieval or simple filtering) that may be performed in parallel by search nodes 506 for execution, and (2) a search results aggregation operation 3206 to be executed by the search head 504 when the results are ultimately collected from the search nodes 506.

During operation, upon receiving search query 3202, a search head 504 determines that a portion of the operations involved with the search query may be performed locally by the search head 504. The search head 504 modifies search query 3202 by substituting "stats" (create aggregate statistics over results sets received from the search nodes 506 at the search head 504) with "prestats" (create statistics by the search node 506 from local results set) to produce search query 3204, and then distributes search query 3204 to distributed search nodes 506, which are also referred to as "search peers" or "peer search nodes." Note that search queries may generally specify search criteria or operations to be performed on events that meet the search criteria. Search queries may also specify field names, as well as search criteria for the values in the fields or operations to be performed on the values in the fields. Moreover, the search head 504 may distribute the full search query to the search peers as illustrated in FIG. 6A, or may alternatively distribute a modified version (e.g., a more restricted version) of the search query to the search peers. In this example, the search nodes 506 are responsible for producing the results and sending them to the search head 504. After the search nodes 506 return the results to the search head 504, the search head 504 aggregates the received results 3206 to form a single search result set. By executing the query in this manner, the system effectively distributes the computational operations across the search nodes 506 while minimizing data transfers.

4.10.2. Keyword Index

As described above with reference to the flow charts in FIG. 5A and FIG. 6A, data intake and query system 108 can construct and maintain one or more keyword indexes to quickly identify events containing specific keywords. This technique can greatly speed up the processing of queries involving specific keywords. As mentioned above, to build a keyword index, an indexing node 404 first identifies a set of keywords. Then, the indexing node 404 includes the identified keywords in an index, which associates each stored keyword with references to events containing that keyword, or to locations within events where that keyword is located. When the query system 214 subsequently receives a keyword-based query, the indexer can access the keyword index to quickly identify events containing the keyword.

4.10.3. High Performance Analytics Store

To speed up certain types of queries, some embodiments of data intake and query system 108 create a high performance analytics store, which is referred to as a "summarization table," that contains entries for specific field-value pairs. Each of these entries keeps track of instances of a specific value in a specific field in the events and includes references to events containing the specific value in the specific field. For example, an example entry in a summarization table can keep track of occurrences of the value "94107" in a "ZIP code" field of a set of events and the entry includes references to all of the events that contain the value "94107" in the ZIP code field. This optimization technique enables the system to quickly process queries that seek to determine how many events have a particular value for a particular field. To this end, the system can examine the entry in the summarization table to count instances of the specific value in the field without having to go through the individual events or perform data extractions at search time. Also, if the system needs to process all events that have a specific field-value combination, the system can use the references in the summarization table entry to directly access the events to extract further information without having to search all of the events to find the specific field-value combination at search time.

In some embodiments, the system maintains a separate summarization table for each of the above-described time-specific buckets that stores events for a specific time range. A bucket-specific summarization table includes entries for specific field-value combinations that occur in events in the specific bucket. Alternatively, the system can maintain a summarization table for the common storage 216, one or more data stores 218 of the common storage 216, buckets cached on a search node 506, etc. The different summarization tables can include entries for the events in the common storage 216, certain data stores 218 in the common storage 216, or data stores associated with a particular search node 506, etc.

The summarization table can be populated by running a periodic query that scans a set of events to find instances of a specific field-value combination, or alternatively instances of all field-value combinations for a specific field. A periodic query can be initiated by a user, or can be scheduled to occur automatically at specific time intervals. A periodic query can also be automatically launched in response to a query that asks for a specific field-value combination.

In some cases, when the summarization tables may not cover all of the events that are relevant to a query, the system can use the summarization tables to obtain partial results for the events that are covered by summarization tables, but may also have to search through other events that are not covered by the summarization tables to produce additional results. These additional results can then be combined with the partial results to produce a final set of results for the query. The summarization table and associated techniques are described in more detail in U.S. Pat. No. 8,682,925, entitled "DISTRIBUTED HIGH PERFORMANCE ANALYTICS STORE", issued on 25 Mar. 2014, U.S. Pat. No. 9,128,985, entitled "SUPPLEMENTING A HIGH PERFORMANCE ANALYTICS STORE WITH EVALUATION OF INDIVIDUAL EVENTS TO RESPOND TO AN EVENT QUERY", issued on 8 Sep. 2015, and U.S. patent application Ser. No. 14/815,973, entitled "GENERATING AND STORING SUMMARIZATION TABLES FOR SETS OF SEARCHABLE EVENTS", filed on 1 Aug. 2015, each of which is hereby incorporated by reference in its entirety for all purposes.

To speed up certain types of queries, e.g., frequently encountered queries or computationally intensive queries, some embodiments of data intake and query system 108 create a high performance analytics store, which is referred to as a "summarization table," (also referred to as a "lexicon" or "inverted index") that contains entries for specific field-value pairs. Each of these entries keeps track of instances of a specific value in a specific field in the event data and includes references to events containing the specific value in the specific field. For example, an example entry in an inverted index can keep track of occurrences of the value "94107" in a "ZIP code" field of a set of events and the entry includes references to all of the events that contain the value "94107" in the ZIP code field. Creating the inverted index data structure avoids needing to incur the computational overhead each time a statistical query needs to be run on a frequently encountered field-value pair. In order to expedite queries, in certain embodiments, the query system 214 can employ the inverted index separate from the raw record data store to generate responses to the received queries.

Note that the term "summarization table" or "inverted index" as used herein is a data structure that may be generated by the indexing system 212 that includes at least field names and field values that have been extracted and/or indexed from event records. An inverted index may also include reference values that point to the location(s) in the field searchable data store where the event records that include the field may be found. Also, an inverted index may be stored using various compression techniques to reduce its storage size.

Further, note that the term "reference value" (also referred to as a "posting value") as used herein is a value that references the location of a source record in the field searchable data store. In some embodiments, the reference value may include additional information about each record, such as timestamps, record size, meta-data, or the like. Each reference value may be a unique identifier which may be used to access the event data directly in the field searchable data store. In some embodiments, the reference values may be ordered based on each event record's timestamp. For example, if numbers are used as identifiers, they may be sorted so event records having a later timestamp always have a lower valued identifier than event records with an earlier timestamp, or vice-versa. Reference values are often included in inverted indexes for retrieving and/or identifying event records.

In one or more embodiments, an inverted index is generated in response to a user-initiated collection query. The term "collection query" as used herein refers to queries that include commands that generate summarization information and inverted indexes (or summarization tables) from event records stored in the field searchable data store.

Note that a collection query is a special type of query that can be user-generated and is used to create an inverted index. A collection query is not the same as a query that is used to call up or invoke a pre-existing inverted index. In one or more embodiments, a query can comprise an initial step that calls up a pre-generated inverted index on which further filtering and processing can be performed. For example, referring back to FIG. 22B, a set of events can be generated at block 2240 by either using a "collection" query to create a new inverted index or by calling up a pre-generated inverted index. A query with several pipelined steps will start with a pre-generated index to accelerate the query.

Figure 23C:
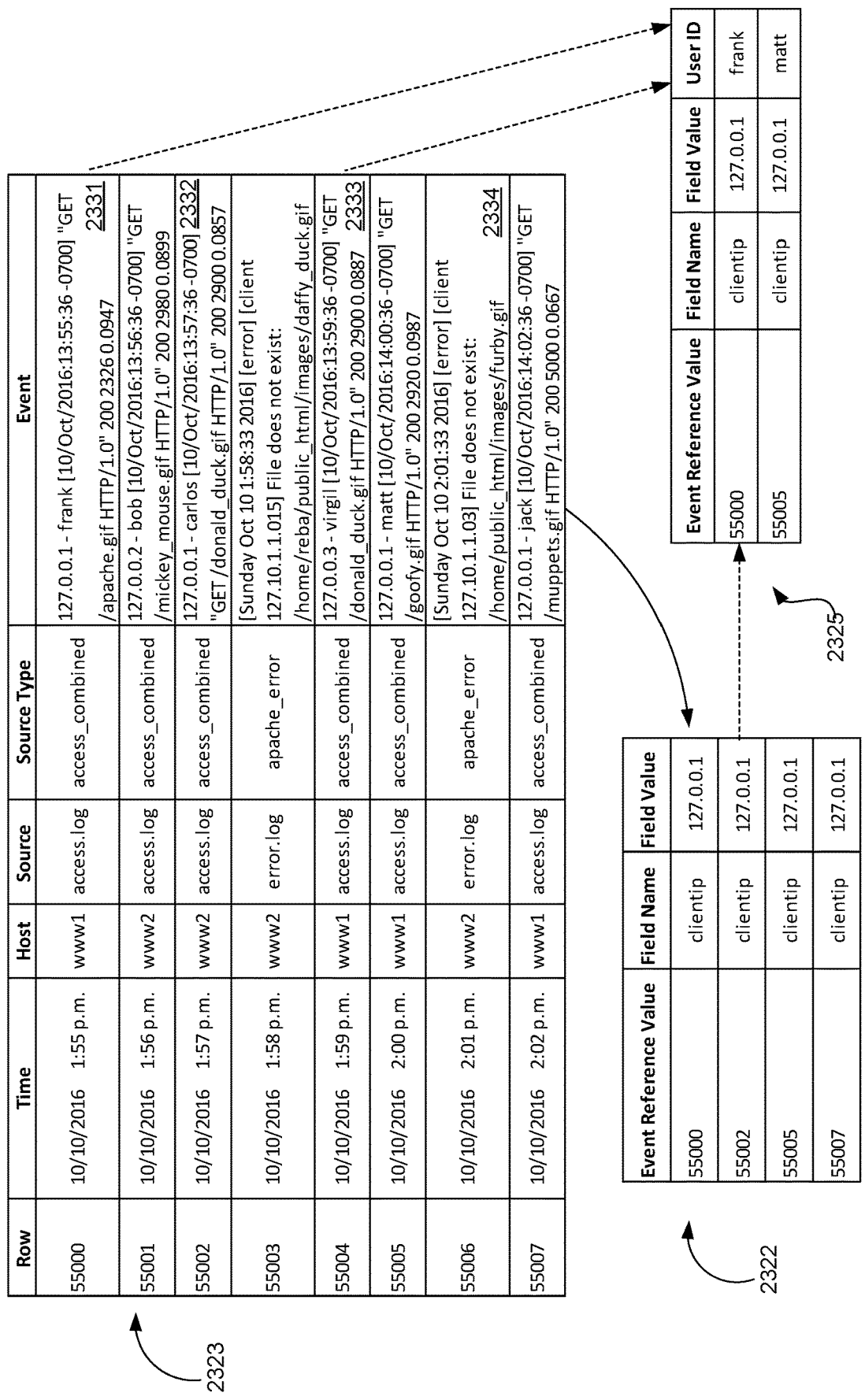
FIG. 23C illustrates an example of creating and using an inverted index, in accordance with example embodiments.

FIG. 23C illustrates the manner in which an inverted index is created and used in accordance with the disclosed embodiments. As shown in FIG. 23C, an inverted index 2322 can be created in response to a user-initiated collection query using the event data 2323 stored in the raw record data store. For example, a non-limiting example of a collection query may include "collect clientip=127.0.0.1" which may result in an inverted index 2322 being generated from the event data 2323 as shown in FIG. 23C. Each entry in inverted index 2322 includes an event reference value that references the location of a source record in the field searchable data store. The reference value may be used to access the original event record directly from the field searchable data store.

In one or more embodiments, if one or more of the queries is a collection query, the one or more search nodes 506 may generate summarization information based on the fields of the event records located in the field searchable data store. In at least one of the various embodiments, one or more of the fields used in the summarization information may be listed in the collection query and/or they may be determined based on terms included in the collection query. For example, a collection query may include an explicit list of fields to summarize. Or, in at least one of the various embodiments, a collection query may include terms or expressions that explicitly define the fields, e.g., using regex rules. In FIG. 23C, prior to running the collection query that generates the inverted index 2322, the field name "clientip" may need to be defined in a configuration file by specifying the "access_combined" source type and a regular expression rule to parse out the client IP address. Alternatively, the collection query may contain an explicit definition for the field name "clientip" which may obviate the need to reference the configuration file at search time.

In one or more embodiments, collection queries may be saved and scheduled to run periodically. These scheduled collection queries may periodically update the summarization information corresponding to the query. For example, if the collection query that generates inverted index 2322 is scheduled to run periodically, one or more search nodes 506 can periodically search through the relevant buckets to update inverted index 2322 with event data for any new events with the "clientip" value of "127.0.0.1."

In some embodiments, the inverted indexes that include fields, values, and reference value (e.g., inverted index 2322) for event records may be included in the summarization information provided to the user. In other embodiments, a user may not be interested in specific fields and values contained in the inverted index, but may need to perform a statistical query on the data in the inverted index. For example, referencing the example of FIG. 23C rather than viewing the fields within the inverted index 2322, a user may want to generate a count of all client requests from IP address "127.0.0.1." In this case, the query system 214 can simply return a result of "4" rather than including details about the inverted index 2322 in the information provided to the user.

The pipelined search language, e.g., SPL of the SPLUNK® ENTERPRISE system can be used to pipe the contents of an inverted index to a statistical query using the "stats" command for example. A "stats" query refers to queries that generate result sets that may produce aggregate and statistical results from event records, e.g., average, mean, max, min, rms, etc. Where sufficient information is available in an inverted index, a "stats" query may generate their result sets rapidly from the summarization information available in the inverted index rather than directly scanning event records. For example, the contents of inverted index 2322 can be pipelined to a stats query, e.g., a "count" function that counts the number of entries in the inverted index and returns a value of "4." In this way, inverted indexes may enable various stats queries to be performed absent scanning or search the event records. Accordingly, this optimization technique enables the system to quickly process queries that seek to determine how many events have a particular value for a particular field. To this end, the system can examine the entry in the inverted index to count instances of the specific value in the field without having to go through the individual events or perform data extractions at search time.

In some embodiments, the system maintains a separate inverted index for each of the above-described time-specific buckets that stores events for a specific time range. A bucket-specific inverted index includes entries for specific field-value combinations that occur in events in the specific bucket. Alternatively, the system can maintain a separate inverted index for one or more data stores 218 of common storage 216, an indexing node 404, or a search node 506. The specific inverted indexes can include entries for the events in the one or more data stores 218 or data store associated with the indexing nodes 404 or search node 506. In some embodiments, if one or more of the queries is a stats query, a search node 506 can generate a partial result set from previously generated summarization information. The partial result sets may be returned to the search head 504 that received the query and combined into a single result set for the query As mentioned above, the inverted index can be populated by running a periodic query that scans a set of events to find instances of a specific field-value combination, or alternatively instances of all field-value combinations for a specific field. A periodic query can be initiated by a user, or can be scheduled to occur automatically at specific time intervals. A periodic query can also be automatically launched in response to a query that asks for a specific field-value combination. In some embodiments, if summarization information is absent from a search node 506 that includes responsive event records, further actions may be taken, such as, the summarization information may generated on the fly, warnings may be provided the user, the collection query operation may be halted, the absence of summarization information may be ignored, or the like, or combination thereof.

In one or more embodiments, an inverted index may be set up to update continually. For example, the query may ask for the inverted index to update its result periodically, e.g., every hour. In such instances, the inverted index may be a dynamic data structure that is regularly updated to include information regarding incoming events.

4.10.3.1. Extracting Event Data Using Posting

In one or more embodiments, if the system needs to process all events that have a specific field-value combination, the system can use the references in the inverted index entry to directly access the events to extract further information without having to search all of the events to find the specific field-value combination at search time. In other words, the system can use the reference values to locate the associated event data in the field searchable data store and extract further information from those events, e.g., extract further field values from the events for purposes of filtering or processing or both.

The information extracted from the event data using the reference values can be directed for further filtering or processing in a query using the pipeline search language. The pipelined search language will, in one embodiment, include syntax that can direct the initial filtering step in a query to an inverted index. In one embodiment, a user would include syntax in the query that explicitly directs the initial searching or filtering step to the inverted index.

Referencing the example in FIG. 31, if the user determines that she needs the user id fields associated with the client requests from IP address "127.0.0.1," instead of incurring the computational overhead of performing a brand new search or re-generating the inverted index with an additional field, the user can generate a query that explicitly directs or pipes the contents of the already generated inverted index 2322 to another filtering step requesting the user ids for the entries in inverted index 2322 where the server response time is greater than "0.0900" microseconds. The query system 214 can use the reference values stored in inverted index 2322 to retrieve the event data from the field searchable data store, filter the results based on the "response time" field values and, further, extract the user id field from the resulting event data to return to the user. In the present instance, the user ids "frank" and "carlos" would be returned to the user from the generated results table 2325.

In one embodiment, the same methodology can be used to pipe the contents of the inverted index to a processing step. In other words, the user is able to use the inverted index to efficiently and quickly perform aggregate functions on field values that were not part of the initially generated inverted index. For example, a user may want to determine an average object size (size of the requested gif) requested by clients from IP address "127.0.0.1." In this case, the query system 214 can again use the reference values stored in inverted index 2322 to retrieve the event data from the field searchable data store and, further, extract the object size field values from the associated events 2331, 2332, 2333 and 2334. Once, the corresponding object sizes have been extracted (i.e. 2326, 2900, 2920, and 5000), the average can be computed and returned to the user.

In one embodiment, instead of explicitly invoking the inverted index in a user-generated query, e.g., by the use of special commands or syntax, the SPLUNK® ENTERPRISE system can be configured to automatically determine if any prior-generated inverted index can be used to expedite a user query. For example, the user's query may request the average object size (size of the requested gif) requested by clients from IP address "127.0.0.1." without any reference to or use of inverted index 2322. The query system 214, in this case, can automatically determine that an inverted index 2322 already exists in the system that could expedite this query. In one embodiment, prior to running any search comprising a field-value pair, for example, a query system 214 can search though all the existing inverted indexes to determine if a pre-generated inverted index could be used to expedite the search comprising the field-value pair. Accordingly, the query system 214 can automatically use the pre-generated inverted index, e.g., index 2322 to generate the results without any user-involvement that directs the use of the index.

Using the reference values in an inverted index to be able to directly access the event data in the field searchable data store and extract further information from the associated event data for further filtering and processing is highly advantageous because it avoids incurring the computation overhead of regenerating the inverted index with additional fields or performing a new search.

The data intake and query system 108 includes an intake system 210 that receives data from a variety of input data sources, and an indexing system 212 that processes and stores the data in one or more data stores or common storage 216. By distributing events among the data stores 218 of common storage 213, the query system 214 can analyze events for a query in parallel. In some embodiments, the data intake and query system 108 can maintain a separate and respective inverted index for each of the above-described time-specific buckets that stores events for a specific time range. A bucket-specific inverted index includes entries for specific field-value combinations that occur in events in the specific bucket. As explained above, a search head 504 can correlate and synthesize data from across the various buckets and search nodes 506.

This feature advantageously expedites searches because instead of performing a computationally intensive search in a centrally located inverted index that catalogues all the relevant events, a search node 506 is able to directly search an inverted index stored in a bucket associated with the time-range specified in the query. This allows the search to be performed in parallel across the various search nodes 506. Further, if the query requests further filtering or processing to be conducted on the event data referenced by the locally stored bucket-specific inverted index, the search node 506 is able to simply access the event records stored in the associated bucket for further filtering and processing instead of needing to access a central repository of event records, which would dramatically add to the computational overhead.

In one embodiment, there may be multiple buckets associated with the time-range specified in a query. If the query is directed to an inverted index, or if the query system 214 automatically determines that using an inverted index can expedite the processing of the query, the search nodes 506 can search through each of the inverted indexes associated with the buckets for the specified time-range. This feature allows the High Performance Analytics Store to be scaled easily.

Figure 23D:
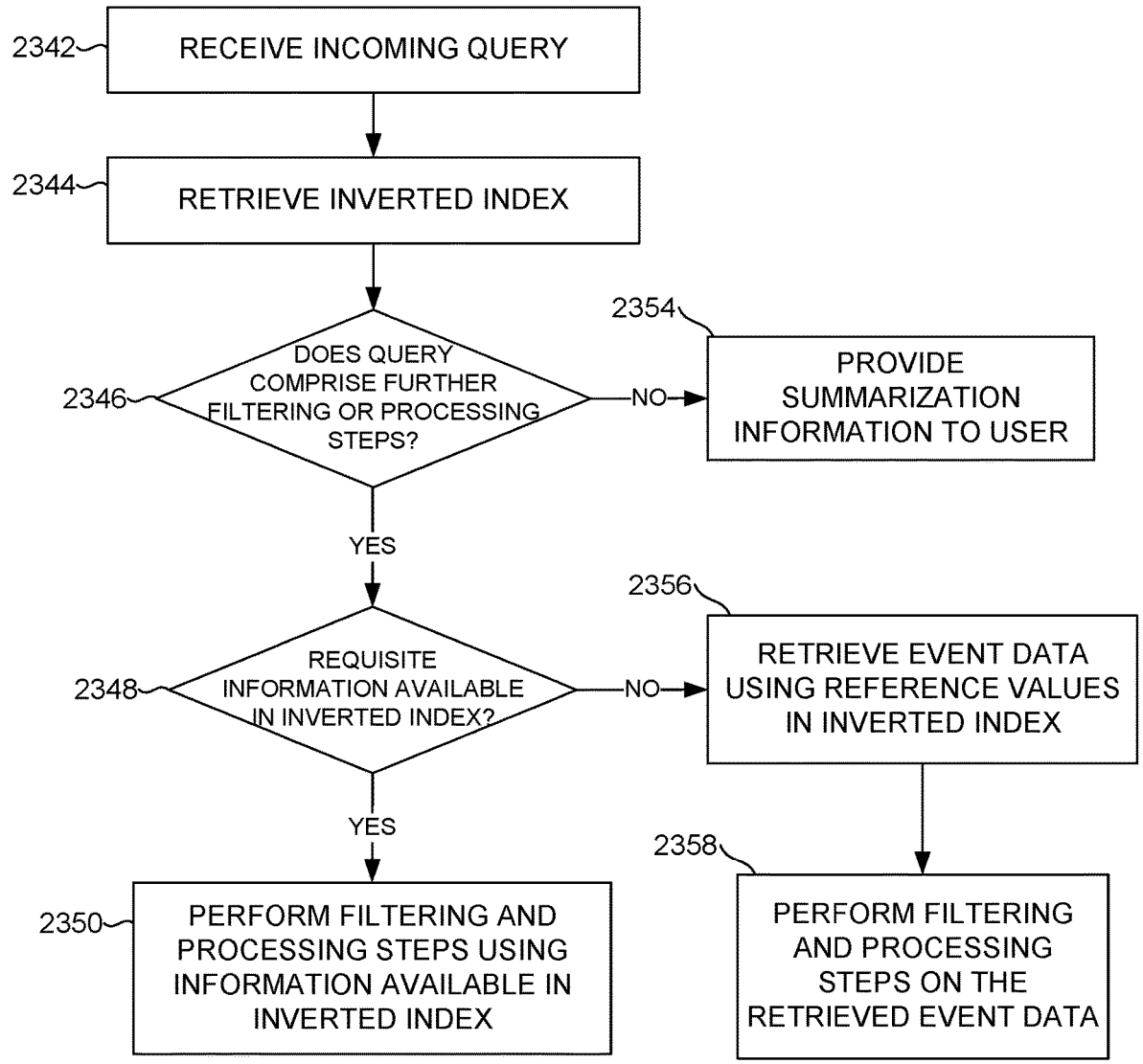
FIG. 23D depicts a flowchart of example use of an inverted index in a pipelined search query, in accordance with example embodiments.

FIG. 23D is a flow diagram illustrating an embodiment of a routine implemented by one or more computing devices of the data intake and query system for using an inverted index in a pipelined search query to determine a set of event data that can be further limited by filtering or processing. For example, the routine can be implemented by any one or any combination of the search head 504, search node 506, search master 512, or search manager 514, etc. However, for simplicity, reference below is made to the query system 214 performing the various steps of the routine.

At block 2342, a query is received by a data intake and query system 108. In some embodiments, the query can be received as a user generated query entered into search bar of a graphical user search interface. The search interface also includes a time range control element that enables specification of a time range for the query.

At block 2344, an inverted index is retrieved. Note, that the inverted index can be retrieved in response to an explicit user search command inputted as part of the user generated query. Alternatively, a query system 215 can be configured to automatically use an inverted index if it determines that using the inverted index would expedite the servicing of the user generated query. Each of the entries in an inverted index keeps track of instances of a specific value in a specific field in the event data and includes references to events containing the specific value in the specific field. In order to expedite queries, in some embodiments, the query system 214 employs the inverted index separate from the raw record data store to generate responses to the received queries.

At block 2346, the query system 214 determines if the query contains further filtering and processing steps. If the query contains no further commands, then, in one embodiment, summarization information can be provided to the user at block 2354.

If, however, the query does contain further filtering and processing commands, then at block 2348, the query system 214 determines if the commands relate to further filtering or processing of the data extracted as part of the inverted index or whether the commands are directed to using the inverted index as an initial filtering step to further filter and process event data referenced by the entries in the inverted index. If the query can be completed using data already in the generated inverted index, then the further filtering or processing steps, e.g., a "count" number of records function, "average" number of records per hour etc. are performed and the results are provided to the user at block 2350.

If, however, the query references fields that are not extracted in the inverted index, the query system 214 can access event data pointed to by the reference values in the inverted index to retrieve any further information required at block 2356. Subsequently, any further filtering or processing steps are performed on the fields extracted directly from the event data and the results are provided to the user at step 2358.

4.10.4. Accelerating Report Generation

In some embodiments, a data server system such as the data intake and query system 108 can accelerate the process of periodically generating updated reports based on query results. To accelerate this process, a summarization engine can automatically examine the query to determine whether generation of updated reports can be accelerated by creating intermediate summaries. If reports can be accelerated, the summarization engine periodically generates a summary covering data obtained during a latest non-overlapping time period. For example, where the query seeks events meeting a specified criteria, a summary for the time period includes may only events within the time period that meet the specified criteria. Similarly, if the query seeks statistics calculated from the events, such as the number of events that match the specified criteria, then the summary for the time period includes the number of events in the period that match the specified criteria.

In addition to the creation of the summaries, the summarization engine schedules the periodic updating of the report associated with the query. During each scheduled report update, the query system 214 determines whether intermediate summaries have been generated covering portions of the time period covered by the report update. If so, then the report is generated based on the information contained in the summaries. Also, if additional event data has been received and has not yet been summarized, and is required to generate the complete report, the query can be run on these additional events. Then, the results returned by this query on the additional events, along with the partial results obtained from the intermediate summaries, can be combined to generate the updated report. This process is repeated each time the report is updated. Alternatively, if the system stores events in buckets covering specific time ranges, then the summaries can be generated on a bucket-by-bucket basis. Note that producing intermediate summaries can save the work involved in re-running the query for previous time periods, so advantageously only the newer events needs to be processed while generating an updated report. These report acceleration techniques are described in more detail in U.S. Pat. No. 8,589,403, entitled "COMPRESSED JOURNALING IN EVENT TRACKING FILES FOR METADATA RECOVERY AND REPLICATION", issued on 19 Nov. 2013, U.S. Pat. No. 8,412,696, entitled "REAL TIME SEARCHING AND REPORTING", issued on 2 Apr. 2011, and U.S. Pat. Nos. 8,589,375 and 8,589,432, both also entitled "REAL TIME SEARCHING AND REPORTING", both issued on 19 Nov. 2013, each of which is hereby incorporated by reference in its entirety for all purposes.

4.12. Security Features

The data intake and query system 108 provides various schemas, dashboards, and visualizations that simplify developers' tasks to create applications with additional capabilities. One such application is the an enterprise security application, such as SPLUNK® ENTERPRISE SECURITY, which performs monitoring and alerting operations and includes analytics to facilitate identifying both known and unknown security threats based on large volumes of data stored by the data intake and query system 108. The enterprise security application provides the security practitioner with visibility into security-relevant threats found in the enterprise infrastructure by capturing, monitoring, and reporting on data from enterprise security devices, systems, and applications. Through the use of the data intake and query system 108 searching and reporting capabilities, the enterprise security application provides a top-down and bottom-up view of an organization's security posture.

The enterprise security application leverages the data intake and query system 108 search-time normalization techniques, saved searches, and correlation searches to provide visibility into security-relevant threats and activity and generate notable events for tracking. The enterprise security application enables the security practitioner to investigate and explore the data to find new or unknown threats that do not follow signature-based patterns.

Conventional Security Information and Event Management (SIEM) systems lack the infrastructure to effectively store and analyze large volumes of security-related data. Traditional SIEM systems typically use fixed schemas to extract data from pre-defined security-related fields at data ingestion time and store the extracted data in a relational database. This traditional data extraction process (and associated reduction in data size) that occurs at data ingestion time inevitably hampers future incident investigations that may need original data to determine the root cause of a security issue, or to detect the onset of an impending security threat.

In contrast, the enterprise security application system stores large volumes of minimally-processed security-related data at ingestion time for later retrieval and analysis at search time when a live security threat is being investigated. To facilitate this data retrieval process, the enterprise security application provides pre-specified schemas for extracting relevant values from the different types of security-related events and enables a user to define such schemas.

The enterprise security application can process many types of security-related information. In general, this security-related information can include any information that can be used to identify security threats. For example, the security-related information can include network-related information, such as IP addresses, domain names, asset identifiers, network traffic volume, uniform resource locator strings, and source addresses. The process of detecting security threats for network-related information is further described in U.S. Pat. No. 8,826,434, entitled "SECURITY THREAT DETECTION BASED ON INDICATIONS IN BIG DATA OF ACCESS TO NEWLY REGISTERED DOMAINS", issued on 2 Sep. 2014, U.S. Pat. No. 9,215,240, entitled "INVESTIGATIVE AND DYNAMIC DETECTION OF POTENTIAL SECURITY-THREAT INDICATORS FROM EVENTS IN BIG DATA", issued on 15 Dec. 2015, U.S. Pat. No. 9,173,801, entitled "GRAPHIC DISPLAY OF SECURITY THREATS BASED ON INDICATIONS OF ACCESS TO NEWLY REGISTERED DOMAINS", issued on 3 Nov. 2015, U.S. Pat. No. 9,248,068, entitled "SECURITY THREAT DETECTION OF NEWLY REGISTERED DOMAINS", issued on 2 Feb. 2016, U.S. Pat. No. 9,426,172, entitled "SECURITY THREAT DETECTION USING DOMAIN NAME ACCESSES", issued on 23 Aug. 2016, and U.S. Pat. No. 9,432,396, entitled "SECURITY THREAT DETECTION USING DOMAIN NAME REGISTRATIONS", issued on 30 Aug. 2016, each of which is hereby incorporated by reference in its entirety for all purposes. Security-related information can also include malware infection data and system configuration information, as well as access control information, such as login/logout information and access failure notifications. The security-related information can originate from various sources within a data center, such as hosts, virtual machines, storage devices and sensors. The security-related information can also originate from various sources in a network, such as routers, switches, email servers, proxy servers, gateways, firewalls and intrusion-detection systems.

During operation, the enterprise security application facilitates detecting "notable events" that are likely to indicate a security threat. A notable event represents one or more anomalous incidents, the occurrence of which can be identified based on one or more events (e.g., time stamped portions of raw machine data) fulfilling pre-specified and/or dynamically-determined (e.g., based on machine-learning)

criteria defined for that notable event. Examples of notable events include the repeated occurrence of an abnormal spike in network usage over a period of time, a single occurrence of unauthorized access to system, a host communicating with a server on a known threat list, and the like. These notable events can be detected in a number of ways, such as: (1) a user can notice a correlation in events and can manually identify that a corresponding group of one or more events amounts to a notable event; or (2) a user can define a "correlation search" specifying criteria for a notable event, and every time one or more events satisfy the criteria, the application can indicate that the one or more events correspond to a notable event; and the like. A user can alternatively select a pre-defined correlation search provided by the application. Note that correlation searches can be run continuously or at regular intervals (e.g., every hour) to search for notable events. Upon detection, notable events can be stored in a dedicated "notable events index," which can be subsequently accessed to generate various visualizations containing security-related information. Also, alerts can be generated to notify system operators when important notable events are discovered.

Figure 33A:
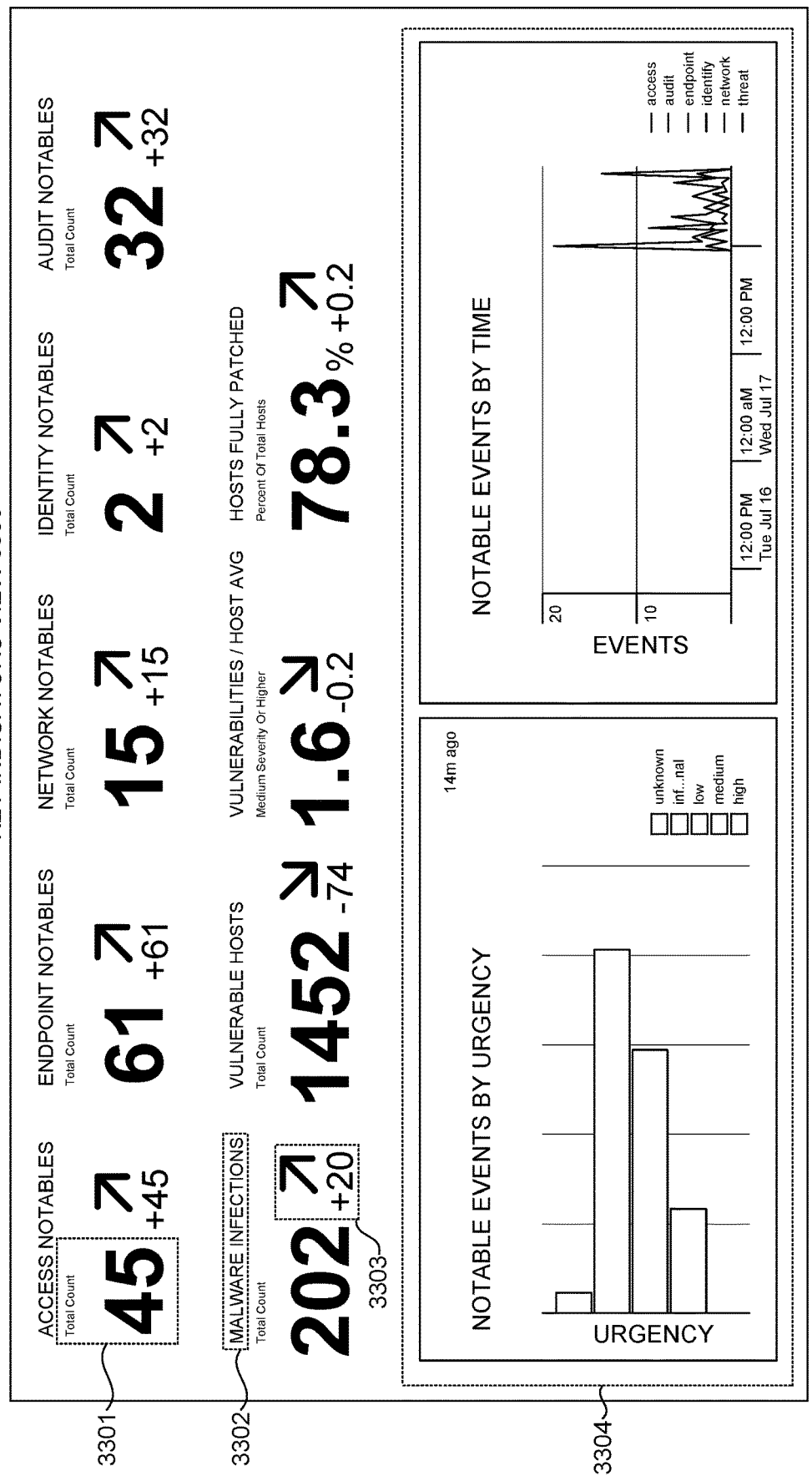
FIG. 33A is an interface diagram of an example user interface of a key indicators view, in accordance with example embodiments.

The enterprise security application provides various visualizations to aid in discovering security threats, such as a "key indicators view" that enables a user to view security metrics, such as counts of different types of notable events. For example, FIG. 33A illustrates an example key indicators view 3300 that comprises a dashboard, which can display a value 3301, for various security-related metrics, such as malware infections 3302. It can also display a change in a metric value 3303, which indicates that the number of malware infections increased by 63 during the preceding interval. Key indicators view 3300 additionally displays a histogram panel 3304 that displays a histogram of notable events organized by urgency values, and a histogram of notable events organized by time intervals. This key indicators view is described in further detail in pending U.S. patent application Ser. No. 13/956,338, entitled "KEY INDICATORS VIEW", filed on 31 Jul. 2013, and which is hereby incorporated by reference in its entirety for all purposes.

Figure 33B:
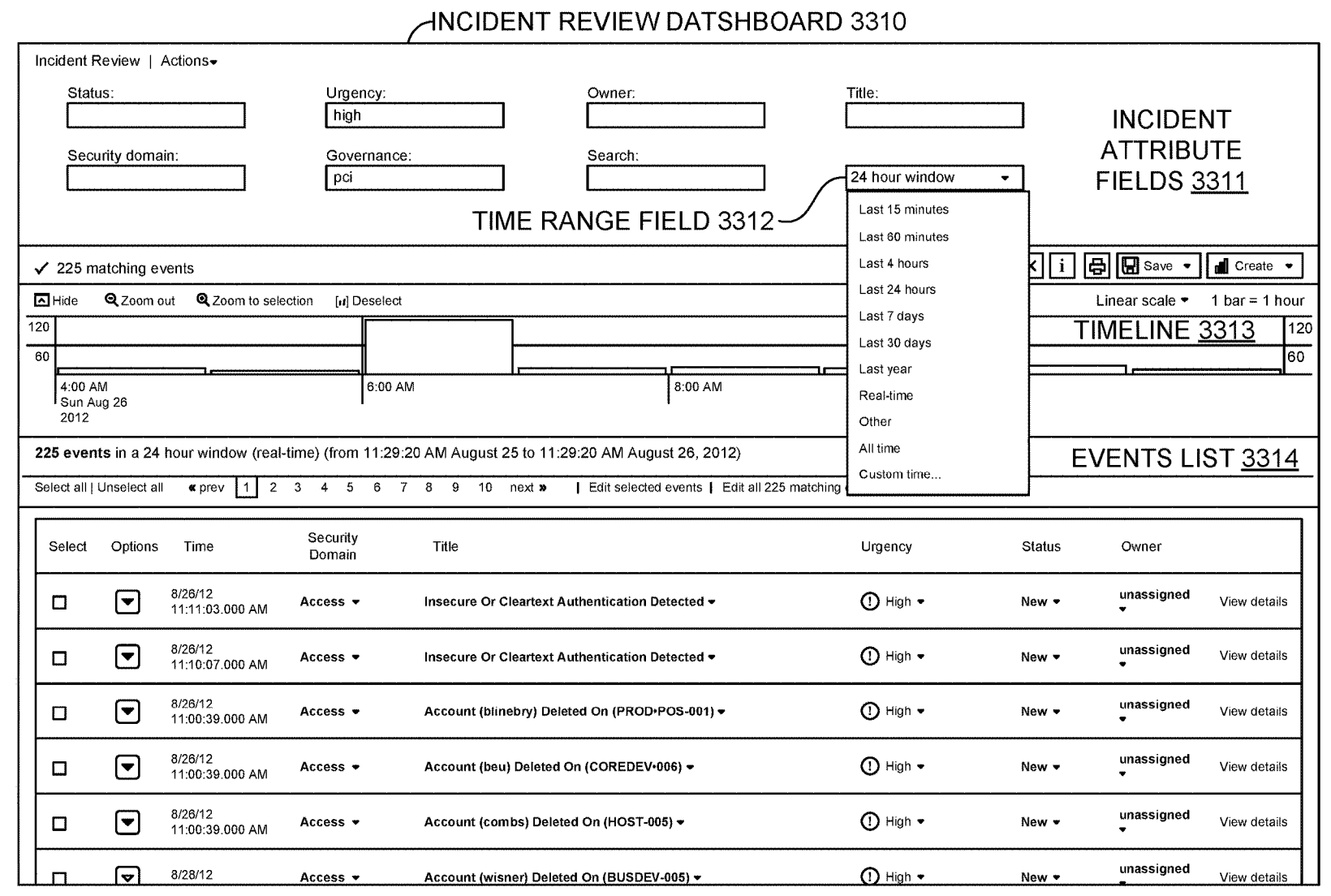

These visualizations can also include an "incident review dashboard" that enables a user to view and act on "notable events." These notable events can include: (1) a single event of high importance, such as any activity from a known web attacker; or (2) multiple events that collectively warrant review, such as a large number of authentication failures on a host followed by a successful authentication. For example, FIG. 33B illustrates an example incident review dashboard 3310 that includes a set of incident attribute fields 3311 that, for example, enables a user to specify a time range field 3312 for the displayed events. It also includes a timeline 3313 that graphically illustrates the number of incidents that occurred in time intervals over the selected time range. It additionally displays an events list 3314 that enables a user to view a list of all of the notable events that match the criteria in the incident attributes fields 3311. To facilitate identifying patterns among the notable events, each notable event can be associated with an urgency value (e.g., low, medium, high, critical), which is indicated in the incident review dashboard. The urgency value for a detected event can be determined based on the severity of the event and the priority of the system component associated with the event.

4.13. Data Center Monitoring

As mentioned above, the data intake and query platform provides various features that simplify the developer's task to create various applications. One such application is a virtual machine monitoring application, such as SPLUNK® APP FOR VMWARE® that provides operational visibility into granular performance metrics, logs, tasks and events, and topology from hosts, virtual machines and virtual centers. It empowers administrators with an accurate real-time picture of the health of the environment, proactively identifying performance and capacity bottlenecks.

Conventional data-center-monitoring systems lack the infrastructure to effectively store and analyze large volumes of machine-generated data, such as performance information and log data obtained from the data center. In conventional data-center-monitoring systems, machine-generated data is typically pre-processed prior to being stored, for example, by extracting pre-specified data items and storing them in a database to facilitate subsequent retrieval and analysis at search time. However, the rest of the data is not saved and discarded during pre-processing.

In contrast, the virtual machine monitoring application stores large volumes of minimally processed machine data, such as performance information and log data, at ingestion time for later retrieval and analysis at search time when a live performance issue is being investigated. In addition to data obtained from various log files, this performance-related information can include values for performance metrics obtained through an application programming interface (API) provided as part of the vSphere Hypervisor™ system distributed by VMware, Inc. of Palo Alto, Calif. For example, these performance metrics can include: (1) CPU-related performance metrics; (2) disk-related performance metrics; (3) memory-related performance metrics; (4) network-related performance metrics; (5) energy-usage statistics; (6) data-traffic-related performance metrics; (7) overall system availability performance metrics; (8) cluster-related performance metrics; and (9) virtual machine performance statistics. Such performance metrics are described in U.S. patent application Ser. No. 14/167,316, entitled "CORRELATION FOR USER-SELECTED TIME RANGES OF VALUES FOR PERFORMANCE METRICS OF COMPONENTS IN AN INFORMATION-TECHNOLOGY ENVIRONMENT WITH LOG DATA FROM THAT INFORMATION-TECHNOLOGY ENVIRONMENT", filed on 29 Jan. 2014, and which is hereby incorporated by reference in its entirety for all purposes.

To facilitate retrieving information of interest from performance data and log files, the virtual machine monitoring application provides pre-specified schemas for extracting relevant values from different types of performance-related events, and also enables a user to define such schemas.

Figure 33C:
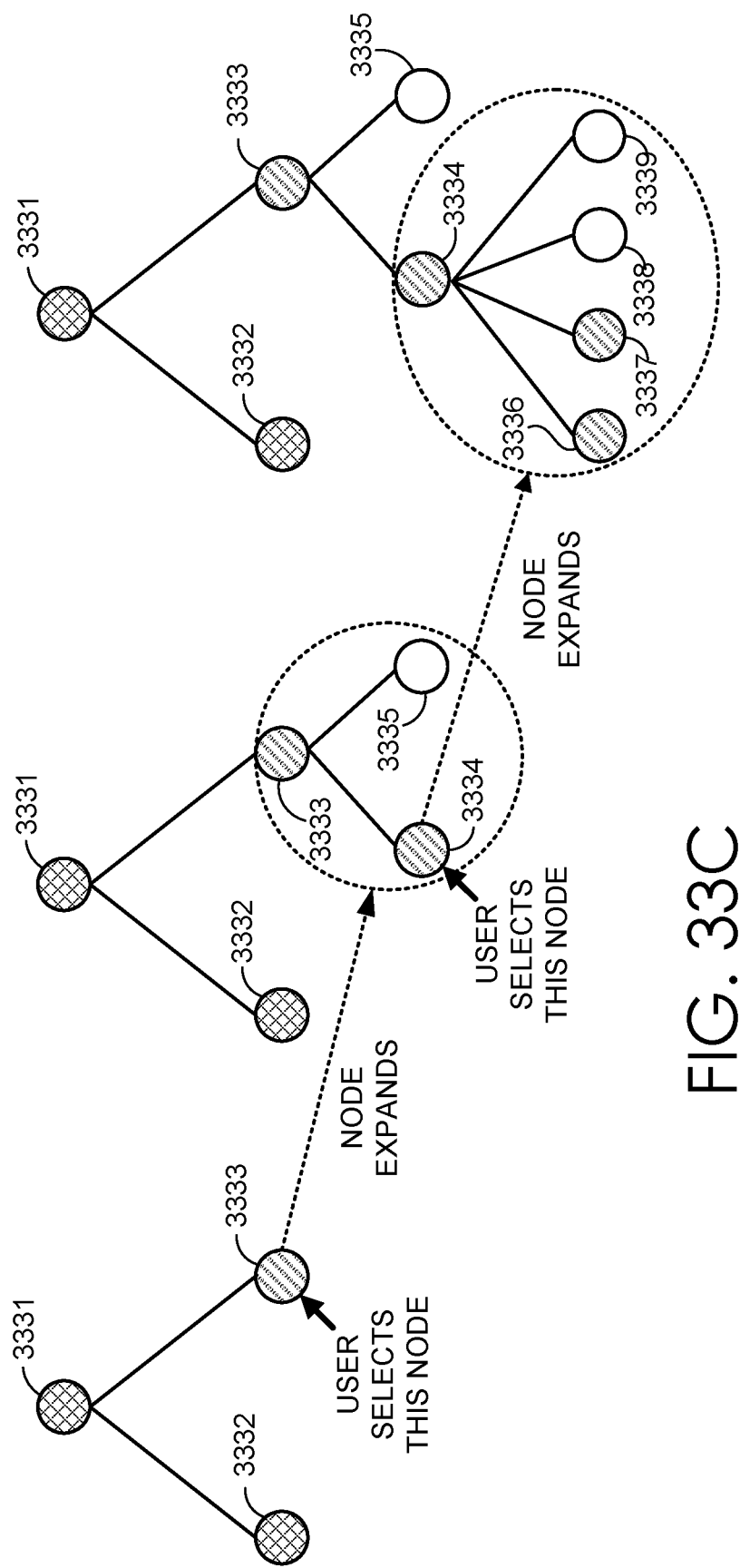
FIG. 33C is a tree diagram of an example a proactive monitoring tree, in accordance with example embodiments.

The virtual machine monitoring application additionally provides various visualizations to facilitate detecting and diagnosing the root cause of performance problems. For example, one such visualization is a "proactive monitoring tree" that enables a user to easily view and understand relationships among various factors that affect the performance of a hierarchically structured computing system. This proactive monitoring tree enables a user to easily navigate the hierarchy by selectively expanding nodes representing various entities (e.g., virtual centers or computing clusters) to view performance information for lower-level nodes associated with lower-level entities (e.g., virtual machines or host systems). Example node-expansion operations are illustrated in FIG. 33C, wherein nodes 3333 and 3334 are selectively expanded. Note that nodes 3331-3339 can be displayed using different patterns or colors to represent different performance states, such as a critical state, a warning state, a normal state or an unknown/offline state. The ease of navigation provided by selective expansion in combination with the associated performance-state information enables a user to quickly diagnose the root cause of a performance problem. The proactive monitoring tree is described in further detail in U.S. Pat. No. 9,185,007, entitled "PROACTIVE MONITORING TREE WITH SEVERITY STATE SORTING", issued on 10 Nov. 2015, and U.S. Pat. No. 9,426,045, also entitled "PROACTIVE MONITORING TREE WITH SEVERITY STATE SORTING", issued on 23 Aug. 2016, each of which is hereby incorporated by reference in its entirety for all purposes.

Figure 33D:
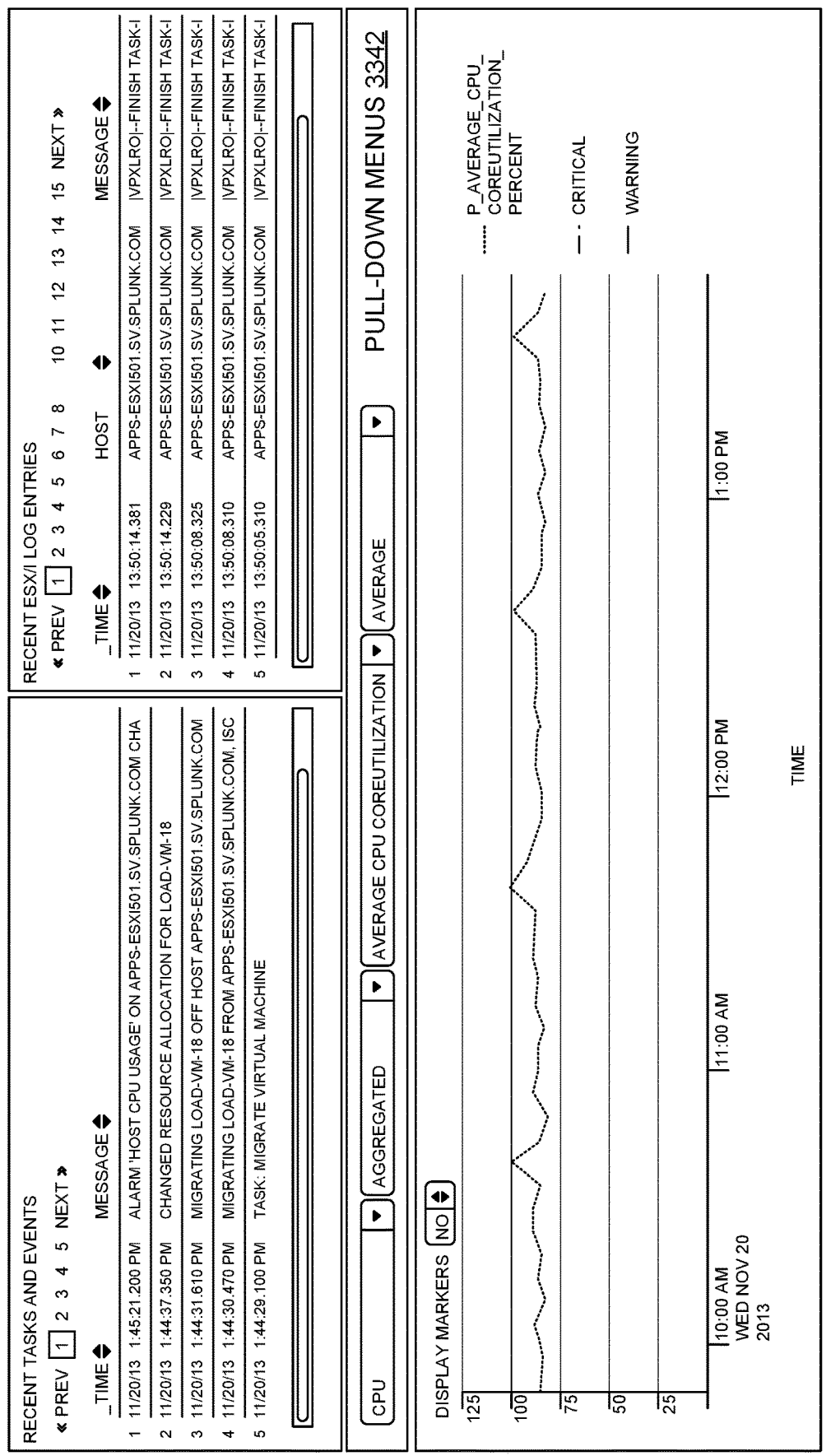
FIG. 33D is an interface diagram of an example a user interface displaying both log data and performance data, in accordance with example embodiments.

The virtual machine monitoring application also provides a user interface that enables a user to select a specific time range and then view heterogeneous data comprising events, log data, and associated performance metrics for the selected time range. For example, the screen illustrated in FIG. 33D displays a listing of recent "tasks and events" and a listing of recent "log entries" for a selected time range above a performance-metric graph for "average CPU core utilization" for the selected time range. Note that a user is able to operate pull-down menus 3342 to selectively display different performance metric graphs for the selected time range. This enables the user to correlate trends in the performance-metric graph with corresponding event and log data to quickly determine the root cause of a performance problem. This user interface is described in more detail in U.S. patent application Ser. No. 14/167,316, entitled "CORRELATION FOR USER-SELECTED TIME RANGES OF VALUES FOR PERFORMANCE METRICS OF COMPONENTS IN AN INFORMATION-TECHNOLOGY ENVIRONMENT WITH LOG DATA FROM THAT INFORMATION-TECHNOLOGY ENVIRONMENT", filed on 29 Jan. 2014, and which is hereby incorporated by reference in its entirety for all purposes.

4.14. It Service Monitoring

As previously mentioned, the data intake and query platform provides various schemas, dashboards and visualizations that make it easy for developers to create applications to provide additional capabilities. One such application is an IT monitoring application, such as SPLUNK® IT SERVICE INTELLIGENCE™, which performs monitoring and alerting operations. The IT monitoring application also includes analytics to help an analyst diagnose the root cause of performance problems based on large volumes of data stored by the data intake and query system 108 as correlated to the various services an IT organization provides (a service-centric view). This differs significantly from conventional IT monitoring systems that lack the infrastructure to effectively store and analyze large volumes of service-related events. Traditional service monitoring systems typically use fixed schemas to extract data from pre-defined fields at data ingestion time, wherein the extracted data is typically stored in a relational database. This data extraction process and associated reduction in data content that occurs at data ingestion time inevitably hampers future investigations, when all of the original data may be needed to determine the root cause of or contributing factors to a service issue.

In contrast, an IT monitoring application system stores large volumes of minimally-processed service-related data at ingestion time for later retrieval and analysis at search time, to perform regular monitoring, or to investigate a service issue. To facilitate this data retrieval process, the IT monitoring application enables a user to define an IT operations infrastructure from the perspective of the services it provides. In this service-centric approach, a service such as corporate e-mail may be defined in terms of the entities employed to provide the service, such as host machines and network devices. Each entity is defined to include information for identifying all of the events that pertains to the entity, whether produced by the entity itself or by another machine, and considering the many various ways the entity may be identified in machine data (such as by a URL, an IP address, or machine name). The service and entity definitions can organize events around a service so that all of the events pertaining to that service can be easily identified. This capability provides a foundation for the implementation of Key Performance Indicators.

One or more Key Performance Indicators (KPI's) are defined for a service within the IT monitoring application. Each KPI measures an aspect of service performance at a point in time or over a period of time (aspect KPI's). Each KPI is defined by a search query that derives a KPI value from the machine data of events associated with the entities that provide the service. Information in the entity definitions may be used to identify the appropriate events at the time a KPI is defined or whenever a KPI value is being determined. The KPI values derived over time may be stored to build a valuable repository of current and historical performance information for the service, and the repository, itself, may be subject to search query processing. Aggregate KPIs may be defined to provide a measure of service performance calculated from a set of service aspect KPI values; this aggregate may even be taken across defined timeframes and/or across multiple services. A particular service may have an aggregate KPI derived from substantially all of the aspect KPI's of the service to indicate an overall health score for the service.

The IT monitoring application facilitates the production of meaningful aggregate KPI's through a system of KPI thresholds and state values. Different KPI definitions may produce values in different ranges, and so the same value may mean something very different from one KPI definition to another. To address this, the IT monitoring application implements a translation of individual KPI values to a common domain of "state" values. For example, a KPI range of values may be 1-100, or 50-275, while values in the state domain may be 'critical,' warning, 'normal,' and 'informational'. Thresholds associated with a particular KPI definition determine ranges of values for that KPI that correspond to the various state values. In one case, KPI values 95-100 may be set to correspond to 'critical' in the state domain. KPI values from disparate KPI's can be processed uniformly once they are translated into the common state values using the thresholds. For example, "normal 80% of the time" can be applied across various KPI's. To provide meaningful aggregate KPI's, a weighting value can be assigned to each KPI so that its influence on the calculated aggregate KPI value is increased or decreased relative to the other KPI's.

One service in an IT environment often impacts, or is impacted by, another service. The IT monitoring application can reflect these dependencies. For example, a dependency relationship between a corporate e-mail service and a centralized authentication service can be reflected by recording an association between their respective service definitions. The recorded associations establish a service dependency topology that informs the data or selection options presented in a GUI, for example. (The service dependency topology is like a "map" showing how services are connected based on their dependencies.) The service topology may itself be depicted in a GUI and may be interactive to allow navigation among related services.

Entity definitions in the IT monitoring application can include informational fields that can serve as metadata, implied data fields, or attributed data fields for the events identified by other aspects of the entity definition. Entity definitions in the IT monitoring application can also be created and updated by an import of tabular data (as represented in a CSV, another delimited file, or a search query result set). The import may be GUI-mediated or processed using import parameters from a GUI-based import definition process. Entity definitions in the IT monitoring application can also be associated with a service by means of a service definition rule. Processing the rule results in the matching entity definitions being associated with the service definition. The rule can be processed at creation time, and thereafter on a scheduled or on-demand basis. This allows dynamic, rule-based updates to the service definition.

During operation, the IT monitoring application can recognize notable events that may indicate a service performance problem or other situation of interest. These notable events can be recognized by a "correlation search" specifying trigger criteria for a notable event: every time KPI values satisfy the criteria, the application indicates a notable event. A severity level for the notable event may also be specified. Furthermore, when trigger criteria are satisfied, the correlation search may additionally or alternatively cause a service ticket to be created in an IT service management (ITSM) system, such as systems available from ServiceNow, Inc., of Santa Clara, Calif.

SPLUNK® IT SERVICE INTELLIGENCE™ provides various visualizations built on its service-centric organization of events and the KPI values generated and collected. Visualizations can be particularly useful for monitoring or investigating service performance. The IT monitoring application provides a service monitoring interface suitable as the home page for ongoing IT service monitoring. The interface is appropriate for settings such as desktop use or for a wall-mounted display in a network operations center (NOC). The interface may prominently display a services health section with tiles for the aggregate KPI's indicating overall health for defined services and a general KPI section with tiles for KPI's related to individual service aspects. These tiles may display KPI information in a variety of ways, such as by being colored and ordered according to factors like the KPI state value. They also can be interactive and navigate to visualizations of more detailed KPI information.

The IT monitoring application provides a service-monitoring dashboard visualization based on a user-defined template. The template can include user-selectable widgets of varying types and styles to display KPI information. The content and the appearance of widgets can respond dynamically to changing KPI information. The KPI widgets can appear in conjunction with a background image, user drawing objects, or other visual elements, that depict the IT operations environment, for example. The KPI widgets or other GUI elements can be interactive so as to provide navigation to visualizations of more detailed KPI information.

The IT monitoring application provides a visualization showing detailed time-series information for multiple KPI's in parallel graph lanes. The length of each lane can correspond to a uniform time range, while the width of each lane may be automatically adjusted to fit the displayed KPI data. Data within each lane may be displayed in a user selectable style, such as a line, area, or bar chart. During operation a user may select a position in the time range of the graph lanes to activate lane inspection at that point in time. Lane inspection may display an indicator for the selected time across the graph lanes and display the KPI value associated with that point in time for each of the graph lanes. The visualization may also provide navigation to an interface for defining a correlation search, using information from the visualization to pre-populate the definition.

The IT monitoring application provides a visualization for incident review showing detailed information for notable events. The incident review visualization may also show summary information for the notable events over a time frame, such as an indication of the number of notable events at each of a number of severity levels. The severity level display may be presented as a rainbow chart with the warmest color associated with the highest severity classification. The incident review visualization may also show summary information for the notable events over a time frame, such as the number of notable events occurring within segments of the time frame. The incident review visualization may display a list of notable events within the time frame ordered by any number of factors, such as time or severity. The selection of a particular notable event from the list may display detailed information about that notable event, including an identification of the correlation search that generated the notable event.

The IT monitoring application provides pre-specified schemas for extracting relevant values from the different types of service-related events. It also enables a user to define such schemas.

4.15. Ingest-Time Processing

As described above, the availability of vastly greater amounts of diverse data on diverse data systems gives rise to technical challenges to search and analyze the data. In particular, a large amount of raw machine data may be ingested into a data intake and query system to provide search and analysis functionality. However, the entirety of the raw machine data may not be of interest. Rather, it may be desirable to analyze certain fields included in the raw machine data. Given the large amount of raw machine data that may be ingested, it can be difficult to identify values corresponding to the desired fields.

One way the data intake and query system can improve an ability to identify values corresponding to desired fields is to extract the fields and/or field values as the raw machine data is being ingested. For example, the raw machine data ingested by the data intake and query system may originate from a push-based and/or pull-based publisher. When the raw machine data is received from a publisher, a log observer system of the data intake and query system can apply one or more processing rules to the raw machine data to extract certain fields and/or field values. In addition, a processing rule applied to raw machine data can define a field or field value to redact, a field or field value to copy, and/or the like. The log observer system can then send the raw machine data and the extracted field or field values (and/or the redacted raw machine data and/or copied field or field values) to other components in the data intake and query system for further data transformations, indexing, and storage.

While the log observer system can use the processing rule(s) to extract field or field values (and/or redact raw machine data and/or copy field or field values), the processing rule(s) may not be applied retroactively. For example, the log observer system may apply the processing rule(s) to some or all of the raw machine data ingested or received after creation of the processing rule(s). The log observer system, however, may discard ingested raw machine data some time after the raw machine data is ingested, such as after existing processing rule(s) are applied to the raw machine data, after the raw machine data and/or extracted fields or field values are provided to another component of the data intake and query system (e.g., the streaming data processor 308), after a threshold period of time has passed since the raw machine data was ingested, and/or the like. Thus, some raw machine data received or ingested prior to creation of the processing rule(s) may no longer be stored by the log observer system. As a result, the log observer system may not be able to apply the processing rule(s) to the discarded raw machine data.

Often, a processing rule is created because of some characteristic observed in raw machine data that has already been ingested. Thus, it may be beneficial to provide a user with an ability to view extracted, redacted, and/or copied fields or field values from raw machine data as the raw machine data is being ingested and/or from historical raw machine data that has already been ingested. Accordingly, described herein is an improved data intake and query system that can perform and display ingest-time and search-time field extraction, redaction, copy, and/or categorization. As described herein, ingest-time field extraction, redaction, copy, and/or categorization may refer to field or field value extraction, redaction, copy, and/or categorization that is performed by the log observer system on raw machine data as the raw machine data is ingested or received from a publisher. As described herein, search-time field extraction, redaction, copy, and/or categorization may refer to field or field value extraction, redaction, copy, and/or categorization that is performed by the log observer system and/or other components of the improved data intake and query system on historical raw machine data that has already been ingested and indexed by the improved data intake and query system.

Figure 34:
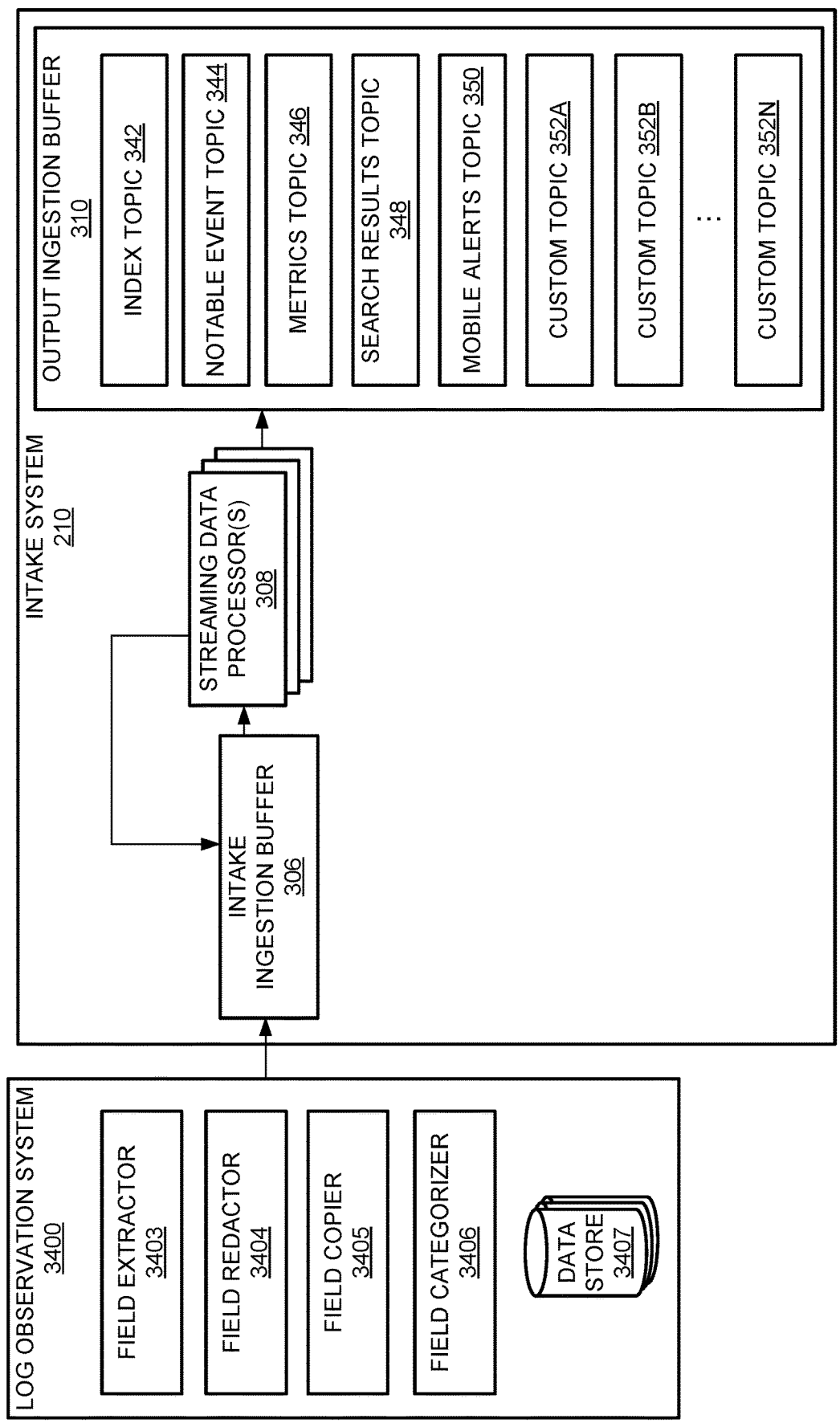
FIG. 34 is a more detailed block diagram of an embodiment of the data intake and query system.

FIG. 34 is a more detailed block diagram of an embodiment of the data intake and query system 108. As illustrated in FIG. 34, the data intake and query system 108 may include the intake system 210 and a log observer system 3400 in communication with the intake system 210. The log observer system 3400 may receive raw machine data from publishers and provide the raw machine data and/or other data elements to the intake ingestion buffer 306. The raw machine data may include log or event data (e.g., fields, parameters, etc.) describing different events.

For example, the log observer system 3400 may include a field extractor 3403, a field redactor 3404, a field copier 3405, a field categorizer 3406, and/or a data store 3407. As explained in greater detail below with respect to FIGS. 35-46, the log observer system 3400 may provide a user interface with which a user can interact (e.g., via the client device 204A) to create one or more processing rules. A processing rule can include a rule defining a field or field value to extract, a rule defining a field or field value to redact, a rule defining a field or field value to copy, and/or a rule defining a field or field value to categorize. The log observer system 3400 may store user-created processing rules in the data store 3407. The data store 3407 may further store one or more pre-packaged processing rules generated by the data intake and query system 108 and available for use by one or more users.

The field extractor 3403 may be configured to create a field extraction processing rule in response to user input. For example, the field extractor 3403 may retrieve historical raw machine data stored in the data store 3407, such as historical raw machine data that was recently ingested and that has not yet been discarded by the log observation system 3400. The field extractor 3403 can cause a user interface to display the historical raw machine data (e.g., historical logs) as a set of sample historical logs from which the user can create a field extraction processing rule. Using the user interface, a user can select one of the sample historical logs and indicate that field extraction is desired. In response, the user interface may allow a user to select a specific type of field extraction to be defined by the field extraction processing rule. For example, field extraction types can include a regex extraction (e.g., a field extraction that uses a regex rule that defines a sequence of characters to search for and extract from a log), a JSON extraction (e.g., a field extraction in which a field or field value is extracted from a JSON message), an event time extraction (e.g., a field extraction in which a timestamp field or timestamp field value is extracted, where the timestamp field or field value can be automatically detected by the log observer system 3400 based on known timestamp formats and/or based on a custom time format provided by a user), or a key-value (KV) parser (e.g., a field extraction in which key-value pairs are extracted, such as fields and field values in the "field=value" format where the field and/or field value is identified by a user).

Once the field extraction type is selected, the user interface may prompt a user to highlight one or more fields and/or one or more field values to extract from the previously-selected sample log. The field extractor 3403 can generate a regex rule (e.g., if the regex extraction field extraction type is selected), a JSON extraction rule (e.g., if the JSON extraction field extraction type is selected), an event time extraction rule (e.g., if the event time extraction field extraction type is selected), or KV parser rule (e.g., if the KV parser field extraction type is selected) based on the highlighted field(s) and/or field value(s). For example, the generated rule may define the operations to perform to extract from logs a sequence of characters that match the highlighted field(s) and/or field value(s).

The user interface may further prompt a user to provide one or more optional filters that can be used to narrow the set of logs to which the field extraction processing rule will be applied. For example, the user may be able to add a filter that defines a matching condition. The matching condition may identify a time period, a field, a field value, and/or the like. Once the field extraction processing rule is fully defined, the field extractor 3403 may apply the field extraction processing rule to only those logs that are ingested and that have a characteristic that satisfies the matching condition (e.g., is ingested or received within the identified time period, includes the identified field, includes the identified field value, etc.).

The field extractor 3403 can generate a preliminary field extraction processing rule based on the rule generated using the highlighted field(s) and/or field value(s) (e.g., the regex rule, the JSON extraction rule, the event time extraction rule, or the KV parser rule) and/or based on any filters set by the user. For example, the preliminary field extraction processing rule may include an instruction that, when executed by the field extractor 3403, causes the field extractor 3403 to extract one or more fields or field values in a manner as defined by the rule generated using the highlighted field(s) and/or field value(s) from logs that satisfy any matching conditions set by the user. As described above, the data store 3407 may store historical raw machine data, such as raw machine data that has been ingested and not yet discarded by the log observer system 3400. The field extractor 3403 can retrieve some or all of the historical raw machine data (e.g., historical logs) and apply the preliminary field extraction processing rule to the retrieved historical logs. Once applied, the field extractor 3403 can cause the user interface to display a preview of the preliminary field extraction processing rule being applied to the historical logs. In particular, the user interface can depict, in a table or other graphical element, the original historical logs and any fields or field values extracted from the original historical logs using the preliminary field extraction processing rule. Thus, the user interface may depict a preview of how the field extraction processing rule may function if applied to actual raw machine data being ingested by the data intake and query system 108. If the user identifies any issues with how field(s) or field value(s) are being extracted from the historical logs as indicated in the preview, the user can make changes to the preliminary field extraction processing rule (e.g., by repeating any of the steps described above that are used to generate the preliminary field extraction processing rule). The user may be able to make any number of changes any number of times until the user is satisfied with the results depicted in the preview.

The user interface may include a prompt allowing the user to finalize and implement the preliminary field extraction processing rule. If the preliminary field extraction processing rule is accepted, the field extractor 3403 may convert the preliminary field extraction processing rule into a field extraction processing rule that will be applied to at least some of the raw machine data that will be ingested going forward.

If a user creates a processing rule or a pre-packaged processing rule is enabled that defines a field or field value to extract, the field extractor 3403 may perform the field or field value extraction on raw machine data in a manner as defined by the processing rule as the log observation system 3400 receives the raw machine data. For example, a field extraction processing rule may include a regex rule, and the field extractor 3403 can apply the regex rule to an ingested log to extract values for a field associated with the regex rule, where the values are extracted by searching the ingested log for the sequence of characters defined in the regex rule. The field extractor 3403 can then forward the ingested log and the extracted field value(s) (and/or extracted field(s)) to the intake ingestion buffer 306. As described herein, the ingested log and extracted items may then be transformed zero or more times by a streaming data processor 308 before being indexed and stored by the indexing system 212 in one or more data stores 218.

As a field extraction processing rule is being applied to ingested logs, a user may request via the user interface to perform a search-time field extraction of a certain set of historical logs using the same field extraction processing rule. In response, the field extractor 3403 can transmit a request to the query system 214 to execute the field extraction processing rule on one or more historical logs that fall within the requested set. In some instances, the field(s) and/or field value(s) to be extracted as defined in the field extraction processing rule may already have been extracted and indexed by the indexing system 212. Thus, the query system 214 can simply query the data store(s) 218 for the requested field(s) and/or field value(s) corresponding to the historical logs falling within the requested set. For some historical logs falling within the requested set, however, the field(s) and/or field value(s) may not have been extracted and indexed. If the field extraction type is a regex extraction, then the field extraction processing rule may include a regex rule, and the regex rule may correspond to logs having a certain sourcetype. Thus, the query system 214 can retrieve the historical logs falling within the requested set for which the requested field(s) and/or field value(s) are not indexed, can evaluate the sourcetype of the historical logs to determine whether the sourcetype of the historical logs corresponds to the sourcetype of the regex rule, and can apply the regex rule to the historical logs if the sourcetype of the historical logs corresponds to the sourcetype of the regex rule to extract the field(s) and/or field value(s). The query system 214 can then return to the field extractor 3403 (1) the historical logs and/or (2) the field(s) and/or field value(s) retrieved from the data store(s) 218 and/or extracted using a rule included in the field extraction processing rule. The field extractor 3403 may cause the user interface to display the returned information. Thus, the user interface may display both ingest-time field extraction (e.g., the results of the field extractor 3403 applying the field extraction processing rule to ingested logs as the logs are being ingested) and search-time field extraction (e.g., the information provided by the query system 214).

The field redactor 3404 may be configured to create a field redaction processing rule in response to user input. For example, the field redactor 3404 may retrieve historical raw machine data stored in the data store 3407, such as historical raw machine data that was recently ingested and that has not yet been discarded by the log observation system 3400. The field redactor 3404 can cause a user interface to display the historical raw machine data (e.g., historical logs) as a set of sample historical logs from which the user can create a field redaction processing rule. Using the user interface, a user can select one of the sample historical logs and indicate that field redaction is desired. In response, the user interface may allow a user to select a specific type of field redaction to be defined by the field redaction processing rule. For example, field redaction types can include an entire field value redaction (e.g., an entire field and/or field value is redacted) and a partial field value redaction (e.g., a selected portion of a field and/or field value is redacted).

If the user selects a partial field value redaction field redaction type, the user interface may prompt a user to highlight one or more fields and/or one or more field values to redact from the previously-selected sample log. The field redactor 3404 can generate a rule that may define the operations to perform to redact from logs a sequence of characters that match the highlighted field(s) and/or field value(s).

Whether the user selects an entire field value redaction field redaction type or a partial field value redaction field redaction type, the user interface may prompt a user to provide one or more optional filters that can be used to narrow the set of logs to which the field redaction processing rule will be applied. For example, the user may be able to add a filter that defines a matching condition. The matching condition may identify a time period, a field, a field value, and/or the like. Once the field redaction processing rule is fully defined, the field redactor 3404 may apply the field redaction processing rule to only those logs that are ingested and that have a characteristic that satisfies the matching condition (e.g., is ingested or received within the identified time period, includes the identified field, includes the identified field value, etc.).

The field redactor 3404 can generate a preliminary field redaction processing rule based on the rule generated using the highlighted field(s) and/or field value(s) and/or based on any filters set by the user. For example, the preliminary field redaction processing rule may include an instruction that, when executed by the field redactor 3404, causes the field redactor 3404 to redact a portion of or all of one or more fields or field values in a manner as defined by the rule generated using the highlighted field(s) and/or field value(s) from logs that satisfy any matching conditions set by the user. As described above, the data store 3407 may store historical raw machine data, such as raw machine data that has been ingested and not yet discarded by the log observer system 3400. The field redactor 3404 can retrieve some or all of the historical raw machine data (e.g., historical logs) and apply the preliminary field redaction processing rule to the retrieved historical logs. Once applied, the field redactor 3404 can cause the user interface to display a preview of the preliminary field redaction processing rule being applied to the historical logs. In particular, the user interface can depict, in a table or other graphical element, a redacted version of the historical logs and an indication of the fields or field values that were redacted from the original historical logs using the preliminary field redaction processing rule. Thus, the user interface may depict a preview of how the field redaction processing rule may function if applied to actual raw machine data being ingested by the data intake and query system 108. If the user identifies any issues with how field(s) or field value(s) are being redacted from the historical logs as indicated in the preview, the user can make changes to the preliminary field redaction processing rule (e.g., by repeating any of the steps described above that are used to generate the preliminary field redaction processing rule). The user may be able to make any number of changes any number of times until the user is satisfied with the results depicted in the preview.

The user interface may include a prompt allowing the user to finalize and implement the preliminary field redaction processing rule. If the preliminary field redaction processing rule is accepted, the field redactor 3404 may convert the preliminary field redaction processing rule into a field redaction processing rule that will be applied to at least some of the raw machine data that will be ingested going forward.

If a user creates a processing rule or a pre-packaged processing rule is enabled that defines a field or field value to redact, the field redactor 3404 may perform the field or field value redaction on raw machine data in a manner as defined by the processing rule as the log observation system 3400 receives the raw machine data. The field redactor 3404 can then forward the redacted log to the intake ingestion buffer 306. In some instances, the field redactor 3404 may discard the redacted data, and therefore the redacted data may not be indexed or stored by the data intake and query system 108. As described herein, the redacted log may then be transformed zero or more times by a streaming data processor 308 before being indexed and stored by the indexing system 212 in one or more data stores 218.

The field copier 3405 may be configured to create a field copy processing rule in response to user input. For example, the field copier 3405 can prompt a user to identify, via a user interface, a field or field value to be copied and to identify a name of a field or field value to which the copying should occur. The field or field value to which the copying should occur can be an existing field or field value or a new field or field value. As an illustrative example, a user may enter in the user interface field X as the field to be copied and may enter field Y as the field to which field X should be copied, where field Y may be an existing field (e.g., a field that the data intake and query system 108 is already extracting or a field that has already been named or defined by a user) or a new field (e.g., a field newly defined by a user).

If a user creates a processing rule or a pre-packaged processing rule is enabled that defines a field or field value to copy, the field copier 3405 may perform the field or field value copy on raw machine data in a manner as defined by the processing rule as the log observation system 3400 receives the raw machine data. The field copier 3405 can then forward the original log, the copied field or field value, and/or the original log modified to include the copied field or field value to the intake ingestion buffer 306. As described herein, the original log, the copied field or field value, and/or the original log modified to include the copied field or field value may then be transformed zero or more times by a streaming data processor 308 before being indexed and stored by the indexing system 212 in one or more data stores 218.

The field categorizer 3406 may be configured to create a field categorization processing rule in response to user input. For example, the field categorizer 3406 can prompt a user to identify, via a user interface, a new field or field value and a condition that, if satisfied, causes the new field or field value to be created. As an illustrative example, a condition could be that the new field or field value is created if a particular field has a certain value. Thus, the field categorizer 3406 can provide additional context in situations in which a field has a value within a certain range of values.

If a user creates a processing rule or a pre-packaged processing rule is enabled that defines a field or field value to categorize, the field categorizer 3406 may perform the field or field value categorization on raw machine data in a manner as defined by the processing rule as the log observation system 3400 receives the raw machine data. The field categorizer 3406 can then forward the original log, the new field or field value if created, and/or the original log modified to include the new field or field value if created to the intake ingestion buffer 306. As described herein, the original log, the new field or field value if created, and/or the original log modified to include the new field or field value if created may then be transformed zero or more times by a streaming data processor 308 before being indexed and stored by the indexing system 212 in one or more data stores 218.

As described herein, the user can create any number of field extraction, field redaction, field copy, and/or field categorization processing rules. The log observation system 3400 may execute the rules in sequence in a pre-defined or user-selected order. For example, a particular window or tab depicted in the user interface can display one or more processing rules in an execution order. In particular, a first processing rule depicted above a second processing rule may be executed by the log observation system 3400 prior to the second processing rule. Using the user interface, a user can drag, move, or otherwise adjust the relative position of the displayed processing rules, thereby adjusting the processing rule execution order.

As described above, the log observation system 3400 can cause a client device 102, 204 to display a user interface that allows a user to create a field extraction, field redaction, field copy, and/or field categorization processing rule. In particular, the log observation system 3400 may generate user interface data that, when transmitted to and processed by a client device 102, 204, causes the client device 102, 204 to render and display the user interface (and any related user interfaces) that allows a user to create a field extraction, field redaction, field copy, and/or field categorization processing rule. For example, the user interface may include a user interface element (e.g., a button, a dropdown menu, a pop-up window, etc.) that, when selected or opened, prompts a user to select which type of processing rule to create. Once selected, the user interface may display the appropriate prompts, requests, information, and/or the like to enable the user to create the selected processing rule. FIGS. 35-42 illustrate user interfaces that can be used to create a regex extraction-based field extraction processing rule, whereas FIGS. 43-46 illustrate user interfaces that can be used to create field redaction processing rules. While user interfaces for creating a field copy or a field categorization processing rule are not explicitly illustrated, user interfaces for creating such processing rules may be similar to some or all of the user interfaces depicted in FIGS. 35-46.

FIGS. 35-42 illustrate an example user interface 3500 that can be used to create a field extraction processing rule. The user interface 3500 may be displayed by a client device 102, 204 in response to receiving user interface data generated by the log observation system 3400 (e.g., the field extractor 3403).

Figure 35:
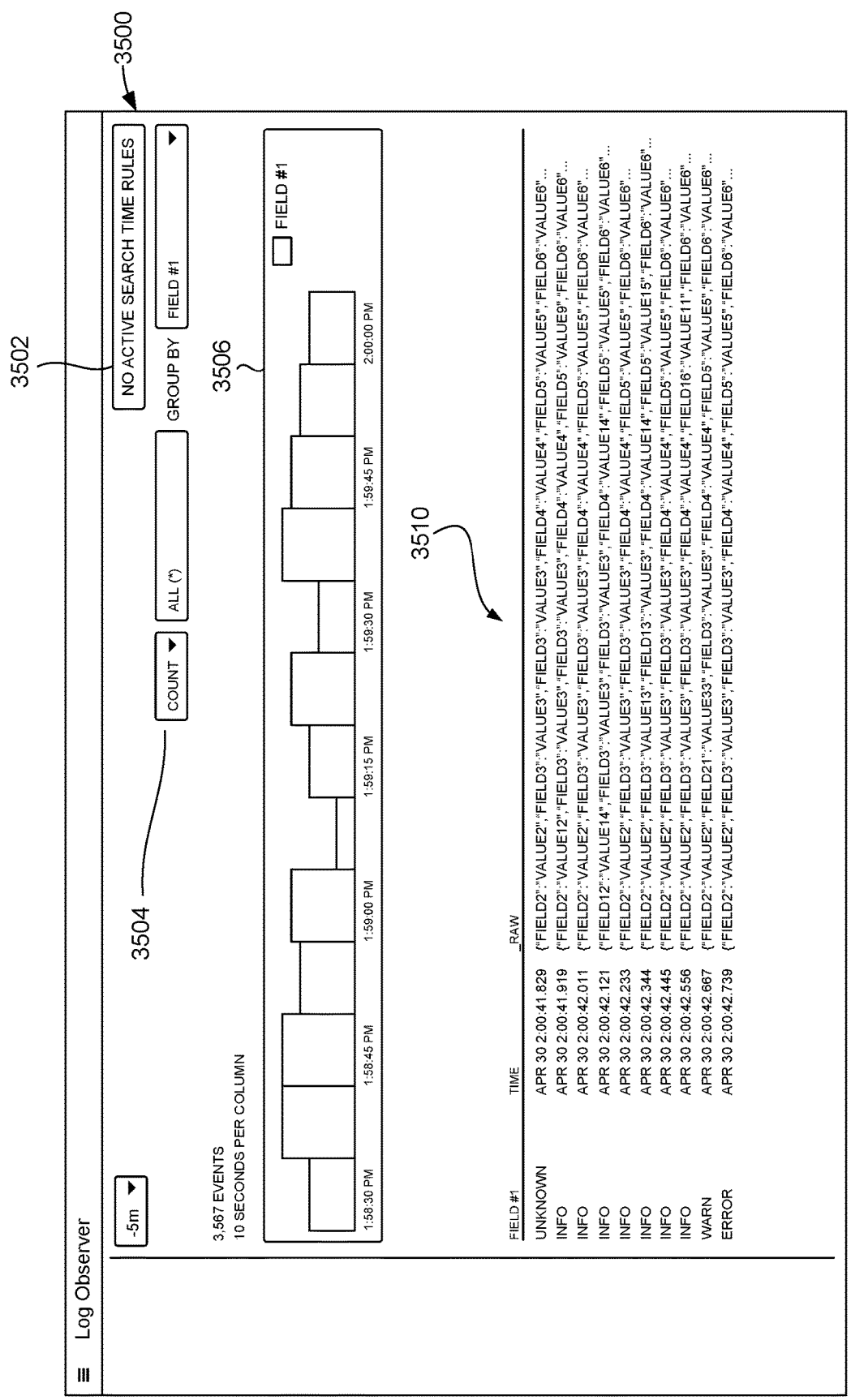
FIGS. 35-42 illustrate an example user interface that can be used to create a field extraction processing rule.

As illustrated in FIG. 35, the user interface 3500 initially depicts a set of logs 3510 recently ingested by the data intake and query system 108. For example, the logs 3510 may have been ingested recently enough such that the logs 3510 are still stored in the data store 3407 (e.g., the logs 3510 have not yet been discarded by the log observation system 3400). One or more field extraction processing rules may already be active, and thus a user may be able to organize the logs 3510 using filter controls 3504. Here, the user has set the filter controls 3504 such that the logs 3510 are grouped by extracted field #1. Per the set filter controls 3504, histogram 3506 depicts a count of the number of logs 3510 that have been ingested that include field #1, where each column in the histogram 3506 corresponds to a portion of the logs 3510 that have a timestamp or that were ingested within a particular 10 second period.

The user interface 3500 may initially display the logs 3510 to allow the user to select one of the logs as a sample that can be used to create a field extraction processing rule. As described above, the field extraction processing rule may be applied by the log observation system 3400 to logs ingested after creation of the rule, but may not be applied by the log observation system 3400 retroactively to logs that have already been ingested, such as the logs 3510. However, the user may be able to enable a search-time field extraction to view application of the field extraction processing rule to those logs that were ingested prior to creation of the rule, where the query system 214 may perform the relevant operations to identify, retrieve, extract, and/or provide the extracted fields to the log observation system 3400. User interface element 3502 may allow the user to enable the search-time field extraction. However, as depicted in FIG. 35 via the text in the user interface element 3502, search-time field extraction is not currently enabled for any existing field extraction processing rule.

Figure 36:
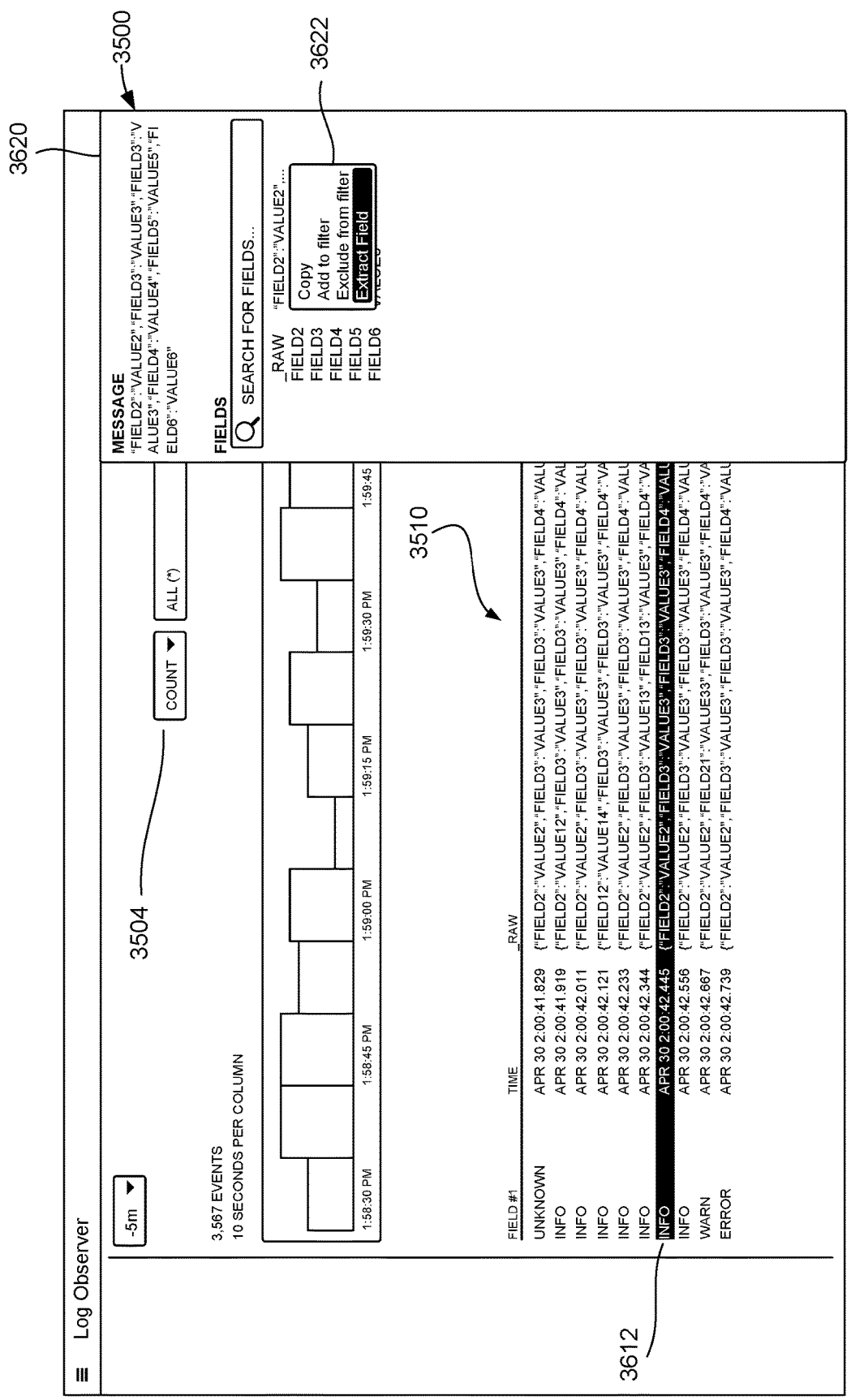

As illustrated in FIG. 36, a user has selected log 3612 from the set of logs 3510. As a result, window 3620 may appear in the user interface 3500. The window 3620 may depict the content of the selected log 3612 and an ability to search for different fields in the log 3612. The user can select any of the fields listed in the window 3620, which may cause window 3622 to appear. The window 3622 includes options to copy the selected field, add a filter to the selected field, exclude the selected field from a filter, or extract the selected field. Here, the user has selected the option to extract the selected field.

Figure 37:
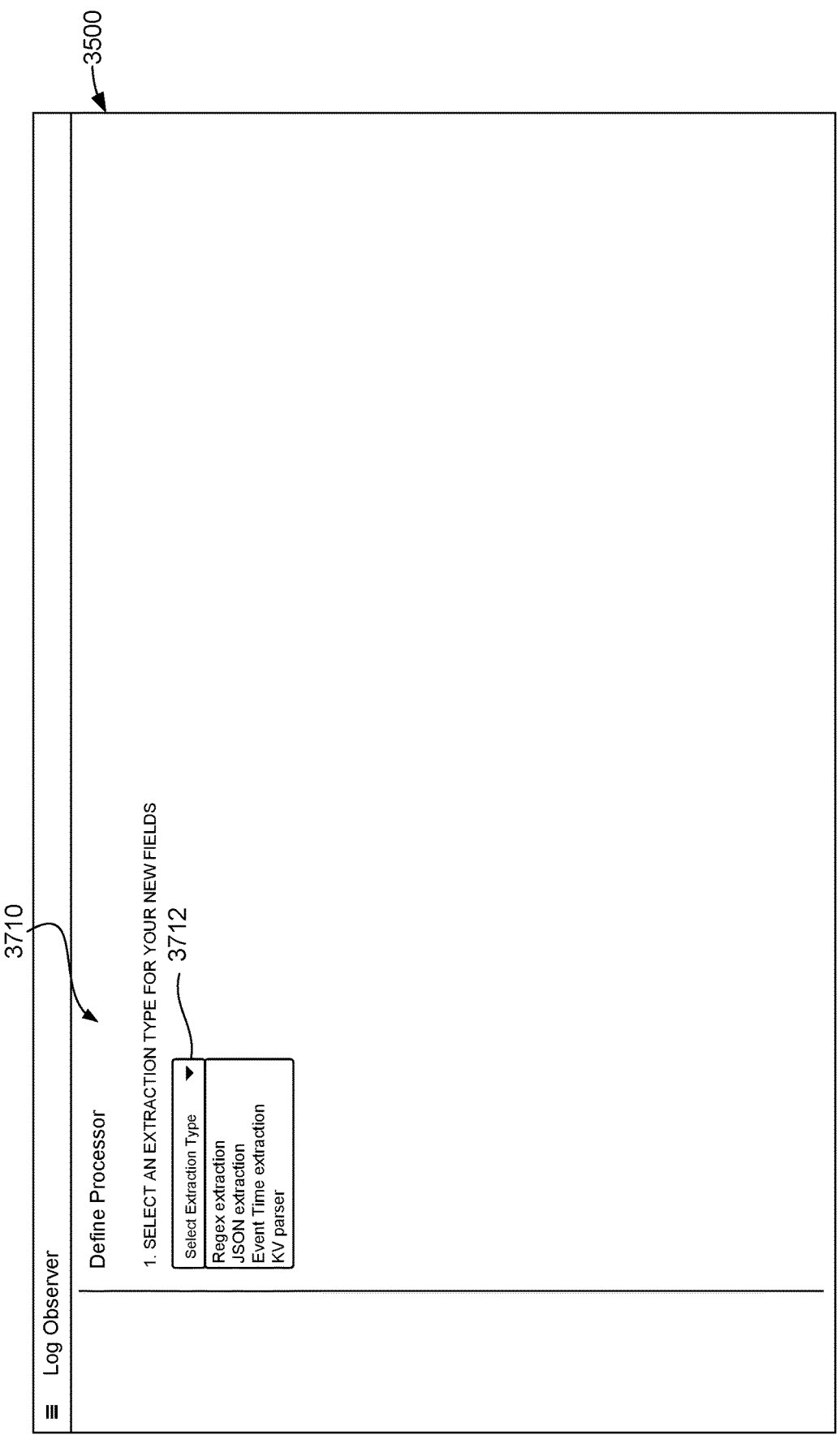

In response, the user interface 3500 depicts a new window or tab 3710 that prompts a user to select an extraction type for the selected field, as illustrated in FIG. 37. For example, via dropdown menu 3712, the user can select a regex field extraction type, a JSON field extraction type, an event time field extraction type, or a KV parser field extraction type.

Figure 38:
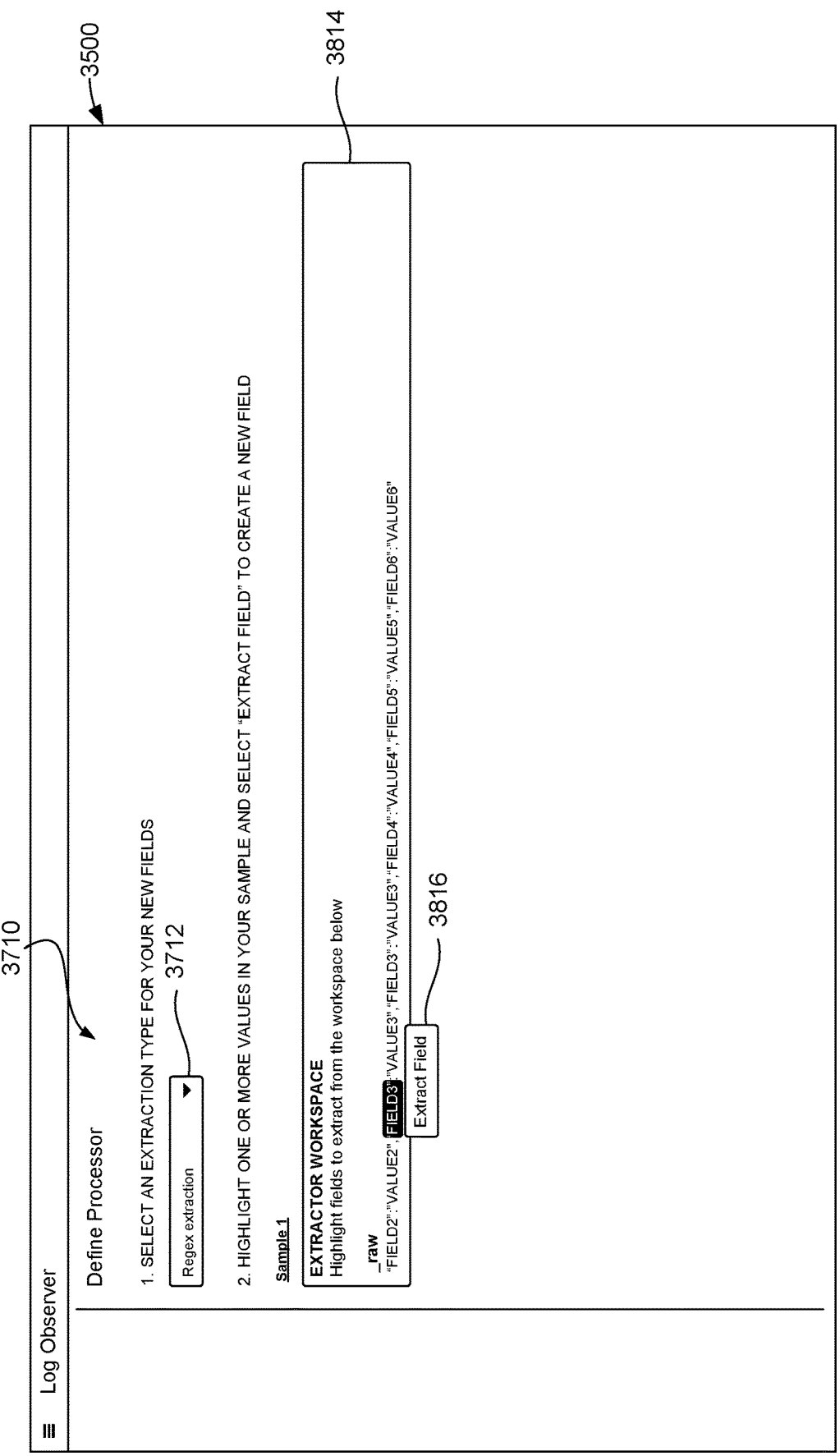

As illustrated in FIG. 38, the user has selected the regex field extraction type via the dropdown menu 3712. In response, the window 3710 depicts an extractor workspace 3814 in which the user is prompted to highlight one or more fields (or field values) to extract from the selected sample log 3612. Here, the user has highlighted FIELD3, which causes user interface element 3816 to appear.

Figure 39:
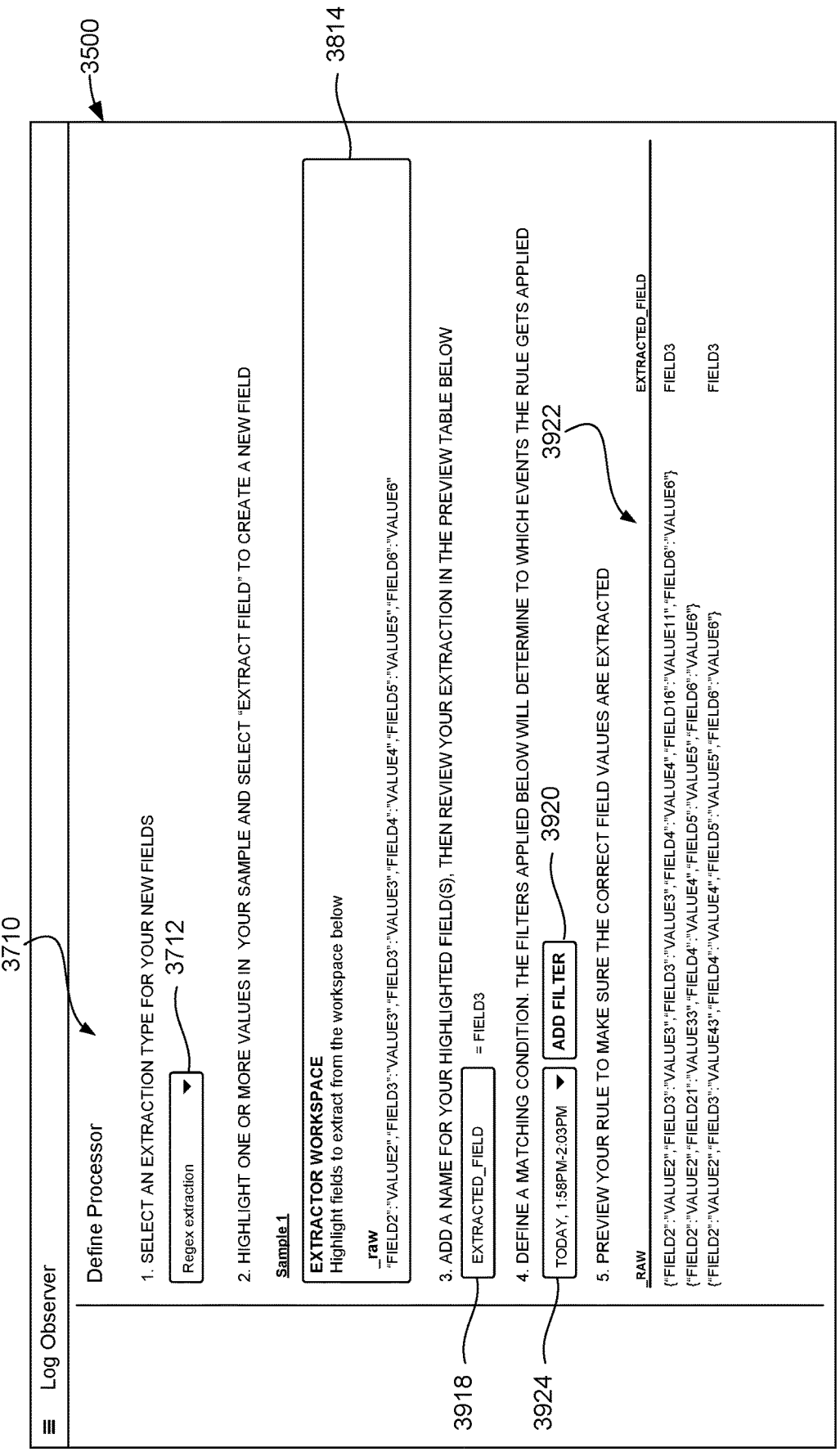

Selection of the user interface element 3816 indicates that the user would like to extract the highlighted field from ingested logs, causing the window 3710 to depict additional information and options, as illustrated in FIG. 39. For example, the user can name the highlighted field(s) or field value(s) via text field 3918, can add one or more filters via user interface element 3920, and can preview logs to which the preliminary field extraction processing rule is applied via table 3922. In particular, the filter that can be added via the user interface element 3920 can be used to define a matching condition, such that the preliminary field extraction processing rule and/or the finalized field extraction processing rule is only applied by the field extractor 3403 to logs that satisfy the matching condition. The user can add any number of filters via the user interface element 3920.

The preview of logs to which the preliminary field extraction processing rule is applied depicted in the table 3922 can help the user view and ensure that the field extraction processing rule is working as intended. For example, the table 3922 can show the original log and the field extracted from the log. If the extracted field is not FIELD3, this may indicate that the field extraction processing rule is not working properly, and the user can add or adjust filters or make other changes to the field extraction processing rule via the user interface 3500 as necessary. To generate the preview depicted in the table 3922, the field extractor 3403 can use the information provided in the dropdown menu 3712, the extractor workspace 3814, the text field 3918, and/or the user interface element 3920 to generate a preliminary field extraction processing rule and apply the preliminary field extraction processing rule to a set of already-ingested logs, such as logs that have already been ingested and that have a timestamp corresponding to the time period indicated in dropdown menu 3924.

Figure 40:
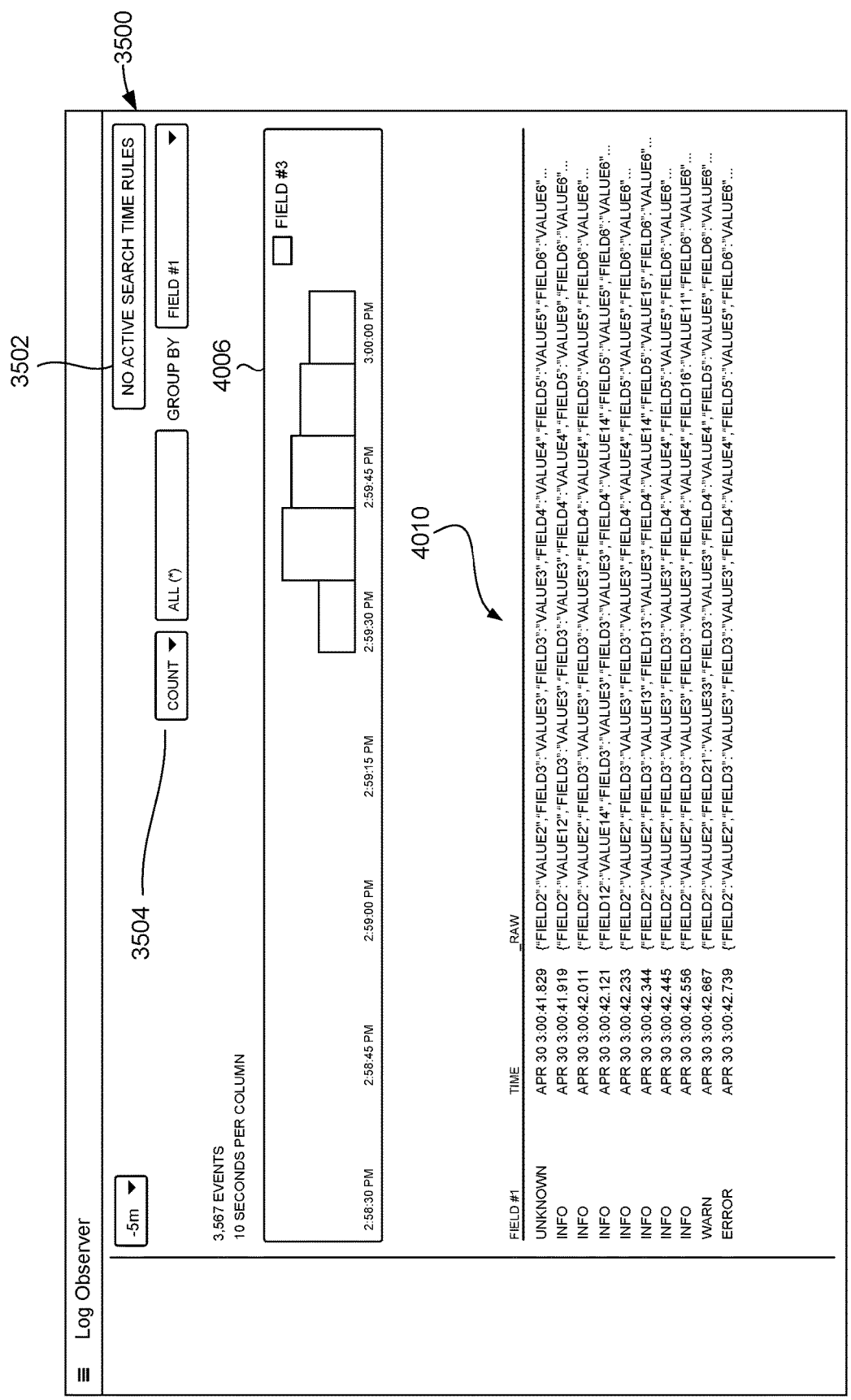

If the user approves the preliminary field extraction processing rule, then the field extractor 3403 may begin applying the field extraction processing rule to newly ingested logs and the results can be depicted in the user interface 3500, as illustrated in FIG. 40. For example, the user interface 3500 depicts a set of logs 4010 recently ingested by the data intake and query system 108 to which the field extraction processing rule has been applied. For example, the logs 4010 may have been ingested subsequent to creation of the field extraction processing rule. Histogram 4006 depicts a count of the number of logs 4010 that have been ingested that include field #3 (or FIELD3), where each column in the histogram 4006 corresponds to a portion of the logs 4010 that have a timestamp or that were ingested within a particular 10 second period. While the histogram 4006 begins at time 2:59:30 PM, logs may have been ingested prior to this time. However, the logs ingested prior to this time may have been ingested prior to creation of the field extraction processing rule.

As described above, the user may be able to enable a search-time field extraction to view application of the created field extraction processing rule to those logs that were ingested prior to creation of the rule (e.g., prior to 2:59:30 PM), where the query system 214 may perform the relevant operations to identify, retrieve, extract, and/or provide the extracted fields to the log observation system 3400. User interface element 3502, when selected, may allow the user to enable the search-time field extraction.

Figure 41:
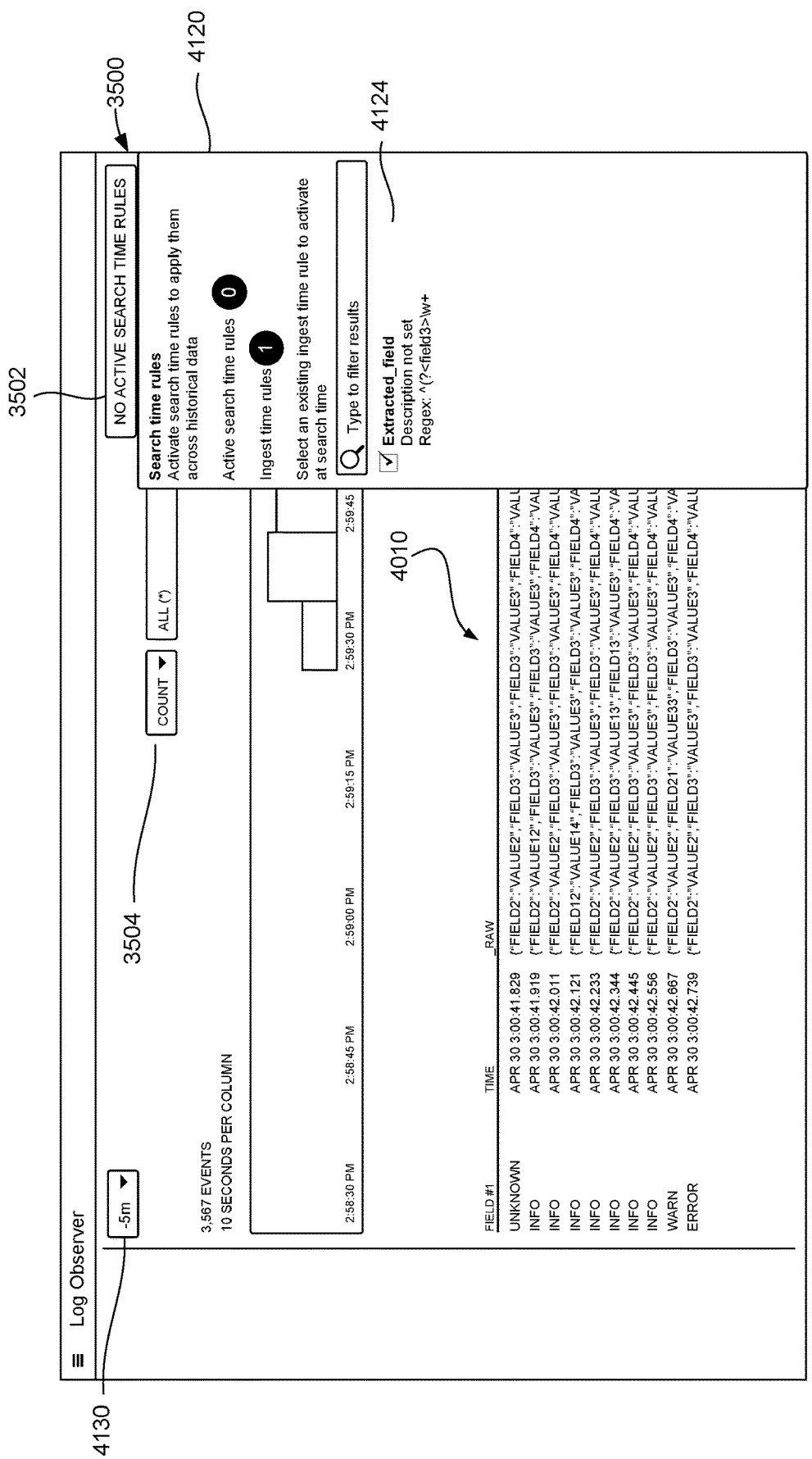

If the user selects the user interface element 3502, a window 4120 may appear that allows a user to enable a search-time field extraction, as illustrated in FIG. 41. For example, the window 4120 may indicate a number of search-time field extractions that are active (e.g., a number of field extraction processing rules for which search-time field extraction is active), a number of field extraction processing rules that are enabled at ingest time (e.g., a number of field extraction processing rules that are applied to logs as the logs are ingested), and a list of field extraction processing rules that exist and that operate at ingest time for which search-time field extraction can be enabled. Here, the field extraction processing rule created using the user interface 3500 as described above with respect to FIGS. 35-39 (e.g., field extraction processing rule 4124) is an available ingest-time rule for which search-time field extraction can be enabled. While a single field extraction processing rule is depicted in FIG. 41, this is not meant to be limiting, as any number of field extraction processing rules can be available and search-time field extraction can be enabled for any number of available field extraction processing rules.

Selection of the field extraction processing rule 4124 via the window 4120 may cause the field extractor 3403 to instruct the query system 214 to generate a query for retrieving and/or extracting the field or field value referenced by the field extraction processing rule 4124 (e.g., FIELD3). As described above, the query system 214 can retrieve the field or field value from the data store(s) 218 (e.g., if the field or field value was previously extracted and indexed) for logs that correspond to the time period indicated by dropdown menu 4130 and/or can extract the field or field value from logs that correspond to the time period indicated by the dropdown menu 4130 using, for example, the regex rule included in the field extraction processing rule 4124 (e.g., if the field or field value was not previously extracted and/or indexed). In some instances, some logs that correspond to the time period may have previously had the field or field value extracted and indexed, whereas other logs that correspond to the time period may not have previously had the field or field value extracted and/or indexed. Thus, the query system 214 may both retrieve field or field values from the data store(s) 218 for some logs and extract the field or field value using the regex rule from other logs. In other instances, the query system 214 may only retrieve field or field values from the data store(s) 218 (e.g., because the logs that correspond to the time period all have previously had the field or field value extracted and indexed) or may only extract the field or field value from the logs (e.g., because none of the logs that correspond to the time period have had the field or field value extracted and/or indexed). The log observation system 3400 can provide the field extraction processing rule 4124 to the query system 214 to enable the extraction. Before applying the regex rule, the query system 214 may check the sourcetype of the logs and apply the regex rule to those logs that have the same sourcetype as the sourcetype corresponding to the regex rule (e.g., the regex rule may define or include an indication of a log sourcetype to which the regex rule can be applied). The query system 214 can provide the results of the field or field value retrieval and/or extraction to the log observation system 3400, including optionally the original logs themselves, such that the information can be displayed via the user interface 3500.

Figure 42:
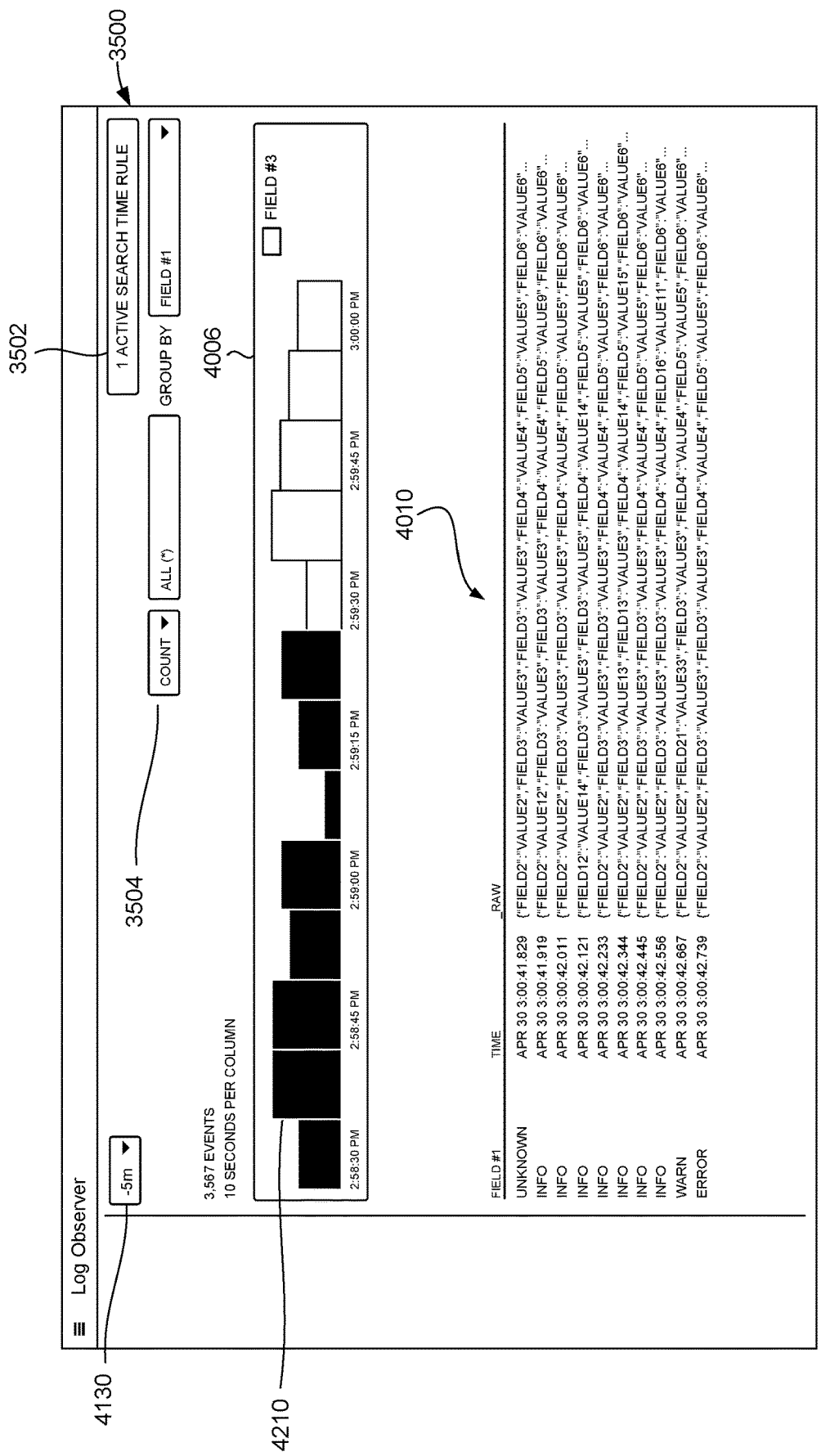

FIG. 42 depicts the results of the search-time field extraction performed by the query system 214 and provided to the log observation system 3400. As illustrated in FIG. 42, the user interface 3500 depicts both the ingest-time field extraction and the search-time field extraction and user interface element 3502 is updated to indicate that 1 search-time field extraction is active. For example, the set of logs 4010 may include both logs that were ingested after creation of the field extraction processing rule 4124 and logs that were ingested before creation of the field extraction processing rule 4124. Similarly, the histogram 4006 may depict a count of the number of logs that have FIELD3 that were ingested after creation of the field extraction processing rule 4124 and that were ingested prior to creation of the field extraction processing rule 4124.

In some instances, the histogram may color-code or otherwise shade the columns differently to indicate which logs were ingested prior to and/or after creation and/or application of the field extraction processing rule 4124. For example, columns 4210 that correspond to a time before 2:59:30 PM may have a darker shading to indicate that such columns 4210 correspond to logs that were ingested prior to creation of the field extraction processing rule 4124. In other instances, columns in the histogram 4006 may not indicate differences between logs ingested prior to or after creation of the field extraction processing rule 4124.

If a user adjusts the time period via the dropdown menu 4130, then the field extractor 3403 may generate an updated instruction and transmit the updated instruction to the query system 214, where the updated instruction indicates the new time period of logs for which field or field values are requested. The field extractor 3403 may not generate or transmit an updated instruction, however, if the new time period falls within any previous time period selected by the user and for which extracted field or field values have already been received from the query system 214. Once any new field or field values (and/or logs) are received from the query system 214, the field extractor 3403 may cause the user interface 3500 to be automatically updated to display the newly received information.

FIGS. 43-46 illustrate an example user interface 4300 that can be used to create a field redaction processing rule. The user interface 4300 may be displayed by a client device 102, 204 in response to receiving user interface data generated by the log observation system 3400 (e.g., the field redactor 3404).

Figure 43:
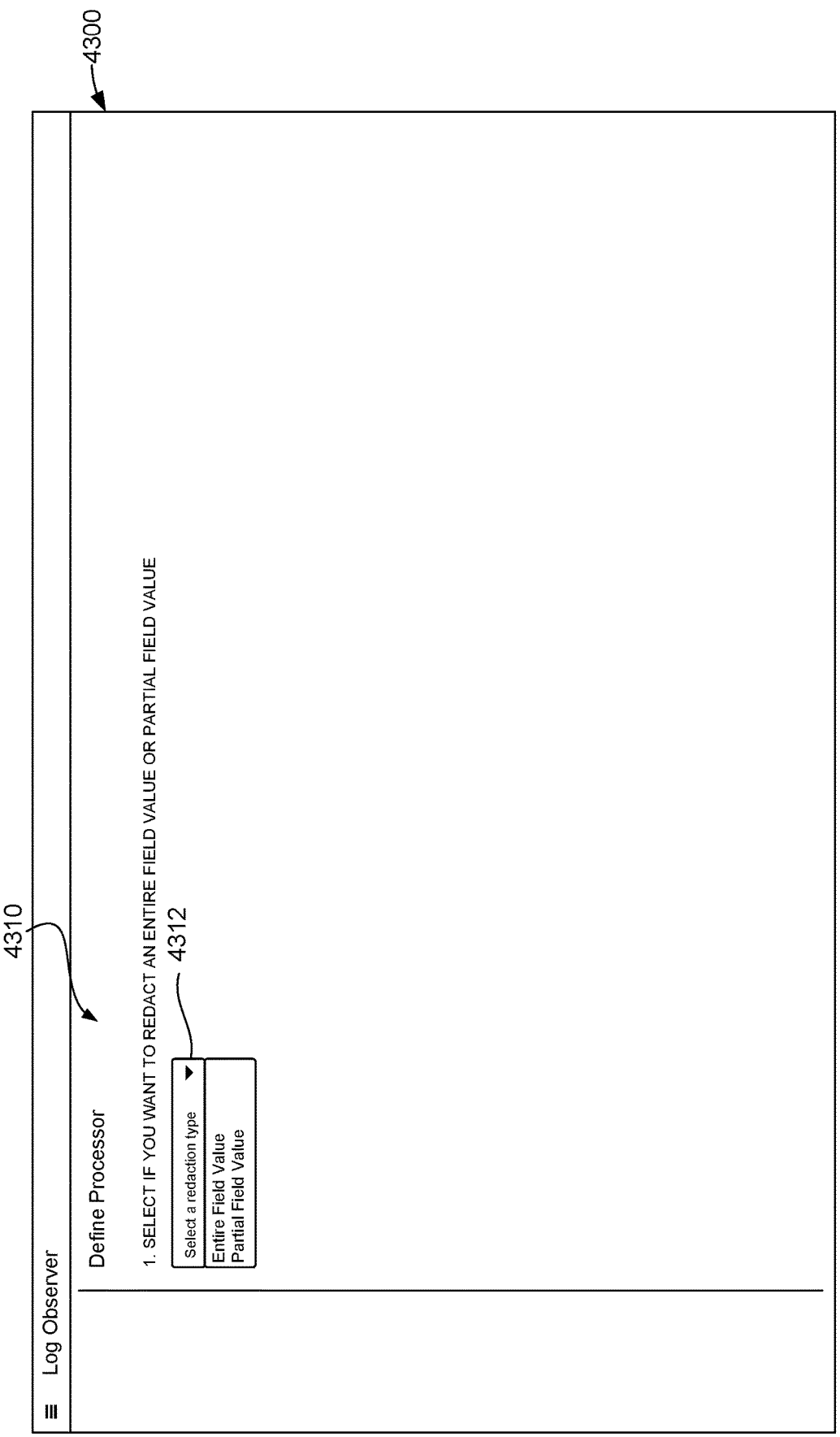
FIGS. 43-46 illustrate an example user interface that can be used to create a field redaction processing rule.

As illustrated in FIG. 43, the user interface 4300 initially depicts a window or tab 4310 that prompts a user to select a redaction type. For example, via dropdown menu 4312, the user can select an entire field value redaction type of a partial field value redaction type.

Figure 44:
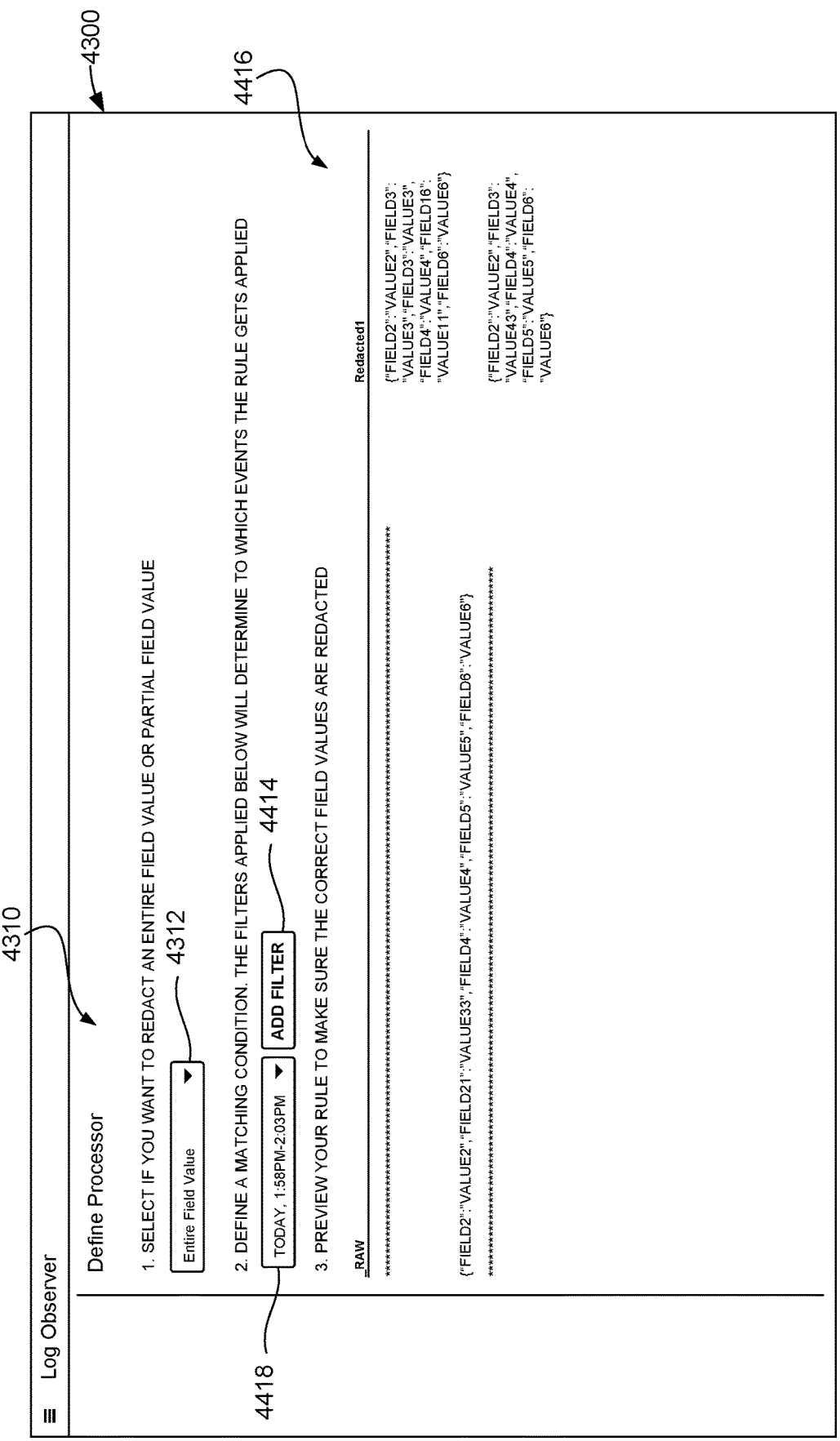

As illustrated in FIG. 44, the user has selected the entire field redaction type via the dropdown menu 4312. In response, the window 4310 depicts additional information and options. For example, the user can add one or more filters via user interface element 4414 and can preview logs to which the preliminary field redaction processing rule is applied via table 4416. In particular, the filter that can be added via the user interface element 4414 can be used to define a matching condition, such that the preliminary field redaction processing rule and/or the finalized field redaction processing rule is only applied by the field redactor 3404 to logs that satisfy the matching condition. The user can add any number of filters via the user interface element 4414.

The preview of logs to which the preliminary field redaction processing rule is applied depicted in the table 4416 can help the user view and ensure that the field redaction processing rule is working as intended. For example, the table 4416 can show the redacted log and the content that was redacted from the redacted log. If the redaction appears incorrect, this may indicate that the field redaction processing rule is not working properly, and the user can add or adjust filters or make other changes to the field redaction processing rule via the user interface 4300 as necessary. To generate the preview depicted in the table 4416, the field redactor 3404 can use the information provided in the dropdown menu 4312 and/or the user interface element 4414 to generate a preliminary field redaction processing rule and apply the preliminary field redaction processing rule to a set of already-ingested logs, such as logs that have already been ingested and that have a timestamp corresponding to the time period indicated in dropdown menu 4418. Application of the preliminary field redaction processing rule may not be permanent, such that any changes to the logs depicted in the preview may not be stored or indexed.

Figure 45:
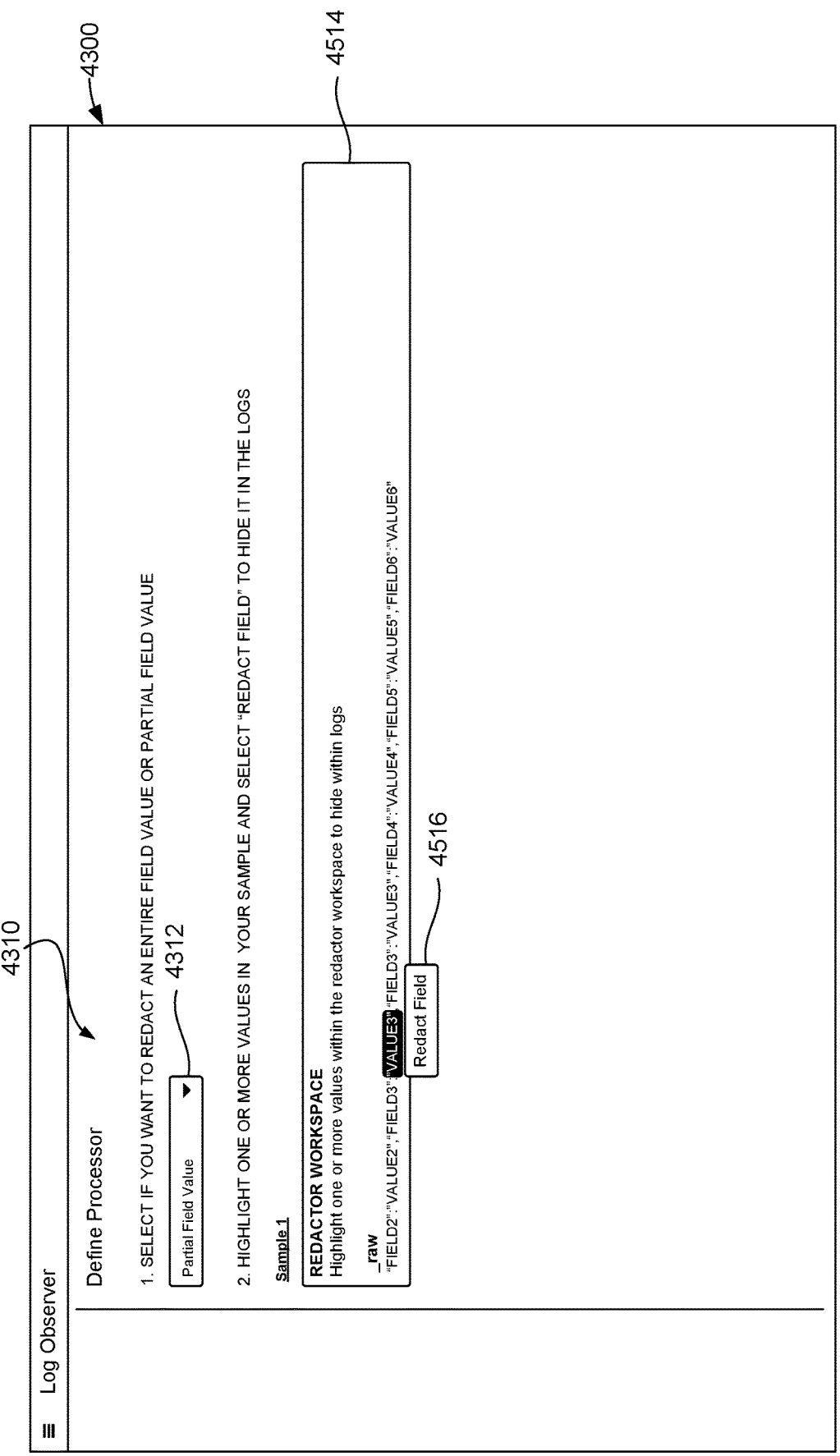

As illustrated in FIG. 45, the user has selected the partial field redaction type via the dropdown menu 4312. In response, the window 4310 depicts a redactor workspace 4514 in which the user is prompted to highlight one or more fields (or field values) to extract from a sample log, such as a sample log selected via the user interface 4300. Here, the user has highlighted VALUE3, which causes user interface element 4516 to appear.

Figure 46:
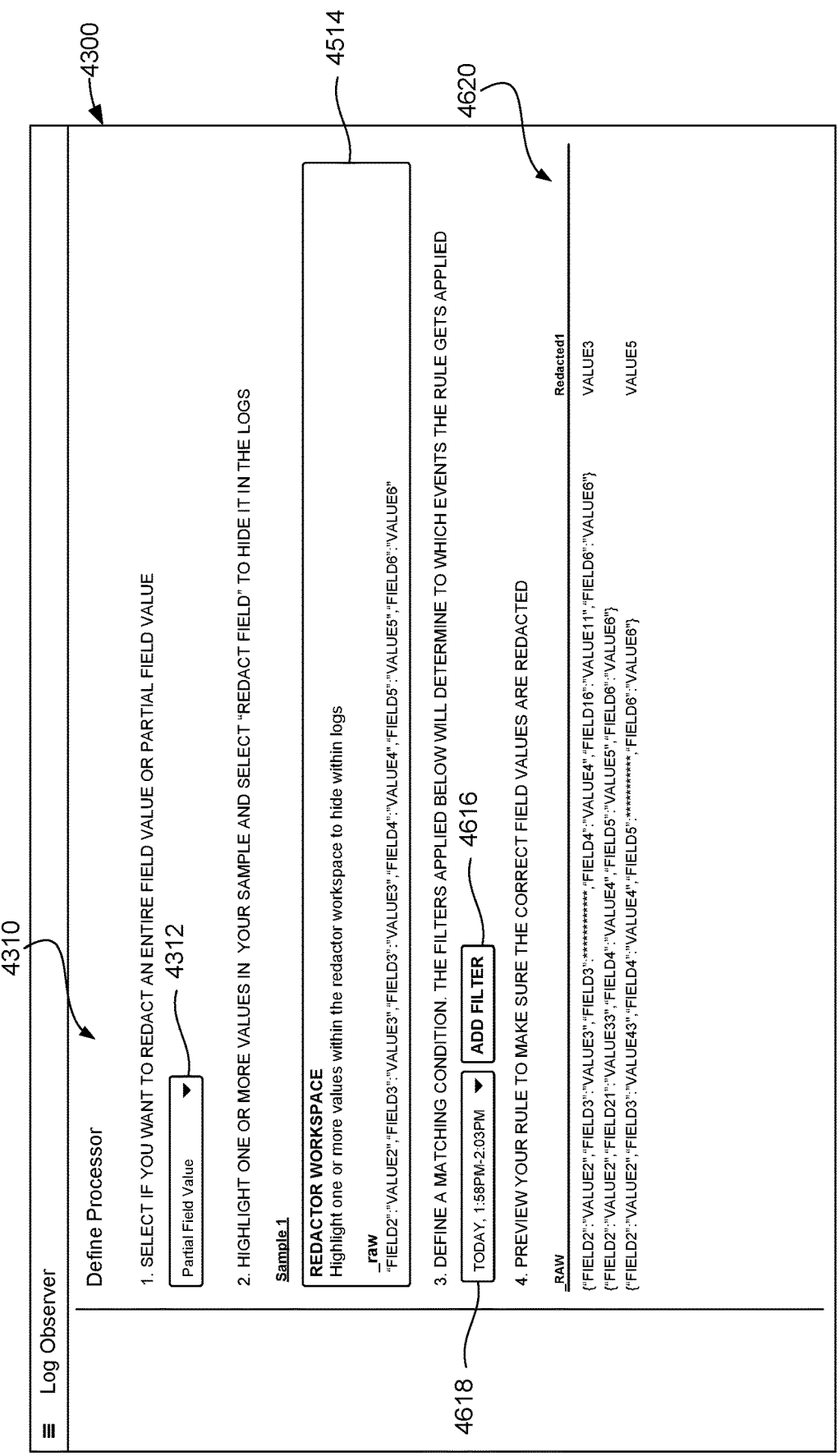

Selection of the user interface element 4516 indicates that the user would like to redact the highlighted field from ingested logs, causing the window 4310 to depict additional information and options, as illustrated in FIG. 46. For example, the user can add one or more filters via user interface element 4616 and can preview logs to which the preliminary field extraction processing rule is applied via table 4620. In particular, the filter that can be added via the user interface element 4616 can be used to define a matching condition, such that the preliminary field redaction processing rule and/or the finalized field redaction processing rule is only applied by the field redactor 3404 to logs that satisfy the matching condition. The user can add any number of filters via the user interface element 4616.

The preview of logs to which the preliminary field redaction processing rule is applied depicted in the table 4620 can help the user view and ensure that the field redaction processing rule is working as intended. For example, the table 4620 can show the redacted log and the content that was redacted from the redacted log. If the redaction appears incorrect, this may indicate that the field redaction processing rule is not working properly, and the user can add or adjust filters or make other changes to the field redaction processing rule via the user interface 4300 as necessary. For example, the table 4620 shows that VALUES, not VALUE3, was redacted from one log, which may indicate that the preliminary field redaction processing rule is not working as intended. To generate the preview depicted in the table 4620, the field redactor 3404 can use the information provided in the dropdown menu 4312, the redactor workspace 4514, and/or the user interface element 4616 to generate a preliminary field redaction processing rule and apply the preliminary field redaction processing rule to a set of already-ingested logs, such as logs that have already been ingested and that have a timestamp corresponding to the time period indicated in dropdown menu 4618. Application of the preliminary field redaction processing rule may not be permanent, such that any changes to the logs depicted in the preview may not be stored or indexed.

If the user approves the preliminary field redaction processing rule, then the field redactor 3404 may begin applying the field redaction processing rule to newly ingested logs and the results can be depicted in the user interface 4300. For example, the user interface 4300 can depict a view similar to the view described above with respect to FIG. 40. In addition, via the user interface 4300, the user may elect to apply the field redaction processing rule to logs that were ingested prior to creation of the field redaction processing rule, which may cause the field redactor 3404 to generate an instruction and transmit the instruction to the query system 214 to redact using the field redaction processing rule and/or provide redacted copies of the logs corresponding to the time period indicated in the user interface 4300 for display.

Figure 47:
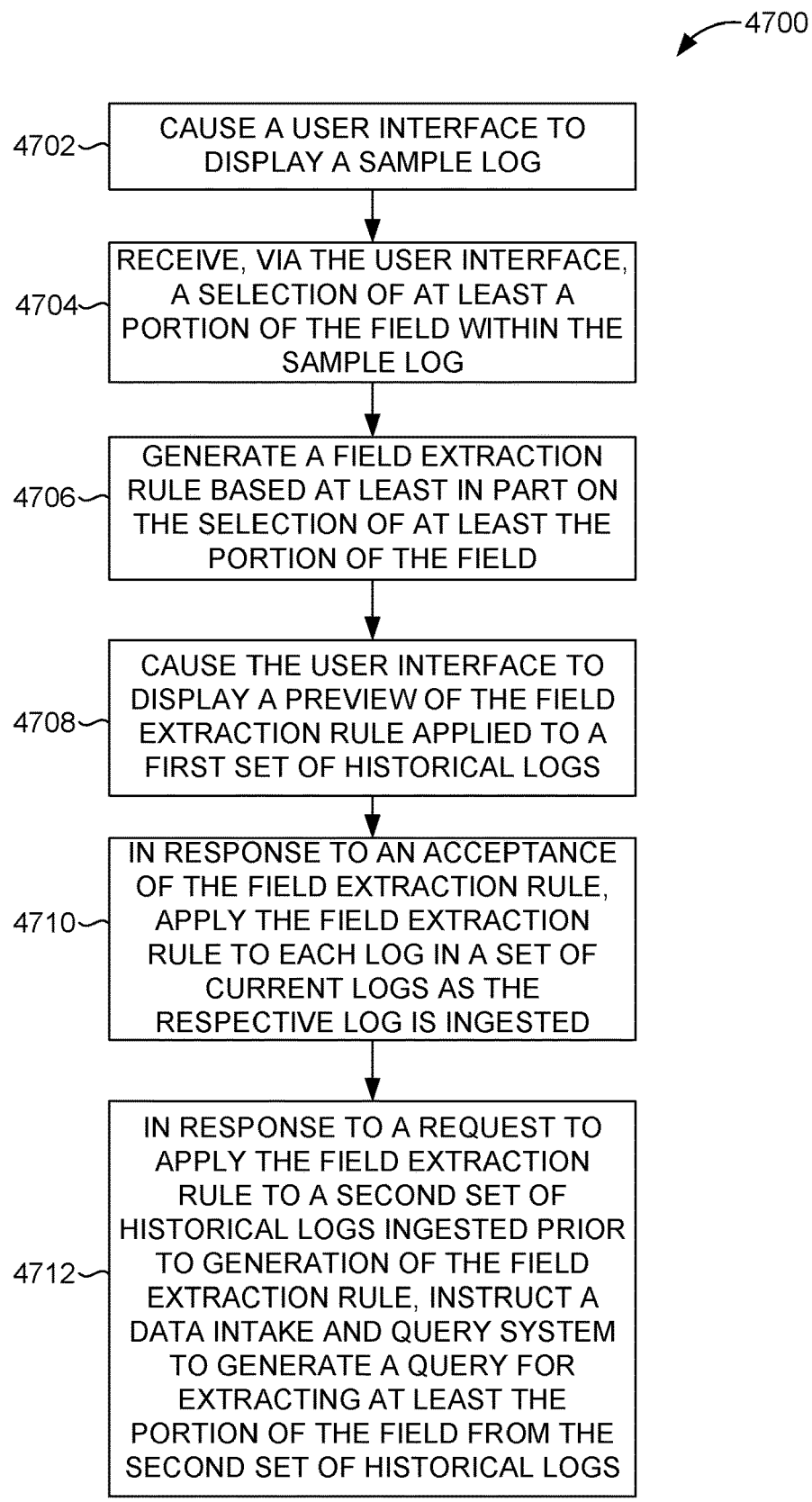
FIG. 47 is a flow diagram illustrative of an implementation of a routine implemented by the log observation system to generate a field extraction processing rule and enable search-time field extraction.

FIG. 47 is a flow diagram illustrative of an implementation of a routine 4700 implemented by the log observation system 3400 to generate a field extraction processing rule and enable search-time field extraction. Although described as being implemented by the log observation system 3400, it will be understood that the elements outlined for routine 4700 can be implemented by one or more computing devices/components that are associated with the data intake and query system 108. Thus, the following illustrative implementation should not be construed as limiting.

At block 4702, a user interface is caused to display a sample log. For example, the sample log may include a field.

At block 4704, a selection of at least a portion of the field within the sample log may be received via the user interface. The selection of the portion of the field may be received after the user has indicated via the user interface of a desire to create a regex field extraction type, a JSON field extraction type, an event time field extraction type, or a KV parser field extraction type.

At block 4706, a field extraction rule is generated based at least in part on the selection of at least the portion of the field. For example, the field extraction rule can be a preliminary field extraction processing rule generated based on a portion of a log highlighted by a user and any filters added by the user that define zero or more matching conditions.

At block 4708, the user interface is caused to display a preview of the field extraction rule applied to a first set of historical logs. The first set of historical logs may be logs that have already been ingested and that have not yet been discarded from the data store 3407. Application of the field extraction rule may not permanently alter the first set of historical logs. Rather, application of the field extraction rule to the first set of historical logs may be for evaluative purposes only. Any fields extracted by applying the rule may not be sent to other components of the data intake and query system 108 for indexing and storage.

At block 4710, in response to acceptance of the field extraction rule, the field extraction rule (e.g., a finalized version of the field extraction processing rule) may be applied to each log in a set of current logs as the respective log is ingested. If the user has set any filters, then the field extraction rule may be applied to each log in the set of current logs that satisfies the corresponding matching condition(s). The application of the field extraction rule may be to those logs in the set of current logs ingested at or after creation of the field extraction rule. Any fields extracted using the field extraction rule may be forwarded to other components of the data intake and query system 108 (e.g., the streaming data processor 308, the intake system 210, the indexing system 212, the data store(s) 218, etc.) for indexing and/or storage.

At block 4712, in response to a request to apply the field extraction rule to a second set of historical logs ingested prior to generation of the field extraction rule, a data intake and query system can be instructed to generate a query for extracting at least the portion of the field from the second set of historical logs. For example, the second set of historical logs may be logs that were ingested prior to generation of the field extraction rule and may or may no longer be stored in the data store 3407. Rather, the second set of historical logs may have already been transformed zero or more times by the streaming data processor 308, field(s) of such logs may have been indexed, and/or the logs and/or field(s) may have been stored. The data intake and query system (e.g., the query system 214) can be instructed to generate a query, where the query is for retrieving extracted field(s) that correspond to the field extraction rule and are from logs that satisfy any matching conditions from the data store(s) 218 and/or for using sourcetype detection and/or a regex rule to extract field(s) that correspond to the field extraction rule from logs that satisfy any matching conditions. The data intake and query system can transmit the results of the query to the log observation system 3400, which can cause the results to be displayed in a user interface. Thus, the user interface may display both the results of the log observation system 3400 applying the field processing rule to logs ingested at or after creation of the field processing rule and the results of the field processing rule being applied (e.g., effectively by the query system 214) to logs that were ingested prior to creation of the field processing rule.

Fewer, more, or different blocks can be used as part of the routine 4700. In some cases, one or more blocks can be omitted. Furthermore, it will be understood that the various blocks described herein with reference to FIG. 47 can be implemented in a variety of orders, or can be performed concurrently.

4.16. Other Architectures

In view of the description above, it will be appreciate that the architecture disclosed herein, or elements of that architecture, may be implemented independently from, or in conjunction with, other architectures. For example, the Parent Applications disclose a variety of architectures wholly or partially compatible with the architecture of the present disclosure.

Generally speaking one or more components of the data intake and query system 108 of the present disclosure can be used in combination with or to replace one or more components of the data intake and query system 108 of the Parent Applications. For example, depending on the embodiment, the operations of the forwarder 204 and the ingestion buffer 4802 of the Parent Applications can be performed by or replaced with the intake system 210 of the present disclosure. The parsing, indexing, and storing operations (or other non-searching operations) of the indexers 206, 230 and indexing cache components 254 of the Parent Applications can be performed by or replaced with the indexing nodes 404 of the present disclosure. The storage operations of the data stores 208 of the Parent Applications can be performed using the data stores 412 of the present disclosure (in some cases with the data not being moved to common storage 216). The storage operations of the common storage 4602, cloud storage 256, or global index 258 can be performed by the common storage 216 of the present disclosure. The storage operations of the query acceleration data store 3308 can be performed by the query acceleration data store 222 of the present disclosure.

As continuing examples, the search operations of the indexers 206, 230 and indexing cache components 254 of the Parent Applications can be performed by or replaced with the indexing nodes 404 in some embodiments or by the search nodes 506 in certain embodiments. For example, in some embodiments of certain architectures of the Parent Applications (e.g., one or more embodiments related to FIGS. 2, 3, 4, 18, 25, 27, 33, 46), the indexers 206, 230 and indexing cache components 254 of the Parent Applications may perform parsing, indexing, storing, and at least some searching operations, and in embodiments of some architectures of the Parent Applications (e.g., one more embodiments related to FIG. 48), indexers 206, 230 and indexing cache components 254 of the Parent Applications perform parsing, indexing, and storing operations, but do not perform searching operations. Accordingly, in some embodiments, some or all of the searching operations described as being performed by the indexers 206, 230 and indexing cache components 254 of the Parent Applications can be performed by the search nodes 506. For example, in embodiments described in the Parent Applications in which worker nodes 214, 236, 246, 3306 perform searching operations in place of the indexers 206, 230 or indexing cache components 254, the search nodes 506 can perform those operations. In certain embodiments, some or all of the searching operations described as being performed by the indexers 206, 230 and indexing cache components 254 of the Parent Applications can be performed by the indexing nodes 404. For example, in embodiments described in the Parent Applications in which the indexers 206, 230 and indexing cache components 254 perform searching operations, the indexing nodes 404 can perform those operations.

As a further example, the query operations performed by the search heads 210, 226, 244, daemons 210, 232, 252, search master 212, 234, 250, search process master 3302, search service provider 216, and query coordinator 3304 of the Parent Applications, can be performed by or replaced with any one or any combination of the query system manager 502, search head 504, search master 512, search manager 514, search node monitor 508, and/or the search node catalog 510. For example, these components can handle and coordinate the intake of queries, query processing, identification of available nodes and resources, resource allocation, query execution plan generation, assignment of query operations, combining query results, and providing query results to a user or a data store.

In certain embodiments, the query operations performed by the worker nodes 214, 236, 246, 3306 of the Parent Applications can be performed by or replaced with the search nodes 506 of the present disclosure. In some embodiments, the intake or ingestion operations performed by the worker nodes 214, 236, 246, 3306 of the Parent Applications can be performed by or replaced with one or more components of the intake system 210.

Furthermore, it will be understood that some or all of the components of the architectures of the Parent Applications can be replaced with components of the present disclosure. For example, in certain embodiments, the intake system 210 can be used in place of the forwarders 204 and/or ingestion buffer 4802 of one or more architectures of the Parent Applications, with all other components of the one or more architecture of the Parent Applications remaining the same. As another example, in some embodiments the indexing nodes 404 can replace the indexer 206 of one or more architectures of the Parent Applications with all other components of the one or more architectures of the Parent Applications remaining the same. Accordingly, it will be understood that a variety of architectures can be designed using one or more components of the data intake and query system 108 of the present disclosure in combination with one or more components of the data intake and query system 108 of the Parent Applications.

Illustratively, the architecture depicted at FIG. 2 of the Parent Applications may be modified to replace the forwarder 204 of that architecture with the intake system 210 of the present disclosure. In addition, in some cases, the indexers 206 of the Parent Applications can be replaced with the indexing nodes 404 of the present disclosure. In such embodiments, the indexing nodes 404 can retain the buckets in the data stores 412 that they create rather than store the buckets in common storage 216. Further, in the architecture depicted at FIG. 2 of the Parent Applications, the indexing nodes 404 of the present disclosure can be used to execute searches on the buckets stored in the data stores 412. In some embodiments, in the architecture depicted at FIG. 2 of the Parent Applications, the partition manager 408 can receive data from one or more forwarders 204 of the Parent Applications. As additional forwarders 204 are added or as additional data is supplied to the architecture depicted at FIG. 2 of the Parent Applications, the indexing node 406 can spawn additional partition manager 408 and/or the indexing manager system 402 can spawn additional indexing nodes 404. In addition, in certain embodiments, the bucket manager 414 may merge buckets in the data store 414 or be omitted from the architecture depicted at FIG. 2 of the Parent Applications.

Furthermore, in certain embodiments, the search head 210 of the Parent Applications can be replaced with the search head 504 of the present disclosure. In some cases, as described herein, the search head 504 can use the search master 512 and search manager 514 to process and manager the queries. However, rather than communicating with search nodes 506 to execute a query, the search head 504 can, depending on the embodiment, communicate with the indexers 206 of the Parent Applications or the search nodes 404 to execute the query.

Similarly the architecture of FIG. 3 of the Parent Applications may be modified in a variety of ways to include one or more components of the data intake and query system 108 described herein. For example, the architecture of FIG. 3 of the Parent Applications may be modified to include an intake system 210 in accordance with the present disclosure within the cloud-based data intake and query system 1006 of the Parent Applications, which intake system 210 may logically include or communicate with the forwarders 204 of the Parent Applications. In addition, the indexing nodes 404 described herein may be utilized in place of or to implement functionality similar to the indexers described with reference to FIG. 3 of the Parent Applications. In addition, the architecture of FIG. 3 of the Parent Applications may be modified to include common storage 216 and/or search nodes 506.

With respect to the architecture of FIG. 4 of the Parent Applications, the intake system 210 described herein may be utilized in place of or to implement functionality similar to either or both the forwarders 204 or the ERP processes 410 through 412 of the Parent Applications. Similarly, the indexing nodes 506 and the search head 504 described herein may be utilized in place of or to implement functionality similar to the indexer 206 and search head 210, respectively. In some cases, the search manager 514 described herein can manage the communications and interfacing between the indexer 210 and the ERP processes 410 through 412.

With respect to the flow diagrams and functionality described in FIGS. 5A-5C, 6A, 6B, 7A-7D, 8A, 8B, 9, 10, 11A-11D, 12-16, and 17A-17D of the Parent Applications, it will be understood that the processing and indexing operations described as being performed by the indexers 206 can be performed by the indexing nodes 404, the search operations described as being performed by the indexers 206 can be performed by the indexing nodes 404 or search nodes 506 (depending on the embodiment), and/or the searching operations described as being performed by the search head 210, can be performed by the search head 504 or other component of the query system 214.

With reference to FIG. 18 of the Parent Applications, the indexing nodes 404 and search heads 504 described herein may be utilized in place of or to implement functionality similar to the indexers 206 and search head 210, respectively. Similarly, the search master 512 and search manager 514 described herein may be utilized in place of or to implement functionality similar to the master 212 and the search service provider 216, respectively, described with respect to FIG. 18 of the Parent Applications. Further, the intake system 210 described herein may be utilized in place of or to implement ingestion functionality similar to the ingestion functionality of the worker nodes 214 of the Parent Applications. Similarly, the search nodes 506 described herein may be utilized in place of or to implement search functionality similar to the search functionality of the worker nodes 214 of the Parent Applications.

With reference to FIG. 25 of the Parent Applications, the indexing nodes 404 and search heads 504 described herein may be utilized in place of or to implement functionality similar to the indexers 236 and search heads 226, respectively. In addition, the search head 504 described herein may be utilized in place of or to implement functionality similar to the daemon 232 and the master 234 described with respect to FIG. 25 of the Parent Applications. The intake system 210 described herein may be utilized in place of or to implement ingestion functionality similar to the ingestion functionality of the worker nodes 214 of the Parent Applications. Similarly, the search nodes 506 described herein may be utilized in place of or to implement search functionality similar to the search functionality of the worker nodes 234 of the Parent Applications.

With reference to FIG. 27 of the Parent Applications, the indexing nodes 404 or search nodes 506 described herein may be utilized in place of or to implement functionality similar to the index cache components 254. For example, the indexing nodes 404 may be utilized in place of or to implement parsing, indexing, storing functionality of the index cache components 254, and the search nodes 506 described herein may be utilized in place of or to implement searching or caching functionality similar to the index cache components 254. In addition, the search head 504 described herein may be utilized in place of or to implement functionality similar to the search heads 244, daemon 252, and/or the master 250 described with respect to FIG. 27 of the Parent Applications. The intake system 210 described herein may be utilized in place of or to implement ingestion functionality similar to the ingestion functionality of the worker nodes 246 described with respect to FIG. 27 of the Parent Applications. Similarly, the search nodes 506 described herein may be utilized in place of or to implement search functionality similar to the search functionality of the worker nodes 234 described with respect to FIG. 27 of the Parent Applications. In addition, the common storage 216 described herein may be utilized in place of or to implement functionality similar to the functionality of the cloud storage 256 and/or global index 258 described with respect to FIG. 27 of the Parent Applications.

With respect to the architectures of FIGS. 33, 46, and 48 of the Parent Applications, the intake system 210 described herein may be utilized in place of or to implement functionality similar to the forwarders 204. In addition, the indexing nodes 404 of the present disclosure can perform the functions described as being performed by the indexers 206 (e.g., parsing, indexing, storing, and in some embodiments, searching) of the architectures of FIGS. 33, 46, and 48 of the Parent Applications; the operations of the acceleration data store 3308 of the architectures of FIGS. 33, 46, and 48 of the Parent Applications can be performed by the acceleration data store 222 of the present application; and the operations of the search head 210, search process maser 3302, and query coordinator 3304 of the architectures of FIGS. 33, 46, and 48 of the Parent Applications can be performed by the search head 504, search node catalog 510, and or search node monitor 508 of the present application. For example, the functionality of the workload catalog 3312 and node monitor 3314 of the architectures of FIGS. 33, 46, and 48 of the Parent Applications can be performed by the search node catalog 510 and search node monitor 508; the functionality of the search head 210 and other components of the search process master 3302 of the architectures of FIGS. 33, 46, and 48 of the Parent Applications can be performed by the search head 504 or search master 512; and the functionality of the query coordinator 3304 of the architectures of FIGS. 33, 46, and 48 of the Parent Applications can be performed by the search manager 514.

In addition, in some embodiments, the searching operations described as being performed by the worker nodes 3306 of the architectures of FIGS. 33, 46, and 48 of the Parent Applications can be performed by the search nodes 506 of the present application and the intake or ingestion operations performed by the worker nodes 3306 of the architectures of FIGS. 33, 46, and 48 of the Parent Applications can be performed by the intake system 210. However, it will be understood that in some embodiments, the search nodes 506 can perform the intake and search operations described in the Parent Applications as being performed by the worker nodes 3306. Furthermore, the cache manager 516 can implement one or more of the caching operations described in the Parent Applications with reference to the architectures of FIGS. 33, 46, and 48 of the Parent Applications.

With respect to FIGS. 46 and 48 of the Parent Applications, the common storage 216 of the present application can be used to provide the functionality with respect to the common storage 2602 of the architecture of FIGS. 46 and 48 of the Parent Applications. With respect to the architecture of FIG. 48 of the Parent Applications, the intake system 210 described herein may be utilized in place of or to implement operations similar to the forwarders 204 and ingested data buffer 4802, and may in some instances implement all or a portion of the operations described in that reference with respect to worker nodes 3306. Thus, the architecture of the present disclosure, or components thereof, may be implemented independently from or incorporated within architectures of the prior disclosures.

5.0 Terminology

Computer programs typically comprise one or more instructions set at various times in various memory devices of a computing device, which, when read and executed by at least one processor, will cause a computing device to execute functions involving the disclosed techniques. In some embodiments, a carrier containing the aforementioned computer program product is provided. The carrier is one of an electronic signal, an optical signal, a radio signal, or a non-transitory computer-readable storage medium.

Any or all of the features and functions described above can be combined with each other, except to the extent it may be otherwise stated above or to the extent that any such embodiments may be incompatible by virtue of their function or structure, as will be apparent to persons of ordinary skill in the art. Unless contrary to physical possibility, it is envisioned that (i) the methods/steps described herein may be performed in any sequence and/or in any combination, and (ii) the components of respective embodiments may be combined in any manner.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims, and other equivalent features and acts are intended to be within the scope of the claims.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly requires otherwise, throughout the description and the claims, the words "comprise," "comprising," and the like are to be construed in an inclusive sense, as opposed to an exclusive or exhaustive sense, i.e., in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

Conjunctive language such as the phrase "at least one of X, Y and Z," unless specifically stated otherwise, is otherwise understood with the context as used in general to convey that an item, term, etc. may be either X, Y or Z, or any combination thereof. Thus, such conjunctive language is not generally intended to imply that certain embodiments require at least one of X, at least one of Y and at least one of Z to each be present. Further, use of the phrase "at least one of X, Y or Z" as used in general is to convey that an item, term, etc. may be either X, Y or Z, or any combination thereof.

In some embodiments, certain operations, acts, events, or functions of any of the algorithms described herein can be performed in a different sequence, can be added, merged, or left out altogether (e.g., not all are necessary for the practice of the algorithms). In certain embodiments, operations, acts, functions, or events can be performed concurrently, e.g., through multi-threaded processing, interrupt processing, or multiple processors or processor cores or on other parallel architectures, rather than sequentially.

Systems and modules described herein may comprise software, firmware, hardware, or any combination(s) of software, firmware, or hardware suitable for the purposes described. Software and other modules may reside and execute on servers, workstations, personal computers, computerized tablets, PDAs, and other computing devices suitable for the purposes described herein. Software and other modules may be accessible via local computer memory, via a network, via a browser, or via other means suitable for the purposes described herein. Data structures described herein may comprise computer files, variables, programming arrays, programming structures, or any electronic information storage schemes or methods, or any combinations thereof, suitable for the purposes described herein. User interface elements described herein may comprise elements from graphical user interfaces, interactive voice response, command line interfaces, and other suitable interfaces.

Further, processing of the various components of the illustrated systems can be distributed across multiple machines, networks, and other computing resources. Two or more components of a system can be combined into fewer components. Various components of the illustrated systems can be implemented in one or more virtual machines or an isolated execution environment, rather than in dedicated computer hardware systems and/or computing devices. Likewise, the data repositories shown can represent physical and/or logical data storage, including, e.g., storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Embodiments are also described above with reference to flow chart illustrations and/or block diagrams of methods, apparatus (systems) and computer program products. Each block of the flow chart illustrations and/or block diagrams, and combinations of blocks in the flow chart illustrations and/or block diagrams, may be implemented by computer program instructions. Such instructions may be provided to a processor of a general purpose computer, special purpose computer, specially-equipped computer (e.g., comprising a high-performance database server, a graphics subsystem, etc.) or other programmable data processing apparatus to produce a machine, such that the instructions, which execute via the processor(s) of the computer or other programmable data processing apparatus, create means for implementing the acts specified in the flow chart and/or block diagram block or blocks. These computer program instructions may also be stored in a non-transitory computer-readable memory that can direct a computer or other programmable data processing apparatus to operate in a particular manner, such that the instructions stored in the computer-readable memory produce an article of manufacture including instruction means which implement the acts specified in the flow chart and/or block diagram block or blocks. The computer program instructions may also be loaded to a computing device or other programmable data processing apparatus to cause operations to be performed on the computing device or other programmable apparatus to produce a computer implemented process such that the instructions which execute on the computing device or other programmable apparatus provide steps for implementing the acts specified in the flow chart and/or block diagram block or blocks.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention. These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain aspects of the invention are presented below in certain claim forms, but the applicant contemplates other aspects of the invention in any number of claim forms. For example, while only one aspect of the invention is recited as a means-plus-function claim under 35 U.S.C sec. 112(f) (AIA), other aspects may likewise be embodied as a means-plus-function claim, or in other forms, such as being embodied in a computer-readable medium. Any claims intended to be treated under 35 U.S.C. § 112(f) will begin with the words "means for," but use of the term "for" in any other context is not intended to invoke treatment under 35 U.S.C. § 112(f). Accordingly, the applicant reserves the right to pursue additional claims after filing this application, in either this application or in a continuing application.

6.0 Example Embodiments

Various example embodiments of methods, systems, and non-transitory computer-readable media relating to features described herein can be found in the following clauses:

Clause 1. A computer-implemented method comprising:
  causing a user interface to display a sample log, wherein the sample log comprises a field;
  receiving, via the user interface, a selection of at least a portion of the field;
  generating a field extraction rule based at least in part on the selection of at least the portion of the field;
  causing the user interface to display a preview of the field extraction rule applied to a first set of historical logs;
  in response to an acceptance of the field extraction rule, applying the field extraction rule to each log in a set of current logs as the respective log is ingested; and
  in response to a request to apply the field extraction rule to a second set of historical logs ingested prior to generation of the field extraction rule, instructing a data intake and query system to generate a query for extracting at least the portion of the field from the second set of historical logs.

Clause 2. The computer-implemented method of Clause 1, wherein the field extraction rule corresponds to one of a regex extraction, a JavaScript Object Notation (JSON) extraction, an event time extraction or a key-value parser extraction.

Clause 3. The computer-implemented method of Clause 1, further comprising receiving, via the user interface, a selection of a filter that defines to which logs in the set of current logs the field extraction rule is applied.

Clause 4. The computer-implemented method of Clause 1, further comprising:
applying the field extraction rule to each log in the first set of historical logs; and
refraining from indexing or storing results of applying the field extraction rule to each log in the first set of historical logs.

Clause 5. The computer-implemented method of Clause 1, wherein applying the field extraction rule to each log in a set of current logs as the respective log is ingested further comprises applying the field extraction rule to each log in the set of current logs as the respective log is ingested and prior to the respective log being transformed in a data processing pipeline.

Clause 6. The computer-implemented method of Clause 1, further comprising transmitting each log in the set of current logs and results of application of the field extraction rule to the respective log to a data intake and query system for indexing.

Clause 7. The computer-implemented method of Clause 1, wherein applying the field extraction rule to each log in a set of current logs as the respective log is ingested further comprises:
applying a second field extraction rule to each log in the set of current logs as the respective log is ingested; and
applying the field extraction rule to each log in the set of current logs as the respective log is ingested after application of the second field extraction rule and prior to a subsequent log in the set of current logs being ingested.

Clause 8. The computer-implemented method of Clause 1, wherein applying the field extraction rule to each log in a set of current logs as the respective log is ingested further comprises:
applying a second field extraction rule to each log in the set of current logs as the respective log is ingested; and
applying the field extraction rule to each log in the set of current logs as the respective log is ingested after application of the second field extraction rule and prior to a subsequent log in the set of current logs being ingested, wherein an order in which the second field extraction rule and the field extraction rule are applied is dependent on an order in which the second field extraction rule and the field extraction rule are depicted in the user interface.

Clause 9. The computer-implemented method of Clause 1, wherein applying the field extraction rule to each log in a set of current logs as the respective log is ingested further comprises:
applying a second field extraction rule to each log in the set of current logs as the respective log is ingested, wherein the second field extraction rule is a prepackaged rule that is automatically enabled based on at least some of the content of at least some of the logs in the set of current logs; and
applying the field extraction rule to each log in the set of current logs as the respective log is ingested after application of the second field extraction rule and prior to a subsequent log in the set of current logs being ingested.

Clause 10. The computer-implemented method of Clause 1, further comprising:
receiving, via the user interface, a request to create a field redaction processing rule;
receiving, via the user interface, a selection of a portion of a field value present in a second sample log;
generating the field redaction processing rule based at least in part on the selection of the portion of the field value present in the second sample log;
causing the user interface to display a preview of the field redaction processing rule applied to a third set of historical logs; and
in response to an acceptance of the field redaction processing rule, applying the field redaction processing rule to each log in a set of second current logs as the respective log is ingested.

Clause 11. The computer-implemented method of Clause 1, further comprising:
receiving, via the user interface, a request to create a field redaction processing rule in which an entire log is redacted;
generating the field redaction processing rule;
causing the user interface to display a preview of the field redaction processing rule applied to a third set of historical logs; and
in response to an acceptance of the field redaction processing rule, applying the field redaction processing rule to each log in a set of second current logs as the respective log is ingested.

Clause 12. The computer-implemented method of Clause 1, wherein the set of current logs are ingested after generation of a field redaction processing rule.

Clause 13. The computer-implemented method of Clause 1, further comprising causing the user interface to display, concurrently, results of applying the field extraction rule to each log in the set of current logs as the respective log is ingested and results of the query generated by the data intake and query system.

Clause 14. The computer-implemented method of Clause 1, wherein the query comprises a request to retrieve the field present in each of the second set of historical logs from a data store that stores indexed data.

Clause 15. The computer-implemented method of Clause 1, wherein the field extraction rule comprises a regex rule that defines a sequence of characters to extract, and wherein the query comprises an application of the regex rule to each of the second set of historical logs that has a sourcetype that matches a sourcetype corresponding to the regex rule.

Clause 16. The computer-implemented method of Clause 1, further comprising receiving, via the user interface, a request to create a field copy processing rule in which a field value of a second field is copied to a third field upon application of the field copy processing rule.

Clause 17. The computer-implemented method of Clause 1, further comprising receiving, via the user interface, a request to create a field categorization processing rule in which a new field is created in response to a field value of a second field satisfying a condition upon application of the field categorization processing rule.

Clause 18. A system comprising:
a data store including computer-executable instructions; and
one or more processors configured to execute the computer-executable instructions, wherein execution of the computer-executable instructions causes the system to:

cause a user interface to display a sample log, wherein the sample log comprises a field;

receive, via the user interface, a selection of at least a portion of the field;

generate a field extraction rule based at least in part on the selection of at least the portion of the field;

cause the user interface to display a preview of the field extraction rule applied to a first set of historical logs;

in response to an acceptance of the field extraction rule, apply the field extraction rule to each log in a set of current logs as the respective log is ingested; and in response to a request to apply the field extraction rule to a second set of historical logs ingested prior to generation of the field extraction rule, instruct a data intake and query system to generate a query for extracting at least the portion of the field from the second set of historical logs.

Clause 19. The system of Clause 18, wherein the field extraction rule corresponds to one of a regex extraction, a JavaScript Object Notation (JSON) extraction, an event time extraction or a key-value parser extraction.

Clause 20. Non-transitory computer-readable media including computer-executable instructions that, when executed by a computing system, cause the computing system to:

cause a user interface to display a sample log, wherein the sample log comprises a field;

receive, via the user interface, a selection of at least a portion of the field;

generate a field extraction rule based at least in part on the selection of at least the portion of the field;

cause the user interface to display a preview of the field extraction rule applied to a first set of historical logs;

in response to an acceptance of the field extraction rule, apply the field extraction rule to each log in a set of current logs as the respective log is ingested; and in response to a request to apply the field extraction rule to a second set of historical logs ingested prior to generation of the field extraction rule, instruct a data intake and query system to generate a query for extracting at least the portion of the field from the second set of historical logs.

Any of the above methods may be embodied within computer-executable instructions which may be stored within a data store or non-transitory computer-readable media and executed by a computing system (e.g., a processor of such system) to implement the respective methods.

What is claimed is:

1. A computer-implemented method comprising:

causing a user interface to display a sample log, wherein the sample log comprises a field;

receiving, via the user interface, a selection of at least a portion of the field;

generating a field extraction rule based at least in part on the selection of at least the portion of the field;

causing the user interface to display a preview of the field extraction rule applied to a first set of historical logs;

in response to an acceptance of the field extraction rule, applying the field extraction rule to each log in a set of current logs as the respective log is ingested; and in response to a request to apply the field extraction rule to a second set of historical logs ingested prior to generation of the field extraction rule, instructing a data intake and query system to generate a query for extracting at least the portion of the field from the second set of historical logs.

2. The computer-implemented method of claim 1, wherein the field extraction rule corresponds to one of a regex extraction, a JavaScript Object Notation (JSON) extraction, an event time extraction or a key-value parser extraction.

3. The computer-implemented method of claim 1, further comprising receiving, via the user interface, a selection of a filter that defines to which logs in the set of current logs the field extraction rule is applied.

4. The computer-implemented method of claim 1, further comprising:

applying the field extraction rule to each log in the first set of historical logs; and refraining from indexing or storing results of applying the field extraction rule to each log in the first set of historical logs.

5. The computer-implemented method of claim 1, wherein applying the field extraction rule to each log in a set of current logs as the respective log is ingested further comprises applying the field extraction rule to each log in the set of current logs as the respective log is ingested and prior to the respective log being transformed in a data processing pipeline.

6. The computer-implemented method of claim 1, further comprising transmitting each log in the set of current logs and results of application of the field extraction rule to the respective log to a data intake and query system for indexing.

7. The computer-implemented method of claim 1, wherein applying the field extraction rule to each log in a set of current logs as the respective log is ingested further comprises:

applying a second field extraction rule to each log in the set of current logs as the respective log is ingested; and applying the field extraction rule to each log in the set of current logs as the respective log is ingested after application of the second field extraction rule and prior to a subsequent log in the set of current logs being ingested.

8. The computer-implemented method of claim 1, wherein applying the field extraction rule to each log in a set of current logs as the respective log is ingested further comprises:

applying a second field extraction rule to each log in the set of current logs as the respective log is ingested; and applying the field extraction rule to each log in the set of current logs as the respective log is ingested after application of the second field extraction rule and prior to a subsequent log in the set of current logs being ingested, wherein an order in which the second field extraction rule and the field extraction rule are applied is dependent on an order in which the second field extraction rule and the field extraction rule are depicted in the user interface.

9. The computer-implemented method of claim 1, wherein applying the field extraction rule to each log in a set of current logs as the respective log is ingested further comprises:

applying a second field extraction rule to each log in the set of current logs as the respective log is ingested, wherein the second field extraction rule is a prepackaged rule that is automatically enabled based on at least some of a content of at least some of the logs in the set of current logs; and applying the field extraction rule to each log in the set of current logs as the respective log is ingested after application of the second field extraction rule and prior to a subsequent log in the set of current logs being ingested.

10. The computer-implemented method of claim 1, further comprising:
receiving, via the user interface, a request to create a field redaction processing rule;
receiving, via the user interface, a selection of a portion of a field value present in a second sample log;
generating the field redaction processing rule based at least in part on the selection of the portion of the field value present in the second sample log;
causing the user interface to display a preview of the field redaction processing rule applied to a third set of historical logs; and
in response to an acceptance of the field redaction processing rule, applying the field redaction processing rule to each log in a set of second current logs as the respective log is ingested.

11. The computer-implemented method of claim 1, further comprising:
receiving, via the user interface, a request to create a field redaction processing rule in which an entire log is redacted;
generating the field redaction processing rule;
causing the user interface to display a preview of the field redaction processing rule applied to a third set of historical logs; and
in response to an acceptance of the field redaction processing rule, applying the field redaction processing rule to each log in a set of second current logs as the respective log is ingested.

12. The computer-implemented method of claim 1, wherein the set of current logs are ingested after generation of a field redaction processing rule.

13. The computer-implemented method of claim 1, further comprising causing the user interface to display, concurrently, results of applying the field extraction rule to each log in the set of current logs as the respective log is ingested and results of the query generated by the data intake and query system.

14. The computer-implemented method of claim 1, wherein the query comprises a request to retrieve the field present in each of the second set of historical logs from a data store that stores indexed data.

15. The computer-implemented method of claim 1, wherein the field extraction rule comprises a regex rule that defines a sequence of characters to extract, and wherein the query comprises an application of the regex rule to each of the second set of historical logs that has a sourcetype that matches a sourcetype corresponding to the regex rule.

16. The computer-implemented method of claim 1, further comprising receiving, via the user interface, a request to create a field copy processing rule in which a field value of a second field is copied to a third field upon application of the field copy processing rule.

17. The computer-implemented method of claim 1, further comprising receiving, via the user interface, a request to create a field categorization processing rule in which a new field is created in response to a field value of a second field satisfying a condition upon application of the field categorization processing rule.

18. A system comprising:
a data store including computer-executable instructions; and
one or more processors configured to execute the computer-executable instructions, wherein execution of the computer-executable instructions causes the system to:
cause a user interface to display a sample log, wherein the sample log comprises a field;
receive, via the user interface, a selection of at least a portion of the field;
generate a field extraction rule based at least in part on the selection of at least the portion of the field;
cause the user interface to display a preview of the field extraction rule applied to a first set of historical logs;
in response to an acceptance of the field extraction rule, apply the field extraction rule to each log in a set of current logs as the respective log is ingested; and
in response to a request to apply the field extraction rule to a second set of historical logs ingested prior to generation of the field extraction rule, instruct a data intake and query system to generate a query for extracting at least the portion of the field from the second set of historical logs.

19. The system of claim 18, wherein the field extraction rule corresponds to one of a regex extraction, a JavaScript Object Notation (JSON) extraction, an event time extraction or a key-value parser extraction.

20. Non-transitory computer-readable media including computer-executable instructions that, when executed by a computing system, cause the computing system to:
cause a user interface to display a sample log, wherein the sample log comprises a field;
receive, via the user interface, a selection of at least a portion of the field;
generate a field extraction rule based at least in part on the selection of at least the portion of the field;
cause the user interface to display a preview of the field extraction rule applied to a first set of historical logs;
in response to an acceptance of the field extraction rule, apply the field extraction rule to each log in a set of current logs as the respective log is ingested; and
in response to a request to apply the field extraction rule to a second set of historical logs ingested prior to generation of the field extraction rule, instruct a data intake and query system to generate a query for extracting at least the portion of the field from the second set of historical logs.

* * * * *